US012607593B2

(12) United States Patent
Merriman et al.

(10) Patent No.: US 12,607,593 B2
(45) Date of Patent: Apr. 21, 2026

(54) MOLECULAR SENSORS AND RELATED METHODS

(71) Applicant: Roswell Biotechnologies, Inc., San Diego, CA (US)

(72) Inventors: Barry L. Merriman, San Diego, CA (US); Paul W. Mola, San Diego, CA (US); Chulmin Choi, San Diego, CA (US)

(73) Assignee: SemiconBio Inc., San Diego, CA (US)

( * ) Notice: Subject to any disclaimer, the term of this patent is extended or adjusted under 35 U.S.C. 154(b) by 0 days.

(21) Appl. No.: 16/070,133

(22) PCT Filed: Dec. 28, 2016

(86) PCT No.: PCT/US2016/068922
§ 371 (c)(1),
(2) Date: Jul. 13, 2018

(87) PCT Pub. No.: WO2017/123416
PCT Pub. Date: Jul. 20, 2017

(65) Prior Publication Data
US 2019/0094175 A1 Mar. 28, 2019

Related U.S. Application Data

(60) Provisional application No. 62/278,907, filed on Jan. 14, 2016, provisional application No. 62/278,889,
(Continued)

(51) Int. Cl.
*G01N 27/414* (2006.01)
*B82Y 15/00* (2011.01)
(Continued)

(52) U.S. Cl.
CPC .......... *G01N 27/4145* (2013.01); *B82Y 15/00* (2013.01); *C12Q 1/6825* (2013.01); *G01N 33/48721* (2013.01); *C12Q 1/6869* (2013.01)

(58) Field of Classification Search
CPC ........... C12Q 1/6825; C12Q 2563/116; C12Q 2565/607; C12Q 2521/101;
(Continued)

(56) References Cited

U.S. PATENT DOCUMENTS

| | | | |
|---|---|---|---|
| 4,923,586 A | 5/1990 | Katayama et al. | |
| 5,082,627 A | 1/1992 | Stanbro | |

(Continued)

FOREIGN PATENT DOCUMENTS

| | | |
|---|---|---|
| CN | 1795376 | 6/2006 |
| CN | 101231287 | 7/2008 |

(Continued)

OTHER PUBLICATIONS

USPTO; Notice of Allowance dated May 11, 2020 in U.S. Appl. No. 16/073,706.

(Continued)

*Primary Examiner* — Jonathan M Hurst
(74) *Attorney, Agent, or Firm* — Spectrum IP Law Group LLC; Dianoosh Salehi

(57) ABSTRACT

Electronic sensors configured to detect single molecules and DNA methods of using and manufacturing same are disclosed. A sensor may include source and drain electrodes spaced apart by a sensor gap; a gate electrode, wherein the source, drain and gate electrodes cooperate to form an electrode circuit; and a bridge molecule bridging across the sensor gap, connecting source and drain electrodes; and a probe coupled to the bridge molecule, wherein interaction of the probe with a nucleic acid is detectable by monitoring a
(Continued)

parameter of the electrode circuit. In various examples, the nucleic acid comprises DNA or RNA.

19 Claims, 94 Drawing Sheets

Specification includes a Sequence Listing.

Related U.S. Application Data filed on Jan. 14, 2016, provisional application No. 62/278,900, filed on Jan. 14, 2016.

(51) Int. Cl.

| | |
|---|---|
| *C12Q 1/6825* | (2018.01) |
| *G01N 33/487* | (2006.01) |
| *C12Q 1/6869* | (2018.01) |

(58) Field of Classification Search
CPC ........ C12Q 2521/107; C12Q 2521/319; C12Q 2521/513; C12Q 1/6869; C12Q 1/701; C12Q 1/6837; B82Y 15/00; G01N 27/4145; G01N 33/48721; G01N 27/3278; G01N 33/5438; G01N 27/3276
See application file for complete search history.

(56) References Cited

U.S. PATENT DOCUMENTS

| | | | |
|---|---|---|---|
| 5,194,133 A | 3/1993 | Clark et al. |
| 5,366,140 A | 11/1994 | Koskenmaki et al. |
| 5,414,588 A | 5/1995 | Barbec, Jr. |
| 5,486,449 A | 1/1996 | Honso et al. |
| 5,532,128 A | 7/1996 | Eggers et al. |
| 5,583,359 A | 12/1996 | Ng et al. |
| 5,639,507 A | 6/1997 | Galvagni et al. |
| 5,646,420 A | 7/1997 | Yamashita |
| 5,767,687 A | 6/1998 | Geist |
| 5,871,918 A | 2/1999 | Thorp et al. |
| 5,881,184 A | 3/1999 | Guidash |
| 5,965,452 A | 10/1999 | Kovacs |
| 5,982,018 A | 11/1999 | Wark |
| 6,051,380 A | 4/2000 | Sosnowski et al. |
| 6,060,023 A | 5/2000 | Maracas |
| 6,094,335 A | 7/2000 | Early |
| 6,110,354 A | 8/2000 | Saban |
| 6,123,819 A | 9/2000 | Peeters |
| 6,144,023 A | 11/2000 | Clerc |
| 6,238,927 B1 | 5/2001 | Abrams et al. |
| 6,440,662 B1 | 8/2002 | Gerwen et al. |
| 6,464,889 B1 | 10/2002 | Lee et al. |
| 6,506,564 B1 | 1/2003 | Mirkin et al. |
| 6,537,747 B1 | 3/2003 | Mills, Jr. et al. |
| 6,670,131 B2 | 12/2003 | Hashimoto |
| 6,673,533 B1 | 1/2004 | Wohlstadter et al. |
| 6,716,620 B2 | 4/2004 | Bashir et al. |
| 6,749,731 B2 | 6/2004 | Kobori |
| 6,762,050 B2 | 7/2004 | Fukushima et al. |
| 6,764,745 B1 | 7/2004 | Karasawa et al. |
| 6,790,341 B1 | 9/2004 | Saban |
| 6,824,974 B2 | 11/2004 | Pisharody et al. |
| 6,861,224 B2 | 3/2005 | Fujita et al. |
| 6,916,614 B1 | 7/2005 | Takenaka et al. |
| 6,958,216 B2 | 10/2005 | Kelley |
| 7,015,046 B2 | 3/2006 | Wohlstadter et al. |
| 7,075,428 B1 | 7/2006 | Oleynik |
| 7,169,272 B2 | 1/2007 | Fritsch et al. |
| 7,183,055 B2 | 2/2007 | Van Der Weide |
| 7,189,435 B2 | 3/2007 | Tuominen et al. |
| 7,202,480 B2 | 4/2007 | Yokoi et al. |
| 7,208,077 B1 | 4/2007 | Albers et al. |
| 7,276,206 B2 | 10/2007 | Augustine et al. |
| 7,399,585 B2 | 7/2008 | Gau |
| 7,432,120 B2 | 10/2008 | Mascolo et al. |
| 7,470,533 B2 | 12/2008 | Xu et al. |
| 7,507,320 B2 | 3/2009 | Hwang et al. |
| 7,531,120 B2 | 5/2009 | Van Rijn et al. |
| 7,579,823 B1 | 8/2009 | Ayliffe |
| 7,691,433 B2 | 4/2010 | Kronholz et al. |
| 7,785,785 B2 | 8/2010 | Pourmand et al. |
| 7,834,344 B2 | 11/2010 | Mascolo et al. |
| 7,851,045 B2 | 12/2010 | Gandon et al. |
| 7,886,601 B2 | 2/2011 | Merassi et al. |
| 7,901,629 B2 | 3/2011 | Calatzis et al. |
| 7,943,394 B2 | 5/2011 | Flandre et al. |
| 8,241,508 B2 | 8/2012 | D'Urso |
| 8,313,633 B2 | 11/2012 | Li et al. |
| 8,351,181 B1 | 1/2013 | Ahn |
| 8,591,816 B2 | 11/2013 | Calatzis et al. |
| 8,652,768 B1 | 2/2014 | Huber et al. |
| 8,753,893 B2 | 6/2014 | Liu et al. |
| 8,927,464 B2 | 1/2015 | Aizenberg et al. |
| 8,940,663 B2 | 1/2015 | Iqbal et al. |
| 9,070,733 B2 | 6/2015 | Rajagopal et al. |
| 9,108,880 B2 | 8/2015 | Jin et al. |
| 9,139,614 B2 | 9/2015 | Medintz |
| 9,306,164 B1 | 4/2016 | Chang et al. |
| 9,829,456 B1 | 11/2017 | Merriman et al. |
| 9,956,743 B2 | 5/2018 | Jin et al. |
| 10,036,064 B2 | 7/2018 | Merriman et al. |
| 10,125,420 B2 | 11/2018 | Jin et al. |
| 10,151,722 B2 | 12/2018 | Jin et al. |
| 10,508,296 B2 | 12/2019 | Merriman et al. |
| 10,526,696 B2 | 1/2020 | Jin et al. |
| 10,584,410 B2 | 3/2020 | Jin et al. |
| 10,597,767 B2 | 3/2020 | Merriman et al. |
| 10,712,334 B2 | 7/2020 | Choi et al. |
| 2002/0022223 A1 | 2/2002 | Connolly |
| 2002/0090649 A1 | 7/2002 | Chan et al. |
| 2002/0137083 A1 | 9/2002 | Kobori et al. |
| 2002/0138049 A1 | 9/2002 | Allen et al. |
| 2002/0142150 A1 | 10/2002 | Baumann et al. |
| 2002/0142477 A1 | 10/2002 | Lewis et al. |
| 2002/0172963 A1 | 11/2002 | Kelley et al. |
| 2002/0184939 A1 | 12/2002 | Yadav |
| 2003/0025133 A1 | 2/2003 | Brousseau |
| 2003/0040000 A1 | 2/2003 | Connolly et al. |
| 2003/0040173 A1 | 2/2003 | Fonash |
| 2003/0064390 A1 | 4/2003 | Schülein et al. |
| 2003/0087296 A1 | 5/2003 | Fujita et al. |
| 2003/0109031 A1 | 6/2003 | Chafin et al. |
| 2003/0141189 A1 | 7/2003 | Lee et al. |
| 2003/0141276 A1 | 7/2003 | Lee et al. |
| 2003/0186263 A1 | 10/2003 | Frey et al. |
| 2003/0224387 A1 | 12/2003 | Kunwar et al. |
| 2004/0012161 A1 | 1/2004 | Chiu |
| 2004/0014106 A1 | 1/2004 | Patno et al. |
| 2004/0023253 A1 | 2/2004 | Kunwar et al. |
| 2004/0038090 A1 | 2/2004 | Faris |
| 2004/0048241 A1 | 3/2004 | Freeman et al. |
| 2004/0063100 A1 | 4/2004 | Wang |
| 2004/0086929 A1 | 5/2004 | Weide et al. |
| 2004/0096866 A1 | 5/2004 | Hoffman et al. |
| 2004/0146863 A1 | 7/2004 | Pisharody et al. |
| 2004/0209355 A1 | 10/2004 | Edman et al. |
| 2004/0209435 A1 | 10/2004 | Patridge et al. |
| 2004/0229247 A1 | 11/2004 | DeBoer et al. |
| 2004/0235016 A1 | 11/2004 | Hamers |
| 2004/0248282 A1 | 12/2004 | Sobha |
| 2005/0029227 A1 | 2/2005 | Chapman |
| 2005/0067086 A1 | 3/2005 | Ito et al. |
| 2005/0074911 A1 | 4/2005 | Kornilovich et al. |
| 2005/0151541 A1 | 7/2005 | Brinz et al. |
| 2005/0156157 A1 | 7/2005 | Parsons et al. |
| 2005/0164371 A1 | 7/2005 | Arinaga |
| 2005/0172199 A1 | 8/2005 | Miller et al. |
| 2005/0181195 A1 | 8/2005 | Dubrow |
| 2005/0221473 A1 | 10/2005 | Dubin et al. |
| 2005/0227373 A1 | 10/2005 | Flandre et al. |
| 2005/0247573 A1 | 11/2005 | Nakamura et al. |
| 2005/0285275 A1 | 12/2005 | Son |
| 2005/0287548 A1 | 12/2005 | Bao et al. |
| 2005/0287589 A1 | 12/2005 | Connolly |

(56)  References Cited

U.S. PATENT DOCUMENTS

| | | | |
|---|---|---|---|
| 2006/0003437 A1* | 1/2006 | Fujihara | C12Q 1/6825 |
| | | | 435/287.1 |
| 2006/0003482 A1 | 1/2006 | Chinthakindi et al. | |
| 2006/0019273 A1 | 1/2006 | Connolly et al. | |
| 2006/0024504 A1 | 2/2006 | Nelson et al. | |
| 2006/0024508 A1 | 2/2006 | D'Urso et al. | |
| 2006/0029808 A1 | 2/2006 | Zhai et al. | |
| 2006/0051919 A1 | 3/2006 | Mascolo et al. | |
| 2006/0051946 A1 | 3/2006 | Mascolo et al. | |
| 2006/0105449 A1 | 5/2006 | Armer et al. | |
| 2006/0105467 A1 | 5/2006 | Niksa et al. | |
| 2006/0128239 A1 | 6/2006 | Nun et al. | |
| 2006/0147983 A1 | 7/2006 | O'uchi | |
| 2006/0154489 A1 | 7/2006 | Tornow | |
| 2006/0275853 A1 | 12/2006 | Matthew et al. | |
| 2007/0026193 A1 | 2/2007 | Luzinov et al. | |
| 2007/0048748 A1 | 3/2007 | Williams et al. | |
| 2007/0140902 A1 | 6/2007 | Calatzis et al. | |
| 2007/0148815 A1 | 6/2007 | Chao et al. | |
| 2007/0184247 A1 | 8/2007 | Simpson et al. | |
| 2007/0186628 A1 | 8/2007 | Curry et al. | |
| 2007/0207487 A1 | 9/2007 | Emig et al. | |
| 2007/0231542 A1 | 10/2007 | Deng | |
| 2008/0012007 A1 | 1/2008 | Li et al. | |
| 2008/0098815 A1 | 5/2008 | Merassi et al. | |
| 2008/0149479 A1 | 6/2008 | Olofsson et al. | |
| 2008/0199657 A1 | 8/2008 | Capron et al. | |
| 2008/0199659 A1 | 8/2008 | Zhao | |
| 2009/0011222 A1 | 1/2009 | Xiu et al. | |
| 2009/0017571 A1 | 1/2009 | Nuckolls | |
| 2009/0020428 A1 | 1/2009 | Levitan | |
| 2009/0027036 A1 | 1/2009 | Nuckolls et al. | |
| 2009/0062684 A1 | 3/2009 | Gregersen et al. | |
| 2009/0152109 A1 | 6/2009 | Whitehead et al. | |
| 2009/0162927 A1 | 6/2009 | Naaman et al. | |
| 2009/0170716 A1 | 7/2009 | Su et al. | |
| 2009/0178935 A1 | 7/2009 | Reymond et al. | |
| 2009/0295372 A1 | 12/2009 | Krstic et al. | |
| 2009/0297913 A1 | 12/2009 | Zhang et al. | |
| 2009/0306578 A1 | 12/2009 | Sivan et al. | |
| 2009/0324308 A1 | 12/2009 | Law et al. | |
| 2010/0038342 A1 | 2/2010 | Lim et al. | |
| 2010/0044212 A1 | 2/2010 | Kim et al. | |
| 2010/0055397 A1 | 3/2010 | Kurihara et al. | |
| 2010/0132771 A1 | 6/2010 | Lu | |
| 2010/0142259 A1 | 6/2010 | Drndic et al. | |
| 2010/0149530 A1 | 6/2010 | Tomaru | |
| 2010/0167938 A1 | 7/2010 | Su et al. | |
| 2010/0184062 A1 | 7/2010 | Steinmueller-Nethl et al. | |
| 2010/0188109 A1 | 7/2010 | Edel et al. | |
| 2010/0194409 A1 | 8/2010 | Gao et al. | |
| 2010/0201381 A1 | 8/2010 | Iqbal et al. | |
| 2010/0206367 A1 | 8/2010 | Jeong et al. | |
| 2010/0227416 A1 | 9/2010 | Koh et al. | |
| 2010/0280397 A1 | 11/2010 | Feldman et al. | |
| 2010/0285275 A1 | 11/2010 | Baca et al. | |
| 2010/0285601 A1 | 11/2010 | Kong et al. | |
| 2010/0288543 A1 | 11/2010 | Hung et al. | |
| 2010/0300899 A1 | 12/2010 | Levine et al. | |
| 2011/0056845 A1 | 3/2011 | Stellacci et al. | |
| 2011/0065588 A1 | 3/2011 | Su et al. | |
| 2011/0076783 A1 | 3/2011 | Liu et al. | |
| 2011/0091787 A1 | 4/2011 | McGrath et al. | |
| 2011/0160077 A1 | 6/2011 | Chaisson et al. | |
| 2011/0166034 A1 | 7/2011 | Kwong et al. | |
| 2011/0217763 A1 | 9/2011 | Rasooly et al. | |
| 2011/0227558 A1* | 9/2011 | Mannion | B82Y 30/00 |
| | | | 324/71.1 |
| 2011/0229667 A1 | 9/2011 | Jin et al. | |
| 2011/0233075 A1 | 9/2011 | Soleymani et al. | |
| 2011/0248315 A1 | 10/2011 | Nam et al. | |
| 2011/0287956 A1 | 11/2011 | Iqbal et al. | |
| 2011/0291673 A1 | 12/2011 | Shibata et al. | |
| 2011/0311853 A1 | 12/2011 | Fratti | |
| 2011/0312529 A1 | 12/2011 | He et al. | |
| 2012/0060905 A1 | 3/2012 | Fogel et al. | |
| 2012/0122715 A1 | 5/2012 | Gao et al. | |
| 2012/0220046 A1 | 8/2012 | Chao | |
| 2012/0258870 A1 | 10/2012 | Schwartz et al. | |
| 2012/0286332 A1 | 11/2012 | Rothberg et al. | |
| 2012/0309106 A1 | 12/2012 | Eichen et al. | |
| 2013/0049158 A1 | 2/2013 | Hong et al. | |
| 2013/0071289 A1 | 3/2013 | Knoll | |
| 2013/0108956 A1 | 5/2013 | Lu et al. | |
| 2013/0109577 A1 | 5/2013 | Korlach et al. | |
| 2013/0162276 A1 | 6/2013 | Lee et al. | |
| 2013/0183492 A1 | 7/2013 | Lee et al. | |
| 2013/0214875 A1 | 8/2013 | Duncan et al. | |
| 2013/0239349 A1 | 9/2013 | Knights et al. | |
| 2013/0245416 A1 | 9/2013 | Yarmush et al. | |
| 2013/0273340 A1 | 10/2013 | Neretina et al. | |
| 2013/0281325 A1 | 10/2013 | Elibol et al. | |
| 2013/0331299 A1 | 12/2013 | Reda et al. | |
| 2014/0001055 A1 | 1/2014 | Elibol et al. | |
| 2014/0011013 A1 | 1/2014 | Jin | |
| 2014/0018262 A1 | 1/2014 | Reda et al. | |
| 2014/0027775 A1 | 1/2014 | Quick et al. | |
| 2014/0048776 A1 | 2/2014 | Huang et al. | |
| 2014/0054788 A1 | 2/2014 | Majima et al. | |
| 2014/0057283 A1 | 2/2014 | Wang et al. | |
| 2014/0061049 A1 | 3/2014 | Lo et al. | |
| 2014/0079592 A1 | 3/2014 | Chang et al. | |
| 2014/0170567 A1 | 6/2014 | Sakamoto et al. | |
| 2014/0174927 A1 | 6/2014 | Bashir et al. | |
| 2014/0197459 A1 | 7/2014 | Kis et al. | |
| 2014/0218637 A1 | 8/2014 | Gao et al. | |
| 2014/0235493 A1 | 8/2014 | Zang et al. | |
| 2014/0253827 A1 | 9/2014 | Gao et al. | |
| 2014/0284667 A1 | 9/2014 | Basker et al. | |
| 2014/0320849 A1 | 10/2014 | Chou et al. | |
| 2014/0367749 A1 | 12/2014 | Bai et al. | |
| 2014/0377900 A1 | 12/2014 | Yann et al. | |
| 2015/0005188 A1* | 1/2015 | Levner | C12Q 1/6804 |
| | | | 506/9 |
| 2015/0017655 A1* | 1/2015 | Huang | C12Q 1/6874 |
| | | | 435/6.19 |
| 2015/0049332 A1 | 2/2015 | Sun et al. | |
| 2015/0057182 A1 | 2/2015 | Merriman et al. | |
| 2015/0065353 A1* | 3/2015 | Turner | C12Q 1/6823 |
| | | | 506/2 |
| 2015/0068892 A1 | 3/2015 | Ueno et al. | |
| 2015/0077183 A1 | 3/2015 | Ciubotaru | |
| 2015/0148264 A1 | 5/2015 | Esfandyarpour et al. | |
| 2015/0177150 A1 | 6/2015 | Rothberg et al. | |
| 2015/0191709 A1 | 7/2015 | Heron et al. | |
| 2015/0263203 A1 | 9/2015 | Lewis et al. | |
| 2015/0293025 A1 | 10/2015 | Ninomiya et al. | |
| 2015/0294875 A1 | 10/2015 | Khondaker et al. | |
| 2015/0344945 A1 | 12/2015 | Mandell et al. | |
| 2016/0017416 A1 | 1/2016 | Boyanov et al. | |
| 2016/0045378 A1 | 2/2016 | Geloen | |
| 2016/0155971 A1 | 6/2016 | Strachan et al. | |
| 2016/0187282 A1 | 6/2016 | Gardner et al. | |
| 2016/0265047 A1 | 9/2016 | van Rooyen et al. | |
| 2016/0284811 A1 | 9/2016 | Yu et al. | |
| 2016/0290957 A1 | 10/2016 | Ram | |
| 2016/0319342 A1 | 11/2016 | Kawai et al. | |
| 2016/0377564 A1 | 12/2016 | Carmignani et al. | |
| 2017/0023512 A1 | 1/2017 | Cummins et al. | |
| 2017/0037462 A1 | 2/2017 | Turner et al. | |
| 2017/0038333 A1 | 2/2017 | Turner et al. | |
| 2017/0043355 A1 | 2/2017 | Fischer | |
| 2017/0044605 A1 | 2/2017 | Merriman | |
| 2017/0131237 A1 | 5/2017 | Ikeda | |
| 2017/0184542 A1 | 6/2017 | Chatelier et al. | |
| 2017/0234825 A1 | 8/2017 | Elibol et al. | |
| 2017/0240962 A1 | 8/2017 | Merriman | |
| 2017/0288017 A1 | 10/2017 | Majima et al. | |
| 2017/0332918 A1 | 11/2017 | Keane | |
| 2018/0014786 A1 | 1/2018 | Keane | |
| 2018/0031508 A1 | 2/2018 | Jin | |
| 2018/0031509 A1 | 2/2018 | Jin | |
| 2018/0045665 A1 | 2/2018 | Jin | |
| 2018/0259474 A1 | 9/2018 | Jin | |

(56) References Cited

U.S. PATENT DOCUMENTS

| | | |
|---|---|---|
| 2018/0297321 A1 | 10/2018 | Jin et al. |
| 2018/0305727 A1 | 10/2018 | Merriman |
| 2018/0340220 A1 | 11/2018 | Merriman |
| 2019/0004003 A1 | 1/2019 | Merriman |
| 2019/0033244 A1 | 1/2019 | Jin |
| 2019/0039065 A1 | 2/2019 | Choi |
| 2019/0041355 A1 | 2/2019 | Merriman |
| 2019/0041378 A1 | 2/2019 | Choi |
| 2019/0194801 A1 | 6/2019 | Jin et al. |
| 2019/0355442 A1 | 11/2019 | Merriman et al. |
| 2019/0376925 A1 | 12/2019 | Choi et al. |
| 2019/0383770 A1 | 12/2019 | Choi et al. |
| 2020/0157595 A1 | 5/2020 | Merriman et al. |
| 2020/0217813 A1 | 7/2020 | Merriman et al. |
| 2020/0242482 A1 | 7/2020 | Merriman et al. |
| 2020/0277645 A1 | 9/2020 | Merriman et al. |
| 2020/0385850 A1 | 12/2020 | Merriman et al. |
| 2020/0385855 A1 | 12/2020 | Jin et al. |
| 2020/0393440 A1 | 12/2020 | Jin et al. |

FOREIGN PATENT DOCUMENTS

| | | |
|---|---|---|
| CN | 102706940 | 10/2012 |
| CN | 104685066 | 6/2015 |
| CN | 104703700 | 6/2015 |
| CN | 108027335 | 5/2018 |
| DE | 102012008375 | 10/2012 |
| DE | 102013012145 | 1/2015 |
| EP | 2053383 | 4/2009 |
| EP | 3403079 | 11/2018 |
| EP | 3408219 | 12/2018 |
| EP | 3408220 | 12/2018 |
| EP | 3414784 | 12/2018 |
| EP | 3420580 | 1/2019 |
| GB | 2485559 | 5/2012 |
| JP | 0233981 | 7/1990 |
| JP | 2008-258594 | 10/2008 |
| JP | 2018-522236 | 8/2018 |
| KR | 20070059880 | 6/2007 |
| KR | 20110104245 | 9/2011 |
| WO | 2001044501 | 6/2001 |
| WO | 2002049980 | 6/2002 |
| WO | 2002074985 | 9/2002 |
| WO | 2003042396 | 5/2003 |
| WO | 2004096986 | 11/2004 |
| WO | 2004099307 | 11/2004 |
| WO | 2005108612 | 11/2005 |
| WO | 2007054649 | 5/2007 |
| WO | 2007102960 | 9/2007 |
| WO | 2007126432 | 11/2007 |
| WO | 2007128965 | 11/2007 |
| WO | 2009003208 | 1/2009 |
| WO | 2009035647 | 3/2009 |
| WO | 2010022107 | 2/2010 |
| WO | 2012083249 | 6/2012 |
| WO | 2012087352 | 6/2012 |
| WO | 2012152056 | 11/2012 |
| WO | 2013096851 | 6/2013 |
| WO | 2014182630 | 7/2014 |
| WO | 2015167019 | 11/2015 |
| WO | 2015176990 | 11/2015 |
| WO | 2015188197 | 12/2015 |
| WO | 2016016635 | 2/2016 |
| WO | 2016100635 | 6/2016 |
| WO | 2016100637 | 6/2016 |
| WO | 2016196755 | 12/2016 |
| WO | 2016210386 | 12/2016 |
| WO | 2017132586 A1 | 1/2017 |
| WO | 2017027518 | 2/2017 |
| WO | 2017041056 | 3/2017 |
| WO | 2017042038 | 3/2017 |
| WO | 2017061129 | 4/2017 |
| WO | 2017123416 | 7/2017 |
| WO | 2017123416 A1 | 7/2017 |
| WO | 2017132567 | 8/2017 |
| WO | 2017132586 | 8/2017 |
| WO | 2017139493 | 8/2017 |
| WO | 2017147187 | 8/2017 |
| WO | 2017151680 | 9/2017 |
| WO | 2017151680 A2 | 9/2017 |
| WO | 2017184677 | 10/2017 |
| WO | 2018022799 | 2/2018 |
| WO | 2018026855 | 2/2018 |
| WO | 2018098286 | 5/2018 |
| WO | 2018132457 | 7/2018 |
| WO | 2018136148 | 7/2018 |
| WO | 2018200687 | 11/2018 |
| WO | 2018208505 | 11/2018 |
| WO | 2003091458 | 1/2019 |
| WO | 2020210832 A1 | 10/2020 |
| WO | 2021195637 A3 | 11/2021 |
| WO | 2021226291 A1 | 11/2021 |
| WO | 2021237180 A1 | 11/2021 |
| WO | 2021237182 A1 | 11/2021 |
| WO | 2021257594 A1 | 12/2021 |
| WO | 2021262739 A1 | 12/2021 |
| WO | 2022051558 A1 | 3/2022 |

OTHER PUBLICATIONS

USPTO; Notice of Allowance dated Jun. 1, 2020 in U.S. Appl. No. 16/076,673.

USPTO; Non-Final Office Action dated Jun. 2, 2020 in U.S. Appl. No. 16/684,338.

USPTO; Non-Final Office Action dated Jun. 15, 2020 in U.S. Appl. No. 16/878,484.

USPTO; Non-Final Office Action dated Jun. 30, 2020 in U.S. Appl. No. 16/479,257.

USPTO; Non-Final Office Action dated Jun. 30, 2020 in U.S. Appl. No. 16/477,106.

EP; European Search Report dated Jun. 18, 2020 in Application No. 16815467.2.

CN; Office Action dated Jun. 5, 2020 in Chinese Patent Application No. 2017800204782.

EP; European Search Report dated Jun. 26, 2020 in Application No. 17874229.2.

Li et al., "Graphene Channel Liquid Container Field Effect Transistor as pH Sensor," Hindawi Publishing Corp., Journal of Nanomaterials 2014.

USPTO; Non-Final Office Action dated Sep. 22, 2020 in U.S. Appl. No. 16/639,716.

USPTO; Non-Final Office Action dated Oct. 2, 2020 in U.S. Appl. No. 16/073,693.

USPTO; Non-Final Office Action dated Nov. 9, 2020 in U.S. Appl. No. 16/731,749.

PCT; International Search Report and Written Opinion dated Jun. 9, 2020 in Application No. PCT/US2020/13218.

PCT; International Search Report and Written Opinion dated Aug. 6, 2020 in Application No. PCT/US2020/25068.

PCT; International Search Report and Written Opinion dated Sep. 4, 2020 in Application No. PCT/US2020/28004.

EP; European Search Report dated Sep. 30, 2020 in Application No. 17893481.6.

JP; Office Action dated Aug. 13, 2020 in Japanese Application No. 2017-566864.

CN; Office Action dated Aug. 14, 2020 in Chinese Patent Application No. 201680083636.4.

Yang et al., "Two-Dimensional Graphene Nanoribbons," J. Am. Chem. Soc. vol. 130, Issue 13 (2008).

USPTO; Final Office Action dated Mar. 6, 2020 in U.S. Appl. No. 16/011,065.

USPTO; Notice of Allowance dated Feb. 20, 2020 in U.S. Appl. No. 16/015,049.

USPTO; Restriction Requirement dated Apr. 8, 2020 in U.S. Appl. No. 16/479,257.

EP; European Search Report dated Jan. 29, 2020 in Application No. 17745013.7.

EP; European Search Report dated Jan. 29, 2020 in Application No. 17750776.1.

(56) References Cited

OTHER PUBLICATIONS

EP; European Search Report dated Feb. 7, 2020 in Application No. 17837566.3.

EP; European Search Report dated Mar. 6, 2020 in Application No. 17835231.6.

Cerofolini et al., "A Hybrid Approach to Nanoelectronics: A Hybrid Approach to Nanoelectrics," Nanotechnology, Institute of Physics Publishing, GB, vol. 16, No. 8, pp. 1040-1047 (2005).

Guo et al., "Conductivity of a single DNA duplex bridging a carbon nanotube gap," Nat. Nanotechnol., vol. 3, No. 3, pp. 1-12 (2008).

Kumar et al., "Terminal Phosphate Labeled Nucleotides: Synthesis, Applications and Linker Effect on Incorporation by DNA Polymerases," Nucleosides, Nucleotides and Nucleic Acids, Taylor and Francis, vol. 24, No. 5-7, pp. 401-408 (2005).

Pugliese et al., "Processive Incorporation of Deoxynucleoside Triphosphate Analogs by Single-Molecule DNA Polymerase I (Klenow Fragment) Nanocircuits," Journal of the American Chemical Society, vol. 137, No. 30, pp. 9587-9594 (2015).

Zafarani et al., "Electrochemical Redox Cycling in a New Nanogap Sensor: Design and Simulation," Journal of Electroanalytical Chemistry, vol. 760, pp. 42-47, (2015).

USPTO; Notice of Allowance dated Nov. 24, 2020 in U.S. Appl. No. 16/477,106.

USPTO; Notice of Allowance dated Dec. 7, 2020 in U.S. Appl. No. 16/878,484.

USPTO; Final Office Action dated Dec. 14, 2020 in U.S. Appl. No. 16/684,338.

USPTO; Final Office Action dated Jan. 11, 2021 in U.S. Appl. No. 16/479,257.

USPTO; Non-Final Office Action dated Dec. 15, 2020 in U.S. Appl. No. 16/831,722.

USPTO; Non-Final Office Action dated Dec. 30, 2020 in U.S. Appl. No. 16/652,672.

EP; European Search Report dated Nov. 19, 2020 in Application No. 18739158.6.

JP; Office Action dated Dec. 2, 2020 in Japanese Patent Application No. 2018-536737.

EP; European Search Report dated Dec. 23, 2020 in Application No. 18790713.4.

EP; European Search Report dated Dec. 14, 2020 in Application No. 18799263.1.

Ali et al., "DNA hybridization detection using less than 10-nm gap silicon nanogap structure," Sensors and Actuators A. vol. 199, pp. 304-309 (2013).

Bornholt et al., "A DNA-Based Archival Storage System", Architectural Support For Programming Languages and Operating Systems, pp. 637-649 (2016).

Chen et al., "Silicon nanowire field-effect transistor-based biosensors for biomedical diagnosis and cellular recording investigation", Nano Today, Elsevier, Amsterdam, NL, vol. 6, No. 2, pp. 131-154 (2011).

Grass et al., "Robust Chemical Preservation of Digital Information on DNA in Silica with Error-Correcting Codes", Angewandte Chemie International Edition, vol. 54, No. 8, pp. 2552-2555 (2015).

Hatcher et al., "PNA versus DNA: Effects of Structural Fluctuations on Electronic Structure and Hole-Transport Mechanisms," J. Amer. Chem. Soc., 130, pp. 11752-11761 (2008).

Korlach et al., "Real-time DNA sequencing from single polymerase molecules," 11, Methods In Enzymology, Academy Press, vol. 472, pp. 431-455 (2010).

Paul et al., "Charge transfer through Single-Stranded Peptide Nucleic Acid Composed of Thymine Nucleotides," J. Phy. Chem. C 2008, 112, pp. 7233-7240 (2008).

Shin et al., "Distance Dependence of Electron Transfer Across Peptides with Different Secondary Structures: The Role of Peptide Energetics and Electronic Coupling," J. Amer. Chem. Soc. 2003, 125, pp. 3722-3732 (2003).

Venkatramani et al., "Nucleic Acid Charge Transfer: Black, White and Gray," Coard Chem Rev., 255(7-8): pp. 635-648 (2011).

Extended European Search Report issued on May 12, 2022 for EP Application No. 18866869.3 [ROS-03505-EP].

USPTO; Non-Final Office Action dated Feb. 26, 2019 in U.S. Appl. No. 15/050,270.

USPTO; Final Office Action dated Mar. 1, 2019 in U.S. Appl. No. 15/979,135.

USPTO; Non-Final Office Action dated Mar. 6, 2019 in U.S. Appl. No. 16/015,049.

USPTO; Non-Final Office Action dated Mar. 7, 2019 in U.S. Appl. No. 15/944,356.

USPTO; Final Office Action dated Apr. 15, 2019 in U.S. Appl. No. 16/015,028.

Antibody Structure Downloaded from https://absoluteantibody.com/antibody-resources/antibody-overview/antibody-structure/ (Mar. 1, 2019).

Bai et al., "Review: Gas Sensors Based on Conducting Polymers," Sensors, vol. 7, pp. 267-307, (2007).

Bailey et al., "DNA-Encoded Antibody Libraries: A Unified Platform for Multiplexed Cell Sorting and Detection of Genes and Proteins," Journal of Am Chem Soc, vol. 129, pp. 1959-1967, (2007).

Khawli et al., "Charge Variants in IgG1-Isolation, Characterization, In Vitro Binding Properties and Pharmacokinetics in Rats," Landes Bioscience, pp. 613-623, (2010).

Schaefer et al., "Stability and Dewetting Kinetics of Thin Gold Films on Ti, TiOx, and ZnO Adhesion Layers," Acta Materialia, vol. 61, pp. 7841-7848, (2013).

USPTO; Notice of Allowance dated Oct. 23, 2019 in U.S. Appl. No. 16/250,929.

USPTO; Non-Final Office Action dated Oct. 24, 2019 in U.S. Appl. No. 16/073,706.

USPTO; Notice of Allowance dated Nov. 8, 2019 in U.S. Appl. No. 16/015,028.

USPTO; Non-Final Office Action dated Nov. 5, 2019 in U.S. Appl. No. 16/015,049.

USPTO; Notice of Allowance dated Dec. 11, 2019 in U.S. Appl. No. 15/979,135.

USPTO; Notice of Allowance dated Jan. 6, 2020 in U.S. Appl. No. 15/050,270.

USPTO; Non-Final Office Action dated Jan. 10, 2020 in U.S. Appl. No. 16/076,673.

EP; European Search Report dated Oct. 24, 2019 in U.S. Appl. No. 17/757,146.

USPTO; Requirement for Restriction dated Jan. 17, 2017 in U.S. Appl. No. 15/336,557.

USPTO; Advisory Action dated Mar. 14, 2017 in U.S. Appl. No. 15/050,270.

USPTO; Non-Final Office Action dated May 16, 2017 in U.S. Appl. No. 15/336,557.

USPTO; Final Office Action date Dec. 30, 2016 in U.S. Appl. No. 15/050,270.

USPTO; Non-Final Office Action dated Sep. 29, 2017 in U.S. Appl. No. 15/050,270.

USPTO; Non-Final Office Action dated Oct. 19, 2016 in U.S. Appl. No. 15/220,307.

USPTO; Notice of Allowance dated Jul. 28, 2017 in U.S. Appl. No. 15/220,307.

USPTO; Requirement for Restriction dated Dec. 1, 2016 in U.S. Appl. No. 13/996,477.

USPTO; Non-Final Office Action dated May 5, 2017 in U.S. Appl. No. 13/996,477.

USPTO; Final Office Action dated Oct. 4, 2017 in U.S. Appl. No. 13/996,477.

USPTO; Notice of Allowance dated Jan. 3, 2018 in U.S. Appl. No. 13/996,477.

USPTO; Non-Final Office Action dated Feb. 9, 2018 in U.S. Appl. No. 15/728,400.

USPTO; Non-Final Office Action dated Feb. 23, 2018 in U.S. Appl. No. 15/728,412.

USPTO; Non-Final Office Action dated Feb. 23, 2018 in U.S. Appl. No. 15/796,080.

USPTO; Final Office Action dated Mar. 8, 2018 in U.S. Appl. No. 15/336,557.

(56)     References Cited

OTHER PUBLICATIONS

USPTO; Notice of Allowance dated May 25, 2018 in U.S. Appl. No. 15/336,557.
USPTO; Final Office Action dated Jun. 13, 2018 in U.S. Appl. No. 15/728,412.
USPTO; Final Office Action dated Jun. 14, 2018 in U.S. Appl. No. 15/796,080.
USPTO; Final Office Action dated Jul. 10, 2018 in U.S. Appl. No. 15/050,270.
USPTO; Final Office Action dated Jul. 10, 2018 in U.S. Appl. No. 15/728,400.
PCT; International Search Report and Written Opinion dated Apr. 8, 2010 in Application No. PCT/US2009/054235.
PCT; International Search Report and Written Opinion dated Nov. 29, 2012 in Application No. PCT/US2011/001995.
PCT; International Search Report and Written Opinion dated Sep. 27, 2016 in Application No. PCT/US2016/039446.
PCT; International Search Report and Written Opinion dated May 25, 2017 in Application No. PCT/US2017/18950.
PCT; International Search Report and Written Opinion dated Jul. 26, 2017 in Application No. PCT/US2017/017231.
PCT; International Search Report and Written Opinion dated Apr. 18, 2017 in Application No. PCT/US2016/068922.
PCT; International Search Report and Written Opinion dated Jan. 27, 2017 in Application No. PCT/US2017/015465.
PCT; International Search Report and Written Opinion dated Jan. 27, 2017 in Application No. PCT/US2017/015437.
PCT; International Search Report and Written Opinion dated Nov. 22, 2017 in Application No. PCT/US2017/044023.
PCT; International Search Report and Written Opinion dated Dec. 26, 2017 in Application No. PCT/US2017/044965.
PCT; International Search Report and Written Opinion dated Mar. 7, 2018 in Application No. PCT/US2017/063105.
PCT; International Search Report and Written Opinion dated Mar. 12, 2018 in Application No. PCT/US2017/063025.
PCT; International Search Report and Written Opinion dated Apr. 13, 2018 in Application No. PCT/US2018/013140.
PCT; International Search Report and Written Opinion dated Jul. 20, 2018 in Application No. PCT/US2018/029382.
PCT; International Search Report and Written Opinion dated Jul. 20, 2018 in Application No. PCT/US2018/029393.
Fink et al., "Electrical Conduction Through DNA Molecules," Nature, vol. 398, pp. 407-410, (Jan. 20, 1999).
Stenning, "The Investigation of Grain Boundary Development and Crystal Synthesis of Thin Gold Films on Silicon Wafers," http://www.ucl.ac.uk/~ucapikr/projects, (Mar. 31, 2009).
Bechelany et al., "Synthesis Mechanisms of Organized Nanoparticles: Influence of Annealing Temperature and Atmosphere," Crystal Growth and Design, vol. 10, pp. 587-596, (Oct. 21, 2010).
H. Nishida, et al., "Self-Oriented Immobilization of DNA Polymerase Tagged by Titanium-Binding Peptide Motif," Langmuir, vol. 31, pp. 732-740, (Dec. 17, 2014).
Niwa, O. et al., "Fabrication and Characteristics of Vertically Separated Interdigitated Array Electrodes," Journal Of Electroanalytical Chemistry and Interfacial Electrochemistry, vol. 267, pp. 291-297, (Aug. 10, 1989) (Abstract Only).
Park, S.J. et al., "Array-Based Electrical Detection of DNA with Nanoparticle Probes," Science, vol. 295, pp. 1503-1506, (Feb. 22, 2002).
Urban, M. et al., "A Paralleled Readout System for an Electrical DNA-Hybridization Assay Based on a Microstructured Electrode Array," Review of Scientific Instruments, vol. 74, pp. 1077-1081, (Jan. 2003) (Abstract Only).
Choi Y.S. et al., "Hybridization by an Electroatomical Genome on Detection on Using an Indicator-Free DNA on a Microelectrode-Array DNA Chip," Bulletin of the Korean Chemistry Society, vol. 26, pp. 379-383, (2005).
Park, C.W. et al., "Fabrication of Poly-Si/ AU Nano-gaps Using Atomic-Layer-Deposited $Al_2O_3$ as a Sacrificial Layer," Nanotechnology, vol. 16, pp. 361-364, (Feb. 1, 2005) (Abstract Only).

Ruttkowski, E. et al., "CMOS Based Arrays of Nanogaps Devices for Molecular Devices," Proceedings of 2005 5th IEEE Conference on Nanotechnology, vol. 1, pp. 438-441, (Jul. 2005) (Abstract Only).
Stagni, C. et al., "CMOS DNA Sensor Array with Integrated A/D Conversation Based on Label-Free Capacitance Measurement," IEEE Journal of Solid-State Circuits, vol. 41, pp. 2956-2964, (Nov. 20, 2006).
Schrott, W. et al., "Metal Electrodes in Plastic Microfluidic Systems," Microelectronic Engineering, vol. 86, pp. 1340-1342, (Jun. 2009).
Roy, S. et al., "Mass-Produced Nanogap Sensor Arrays for Ultra-Sensitive Detection of DNA," Journal of the American Chemical Society, vol. 131, pp. 12211-12217, (Aug. 5, 2009) (Abstract Only).
Choi, J. E. et al., "Fabrication of Microchannel with 60 Electrodes and Resistance Measurement," Flow Measurement and Instrumentation, vol. 21, pp. 178-183, (Sep. 2010) (Abstract Only).
Lee, K. H. et al., "One-Chip Electronic Detection of DNA Hybridization using Precision Impedance-Based CMOS Array Sensor," Biosensors and Bioelectronics, vol. 26, pp. 1373-1379, (Dec. 15, 2010).
Chen, X. et al., "Electrical Nanogap Devices for Biosensing," Materials Today, vol. 13, pp. 28-41, (Nov. 2010).
Ghindilis, A. et al., "Real Time Biosensor Platforms Fully Integrated Device for Impedimetric Assays," ECS Transactions, vol. 33, pp. 59-68, (2010).
Su, Y., "Modeling and Characteristic Study of Thin Film Based Biosensor Based on COMSOL," Mathematical Problems in Engineering, Article 581063 (6 Pages), (Apr. 7, 2014).
Blossey, R., "Self-Cleaning Surfaces-Virtual Realities," Nature Materials, vol. 2(5), pp. 301-306, (May 2006).
Cassie, A.B.D. et al., "Wettability of Porous Surfaces," Transitions of the Faraday Society, vol. 40, pp. 546-551, (Jan. 1944) (Abstract Only).
Choi, C. et al., "Strongly Superhydrophobic Silicon Nanowires by Supercritical CO2 Drying," Electronic Materials Letters, vol. 6 (2), pp. 59-64, (Jun. 2010).
Coulson S.R. et al., "Super-Repellent Composite Fluoropolymer Surfaces," The Journal Of Physical Chemistry B., vol. 104(37), pp. 8836-8840, (Aug. 2000).
Gapin, A.I. et al., "CoPt Patterned Media in Anodized Aluminum Oxide Templates," Journal Of Applied Physics, vol. 99(8), pp. 08G902 (1-3), (Apr. 2006).
Parkin, I. P. et al., "Self-Cleaning Coatings," Journal of Materials Chemistry, vol. 15(17), pp. 1689-1695, (Dec. 2004).
Shimoda, T. et al., "Solution-Processed Silicon Films and Transistors," Nature, vol. 440(7085), pp. 783-786, (Apr. 2006).
Kim, J. Y. et al., "Optically Transparent Glass with Vertically Aligned Surface Al203 Nanowires Having Superhydrophobic Characteristics," NANO: Brief Reports and Reviews, vol. 5(2), pp. 89-95, (Apr. 2010) (Abstract Only).
Han, "Energy Band Gap Engineering of Graphene Nanoribbons," Physical Review Letters, vol. 98, pp. 1-7, (May 16, 2007).
Prins et al., "Room-Temperature Gating of Molecular Junctions Using Few-Layer Graphene Nanogap Electrodes," Nano Letters, vol. 11, pp. 4607-4611, (Oct. 21, 2011).
Heerema et al., "Graphene Nanodevices for DNA Sequencing," Nature Nanotechnology, vol. 11, pp. 127-136, (Feb. 3, 2016).
Liu et al., "Atomically Thin Molybdenum Disulfide Nanopores with High Sensitivity for DNA Translocation," ACS Nano, vol. 8, pp. 2504-2511, (Feb. 18, 2014).
Kim et al., "Rapid Fabrication of Uniformly Sized Nanopores and Nanopore Arrays for Parallel DNA Analysis," Advances Materials, vol. 18, pp. 3149-3153, (Dec. 4, 2006).
Wang et al., "Electronics and Optoelectronics of Two-Dimensional Transition Metal Dichalcogenides," Nature Nanotechnology, vol. 7, pp. 699-712, (Nov. 6, 2012).
Liu et al., "An Enzyme-Based E-DNA Sensor for Sequence-Specific Detection of Femtomolar DNA Targets," J. Am. Chem. Soc., vol. 130(21), pp. 6820-6825, (2008).
Mirando-Castro et al., "Hairpin-DNA Probe for Enzyme-Amplified Electrochemical Detection of Legionella Pnuemophila," Anal. Chem., vol. 79, pp. 4050-4055, (Jun. 1, 2007).

(56)  References Cited

OTHER PUBLICATIONS

Shimanovsky et al., "Hiding Data in DNA," International Workshop on Information Hiding, Lecture Notes in Computer Science, pp. 373-386, (Dec. 18, 2012).
Church et al., "Next-Generation Digital Information Storage in DNA," Science, vol. 337(6102), p. 6102, (Sep. 28, 2012).
Fuller et al., "Real-Time Single-Molecule Electronic DNA Sequencing by Synthesis Using Polymer-Tagged Nucleotides on a Nanopore Array," Proceedings of the National Academy of Sciences, vol. 113(19), pp. 5233-5523, (May 10, 2016).
Hanief, Topic, Pineda-Vargas, "Solid State Dewetting of Continuous Thin Platinum Coatings," Nuclear Instruments and Methods in Physics Research, vol. 363, pp. 173-176, (2015).
Sholders et al., "Distinct Conformations of a Putative Translocation Element in Poliovirus Polymerase," Journal of Molecular Biology, vol. 426(7), pp. 1407-1419, (Apr. 3, 2014).
USPTO; Non-Final Office Action dated Jul. 30, 2019 in the U.S. Appl. No. 16/015,028.
USPTO; Non-Final Office Action dated Aug. 22, 2019 in the U.S. Appl. No. 16/011,065.
USPTO; Restriction Requirement dated Sep. 19, 2019 in U.S. Appl. No. 16/073,706.
USPTO; Non-Final Office Action dated Aug. 19, 2019 in U.S. Appl. No. 12/667,583.
CN; Notice of the First Office Action dated Sep. 2, 2019 in Chinese Application No. 201680049272.8.
EP; European Search Report dated Aug. 2, 2019 in Application No. EP16885434.7.
EP; European Search Report dated Aug. 2, 2019 in Application No. EP17745026.9.
USPTO; Advisory Action dated May 22, 2019 in U.S. Appl. No. 15/979,135.
USPTO; Restriction Requirement dated May 29, 2019 in U.S. Appl. No. 16/250,929.
USPTO; Notice of Allowance dated May 30, 2019, in U.S. Appl. No. 16/152,190.
USPTO; Non-Final Office Action dated Jun. 25, 2019 in U.S. Appl. No. 15/979,135.
USPTO; Final Office Action dated Jun. 19, 2019 in U.S. Appl. No. 16/015,049.
USPTO; Final Office Action dated Jul. 10, 2019 in U.S. Appl. No. 15/050,270.
PCT; International Search Report and Written Opinion dated Jan. 18, 2019 in Application No. PCT/US2018/055264.
EP; European Search Report dated Jan. 30, 2019 in Application No. EP16815467.2.
Briglin et al., "Exploitation of Spatiotemporal Information and Geometric Optimization of Signal/Noise Performance Using Arrays of Carbon Black-Polymer Composite Vapor Detectors," Sensors and Actuators B, vol. 82, pp. 54-74, (2002).
Cosofret et al., "Microfabricated Sensor Arrays Sensitive to pH and K+ for Ionic Distribution Measurements in the Beating Heart," Analytical Chemistry, vol. 67, pp. 1647-1653, (1995).
Henry et al., "Microcavities Containing Individually Addressable Recessed Microdisk and Tubular Nanoband Electrodes," Journal of The Electrochemical Society, vol. 146(9), pp. 3367-3373, (1999).
Lin at al., "An Addressable Microelectrode Array for Electrichemiul Detection," Analytical Chemistry, vol. 80, pp. 6830-6833, (2008).
Thompson, "Solid-State Dewetting of Thin Films," Department of Materials Science and Engineering, vol. 42, pp. 399-434, (2012).
USPTO; Advisory Action dated Sep. 4, 2018 in U.S. Appl. No. 15/796,080.
USPTO; Non-Final Office Action dated Sep. 4, 2018 in U.S. Appl. No. 15/979,135.
USPTO; Notice of Allowance dated Sep. 12, 2018 in U.S. Appl. No. 15/728,412.
USPTO; Advisory Action dated Sep. 26, 2018 in U.S. Appl. No. 15/050,270.
USPTO; Notice of Allowance dated Oct. 11, 2018 in U.S. Appl. No. 15/796,080.

USPTO; Advisory Action dated Oct. 12, 2018 in U.S. Appl. No. 15/728,400.
USPTO; Requirement for Restriction dated Oct. 15, 2018 in U.S. Appl. No. 16/015,028.
PCT; International Preliminary Report on Patentability received Aug. 14, 2018 in Application No. PCT/US2017/017231.
USPTO; Requirement for Restriction dated Nov. 2, 2011 in U.S. Appl. No. 12/667,583.
USPTO; Non-Final Office Action dated Sep. 28, 2018 in U.S. Appl. No. 12/667,583.
USPTO; Advisory Action dated Nov. 14, 2018 in U.S. Appl. No. 15/728,400.
USPTO; Non-Final Office Action dated Nov. 30, 2018 in U.S. Appl. No. 15/979,135.
USPTO; Notice of Allowance dated Dec. 6, 2018 in U.S. Appl. No. 15/728,400.
USPTO; Requirement for Restriction dated Dec. 17, 2018 in U.S. Appl. No. 16/015,049.
USPTO; Non-Final Office Action dated Dec. 26, 2018 in U.S. Appl. No. 16/015,028.
USPTO; Non-Final Office Action dated Feb. 1, 2019 in U.S. Appl. No. 16/152,190.
USPTO; Final Office Action dated Feb. 19, 2019 in U.S. Appl. No. 12/667,583.
PCT; International Search Report in Application No. PCT/US2018/048873.
PCT; Written Opinion in Application No. PCT/US2018/048873.
Mastrototaro et al., "Thin-Film Flexible Multielectrode Arrays for Voltage Measurements in the Heart," IEEE Engineering in Medicine & Biology Society 11th Annual International Conference, I Page, (1989).
Mastrototaro et al., "Rigid and Flexible Thin-Film Multielectrode Arrays for Transmural Cardiac Recording," IEEE Transactions on Biomedical Engineering, vol. 39, pp. 217-279, (1992).
Van Gerwin et al., "Nanoscaled Interdigitated Electrode Arrays for Biochemical Sensors," Sensors and Actuators B, vol. 49, pp. 73-80, (1998).
Santschi et al., "Interdigitated 50nm Ti Electrode Arrays Fabricated using $XeF_2$ Enhanced Focused Ion Beam Etching," Nanotechnology, vol. 17, pp. 2722-2729, (2006).
Javey et al., "Layer-By-Layer Assembly of Nanowires for Three-Dimensional, Multifunctional Electronics," Nano Letters, vol. 7, pp. 773-777, (2007).
Fan et al., "Detection of MicroRNAs Using Target-Guided Formation of Conducting Polymer Nanowires in Nanogaps," Journal of the American Chemical Society, vol. 129, pp. 5437-5443, (2007).
Kitsara et al., "Single Chip Interdigitated Electrode Capacitive Chemical Sensor Arrays," Sensors and Actuators B, vol. 127, pp. 186-192, (2007).
Xu et al., "Fabrication of Complex Metallic Nanostructures by Nanoskiving," American Chemical Society Nano, vol. 1(3), pp. 215-227, (2007).
Berdat et al., "Label-Free Detection of DNA with Interdigitated Micro-Electrodes in a Fluidic Cell," Lab on a Chip, vol. 8, pp. 302-308, (2008).
Dickey et al., "Electrically Addressable Parallel Nanowires with 30 NM Spacing from Micromolding and Nanoskiving," Nano Letters, vol. 8(12), pp. 4568-4573, (2008).
Singh et al., "3D Nanogap Interdigitated Electrode Array Biosensors," Analytical and Bioanalytical Chemistry, vol. 397, pp. 1493-1502, (2010).
Bhura, "3D Interdigitated Electrode Array (IDEA) Biosensor for Detection of Serum Biomarker," Master Thesis, Portland State University, 68 Pages, (2011).
Ino et al., "Addressable Electrode Array Device with IDA Electrodes for High-Throughput Detection," Lab on a Chip, vol. 11, p. 385-388, (2011).
Bonilla et al., "Electrical Readout of Protein Microarrays on Regular Glass Slides," Analytical Chemistry, vol. 83, pp. 1726-1731, (2011).
Ahn et al., "Electrical Immunosensor Based on a Submicron-Gap Interdigitated Electrode and Gold Enhancement," Biosensors and Bioelectronics, vol. 26, pp. 4690-4696, (2011).

(56)          References Cited

OTHER PUBLICATIONS

Singh et al., "Evaluation of Nanomaterials-Biomolecule Hybrids for Signals Enhancement of Impedimetric Biosensors," 11th IEEE International Conference on Nanotechnology, pp. 707-710, (2011).

Singh et al., "Nanoparticle-Enhanced Sensitivity of a Nanogap-Interdigitated Electrode Array Impedimetric Biosensor," Langmuir, vol. 27, pp. 13931-13939, (2011).

Chen et al., "Fabrication of Submicron-Gap Electrodes by Silicon Volume Expansion for DNA-Detection," Sensors and Actuators A, vol. 175, pp. 73-77, (2012).

Branagan et al., "Enhanced Mass Transport of Electroactive Species to Annular Nanoband Electrodes Embedded in Nanocapillary Array Membranes," Journal of the American Chemical Society, vol. 134, pp. 8617-8624, (2012).

Ino et al., "Local Redox-Cycling-Based Electrochemical Chip Device with Seep Microwells for Evaluation of Embryoid Bodies," Angewandte Chemie International Edition, vol. 51, pp. 6648-6652, (2012).

Botsialas et al., "A Miniaturized Chemocapacitor System for the Detection of Volatile Organic Compounds," Sensors and Actuators B, Chemical, vol. 177, pp. 776-784, (2013).

Sanguino et al., "Interdigitated Capacitive Immunosensors with PVDF Immobilization Layers," IEEE Sensors Journal, vol. 14(4), pp. 1260-1265, (Apr. 2014).

Van Megan et al., "Submicron Electrode Gaps Fabricated by Gold Electrodeposition at Interdigitated Electrodes," Key Engineering Materials, vol. 605, pp. 107-110, (2014).

MacNaughton et al., "High-Throughput Heterogeneous Integration of Diverse Nanomaterials on a Single Single Chip for Sensing Applications," PLOS One, vol. 9(10), e111377, 7 Pages, (2014).

Kitsara et al., "Small-Volume Multiparametric Electrochemical Detection at Low Cost Polymeric Devices Featuring Nanoelectrodes," SPIE, vol. 9518, 9 Pages, (2015).

Alayo et al., "Gold Interdigitated Nanoelectrodes as a Sensitive Analytical Tool for Selective Detection of Electroactive Species via Redox Cycling," Microchim Acta, vol. 183, pp. 1633-1639, (2016).

Han et al., "Redox Cycling in Nanopore-Confined Recessed Dual-Ring Electrode Arrays," Journal of Physical Chemistry C, vol. 120, pp. 20634-20641, (2016).

Okinaka et al., ""Polymer" Inclusions in Cobalt-Hardened Electroplated Gold," Journal the of Electrochemical Society, vol. 125, p. 1745, (1978).

Braun et al., "DNA-Templated Assembly and Electrode Attachment of a Conducting Silver Wire," Letters to Nature, vol. 391(6669), pp. 775-778, (Feb. 1998).

Chen et al., "Electrochemical Approach for Fabricating Nanogap Electrodes with Well Controllable Separation," Applied Physics Letters, vol. 86, pp. 123105.1-123105.3, (2005).

Hashioka et al., "Deoxyribonucleic Acid Sensing Device with 40-NM-Gap-Electrodes Fabricated by Low-Cost Conventional Techniques," Applied Physics Letters, vol. 85(4), p. 687-688, (Jul. 2004).

He et al., "Electromechanical Fabrication of Atomically Thin Metallic Wires and Electrodes Separated with Molecular-Scale Gaps," Journal of Electroanalytical Chemistry, vol. 522, pp. 167-172, (Jan. 2002).

Hwang et al., "Electrical Transport Through 60 Base Pairs of Poly (dG)-Poly (dC) DNA Molecules," Applied Physics Letters, vol. 81(6), p. 1134-1136, (Aug. 2002).

Iqbal et al., "Direct Current Electrical Characterization of ds-DNA in Nanogap Junctions," Applied Physics Letter, vol. 86, p. 153901-1-153901-3, (Apr. 2005).

Liu et al., "Controllable Nanogap Fabrication on Microchip by Chronopotentiometry," Electrochimica Acta, vol. 50, pp. 3041-3047, (2005).

Qing et al., "Finely Tuning Metallic Nanogap Size with Electrodeposition by Utilizing High-Frequency Impedance in Feedback," Angewandte Chemie Int ed, vol. 44, pp. 7771-7775, (2005).

Reichert et al., "Driving Current Through Single Organic Molecules," Physical Review Letters, vol. 88(17), pp. 176804-1-176804-4, (Apr. 2002).

Reed et al., "Conductance of a Molecular Junction Reports," Science, vol. 278, pp. 252-254, (Oct. 1997).

Roppert et al., "A New Approach for an Interdigitated Electrodes DNA-Sensor," XVIIIth International Symposium on Bioelectrochemistry and Bioenergetics, Bioelectrochemistry, p. 143, (2005).

Kraft, "Doped Diamond: A Compact Review on a New, Versatile Electrode Material," International Journal of Electrochemistry, vol. 2, pp. 355-385, (May 2007).

* cited by examiner

200

301

1000

LITHOGRAPH STEP TO DEFINE CONTACT LOCATIONS ⟶ 910

DEVELOP RESIST ⟶ 920

DEPOSITION OF PREFORMED CONTACT PARTICLES ⟶ 1030

LIFT-OFF ⟶ 940

ANNEALING ⟶ 950

1087   1087

1006   1007

1200

Time (s)

Time (s)

(a) SPIN-COATING RESIST (b) EXPOSE BY E-BEAM (c) DEVELOPMENT (d) DEPOSITION OF Au 2 nm / PT 20 NM / TI 3 NM BY SPUTTERING (e) LIFT-OFF (f) ANNEALING PROCESS TO BREAK THE Au 2 nm LAYER (g) TOP VIEW

| | ONLY GNP | AFFINITY PURIFIED ANTI-GNP(5nm) MOUSE IgG, PAS 18037-18041 | MOUSE NAÏVE SERUM | MOUSE CONTROL IgG |
|---|---|---|---|---|
| | COLUMNS 1-3 | COLUMNS 4-6 | COLUMNS 7-9 | COLUMNS 10-12 |
| A | ONLY BUFFER (NO GNP, NO PRIMARY Ab) | ONLY Ab (1:20) (NO GNP) | ONLY Ab (1:20) (NO GNP) | ONLY Ab (1:20) (NO GNP) |
| B | ONLY 5 nm GNP (1 µg/mL), (NO PRIMARY Ab) | 5 nm GNP (1 µg/mL) + Ab (1:20) | 5 nm GNP (1 µg/mL) + Ab (1:20) | 5 nm GNP (1 µg/mL) + Ab (1:20) |
| C | ONLY 5 nm GNP (10 µg/mL), (NO PRIMARY Ab) | 5 nm GNP (10 µg/mL) + Ab (1:20) | 5 nm GNP (10 µg/mL) + Ab (1:20) | 5 nm GNP (10 µg/mL) + Ab (1:20) |
| D | ONLY 5 nm GNP (100 µg/mL), (NO PRIMARY Ab) | 5 nm GNP (100 µg/mL) + Ab (1:20) | 5 nm GNP (100 µg/mL) + Ab (1:20) | 5 nm GNP (100 µg/mL) + Ab (1:20) |
| E | ONLY 5 nm GNP (300 µg/mL), (NO PRIMARY Ab) | 5 nm GNP (300 µg/mL) + Ab (1:20) | 5 nm GNP (300 µg/mL) + Ab (1:20) | 5 nm GNP (300 µg/mL) + Ab (1:20) |
| F | ONLY 10 nm GNP (10 µg/mL), (NO PRIMARY Ab) | 10 nm GNP (10 µg/mL) + Ab (1:20) | 10 nm GNP (10 µg/mL) + Ab (1:20) | 10 nm GNP (10 µg/mL) + Ab (1:20) |
| G | ONLY 20 nm GNP (10 µg/mL), (NO PRIMARY Ab) | 20 nm GNP (10 µg/mL) + Ab (1:20) | 20 nm GNP (10 µg/mL) + Ab (1:20) | 20 nm GNP (10 µg/mL) + Ab (1:20) |
| H | | | | |

FIG. 46A

| | 1 | 2 | 3 | 4 | 5 | 6 | 7 | 8 | 9 | 10 | 11 | 12 |
|---|---|---|---|---|---|---|---|---|---|---|---|---|
| A | 0.038 | 0.038 | 0.037 | 0.602 | 0.581 | 0.722 | 0.264 | 0.274 | 0.275 | 0.333 | 0.357 | 0.343 |
| B | 0.038 | 0.038 | 0.038 | 0.938 | 1.079 | 0.939 | 0.275 | 0.307 | 0.239 | 0.546 | 0.541 | 0.432 |
| C | 0.038 | 0.039 | 0.038 | 2.056 | 1.984 | 1.798 | 0.257 | 0.285 | 0.314 | 1.224 | 1.284 | 0.940 |
| D | 0.042 | 0.039 | 0.039 | 2.317 | 2.314 | 1.874 | 0.280 | 0.339 | 0.377 | 1.557 | 1.694 | 1.620 |
| E | 0.042 | 0.043 | 0.039 | 2.394 | 2.224 | 2.130 | 0.298 | 0.353 | 0.363 | 1.667 | 1.655 | 1.715 |
| F | 0.041 | 0.042 | 0.040 | 1.536 | 1.291 | 1.322 | 0.290 | 0.318 | 0.343 | 1.089 | 1.013 | 0.909 |
| G | 0.042 | 0.041 | 0.042 | 1.566 | 1.567 | 1.440 | 0.350 | 0.338 | 0.327 | 1.212 | 1.094 | 1.108 |
| H | | | | | | | | | | | | |

See FIG. 71C

FIG. 71B 10 mm

Chip: 20 electrode devices

Zoom in...

Zoom in...

1 mm

5 µm 10 nm gap 500 nm

ELECTRONIC MONITORING OF DEVICE ASSEMBLY PHASES

ASSEMBLY PHASE 1:
BRIDGE BINDING TO ELECTRODES

ASSEMBLY PHASE 2:
POLYMERASE BINDING TO BRIDGE

ASSEMBLY PHASE 3:
DNA TEMPLATE BINDING TO COMPLEX dCP4-LACTOSE dC

TETRA PHOSPHATE

LACTOSE

DBCO-CLICK

FIG.84A dCP4-Cy7

FIG.84B

SEQUENCE LISTING

```
<160> NUMBER OF SEQ ID NOS: 23

<210> SEQ ID NO 1
<211> LENGTH: 60
<212> TYPE: DNA
<213> ORGANISM: Artificial Sequence
<220> FEATURE:
<223> OTHER INFORMATION: thiol-modified oligonucleotide
<220> FEATURE:
<221> NAME/KEY: misc_feature
<222> LOCATION: (1)..(1)
<223> OTHER INFORMATION: n = 5'-thiol modified thymine

<400> SEQUENCE: 1
ngcgtacgta tgtcatgaat ggcgcagact gatgtcctat gacgtcgcta ctgcagtact      60

<210> SEQ ID NO 2
<211> LENGTH: 60
<212> TYPE: DNA
<213> ORGANISM: Artificial Sequence
<220> FEATURE:
<223> OTHER INFORMATION: thiol-modified oligonucleotide
<220> FEATURE:
<221> NAME/KEY: misc_feature
<222> LOCATION: (1)..(1)
<223> OTHER INFORMATION: n = 5'-thiol modified thymine
<220> FEATURE:
<221> NAME/KEY: misc_feature
<222> LOCATION: (29)..(29)
<223> OTHER INFORMATION: internal biotin-modified deoxythymidine

<400> SEQUENCE: 2
ngtactgcag tagcgacgtc ataggacanc agtctgcgcc attcatgaca tacgtacgca      60

<210> SEQ ID NO 3
<211> LENGTH: 14
<212> TYPE: PRT
<213> ORGANISM: Artificial Sequence
<220> FEATURE:
<223> OTHER INFORMATION: peptide biopolymer bridge molecule

<400> SEQUENCE: 3

Met His Gly Lys Thr Gln Ala Thr Ser Gly Thr Ile Gln Ser
1               5                   10

<210> SEQ ID NO 4
<211> LENGTH: 8
<212> TYPE: PRT
<213> ORGANISM: Artificial Sequence
<220> FEATURE:
<223> OTHER INFORMATION: peptide biopolymer bridge molecule

<400> SEQUENCE: 4

Val Ser Gly Ser Ser Pro Asp Ser
1               5

<210> SEQ ID NO 5
<211> LENGTH: 12
<212> TYPE: PRT
```

-continued

```
<213> ORGANISM: Artificial Sequence
<220> FEATURE:
<223> OTHER INFORMATION: peptide biopolymer bridge molecule

<400> SEQUENCE: 5

Leu Lys Ala His Leu Pro Pro Ser Arg Leu Pro Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: peptide biopolymer bridge molecule

<400> SEQUENCE: 6

Val Pro Ser Ser Gly Pro Gln Asp Thr Arg Thr Thr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: peptide biopolymer bridge molecule

<400> SEQUENCE: 7

Met Ser Pro His Pro His Pro Arg His His His Thr
1               5                   10

<210> SEQ ID NO 8
<211> LENGTH: 5
<212> TYPE: PRT
<213> ORGANISM: Artificial Sequence
<220> FEATURE:
<223> OTHER INFORMATION: amino acid motif in a peptide biopolymer bridge
      molecule

<400> SEQUENCE: 8

Glu Ala Ala Ala Arg
1               5

<210> SEQ ID NO 9
<211> LENGTH: 5
<212> TYPE: PRT
<213> ORGANISM: Artificial Sequence
<220> FEATURE:
<223> OTHER INFORMATION: amino acid motif in a peptide biopolymer bridge
      molecule

<400> SEQUENCE: 9

Glu Ala Ala Ala Lys
1               5

<210> SEQ ID NO 10
<211> LENGTH: 8
<212> TYPE: PRT
<213> ORGANISM: Artificial Sequence
<220> FEATURE:
<223> OTHER INFORMATION: amino acid motif in a peptide biopolymer bridge
      molecule

<400> SEQUENCE: 10

Glu Glu Glu Glu Arg Arg Arg Arg
1               5

<210> SEQ ID NO 11
```

<211> LENGTH: 8
<212> TYPE: PRT
<213> ORGANISM: Artificial Sequence
<220> FEATURE:
<223> OTHER INFORMATION: amino acid motif in a peptide biopolymer bridge
      molecule

<400> SEQUENCE: 11

Glu Glu Glu Glu Lys Lys Lys Lys
1               5

<210> SEQ ID NO 12
<211> LENGTH: 34
<212> TYPE: DNA
<213> ORGANISM: Artificial Sequence
<220> FEATURE:
<223> OTHER INFORMATION: unpaired base nucleotide sequence
<220> FEATURE:
<221> NAME/KEY: misc_feature
<222> LOCATION: (1)..(13)
<223> OTHER INFORMATION: n = any standard nucleotide
<220> FEATURE:
<221> NAME/KEY: misc_feature
<222> LOCATION: (15)..(23)
<223> OTHER INFORMATION: n = 5-methylcytosine

<400> SEQUENCE: 12
nnnnnnnnnn nnngngngng ngngcgcgcg cgcg                                    34

<210> SEQ ID NO 13
<211> LENGTH: 34
<212> TYPE: DNA
<213> ORGANISM: Artificial Sequence
<220> FEATURE:
<223> OTHER INFORMATION: complementary synthesized strand based on
      unpaired base nucleotide sequence
<220> FEATURE:
<221> NAME/KEY: misc_feature
<222> LOCATION: (22)..(34)
<223> OTHER INFORMATION: n = any standard nucleotide

<400> SEQUENCE: 13
cgcgcgcgcg cgcgcgcgcg cnnnnnnnnn nnnn                                    34

<210> SEQ ID NO 14
<211> LENGTH: 63
<212> TYPE: PRT
<213> ORGANISM: Artificial Sequence
<220> FEATURE:
<223> OTHER INFORMATION: protein alpha helix bridge molecule
<220> FEATURE:
<221> NAME/KEY: MOD_RES
<222> LOCATION: (32)..(32)
<223> OTHER INFORMATION: Xaa = lysine modified to include biotin on an
      Ahx (six carbon linear aminohexanoic) linker (Lys-Ahx-Biotin)

<400> SEQUENCE: 14

Cys Ala Glu Ala Ala Ala Arg Glu Ala Ala Ala Arg Glu Ala Ala Ala
1               5                   10                  15

Arg Glu Ala Ala Ala Arg Glu Ala Ala Ala Arg Glu Ala Ala Ala Xaa
            20                  25                  30

Glu Ala Ala Ala Arg Glu Ala Ala Ala Arg Glu Ala Ala Ala Arg Glu
        35                  40                  45

Ala Ala Ala Arg Glu Ala Ala Ala Arg Glu Ala Ala Ala Arg Cys
    50                  55                  60

<210> SEQ ID NO 15
<211> LENGTH: 89

-continued

```
<212> TYPE: DNA
<213> ORGANISM: Artificial Sequence
<220> FEATURE:
<223> OTHER INFORMATION: GT repeat tracts of template sequence

<400> SEQUENCE: 15
gtgtgtgtgt gtgtgtgtgt tttgtgtgtg tgtgtgtgtg tgtaaagtgt gtgtgtgtgt      60
gtgtgtcccg tgtgtgtgtg tgtgtgtgtgt                                       89

<210> SEQ ID NO 16
<211> LENGTH: 50
<212> TYPE: DNA
<213> ORGANISM: Artificial Sequence
<220> FEATURE:
<223> OTHER INFORMATION: oligonucleotide sequence featuring a poly-A
      region

<400> SEQUENCE: 16
cgccgcggag ccaagaaaaa aaaaaaaaaa aaaaattgca tgtcctgtga                  50

<210> SEQ ID NO 17
<211> LENGTH: 15
<212> TYPE: DNA
<213> ORGANISM: Artificial Sequence
<220> FEATURE:
<223> OTHER INFORMATION: primer

<400> SEQUENCE: 17
tcacaggaca tgcaa                                                        15

<210> SEQ ID NO 18
<211> LENGTH: 4
<212> TYPE: PRT
<213> ORGANISM: Artificial Sequence
<220> FEATURE:
<223> OTHER INFORMATION: linker group

<400> SEQUENCE: 18

Gly Gly Gly Ser
1

<210> SEQ ID NO 19
<211> LENGTH: 5
<212> TYPE: PRT
<213> ORGANISM: Artificial Sequence
<220> FEATURE:
<223> OTHER INFORMATION: portion of derivatizing peptide

<400> SEQUENCE: 19

Cys Ala Leu Asn Asn
1               5

<210> SEQ ID NO 20
<211> LENGTH: 8
<212> TYPE: PRT
<213> ORGANISM: Artificial Sequence
<220> FEATURE:
<223> OTHER INFORMATION: "FLAG-tag" antigen peptide

<400> SEQUENCE: 20

Asp Tyr Lys Asp Asp Asp Asp Lys
1               5

<210> SEQ ID NO 21
<211> LENGTH: 17
<212> TYPE: PRT
```

-continued

```
<213> ORGANISM: Artificial Sequence
<220> FEATURE:
<223> OTHER INFORMATION: derivatizing peptide

<400> SEQUENCE: 21

Cys Ala Leu Asn Asn Gly Ser Gly Ser Asp Tyr Lys Asp Asp Asp Asp
1               5                   10                  15

Lys

<210> SEQ ID NO 22
<211> LENGTH: 14
<212> TYPE: DNA
<213> ORGANISM: Artificial Sequence
<220> FEATURE:
<223> OTHER INFORMATION: example output sequence

<400> SEQUENCE: 22
gattacagat taca                                                          14

<210> SEQ ID NO 23
<211> LENGTH: 13
<212> TYPE: DNA
<213> ORGANISM: Artificial Sequence
<220> FEATURE:
<223> OTHER INFORMATION: example output sequence

<400> SEQUENCE: 23
acgtacgtac gta                                                           13
```

MOLECULAR SENSORS AND RELATED METHODS

CROSS-REFERENCE TO RELATED APPLICATIONS

This application is a U.S. national phase filing under 35 U.S.C. § 371 of PCT/US2016/068922 filed on Dec. 28, 2016, which claims priority to U.S. Provisional Patent Application No. 62/278,889 filed on Jan. 14, 2016, entitled "MANUFACTURE OF MOLECULAR BRIDGES FOR NANOSCALE DEVICES"; U.S. Provisional Patent Application No. 62/278,900 filed on Jan. 14, 2016 entitled "METHODS FOR MANUFACTURE OF BEADS ON A SUBSTRATE FOR NANOSCALE DEVICES"; and U.S. Provisional Patent Application No. 62/278,907 filed on Jan. 14, 2016 entitled "METHODS OF NUCLEIC ACID ANALYSIS USING MOLECULAR ELECTRONICS SENSORS, the disclosures of which are incorporated herein by reference.

FIELD

The present disclosure relates to electronic sensor devices. In particular, the disclosure relates to electronic sensor devices that comprise one or more biomolecule components in a measurement circuit, and can be used for nucleic acid sequencing.

BACKGROUND

Measuring properties at the molecular scale presents numerous challenges, due to the sensitivity required, and the presence of many potential sources of noise. In describing sensors for this purpose, it is therefore helpful to be clear about all sources of measurement error. In general, for any system or object that may be measured, a measured state, m, will only be an approximation of the actual system state, a. This may be due to any of a number of factors, such as imperfect signal interpretation reflecting error due to the operation of the sensor, the readout process, or the signal interpretation, and also because contacting the sensor to the system in some cases may perturb the state of the system. That the measured state m is different than the actual state a reflects the measurement error of the combined sensor, readout, and interpretation. Ideally, a sensor system will be constructed to make this measurement error as small as possible.

To measure states at a molecular scale, such as in the case of sequencing a DNA molecule, various efforts have been directed to create sensor systems in which the sensor device has a "probe" that contacts the molecules of interest, preferably on a single-molecule scale, while other features of the sensor device are on larger nano- or micro-scales for purposes of manufacturing the sensor devices or integrating them into a signal transduction system.

In particular, a biosensor is an analytical device that functionally integrates a biological recognition component into a signal transduction system, to measure properties of biologically relevant molecules, such as DNA, RNA or proteins. That integration provides rapid and convenient conversion of biological events to detectable electrical signals. Of the various electrical biosensing architectures that have been devised, systems based on field-effect transistors (FETs) appear promising because they can directly translate interactions between target molecules (e.g., biological molecules) and the FET surface into detectable electrical signals. In a typical FET device, current flows along a channel that is connected to two electrodes (also referred to as the source and the drain). The channel conductance between the source and the drain can be modulated by a third electrode (also referred to as the gate) that is coupled to the channel through a thin dielectric insulating layer. FETs can be used to detect target chemicals and measure chemical concentrations for a wide range of commercial applications. A classical and widely used example is a FET-based pH sensor, used to measure hydrogen ion concentration. This was introduced by Bergveld in the 1970's, and is used in solid-state pH sensors. The general field of ion-sensitive FET (ISFET) devices expands upon that concept for other chemical concentration measurements.

A limitation of current FET-type biosensor systems is their sensitivity. Current biosensor systems are unable to perform single molecule detection and identification. Likewise, they are unable to monitor single molecule reaction dynamics. These sensitivity limitations of FET-type biosensors prevent their use as detectors in important biochemical assays, such as in single molecule sequencing reactions.

Some efforts to improve FET biosensor sensitivity have focused on use of carbon nanostructures, such as carbon nanotubes, to form the channel between electrodes. However, carbon nanostructures pose various obstacles with respect to biosensor functionalization. In particular, there is no way to engineer in attachments sites at specific, desired atomic locations, for the purpose of attaching functional or sensitizing probe molecules. Additionally, present limits on precision, control, and scale of the synthesis of carbon nanostructures pose further challenges with respect to sensitivity and reliable production of individual sensors, establishing high density scalable arrays of sensors, and commercial viability of sensor manufacturing. Current carbon nanotube synthesis methods typically produce structures on a scale of around 100 nm or longer in length, a scale that is likely to pose limitations with respect to sensitivity as well as sensor density on a multi-sensor platform.

Thus, molecular-scale electronic biosensor devices with architectures compatible with increased sensitivity and precision, reliable engineering, and that are further compatible with efficient and commercially-viable manufacturing methods for achieving increased sensor density on a multi-sensor platform, are desirable. Likewise, improved methods of manufacturing such sensor devices are also desirable.

SUMMARY

The present disclosure generally relates to sensors, systems including the sensors, and to methods of forming and using the sensors and systems. Exemplary sensors can be used to, for example, sequence molecules such as DNA, RNA, or other oligonucleotides. While the ways in which various embodiments of the disclosure address the drawbacks of the prior art sensors are discussed in more detail below, in general, the disclosure provides sensors that are relatively easy and inexpensive to manufacture.

In various embodiments of the present disclosure, a sensor comprises: a source electrode; a drain electrode spaced apart from the source electrode by a sensor gap; a gate electrode, wherein the source, drain and gate electrode cooperate to form an electrode circuit; and a bridge molecule bridging across said sensor gap, connecting the source and drain electrodes; and a probe coupled to the bridge molecule, wherein interaction of the probe with a nucleic acid is detectible by monitoring at least one parameter of the electrode circuit. In various examples, the nucleic acid comprises DNA or RNA, or variants thereof.

In various embodiments, the probe of the sensor comprises an enzyme, such as, for example, a DNA polymerase, a reverse transcriptase, an exonuclease, or a helicase. In some cases, the probe may comprise a DNA polymerase, such as, for example, Phi29, PolI, or a mutant thereof.

In various embodiments, the bridge molecule may comprise an antibody, double-stranded DNA or a protein alpha-helix. For example, the antibody may comprise an IgG antibody, such as an IgG antibody that recognizes at least one contact point on the source or drain electrode or that recognizes contact points on the source and drain electrodes. Other bridge molecules may include a nucleic acid duplex, such as, for example, a DNA duplex, a DNA-RNA hybrid duplex, a DNA-PNA hybrid duplex, a PNA-PNA duplex, or a DNA-LNA hybrid duplex.

In accordance with various embodiments of the disclosure, a sensor includes a first contact coupled to a first electrode, a second contact coupled to a second electrode, a sensor gap defined between one of the first contact and the first electrode and one of the second contact and the second electrode, and a bridge molecule comprising a first end and a second end, wherein the bridge molecule is coupled to the first contact at the first end and coupled to the second contact at the second end. In accordance with various aspects of these embodiments, the bridge molecule is a biopolymer, or the bridge molecule is chemically synthesized. In accordance with additional aspects, the sensor includes a third or gate electrode. In these cases, the gate electrode can be used to tune and/or activate the sensor device. In accordance with further aspects, the sensor gap has a sensor gap dimension of between about 5 nm and about 30 nm. In accordance with additional aspects, the first end or the bridge molecule comprises a first self-assembling anchor; in accordance with further aspects, the second end comprises a second self-assembling anchor. Exemplary bridge molecules can include one or more of the following attributes: the bridge molecule can be linear (e.g., a linear biopolymer), the bridge molecule has an end-to-end length that is less than a persistence length of the bridge molecule, and the bridge molecule includes an end-to-end length configured to approximate the dimension of the sensor gap. Exemplary bridge molecules include a nucleic acid duplex, such as, for example, a DNA duplex, a DNA-RNA hybrid duplex, a DNA-PNA hybrid duplex, a PNA-PNA duplex, or a DNA-LNA hybrid duplex. Exemplary sensors include a probe attached to the bridge molecule. The probe can be configured to engage a single target molecule. Exemplary probes can include or be an enzyme configured to engage the target molecule during a reaction in a solution.

In accordance with additional embodiments of the disclosure, a sensor includes a first electrode overlying a substrate surface, a second electrode overlying a substrate surface, a sensor gap defined between the first electrode and the second electrode (or between contacts attached to the electrodes), and a bridge molecule comprising a first end and a second end, wherein the bridge molecule is coupled to a first contact at the first end and coupled to a second contact at the second end. The sensor gap can include a sensor gap dimension of between about 5 nm and about 30 nm. In accordance with various aspects of these embodiments, the bridge molecule is a biopolymer, or the bridge molecule is chemically synthesized. In accordance with additional aspects, the sensor includes a third or gate electrode. In these cases, the gate electrode can be used to tune and/or activate the sensor device. In accordance with additional aspects, the first end or the bridge molecule comprises a first self-assembling anchor; in accordance with further aspects, the second end comprises a second self-assembling anchor. Exemplary bridge molecules can include one or more attributes noted herein. Exemplary bridge molecules include a nucleic acid duplex, such as, for example, a DNA duplex, a DNA-RNA hybrid duplex, a DNA-PNA hybrid duplex, a PNA-PNA duplex, or a DNA-LNA hybrid duplex. Exemplary sensors include a probe attached to the bridge molecule. Exemplary sensors include a probe attached to the bridge molecule. The probe can be configured to engage a single target molecule. Exemplary probes can include or be an enzyme configured to engage the target molecule during a reaction in a solution.

In accordance with additional exemplary embodiments, a system includes a sensor as described herein. The system can additionally include one or more circuits, such as a circuit formed using a substrate used to form the sensor or upon which the sensor resides. Systems can additionally or alternatively include additional circuits and/or devices to, for example, remove noise from a signal and/or assist with interpretation of the signal.

In accordance with yet additional embodiments of the disclosure, a method includes providing a sensor, such as a sensor described herein; contacting a nucleic acid template with a polymerase, wherein the polymerase is coupled to a bridge molecule comprising a portion of a sensor; providing a nucleotide base mix; performing, by the polymerase, an incorporation event comprising incorporation of a nucleotide from the nucleotide base mix into a synthesized nucleic acid; and detecting a signal produced by the incorporation event. In accordance with various aspects of these embodiments, a method can additionally include a step of applying an electrical potential to the sensor—e.g., to tune or activate the sensor. In accordance with further aspects, noise can be removed from the signal.

In accordance with yet additional embodiments, a method of manufacturing a biomolecular sensing device includes the steps of forming a first electrode and a second electrode on a substrate surface, wherein the first electrode and the second electrode are separated by an electrode gap; placing a first contact on the first electrode and a second contact on the second electrode, wherein the first contact and the second contact are separated by a contact gap; and attaching a bridge molecule to the first contact and the second contact. Exemplary methods can further include the step of contacting the bridge molecule with a probe to couple the probe to the bridge molecule.

And, in accordance with further embodiments of the disclosure, a method of sequencing an oligonucleotide comprises using one or more sensors as described herein.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures.

FIG. 21 illustrates a chemically synthesized bridge molecule in accordance with various embodiments;

FIG. 46A shows the plate map, setting forth the various concentrations of gold nanoparticles deposited into wells, with triplicate columnar repeats of buffer, affinity antibodies, naïve serum, and control non-specific mouse IgG, at various dilutions indicated in rows;

FIG. 46C is the corresponding table of numeric ELISA readings;

FIG. 48 sets forth commonly occurring methylated forms of nucleic acid bases. When these are present in DNA, it is desirable to be able to read out their presence in the sequence as well, as this may have biological relevance;

FIG. 67 illustrates one example of enhancing the primary hybridization signal, by using enzymatic extension (3' extendible end of the probe indicated by blue arrow) to incorporate one or more bases, perhaps including detectible groups (purple) to enhance the signal. Such enzymatic extension both adds stringency/checks for proper pairing, as well as the means of enhancing the electronic sensor signal, as indicated by the three levels in the current plot (no hybridization, hybridization, extension product present). In the case of single base extension, if the base identity is detectible (either from the four dNTPs together, or through a series of individual dNTP extension trials) it can also add one more base of sequence information, enhancing the sequencing capacity of the method;

Figure 68:
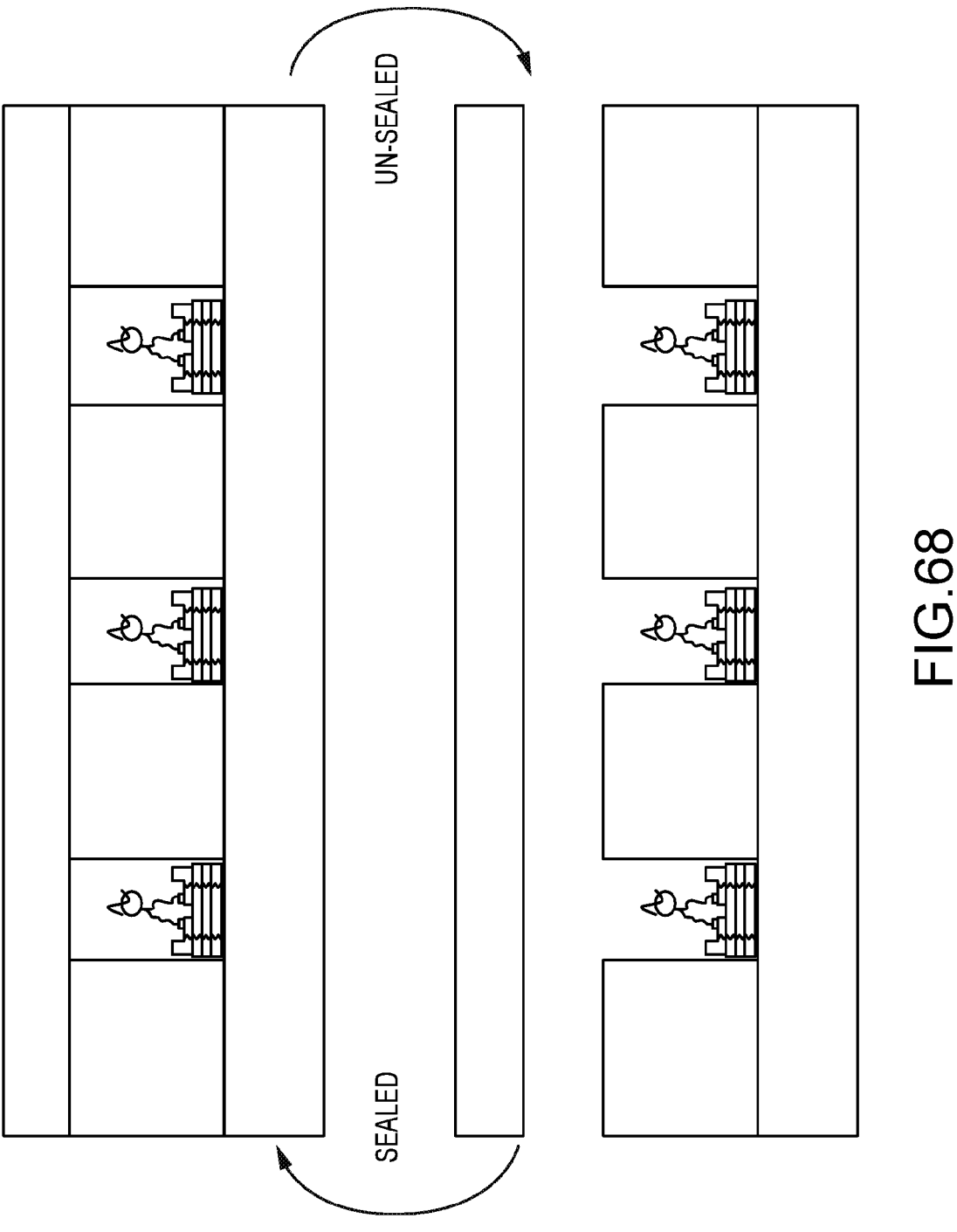
Figure 69:
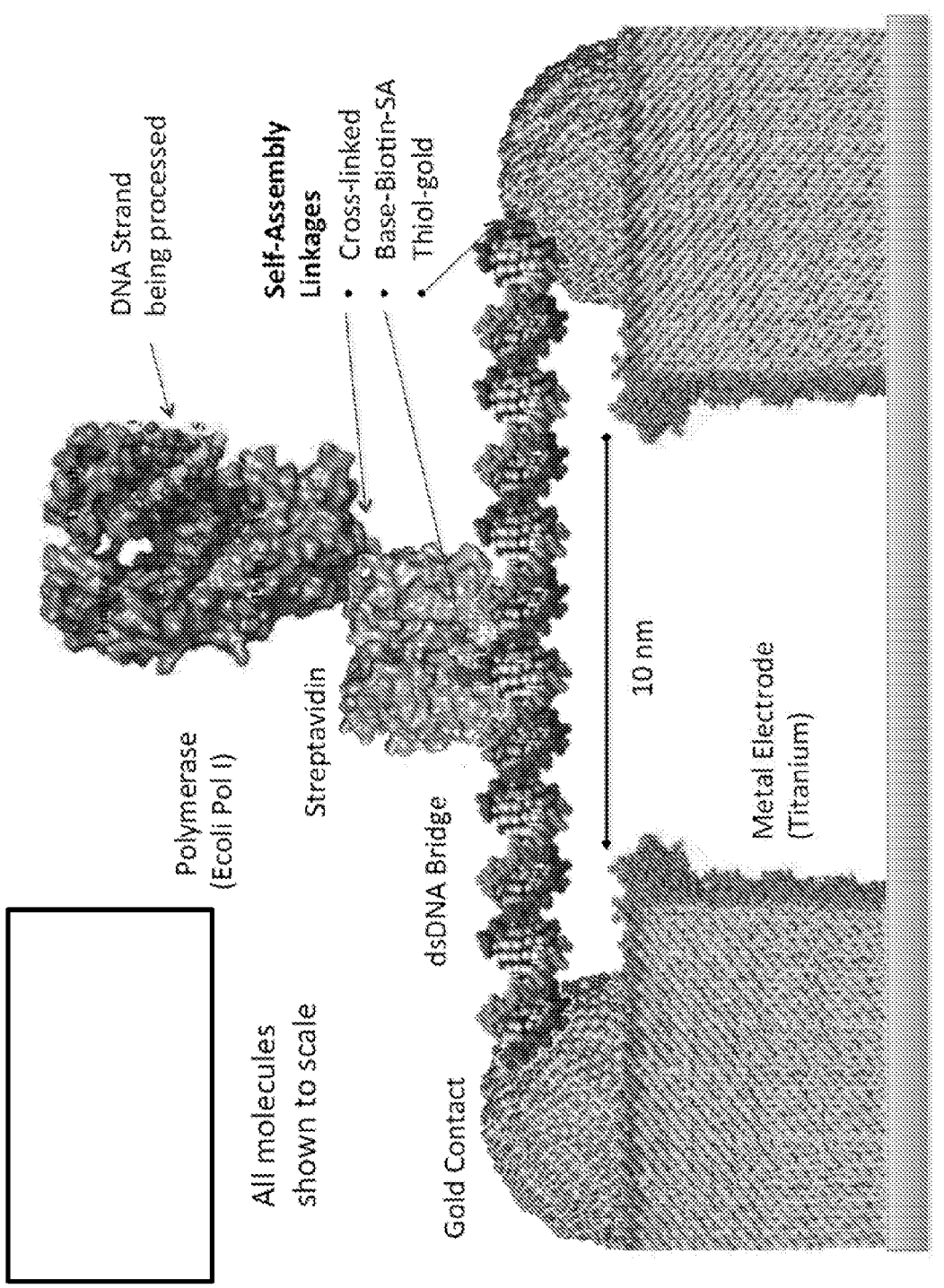
Figure 70:
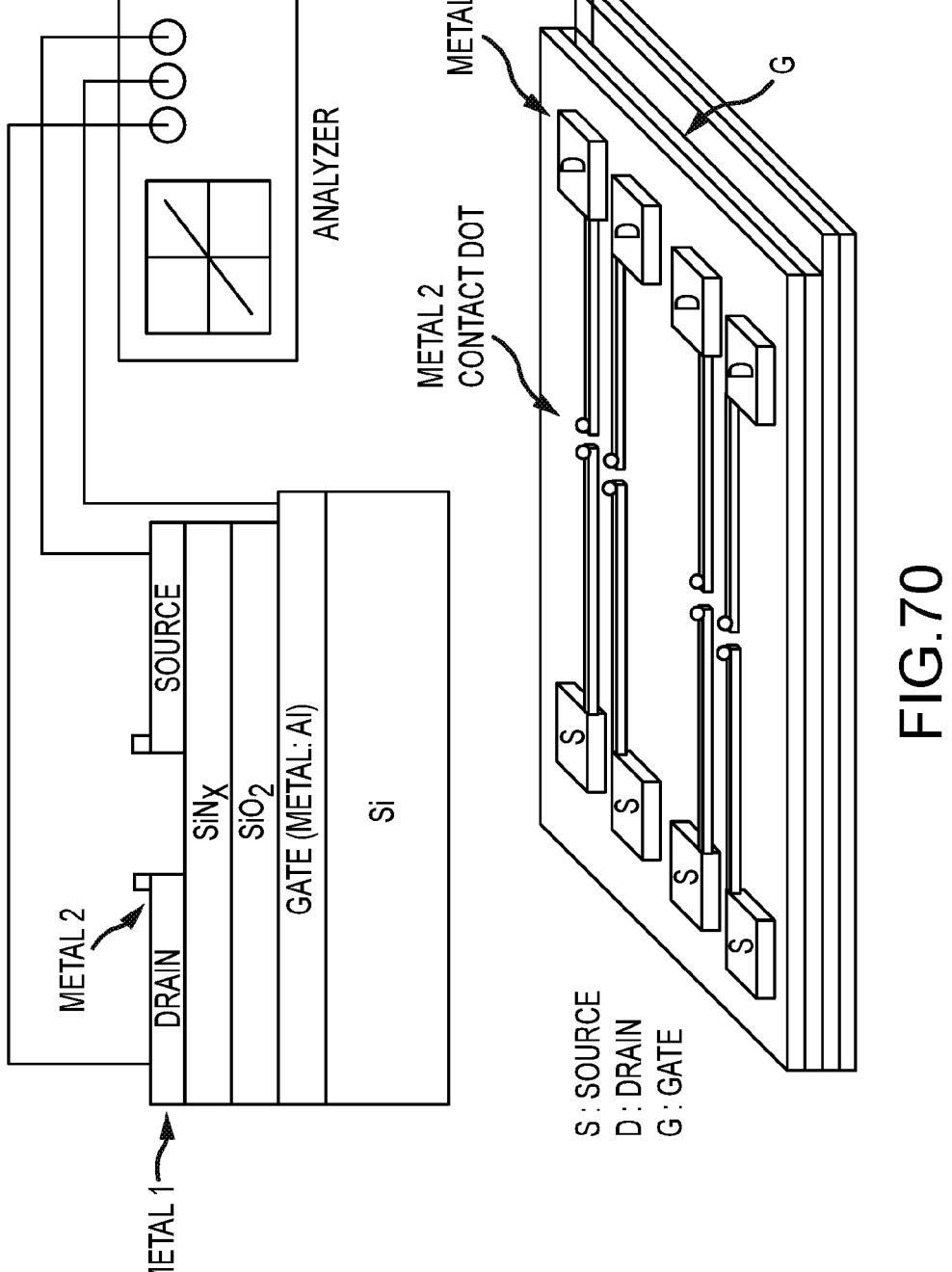
Figure 71A:
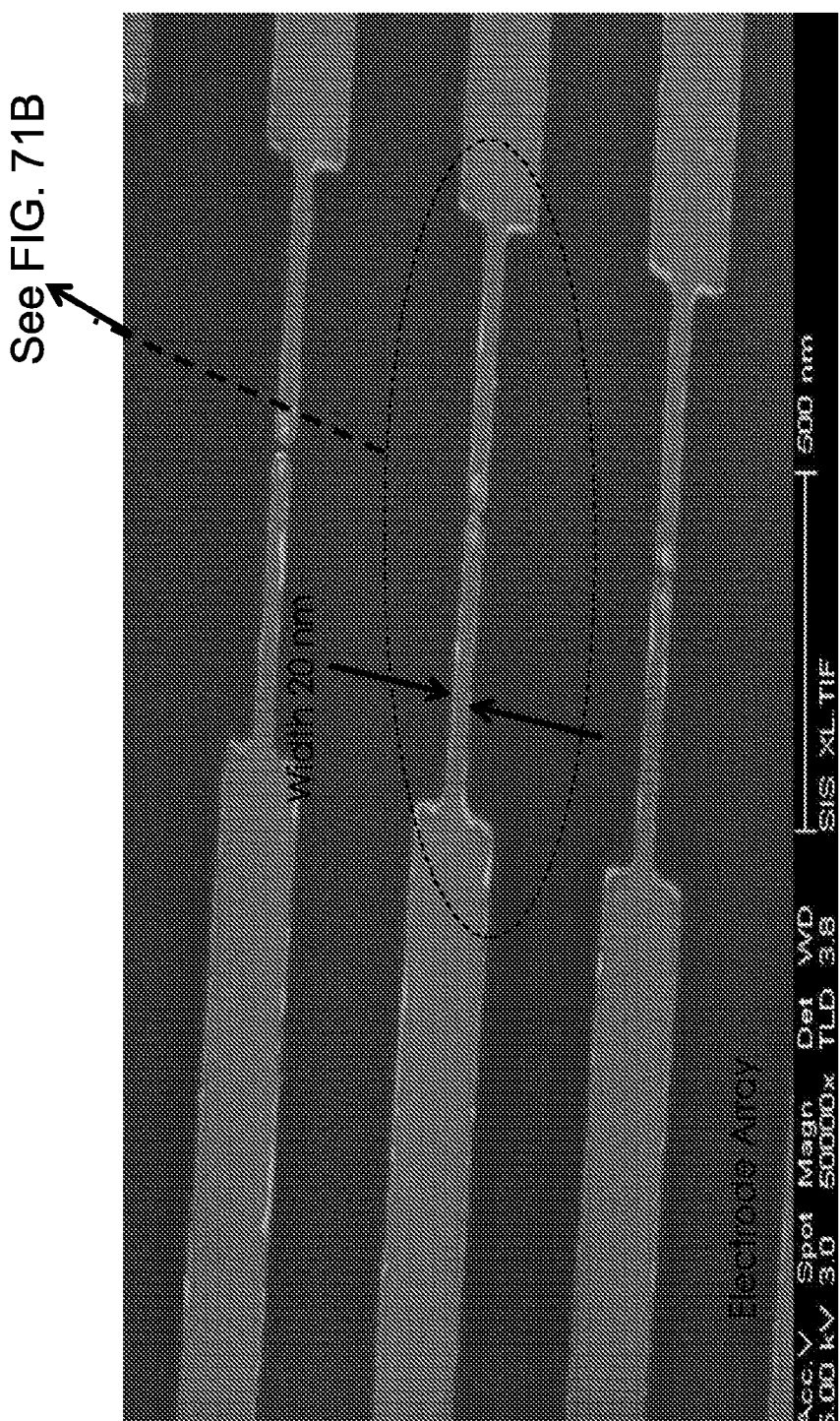
Figure 71C:
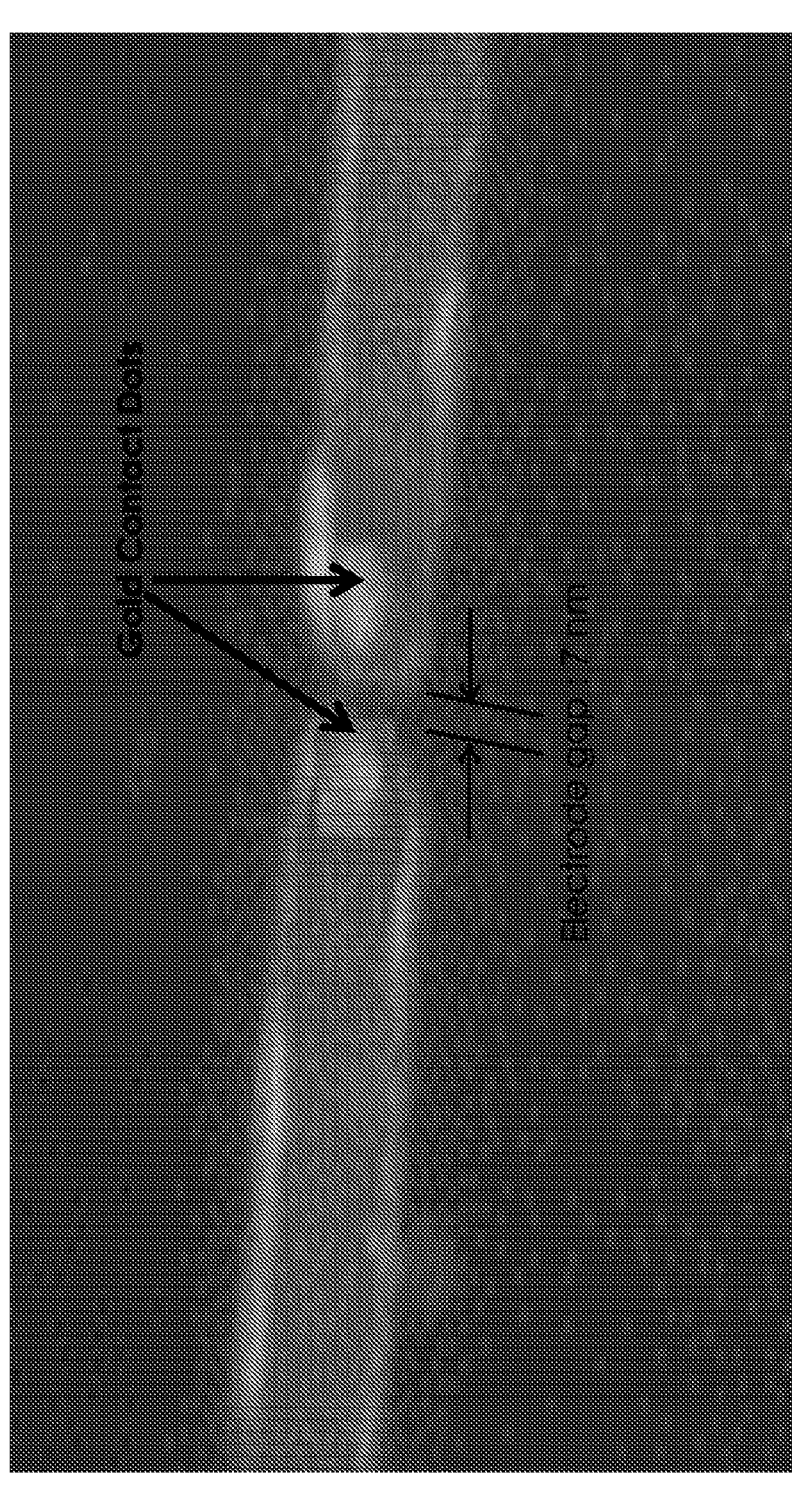
Figure 72:
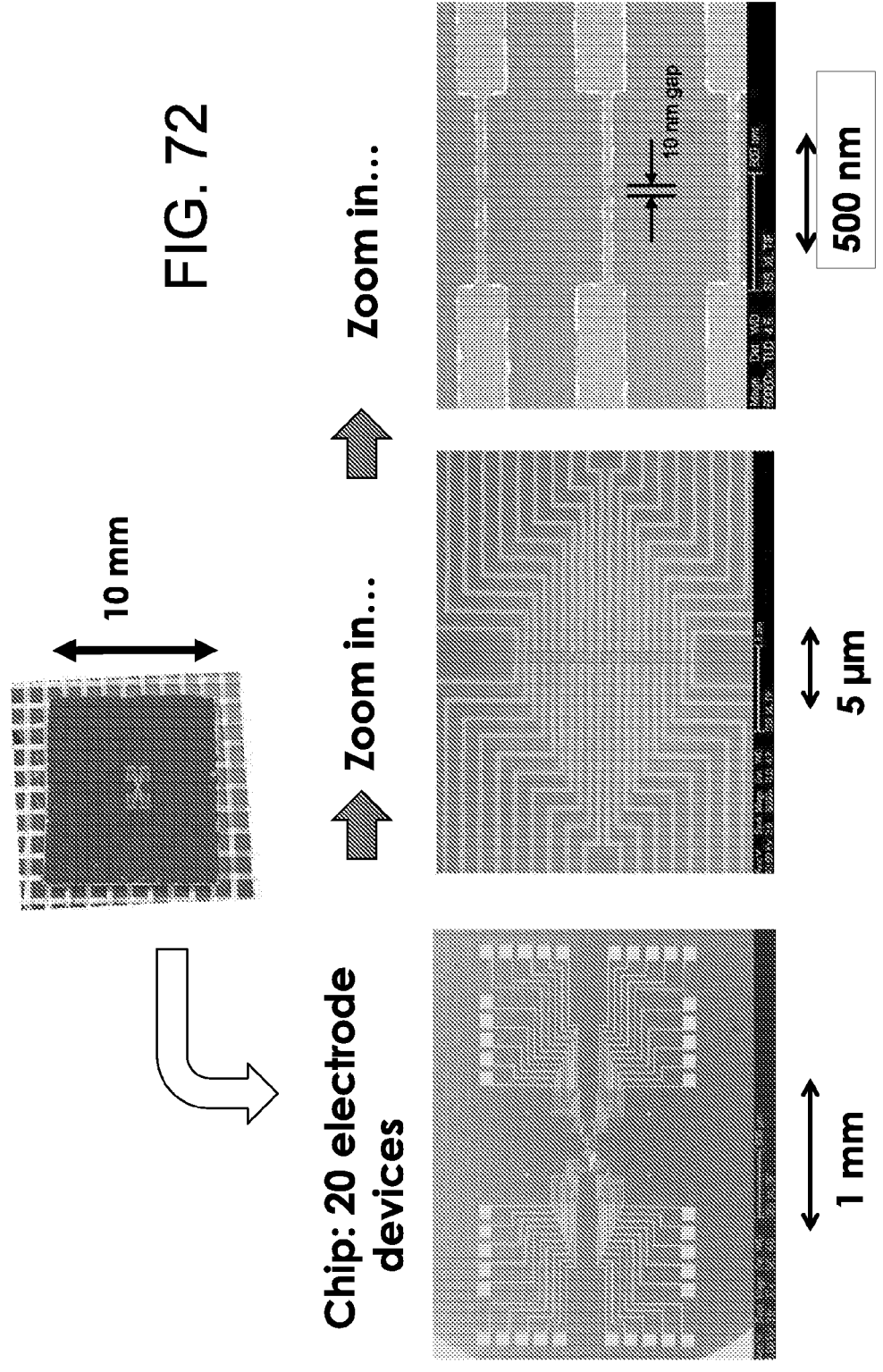
Figure 73:
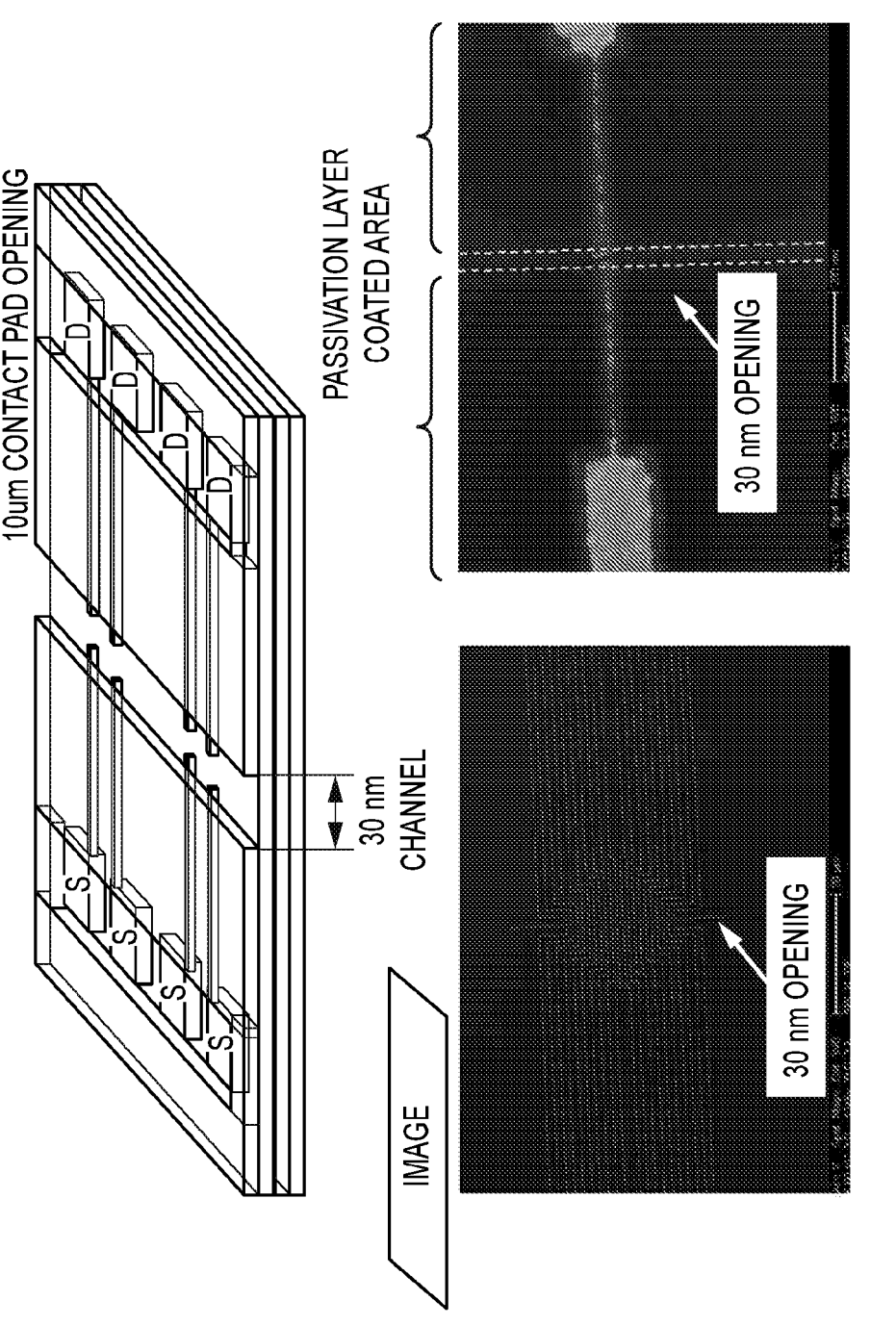
Figure 74:
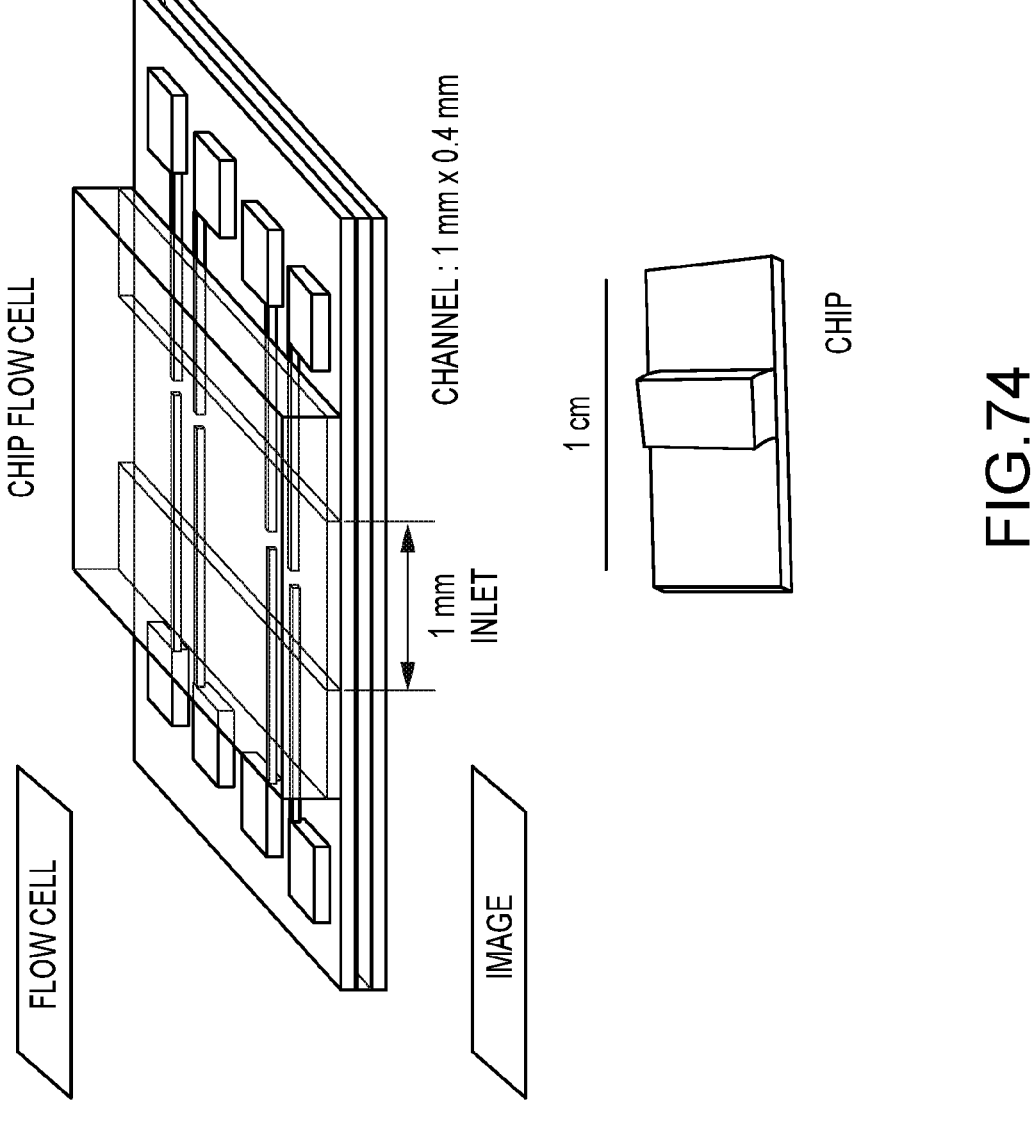
Figure 75:
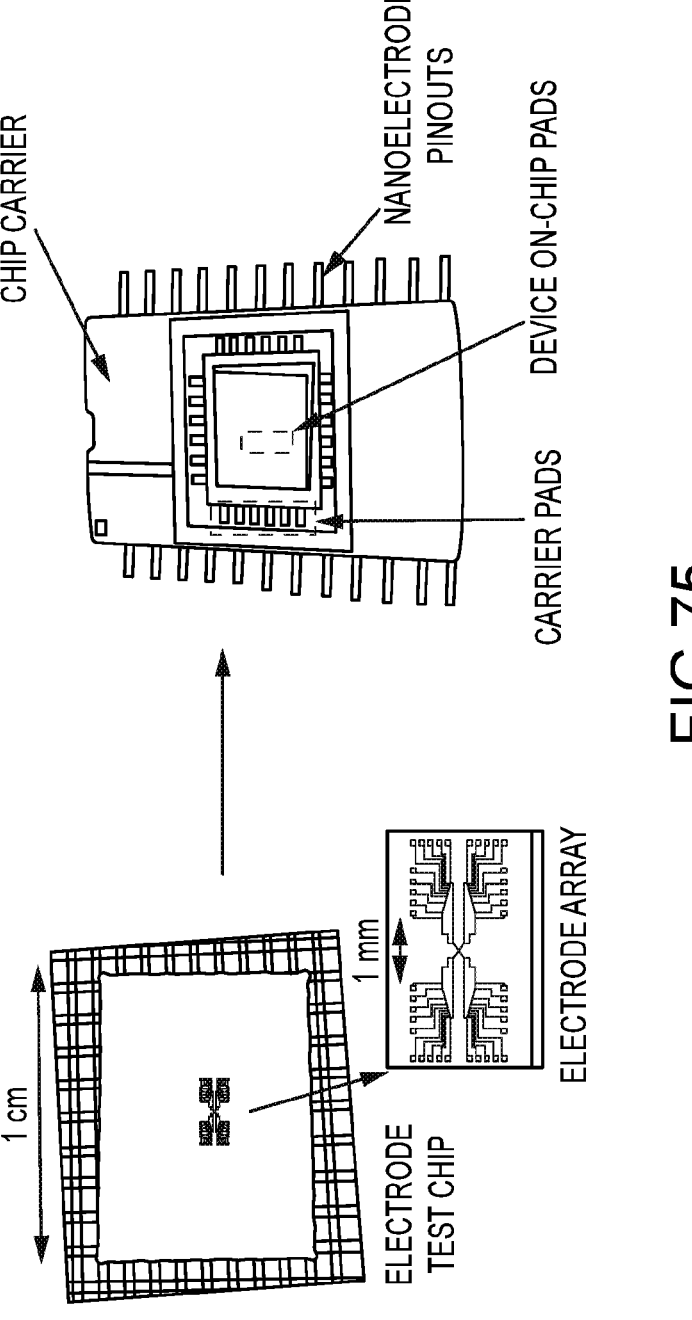
Figure 76:
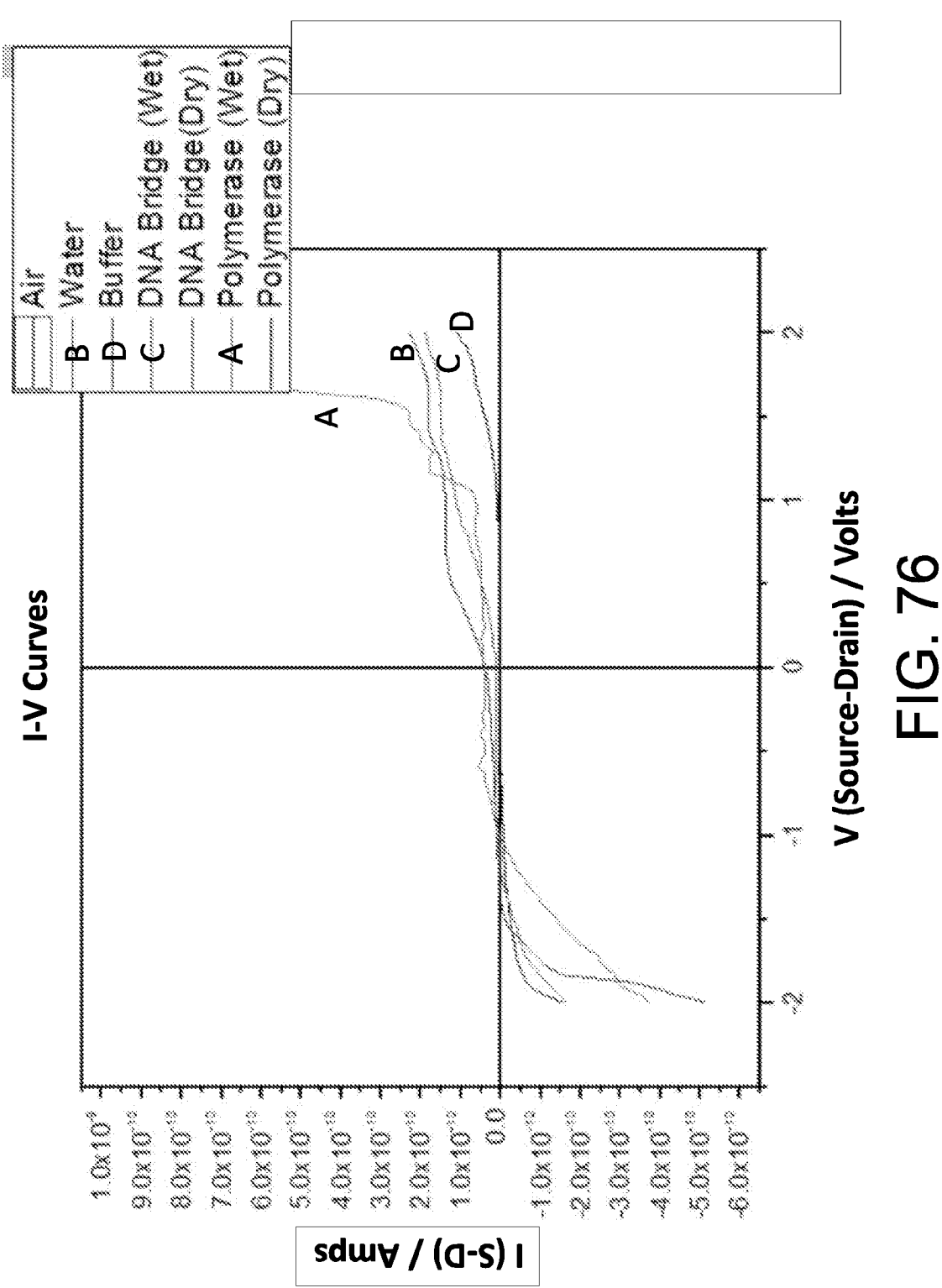
Figure 77:
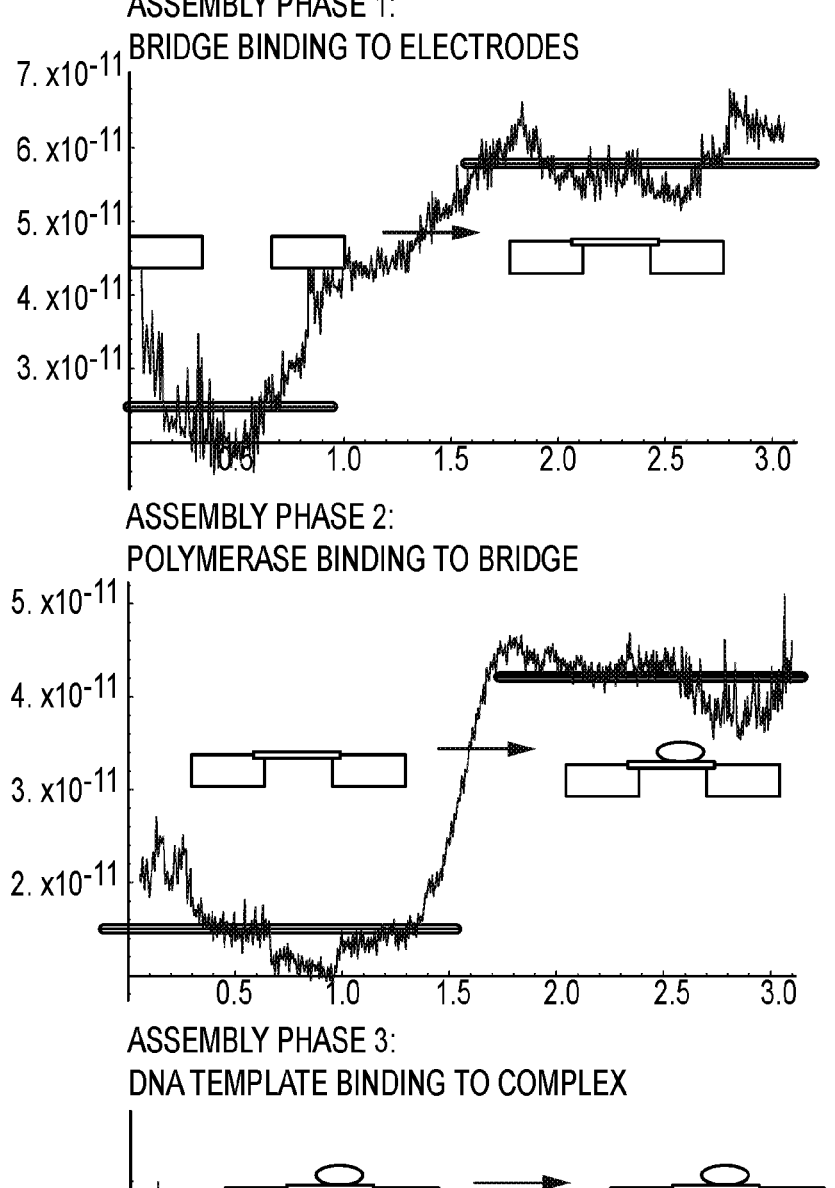
Figure 78:
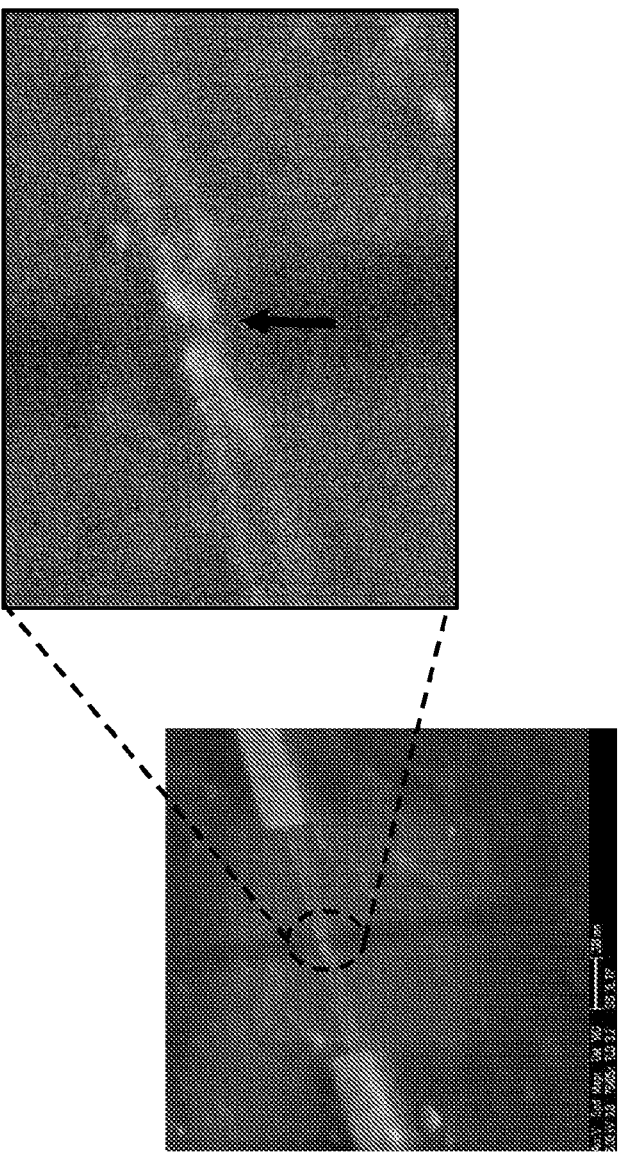
Figure 79:
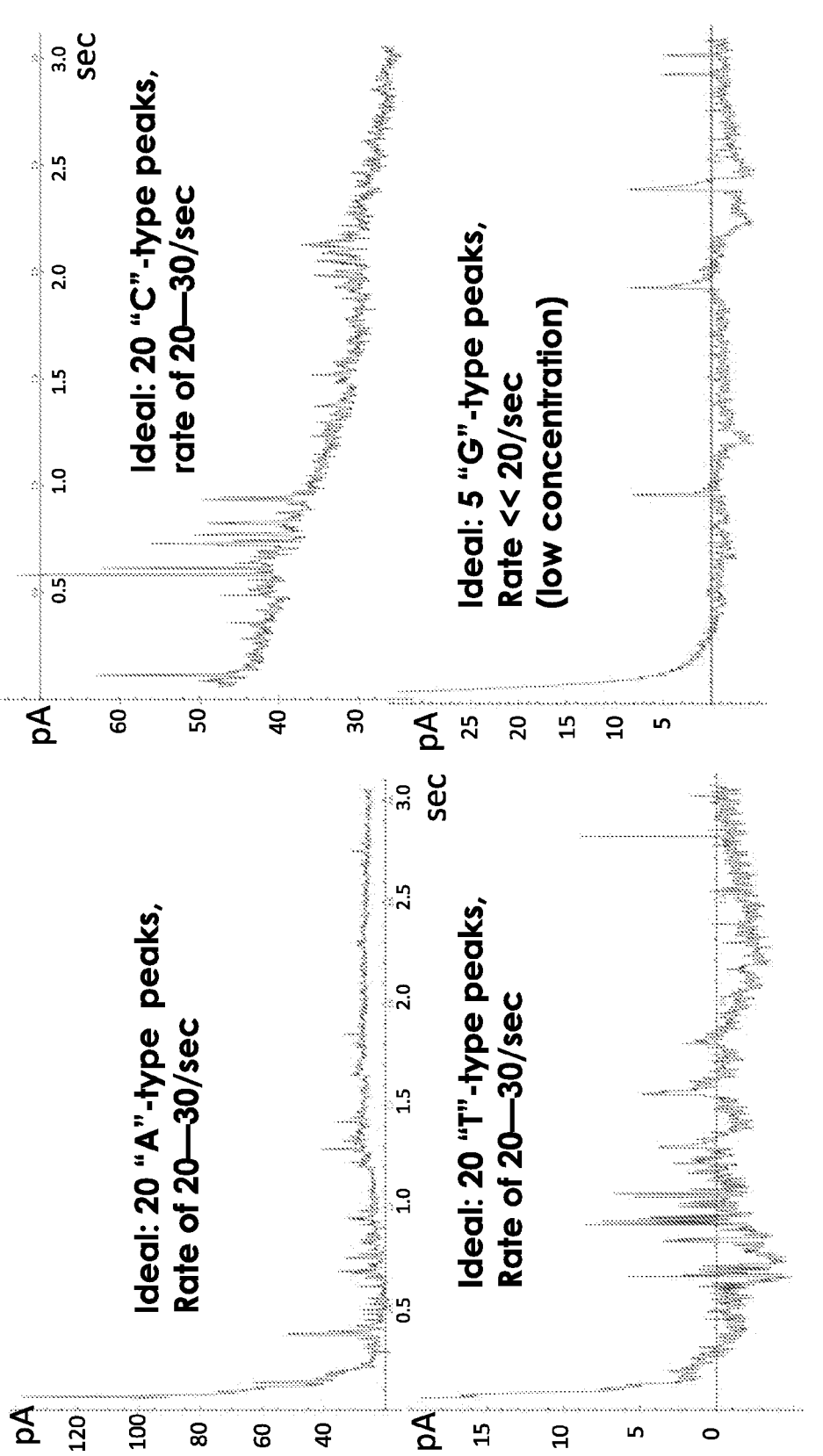
Figure 80:
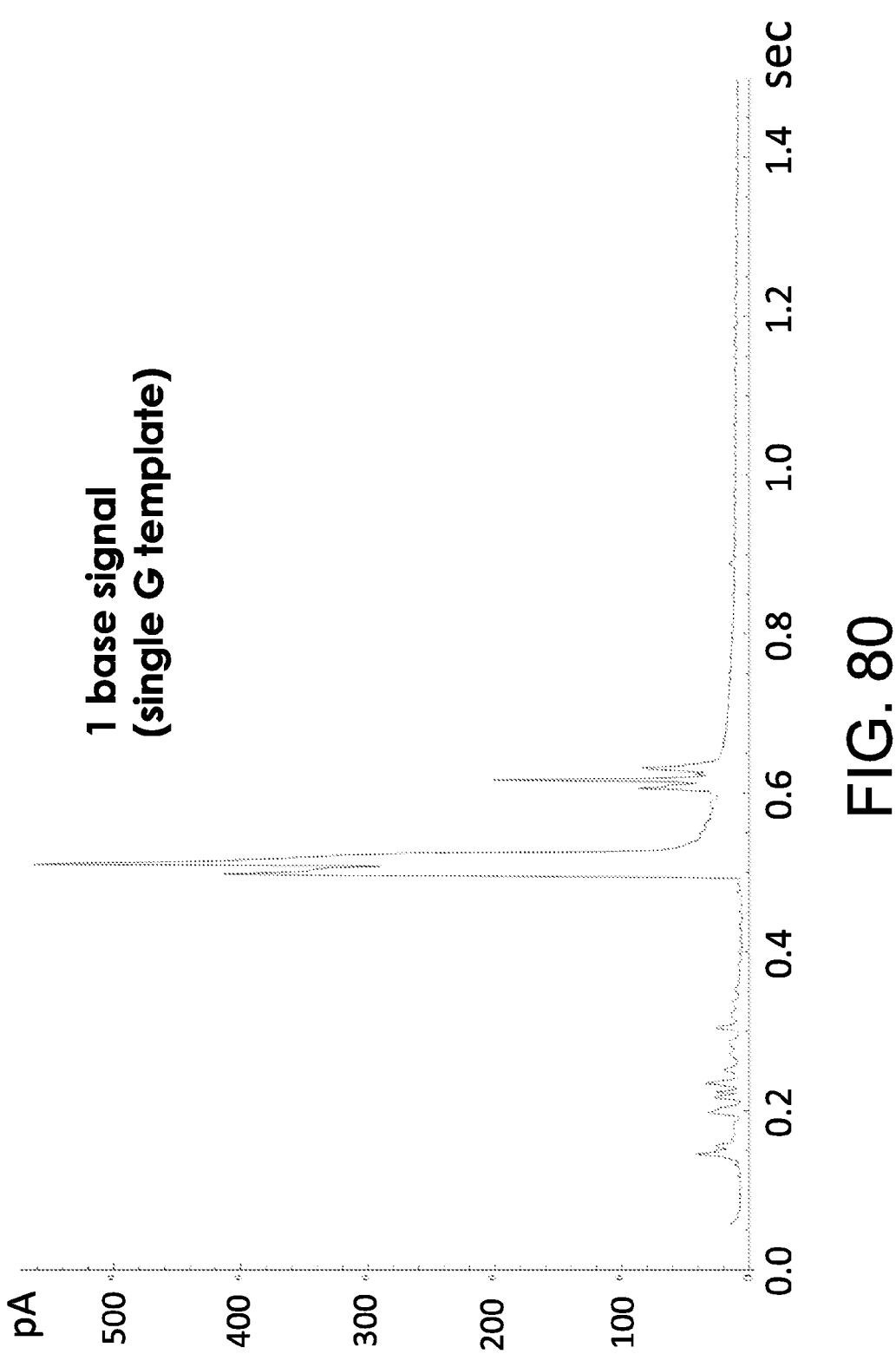
Figure 81:
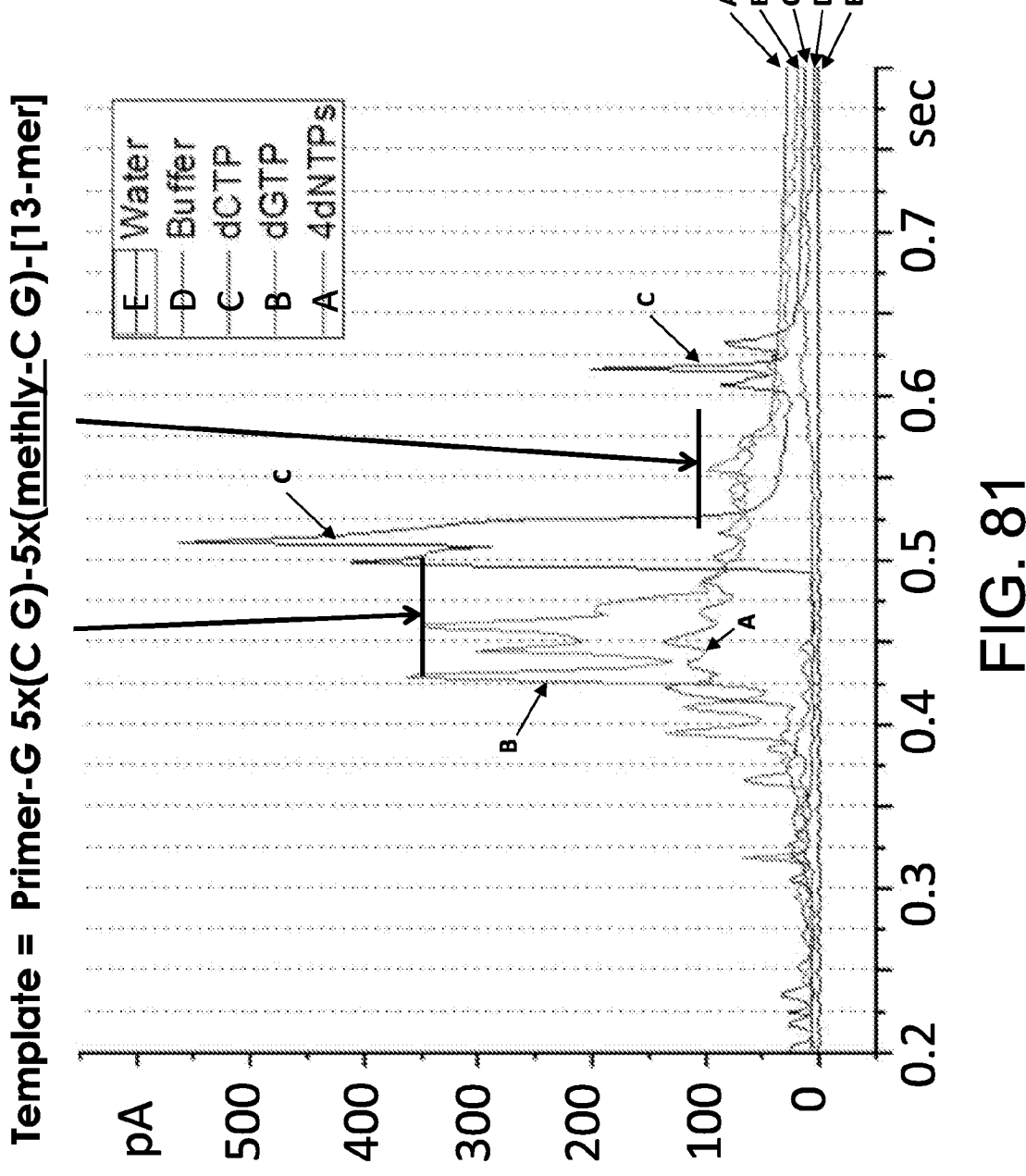
Figure 82:
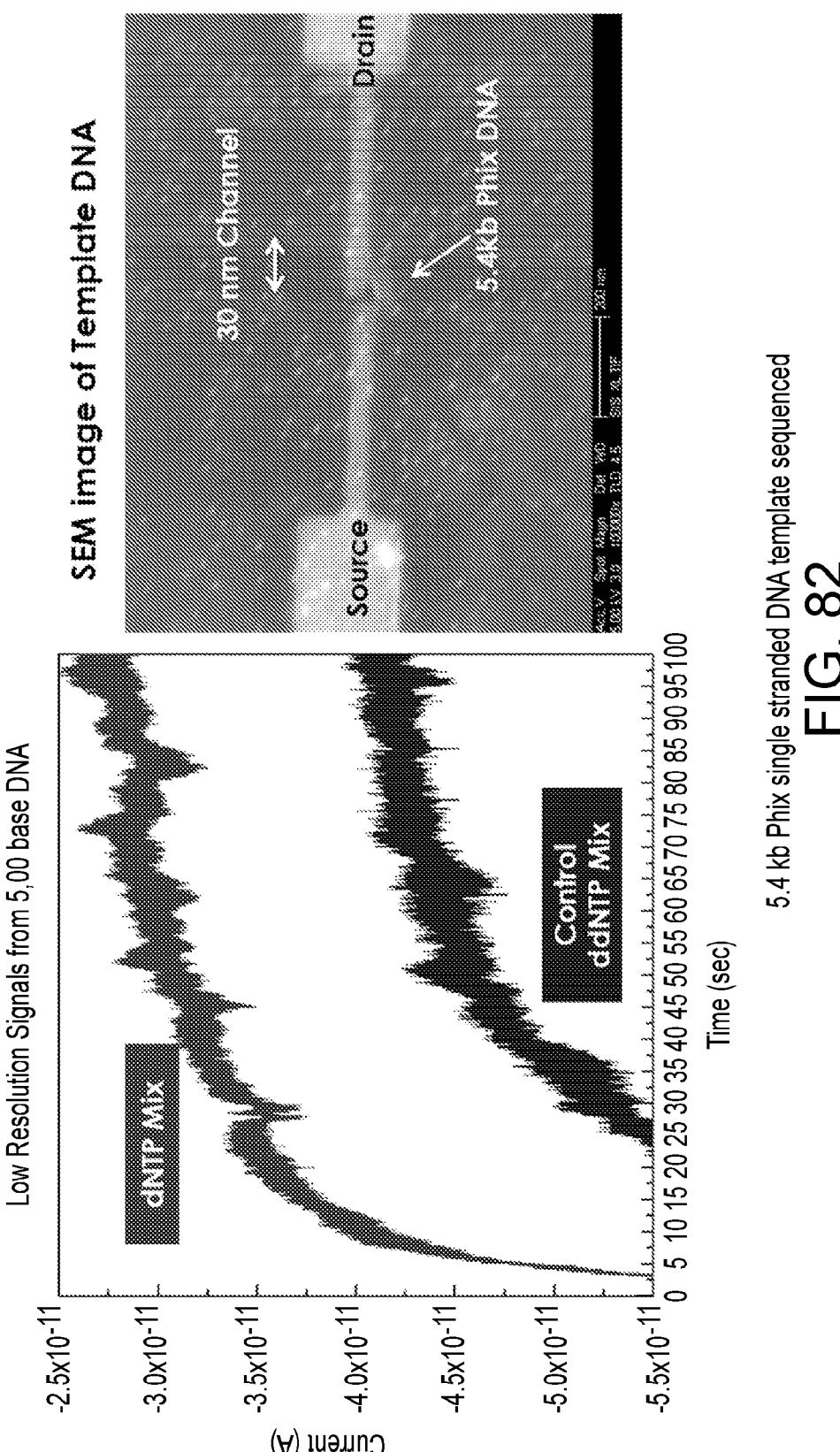
Figures 83A, 83B:
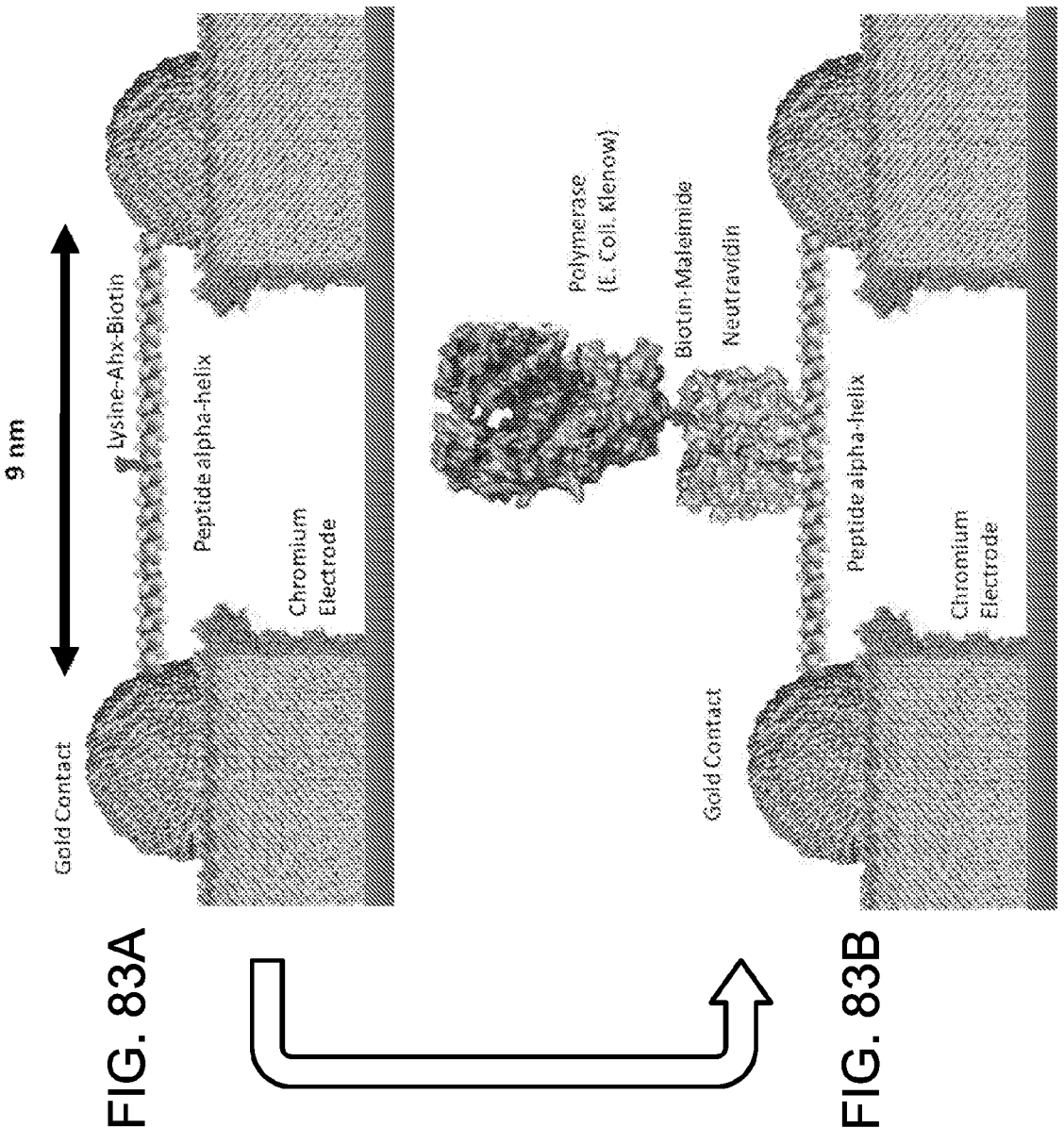
Figure 85A:
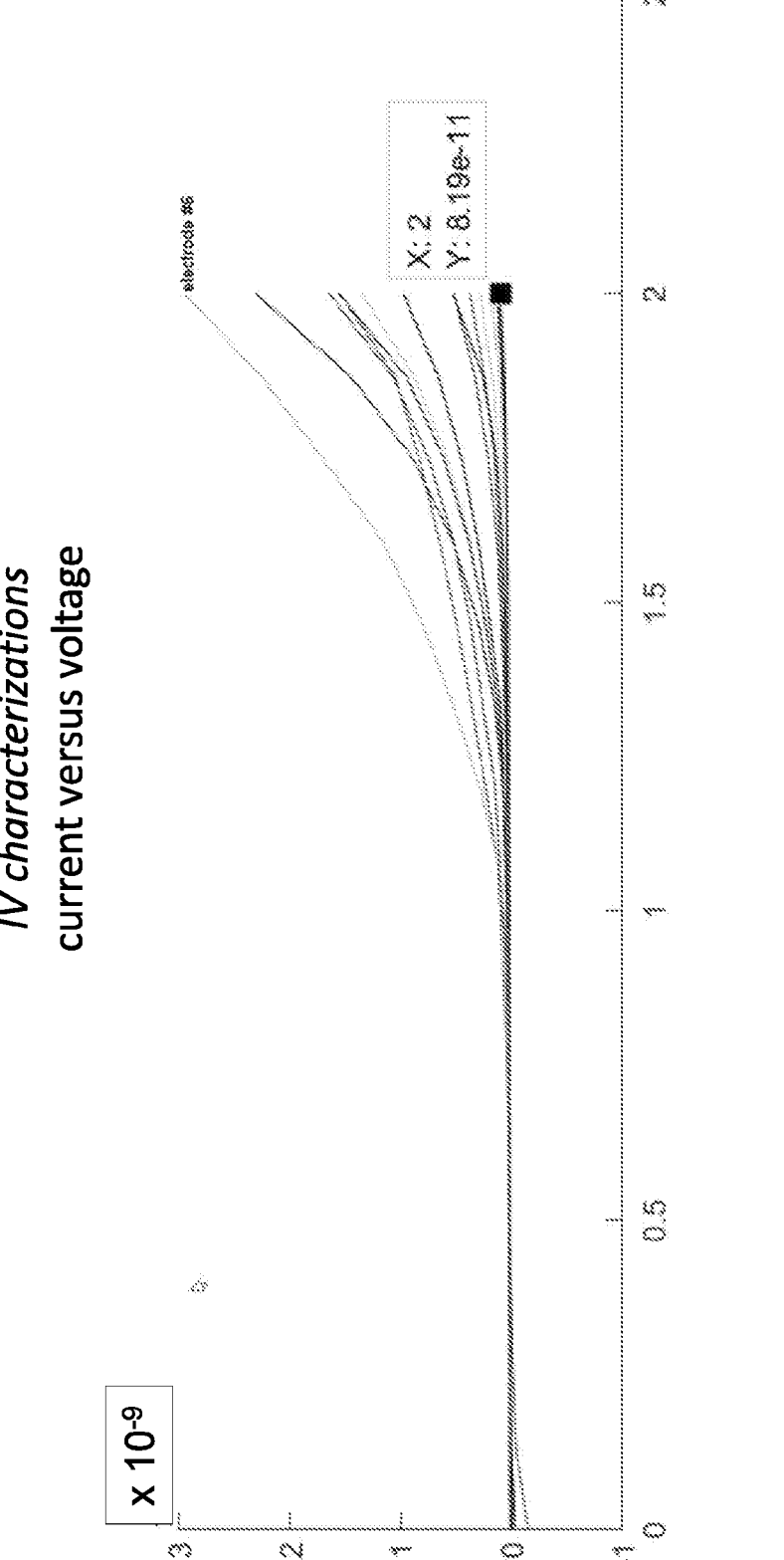
Figure 85B:
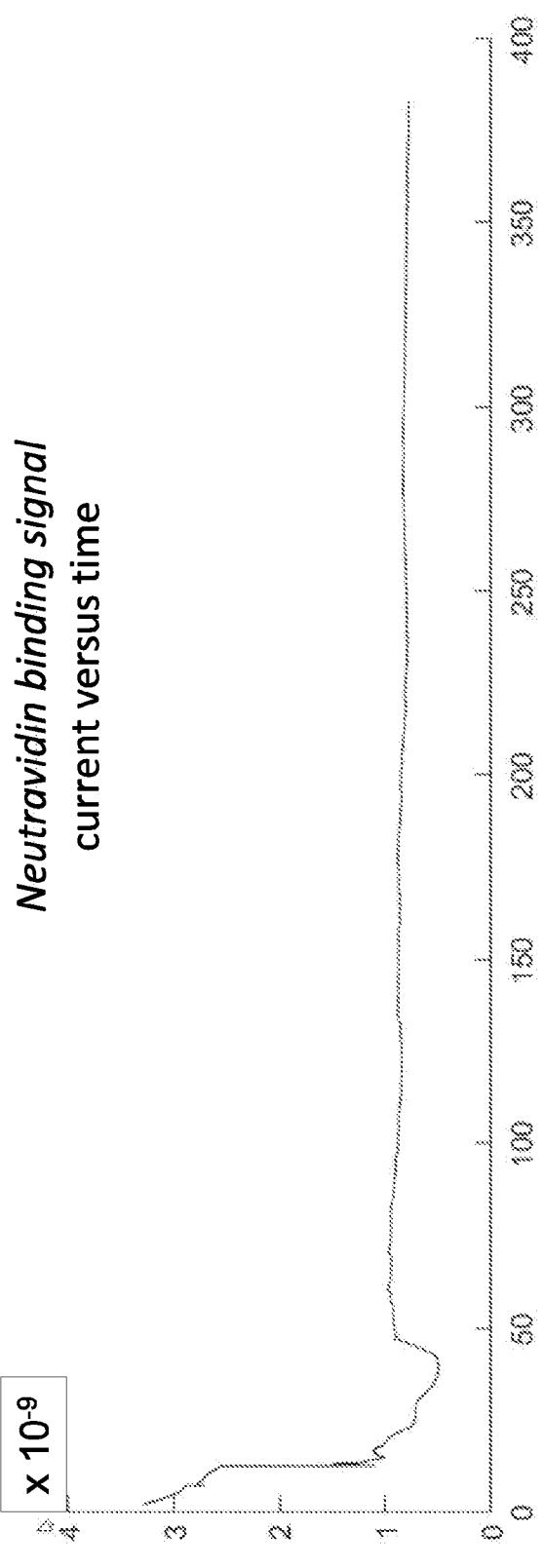
Figure 85C:
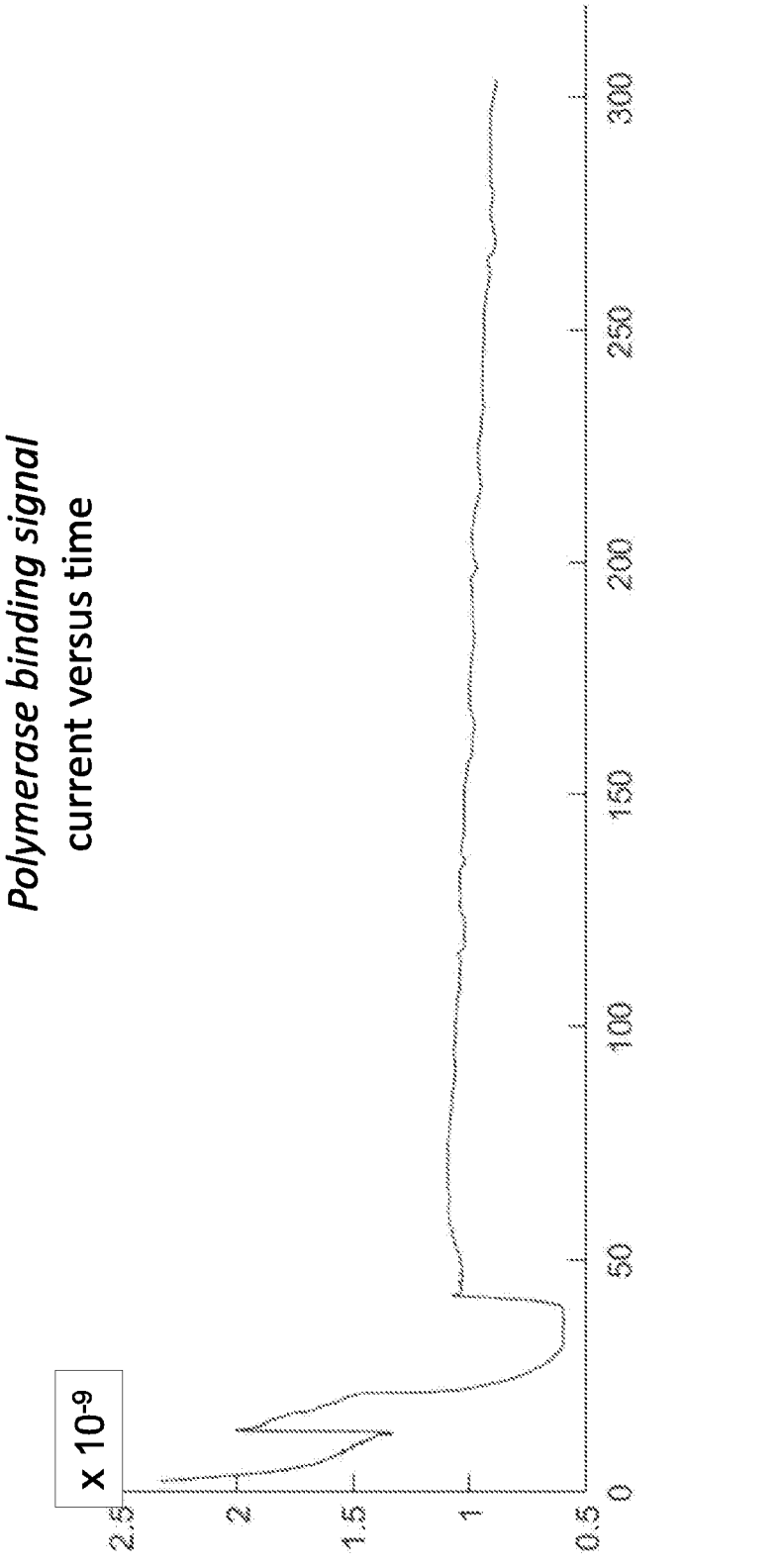
Figure 85D:
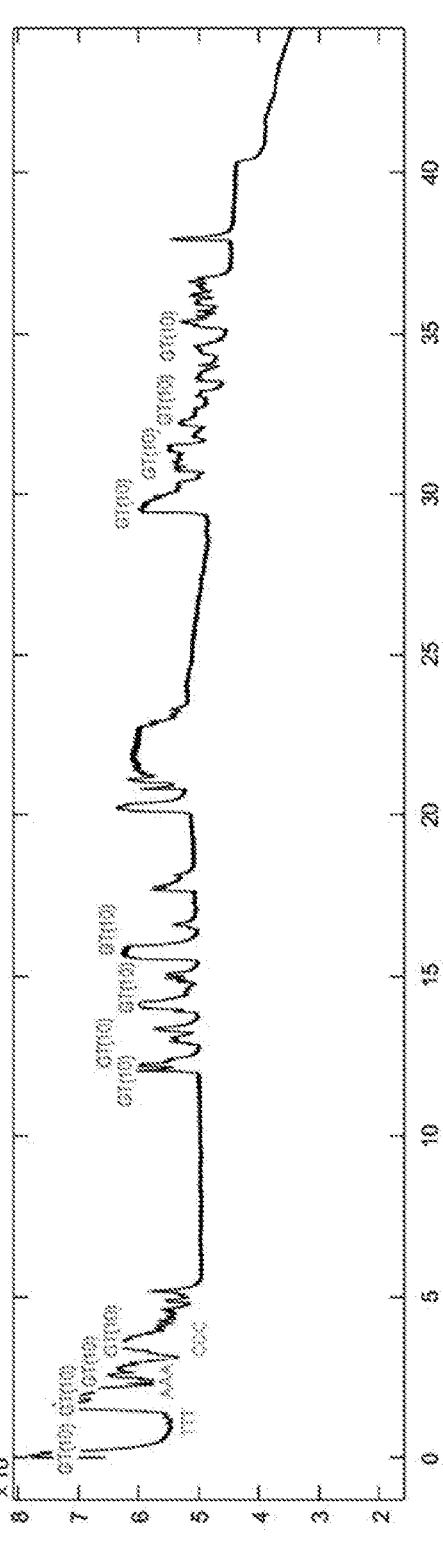

FIG. 68 illustrates a sensor enclosed in microwells or nanowells that can be sealed and unsealed in a bulk/macroscopic process. This localizes reactants and reaction products, to facilitate other modes of detection. This may also benefit from multiple sensor types per well, or multiple probe molecules per sensor, so that a processive enzyme can be present with a probe to detect a reaction product;

FIG. 69 illustrates details of the bridge and probe molecule structure typically used for experimental work. The bridge in this case is double stranded DNA molecule, of 20 nm length shown (60 bases), with thiol groups at both 5' ends for coupling to gold contacts on a metal electrode;

FIG. 70 illustrates a schematic of a test set-up for electrical measurements on molecular sensors is shown. In the upper portion of FIG. 70, a cross-section of the electrode-substrate structure and attachment to an analyzer for applying voltages and measuring currents through the bridge molecule is shown. In the lower portion of FIG. 70, a perspective view of an electrode array for bridging circuits is illustrated;

Figure 71B:
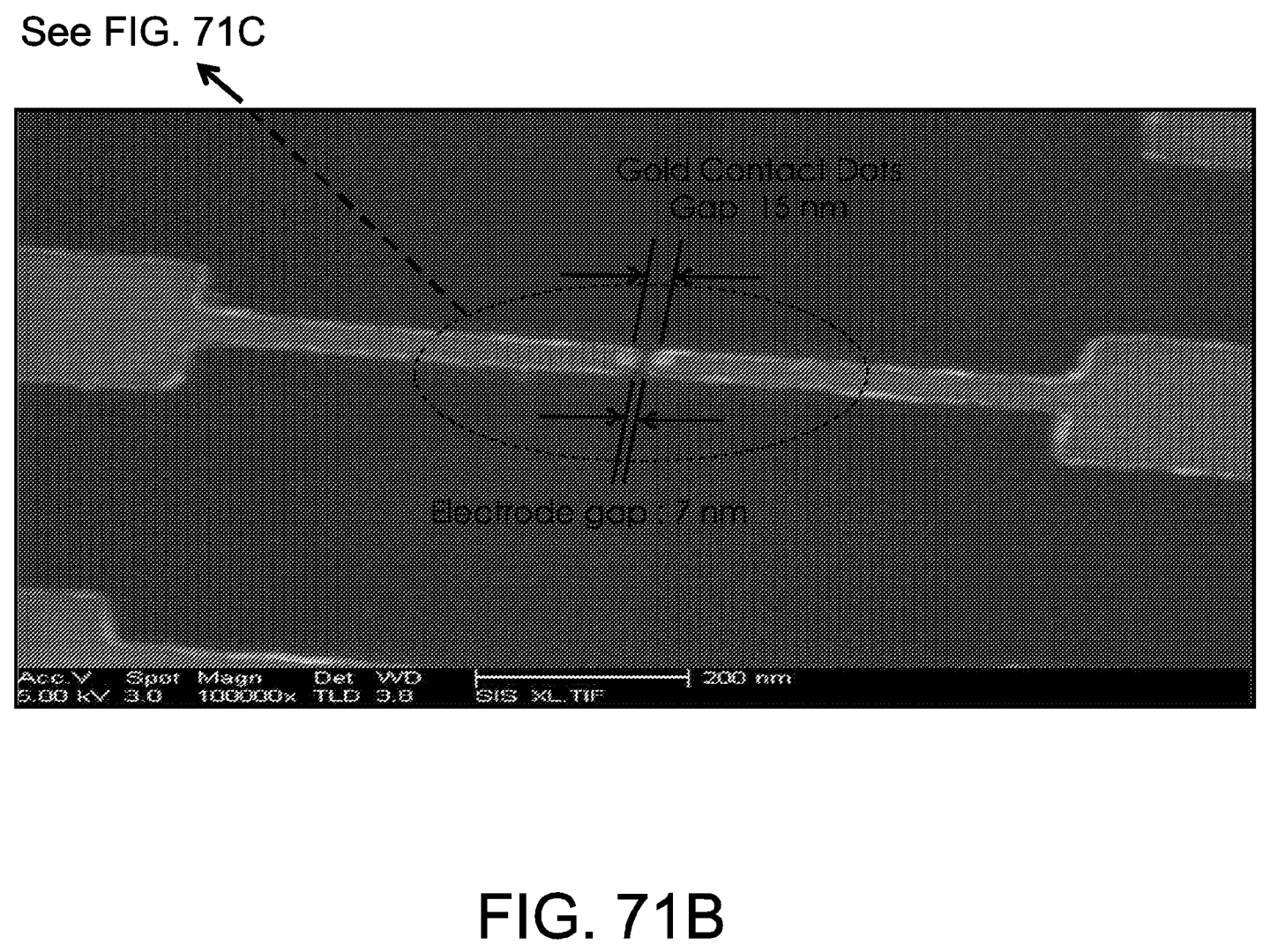

FIG. 71A is an electron microscope image of an array of titanium electrodes with gold metal dot contacts for bridge binding. Electrodes are on a silicon substrate and were produced by e-beam lithography;

FIG. 71B is an electron microscope close-up image of one of the electrode gaps in FIG. 71A, showing an electrode gap of 7 mm and a gold dot contact gap of 15 mm gold-to-gold spacing;

FIG. 71C is an electron microscope close-up image of a single electrode gap from FIG. 71B, showing approximately 10 nm diameter gold dots at the tips of the two electrodes;

FIG. 72 illustrates electrode test chip architecture. In this case, the electrode array was formed on a 1 cm silicon substrate, using e-beam lithography. The series of three SEM images in FIG. 72 shows the 20 electrode pairs at increasing resolution, down to the 10 nm scale of the electrode gap;

FIG. 73 illustrates an embodiment of the sensor device wherein a silicon oxide passivation layer is used to protect electrodes from solution. The openings in passivation expose the electrode area on the nm scale, and the electrical contact pads on a 10 micron scale;

FIG. 74 illustrates an embodiment of a flow cell to support controlled exposure of liquid solutions to the sensor chip surface. The flow cell is molded PDMS polymer;

FIG. 75 illustrates a chip mounted in a chip carrier for electrical measurements;

FIG. 76 illustrates conductivity of an assembled sensor complex, showing measured Current-versus-Voltage (I-V) Characteristics of DNA bridge molecules and complete sensor complexes (bridge with polymerase) in wet (dilute salt buffer) and dry (air) conditions, along with controls of open circuit electrodes in air, water and dilute salt buffer. The figure shows that the bridge and sensor complex conduct on the order of 100 mpico-Amp currents at 1 Volt of applied source-drain voltage. Measurements are done on semiconductor parameter analyzer via an SMU;

FIG. 77 illustrates electronic monitoring of a molecular sensor self-assembly onto gold-dot contact electrodes. Current versus time measurements are used to monitor assembly of bridge and molecular sensor complex. Upper left: Phase 1: double stranded DNA bridge assembles with thiol groups on 5' ends assembles onto electrode gold contact point, as indicated by jump in current. Upper right: Phase 2: polymerase-streptavidin complex binds to biotinylated site on the dsDNA bridge, as indicated by jump up in current. Lower right: Phase 3: primed single-stranded DNA template binds to polymerase to complete the complex, as indicated by spike in current versus time;

FIG. 78 shows electron microscope images of a final assembly structure at two levels of magnification. In the close-up image, the bridge-complex is visible without any labeling, seen as the blurry high contrast region joining the electrodes (pointed to by the green arrow);

FIG. 79 are four plots measuring incorporation signals with the sensor, illustrating measuring incorporation signals with the sensor, and shows the current signals resulting from the sensor being supplied with various primed, single stranded DNA sequencing templates and dNTPs for incorporation and polymerization. In each case, the major signal spikes represent signals from discrete incorporation events, wherein the polymerase enzyme adds another base to the extending strand. Upper left: template is 20 T bases; upper right, template is 20 G bases; lower left, template is 20 A bases; lower right, template is 20 C bases. The approximate rate of incorporation observed is 10-20 bases per second, consistent with standard enzyme kinetics, except for the lower rate of ~1 base per second due to rate limiting factors (e.g. lower dNTP concentration);

FIG. 80 illustrates a close up of the signal produced from a single base incorporation event. The signal has a double-peak structure which could potentially be used to help characterize the identity of the base, in addition to detecting the incorporation event;

FIG. 81 illustrates an embodiment of sensing methylated bases. This figure shows the potential use of the sensor to sense the methylation state or individual methylated bases in the template. The figure shows different signals result from un-methylated versus methylated portion of the template (green trace). Higher signal results from the un-methylated portion, rather than methylated portion. The experiment shown consists of measuring traces for a series of different solution additions onto the sensor chip as indicated, for the template sequence indicated. The dCTP flow produced a single base incorporation spike, and the addition of dGTP then enabled incorporation to proceed across the CG tract of the template, highlighting a difference in signal from methylated versus un-methylated template;

FIG. 82 illustrates the long reads capability of the sensor. This figure shows the potential to read or analyze long DNA fragments, which is important for applications where long range continuity of the data is important, such as de novo assembly of whole genome sequences. The DNA template is the 5.4 kb PhiX viral genome. At left: differential signals from a low-time-resolution read of the template (dNTP mix), versus a follow on control (terminator ddNTP mix, polymerase activity blocked) without polymerization. At right: SEM image of the electrodes with the long template DNA visible;

FIG. 83A illustrates an embodiment of a sensor comprising a peptide alpha-helix bridge molecule. The bridge molecule in one specific preferred embodiment reduced to practice comprises a peptide having a 66 amino acid sequence;

FIG. 83B illustrates an embodiment of a fully assembled sensor comprising an alpha-helix bridge coupled to a neutravidin molecule via the known biotin-neutravidin binding reaction, and also the polymerase attached via an additional biotin-maleimide linker that has been conjugated to a surface cysteine on the polymerase via the known maleimide-cysteine covalent coupling reaction;

Figure 84A:
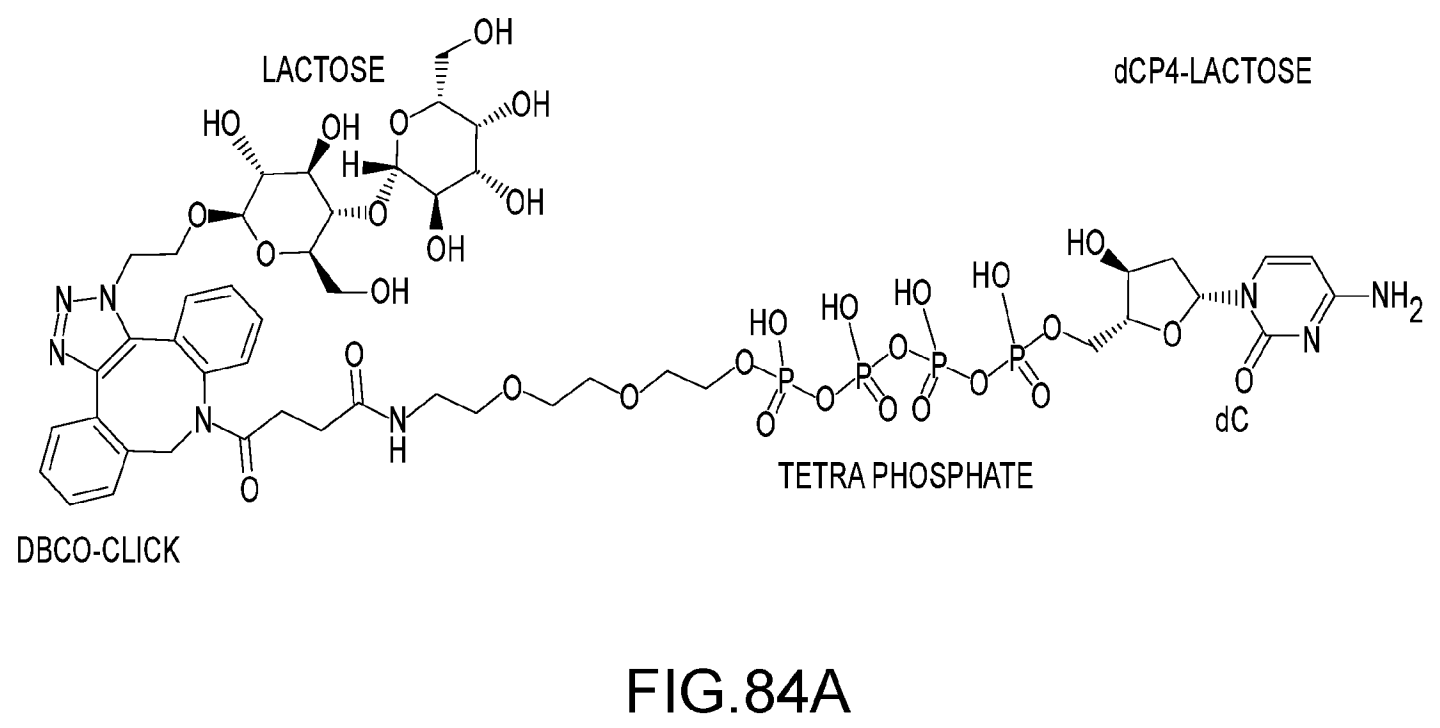
Figure 84B:
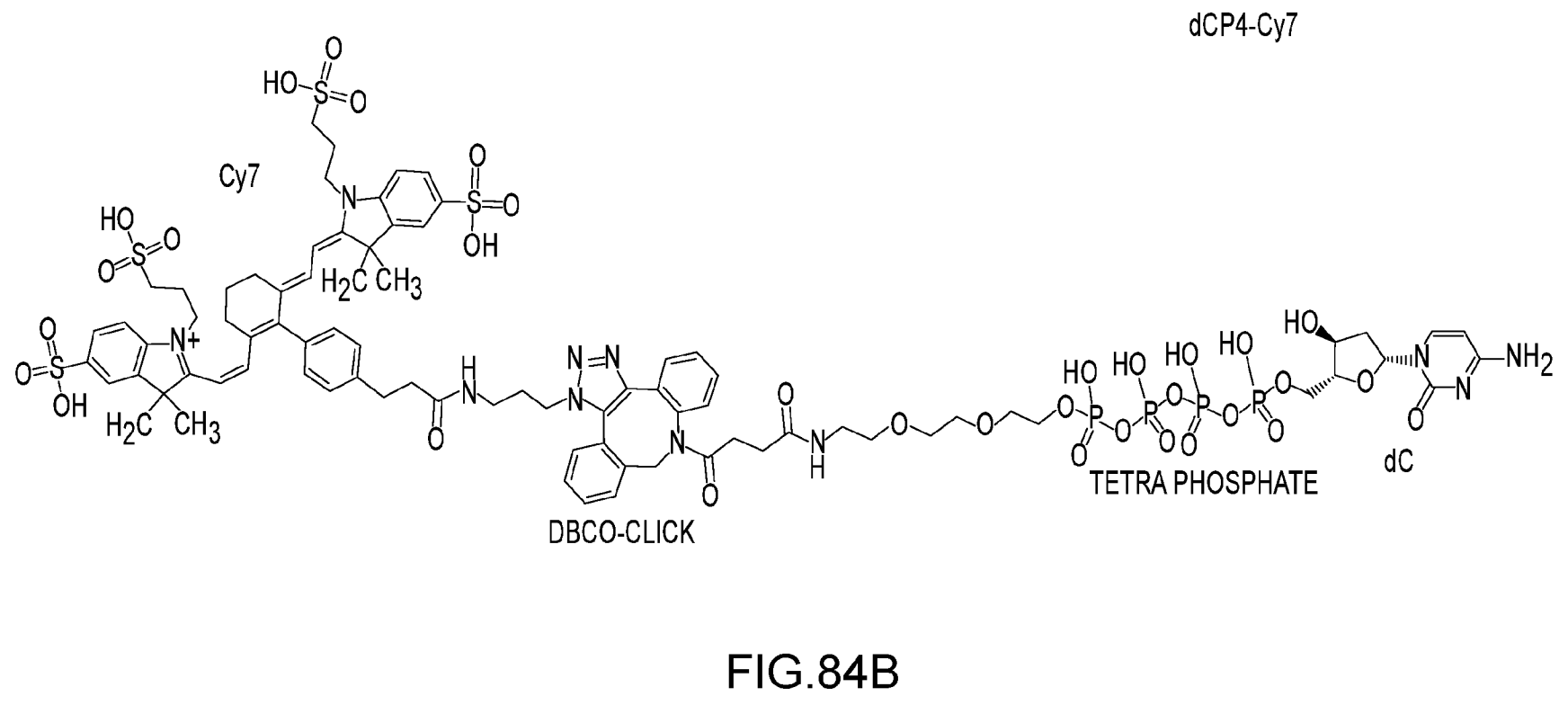

FIG. 84A illustrates a modified C nucleotide used in EXAMPLE 9 (as a mixture with dCP4-Cy7 depicted in FIG. 84B) in order to enhance signals from the polymerase incorporations;

FIG. 84B illustrates a modified C nucleotide used in EXAMPLE 9 (as a mixture with dCP4-lactose depicted in FIG. 84A) in order to enhance signals from the polymerase incorporations;

FIG. 85A depicts data from s Sequence Sensing Experiment with the alpha-helix peptide bridge. The plot is Current-vs-Voltage traces for the electrodes on a test chip that has been incubated with the peptide bridge molecule for 1 hour in PBS buffer, at 1 μM peptide concentration, in order to attach bridge to gold contacts. The highest current trace, which achieves a 3 nano-amp current at 2 volts applied source-drain, indicates an electrode with a bridge molecule in place;

FIG. 85B depicts additional data from s Sequence Sensing Experiment with the alpha-helix peptide bridge. The plot is Current-vs-Time trace showing the signature of the subsequent neutravidin binding to the bridge, at time of approximately 10 seconds to 50 seconds, when bridged sensor is exposed to a neutravidin solution with applied source-drain voltage of 2 volts;

FIG. 85C depicts additional data from s Sequence Sensing Experiment with the alpha-helix peptide bridge. The plot is Current-vs-Time trace showing the signature of the polymerase-maleimide-biotin binding the neutravidin-bridge complex, at the time of 10-20 seconds, when the latter is exposed to a solution of the former; and FIG. 85D depicts additional data from s Sequence Sensing Experiment with the alpha-helix peptide bridge. The plot sets forth the resulting sequencing signals when the assembled sensor is provided with solution containing a template DNA, with sequence having a series of GT repeats: (10×GT) TTT (10×GT) AAA (10× GT) CCC (10×GT). Figure is annotated with one possible interpretation of these signals, where major spikes corresponding to the GT repeat tracts of the template, and overall three different template DNA molecules engage with the sensor during the 45 seconds shown.

DETAILED DESCRIPTION

The detailed description of exemplary embodiments herein makes reference to the accompanying drawings, which show exemplary embodiments by way of illustration and their best mode. While these exemplary embodiments are described in sufficient detail to enable those skilled in the art to practice the invention, it should be understood that other embodiments may be realized and that logical, chemical, and mechanical changes may be made without departing from the spirit and scope of the inventions. Thus, the detailed description herein is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

In various embodiments, a single molecule biosensor device can comprise a first electrode and a second electrode. The first electrode and the second electrode are separated by a sensor gap defined by the electrodes and/or contacts attached to the electrodes. The first and second electrodes can be coupled by a bridge molecule spanning the sensor gap. The bridge molecule can comprise a biopolymer, such as nucleic acid or amino acid polymers. The bridge may also comprise a chemically synthesized molecule, which may include a synthetic organic molecule, a polymer comprising synthetic analogs of biopolymer monomers, or other wholly synthetic monomers not derived from a biological molecule. The differences between a "biopolymer" and a "chemically synthesized molecule" is not meant to be so strictly literal as to exclude the possibility for synthetic transformations that modify an otherwise natural biopolymer into a useful bridge molecule, such as, for example, synthetically modifying the 3' and 5' ends of an otherwise naturally occurring polynucleic acid sequence for subsequent binding and bridging. A bridge molecule, whether comprised of a biopolymer or a synthetic molecule, may have a known, atomically precise molecular structure. The bridge molecule attachment to the electrodes may be mediated by a contact. A probe molecule or molecular complex can be coupled to the bridge molecule. The probe can be a biomolecule such as an enzyme configured to interact with a single target molecule. In various embodiments, a sensor device can comprise multiple single molecule biosensors arrayed in parallel. Such multi-sensor devices can be used to perform parallel detection, discrimination, and/or characterization or identification of multiple individual target molecules in a complex mixture of target and other molecules.

Figure 1:
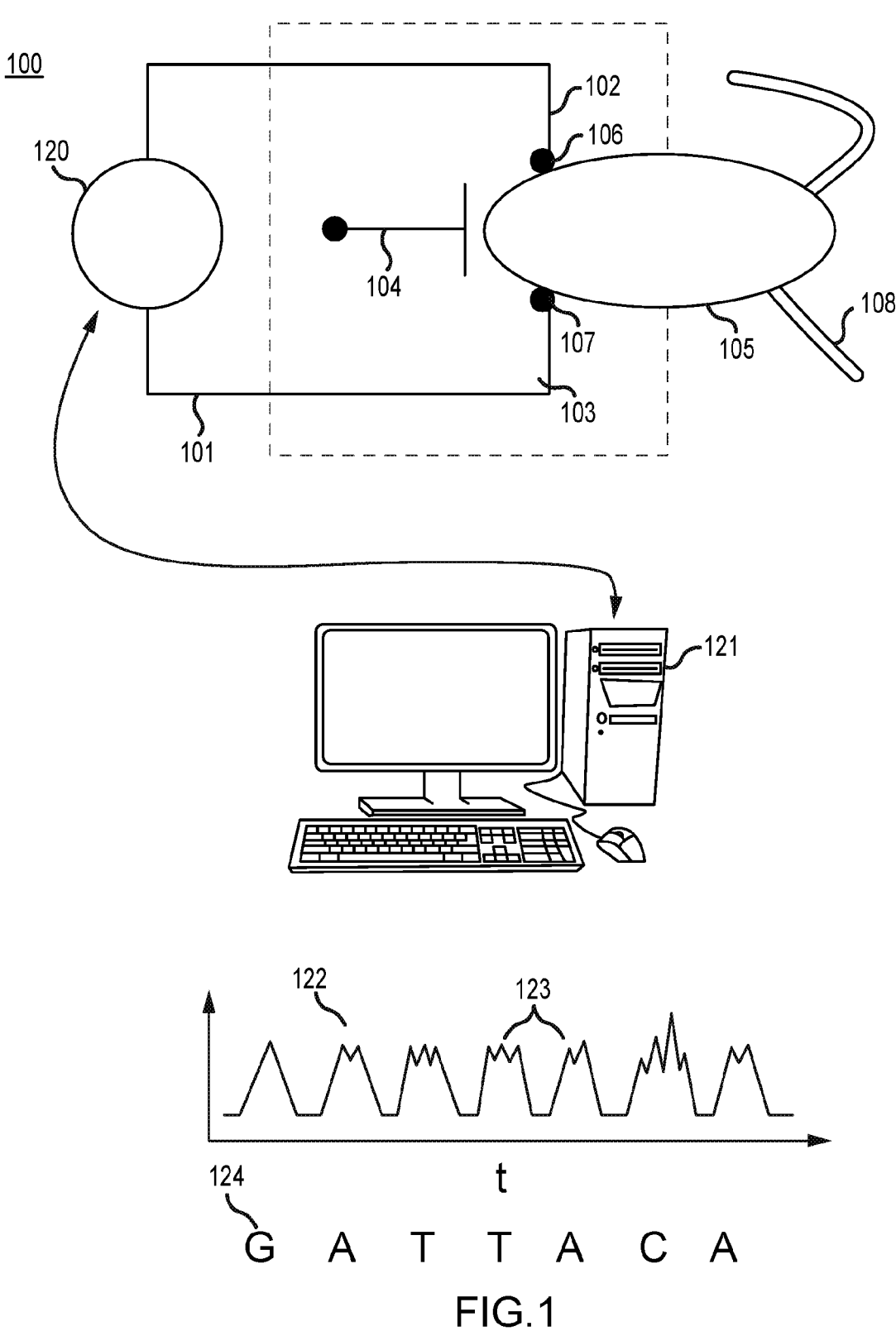
FIG. 1 illustrates a schematic representation of a sensor in accordance with various embodiments.

FIG. 1 illustrates a schematic representation of a sensor device 100 comprising a sensor 101 in accordance with various embodiments. Sensor 101 includes a first electrode 102 and a second electrode 103. Sensor 101 may also include a gate 104, as described in greater detail below. Sensor 101 can further comprise a sensor complex 105 functionally coupled to the first electrode 102 and the second electrode 103. In various embodiments, the sensor complex may be coupled to the electrodes via first contact 106 and second contact 107 attached to the respective electrodes. Sensor complex 105 can comprise multiple components, such as a bridge molecule and a probe molecule, as described in greater detail below. Sensor complex 105 can interact with the surrounding environment, thereby enabling sensor 101 to perform a sensing function. For example, as illustrated in FIG. 1, sensor complex 105 may interact with a target molecule 108 such as a DNA molecule, and the sensor device can be used to detect the presence of and/or properties of the target molecule.

In various embodiments, sensor device 100 and sensor 101 may be operatively connected to circuit 120 to detect a change of an electrical property of sensor 101. Circuit 120 is preferably an integrated circuit with micro-scale proximity to the sensor 101, but circuit 120 could also be embodied as an external electrical meter, such as a bench-top current meter. Sensor device 100 can comprise a plurality of sensors 101. Integrated circuit 120 can comprise a circuit architecture that may be fabricated using CMOS fabrication methods. Integrated circuit 120 can comprise an electronic measurement circuit for each sensor 101 that is fabricated within the same chip that provides support for the sensor. Expressed differently, a sensor device 100 can comprise a sensor 101 and an integrated circuit 120 in an integrated microcircuit. Integrated circuit 120 can further comprise readout circuitry and input/output features for connection to an external signal processing system 121.

In various embodiments, use of an integrated circuit 120 residing on a common semiconductor chip with sensor 101 can reduce sources of electronic noise in readings that can be produced by macroscopic, external circuit elements. For example, such a circuit may be a mixed signal CMOS sensor, comprising a small number of transistors, in the range of 1 to 200 depending on the performance requirements for sensitivity and readout. Such a circuit can function to measure current in a single sensor 101 in various embodiments. Further, a sensor device 100 can comprise an integrated circuit 120 comprising sensor/readout circuits for an array of sensors 101 so as to support the simultaneous operation of a large number of sensors in contact with the same sample.

In various embodiments, a sample contacted by a sensor 101 will comprise a liquid-phase sample. The solution comprising the sample may be extremely dilute and at low ionic strength to reduce the noise in electrical measurements performed using the sensor. The acquired signal will typically be the current flowing between electrodes 102 and 103 in the sensor, although it could be a related observable electronic parameter such as the voltage between electrodes, resistance/conductance between electrodes, or gate voltage.

In various embodiments, the configuration of sensor 101 and integrated circuit 120 in an integrated microchip format amenable to fabrication using modern CMOS fabrication methods can facilitate production of sensor devices with a highly compact architecture. In various embodiments, the integrated circuit for a sensor may be located within about 100 μm of the sensor gap, or within about 50 μm of the sensor gap, or within about 20 μm of the sensor gap, or within about 10 μm of the sensor gap, or within about 5 μm of the sensor gap, or within about 1 μm of the sensor gap. Moreover, in various embodiments, a sensor device can comprise a plurality of sensors, each sensor having an associated integrated circuit located within the parameters specified above.

Signal processing system 121 can be configured to provide electronic control of sensor device 100 and to receive, store, and analyze signal received from the sensor device and each sensor 101 therein. Signal processing system 121 can comprise a computer system with a processor and/or software configured to perform the electronic control functions, including control of the voltage and current applied to each sensor 101, and to perform the signal processing functions for signal received from each sensor 101.

For example and as illustrated in FIG. 1, a sensor device 100 comprising a sensor 101 may be used to perform a nucleic acid sequencing reaction. During operation of the device, a voltage may be applied between the first electrode and the second electrode of sensor 101, with interactions of the sensor with a target producing modulation of current flow through a biopolymer bridge molecule (see, e.g., 333, FIG. 3) that can be measured using integrated circuit 120 and signal processing system 121. Sensor 101 may produce a signal pattern 122 over time t with signal features 123 produced by the sensor in response to the sensor complex interaction with features of target molecule 108. Signal processing system 121 can receive and process the signal pattern and provide a sequence output 124 in response to the signal pattern, which in this context is the interpretation of the signal.

In various embodiments, a single molecule biosensor can take the form of a transistor, such as a field effect transistor (FET), with the attached bridge molecule and/or probe, and/or target molecule and/or solution-phase molecules in close proximity to these components, serving as a channel or conductive path in an electrical circuit. In such an embodiment, a sensor complex comprising a single probe molecule may be configured to bind or interact with a single target molecule as explained in greater detail below, thereby providing the biosensor with single molecule sensitivity. Such a transistor embodiment may include a two or three terminal transistor, or potentially more terminals, such as in the case of multi-gate devices.

Figure 2A:
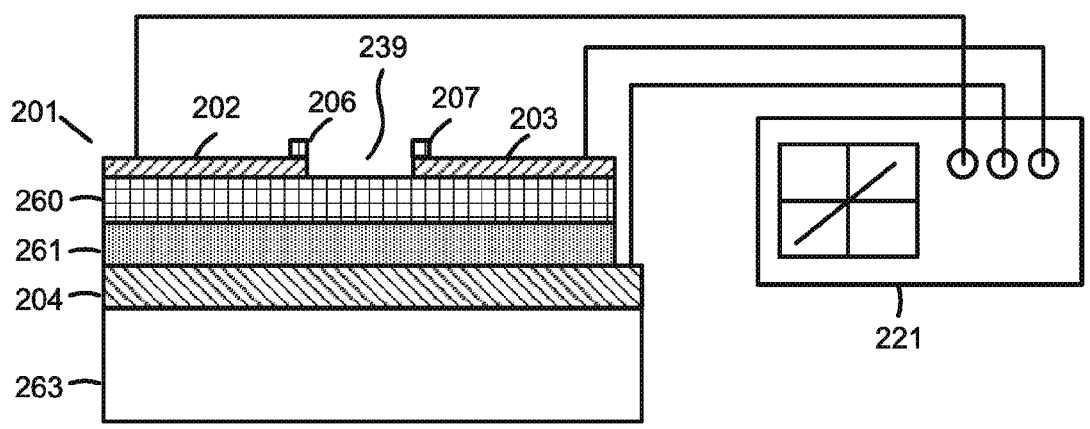
FIGS. 2A and 2B illustrate views of a sensor device in accordance with various embodiments.
Figure 2B:
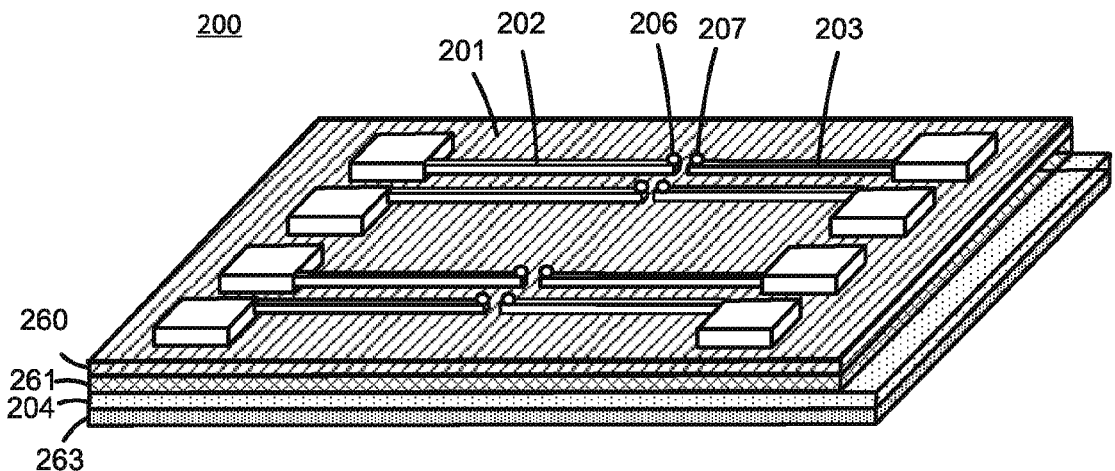

FIGS. 2A and 2B illustrate views of a sensor device 200 in accordance with various embodiments. Sensor complexes are not shown in the illustrated views of sensor device 200. Sensor device 200 comprises a plurality of sensors 201, with each sensor comprising a first electrode 202 and a second electrode 203. Each sensor can further comprise a sensor gap 239. In the illustrated embodiment, each sensor comprises a first contact 206 attached to the first electrode and a second contact 207 attached to the second electrode. In various embodiments, the electrodes can be disposed on a semiconductor substrate surface. For example, sensor device 200 can comprise a silicon nitride layer 260 overlying a silicon dioxide layer 261. Sensor device 200 can further comprise buried gate 204 underlying the semiconductor substrate layer(s) on which the electrodes are disposed. The various components described above can be fabricated on a support such as a silicon chip 263. As illustrated schematically in FIG. 2A, each of the first electrode 201, the second electrode 202, and the gate 204 may be connected to a signal processing system 221, which may be an external meter, as depicted in the illustration, but which could alternatively be integrated circuitry (details not shown).

Figure 3:
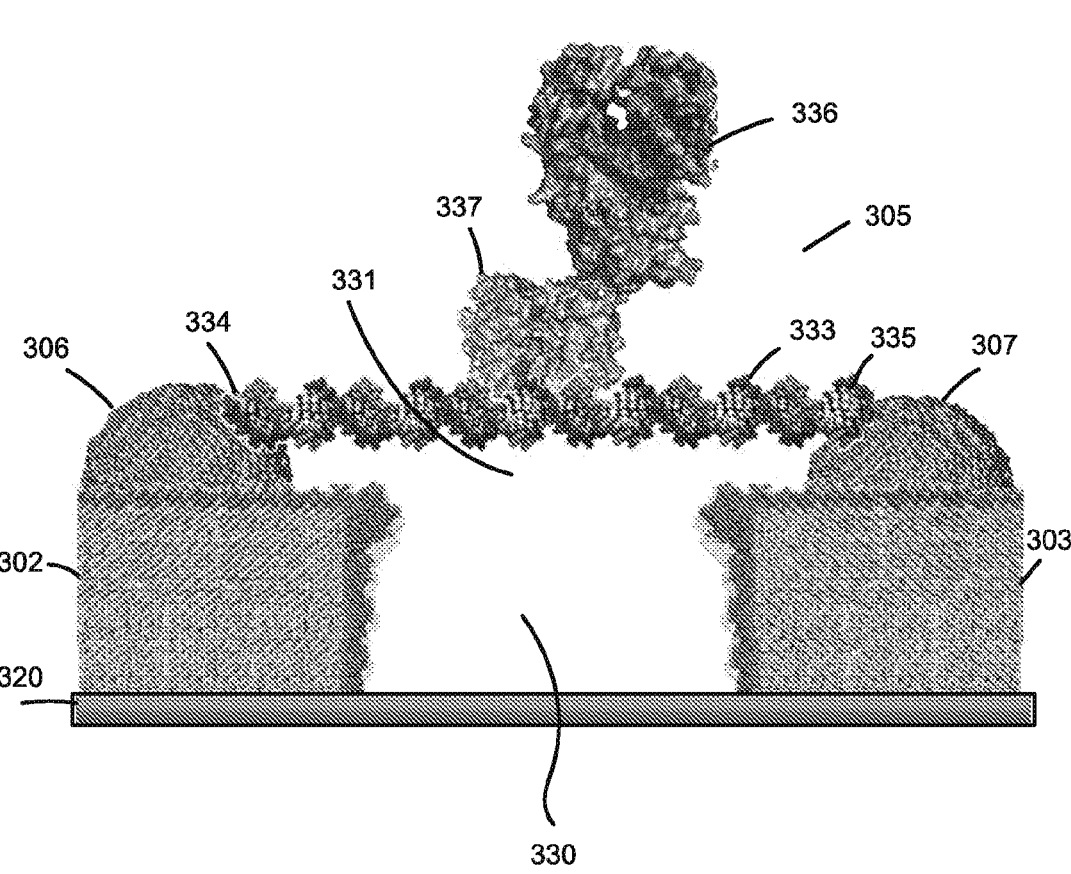
FIG. 3 illustrates a profile view of a portion of a sensor in accordance with various embodiments.

With reference now to FIG. 3, a profile view of a portion of a sensor 301 and sensor complex 305 are illustrated in greater detail. Sensor 301 comprises first electrode 302 and second electrode 303. First electrode 302 and second electrode 303 may be disposed on a substrate 320. In various embodiments, sensor 301 can further comprise a first contact 306 and a second contact 307 operatively coupled to first electrode 302 and second electrode 303, respectively. However, contacts are not strictly required, and a sensor in accordance with the present disclosure need not comprise a first and second contact. The ends of first electrode 302 and second electrode 303 define an electrode gap 330. Likewise, for a sensor comprising contacts such as sensor 301, the distance between first contact 306 and second contact 307 defines a contact gap 331. The actual dimension of a contact gap for any given first contact and second contact may vary dependent on the configuration of the contact and the point of the contact used for reference. For example, for the hemispherical first contact 306 and second contact 307 illustrated in FIG. 3, the dimension of contact gap 331 may be measured between the nearest points of the contact or from center to center. In various embodiments, one of the electrode gap and the contact gap, or the gap defined collectively or by various combinations of the electrodes and/or contacts, may be referred to as a sensor gap.

With continued reference to FIG. 3, sensor 301 further comprises sensor complex 305. In various embodiments, a sensor complex 305 can comprise a bridge molecule 333 and a probe 334. Probe 334 can be coupled to bridge molecule 333 via a linker 337, which here is shown as a streptavidin-biotin complex, with the biotin covalently incorporated into a nucleotide of the DNA bridge 333, and the streptavidin chemically, covalently cross-linked to the polymerase 334. Each of the various components of sensor complex 305 are described in greater detail below.

In various embodiments, a bridge molecule 333 can comprise a chemically synthesized bridge molecule or a biopolymer bridge molecule. A chemically synthesized bridge molecule or a biopolymer bridge molecule may be configured to span a sensor gap both structurally and functionally. For example, a chemically synthesized molecule or biopolymer molecule may be configured through selection and use of atomically precise molecular subunits (e.g., monomeric units for incorporation into a polymeric bridge molecule) that provide for construction of a bridge molecule with known or predictable structural parameters, incorporation of features that facilitate self-assembly to contact points and self-assembly of a probe molecule to a bridge molecule, as well as suitable electrochemical properties for electrical connection of electrodes.

Figure 21:
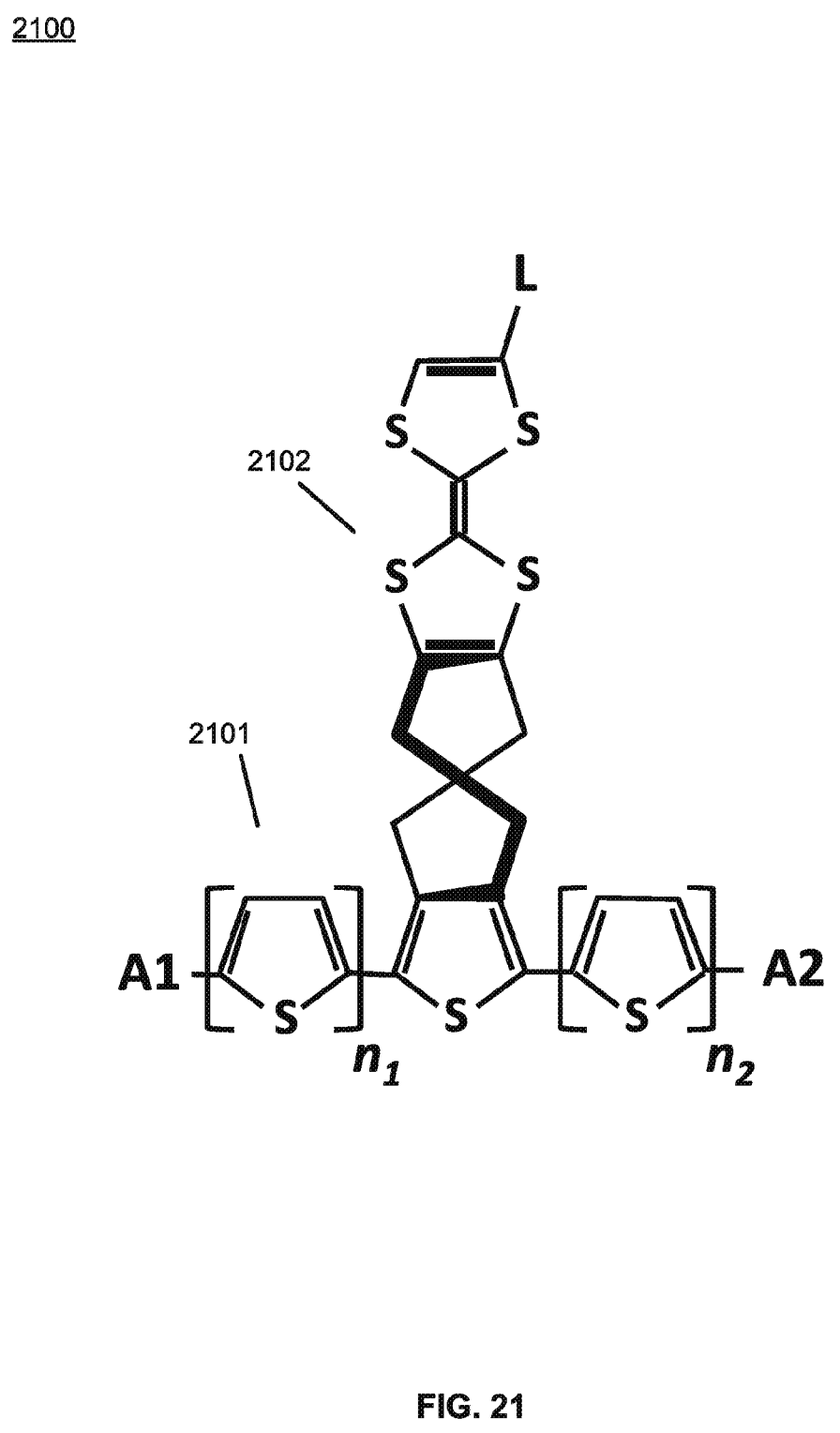

A chemically synthesized bridge molecule is a molecule that can be assembled by a person of skill in the art of synthetic organic chemistry. For example, a chemically synthesized molecule can comprise a polypyrrole, polyaniline, or polythiophene backbone. With reference briefly to FIG. 21, an example of a general structure of a polythiophene-based chemically synthesized bridge molecule 2100 is illustrated. Chemically synthesized bridge molecule 2100 can comprise a chain of thiophene rings 2101 forming the backbone of the bridge molecule, with $n_1$ and $n_2$ thiophene rings on either side of a probe support moiety 2102 that may be configured at a specific location in the bridge molecule 2100. Since each thiophene ring 2101 is approximately 0.3 nm wide, a chemically synthesized bridge molecule comprising about 10 to about 100 rings could be constructed to span an about 3 nm to an about 30 nm gap. The termini (e.g., A1 and A2) of a chemically synthesized bridge molecule can comprise thiol or amine groups, or other groups configured to bind to electrode or contact materials. A chemically synthesized bridge molecule can also be configured with a linker (e.g., L) suitable to provide attachment of a probe molecule. Any other chemically synthesized bridge molecule configuration, comprised of any suitable backbone moiety now known to, or that may be hereinafter devised by, a person of ordinary skill in the art, may be used in accordance with various embodiments of the present disclosure.

As used herein, the term "biopolymer" can include any molecule comprising at least one monomeric unit that can be produced by a living organism, although the actual monomeric unit comprising a biopolymer or the polymer itself need not be produced by an organism and can be synthesized in vitro. Examples of biopolymers include polynucleotides, polypeptides, and polysaccharides, including well known forms of these such as DNA, RNA and proteins. Bridge molecules that comprise a biopolymer can include multi-chain polymeric proteins in a simple "coiled-coil" configuration, as occurs in collagen proteins, or a more complex folding of heavy and light chain polymeric proteins, such as in immunoglobin molecules (e.g. IgG). Such complexes that comprise biopolymers also include common nucleic acid duplex helices, such as a DNA double helix, which is two DNA single strand molecules bound into a helical double strand by hydrogen bonding, PNA-PNA duplexes, as well as DNA-RNA, DNA-PNA, and DNA-LNA hybrid duplexes. A biopolymer molecule need not be naturally occurring or produced by an organism to be classified as a biopolymer. Instead, for purposes of the present disclosure, the term "biopolymer" can include molecules that are synthesized enzymatically as well as non-enzymatically and can likewise include molecules comprising synthetic analogues of naturally-occurring monomeric units. For example, biopolymers can comprise peptide nucleic acids (PNAs) and locked nucleic acids (LNAs), synthetic analogues of DNA and RNA that have enhanced stability properties. In addition, a biopolymer can comprise any of a variety of modifications that may be added to a molecule. The use of biopolymer bridge molecules can provide various benefits, including synthesis of precisely controlled structures having suitable size and chemistry for sensor function, they may be naturally compatible with the target molecules for the sensor (e.g., compatible with the same liquid buffer medium), and the biotech industry has developed extensive capabilities to design, engineer and synthesize such molecules, and to manufacture them economically and with high quality control.

A bridge molecule can be configured to span a sensor gap and be coupled to an electrode and/or a contact on either side of the sensor gap in a manner suitable to provide electronic communication between the bridge molecule and the electrode and/or contact.

In various embodiments, a bridge molecule can comprise a linear biopolymer such as a double-stranded DNA helix or an α-helical polypeptide. As illustrated in FIG. 3, bridge molecule 333 comprises a linear biopolymer double-stranded DNA bridge molecule with a first end 334 coupled to first contact 306 and a second end 335 coupled to second contact 307.

In various embodiments, a rigid bridge structure may provide advantages in terms of taking on a well-defined configuration during and after assembly of the sensor complex. Without wishing to be bound by theory, a linear biopolymer can comprise a semi-flexible polymer that may be described by its bending rigidity. On a short length scale, a linear biopolymer may behave as a rigid polymer, requiring a strong force to bend the polymer, while on a longer scale, the linear biopolymer may be bent or curved more easily. The characteristic bending length measure within which a linear biopolymer essentially behaves as a rigid molecule in a certain set of environmental conditions is referred to as the persistence length. The persistence length can depend on the environmental conditions in which a bending force is exerted on the polymer, with variables such as the temperature and ionic conditions of the surrounding environment affecting the persistence length. The persistence length of a linear biopolymer such as double-stranded DNA may be estimated based on theoretical modeling or it may be measured empirically for a set of environmental conditions corresponding to a predetermined experimental condition in which a device in accordance with various embodiments may be used. For example, the persistence length of double-stranded DNA has been calculated at about 30 nm to about 80 nm, and the persistence length of an α-helical peptide calculated at about 80 nm to about 100 nm in various conditions that may approximate the conditions in which a sensor in accordance with various embodiments of the present disclosure may be used. Thus, in various embodiments, a double-stranded DNA molecule or an α-helical peptide having an end-to-end length, as measured along its major axis, of less than the respective persistence length parameters described above may behave as an essentially rigid polymer, thereby providing certain advantages or benefits with respect to device assembly and performance.

In various embodiments, use of linear biopolymers comprised of DNA or amino acids permits the straightforward construction of nano-scale sensor components having a predetermined length based on the monomeric composition (i.e., the primary structure) of the biopolymer. Without wishing to be bound by theory, use of a linear biopolymer with an end-to-end length of less than the persistence length may enhance the efficiency of a self-assembly step during construction of a biomolecular sensing device in accordance with various embodiments. Use of such linear biopolymers provides an ability to maintain the specifications of a biopolymer bridge molecule within parameters in which their micromechanical properties are more predictable than for longer linear biopolymers that may bend or fold, thereby reducing the influence of undesirable stochastic effects, for example, during bridge molecule synthesis, handling, self-assembly, or sensor operation. Moreover, the use of linear biopolymers permits precise specification of the bridge molecule length to the sensor gap (i.e., the electrode gap and/or contact gap dimension and architecture), providing a further ability to readily test the performance of theoretical structural models and device improvements and to make incremental, well-controlled, and empirically-testable modifications. In various embodiments, a linear biopolymer bridge molecule may be configured to provide a reduced rate of miscoupling of both the first self-assembling anchor at the first and the second self-assembling anchor and the second end to one of the first contact and the second contact due to the essentially rigid nature of the linear biopolymer bridge molecule at the scale used in the sensor device (e.g., an end-to-end length of between about 5 nm and about 30 nm). Similarly, a biopolymer bridge molecule may be configured to provide a reduced rate of single-end coupling. This may result when the substantially rigid bridge molecule, once coupled at a first contact, restricts the second end to spend more time in the proximity of the desired second contact point, owing to the spacing of contacts, thereby increasing the rate of the desired second coupling reaction.

As mentioned above, a biopolymer bridge molecule can comprise a double-stranded DNA molecule. In various embodiments, a double-stranded DNA can comprise a thiol-modified oligo comprising a thiol-modified nucleotide or base. A thiol-modified nucleotide can comprise a self-assembling anchor configured to bind to a gold nanobead or similar surface contact. In various embodiments, a self-assembling anchor can comprise a 5'-thiol modified nucleotide, which can be located at or near the 5' terminus of an oligonucleotide. A double-stranded DNA molecule can comprise a complementary pair of oligonucleotides, with each oligonucleotide comprising a 5'-thiol modified nucleotide, such that the assembled double-stranded DNA comprises a self-assembling anchor located at both termini of a double-stranded DNA molecule. For example, in various embodiments, a double-stranded DNA molecule can comprises oligonucleotides with the following sequences:

5'-/5ThioMC6-D/TGC GTA CGT ATG TCA TGA ATG GCG CAG ACT GAT GTC CTA TGA CGT CGC TAC TGC AGT ACT-3' (SEQ ID NO: 1), and 5'-/5ThioMC6-D/AGT ACT GCA GTA GCG ACG TCA TAG GAC A/iBiodT/C AGT CTG CGC CAT TCA TGA CAT ACG TAC GCA-3' (SEQ ID NO: 2), with the "/5ThioMC6-D/" denoting a 5'-thiol modifier and "/iBiodT/" denoting an internal biotin-modified deoxythymidine nucleotide (Integrated DNA Technologies, Inc., Coralville, IA). When annealed to one another, these oligos provide a double-stranded DNA molecule with a 5'-thiol modified nucleotide located at each end of the molecule as the first and second self-assembling anchors.

A double-stranded DNA molecule bridge can also further comprise a biotin linker component to facilitate linking a probe molecule to the bridge with a complementary avidin-type linker component. In various embodiments and as illustrated in the reverse oligonucleotide sequence described above, a biotin-modified oligonucleotide can be incorporated into one of the oligos of a double-stranded DNA molecule bridge. In various embodiments, the biotin-modified oligo is an internal modification, such as via a modified thymidine residue (biotin-dT). A variety of biotin modification configurations may be used, including attachment to thymidine via a C6 spacer, attachment via a triethyleneglycol spacer, attachment via a photocleavable spacer arm, dual biotin modifications, desthiobiotin modifications, and biotin azide modifications. Other modifications that are now known to a person of skill in the art or may be hereinafter devised and may be made to an oligonucleotide to facilitate linkage to a probe molecule are within the scope of the present disclosure. Similarly, other common small molecules with a protein binding partner, such digoxigenin, can play a similar role to that of biotin for such purposes of conjugation to probe molecules at precisely atomically specified points in the bridge molecule.

In various embodiments, a peptide biopolymer bridge molecule can comprise various configurations and/or features suitable to provide various desirable bridge molecule structure and performance characteristics, including electrode or contact binding characteristics, structural characteristics, electrical performance characteristics, and the like. For example, a peptide biopolymer bridge can comprise an L-cysteine residue at one or both of the amino terminus and the carboxyl terminus to serve as a self-assembling anchor via thiol-metal binding to specific metal contacts that engage in strong thiol binding, such as gold, palladium or platinum. In other embodiments, a biopolymer bridge molecule can comprise a peptide with the known capacity to selectively and strongly bind gold contacts for purposes of self-assembly and electro-mechanical connection into the circuit. Specific such peptides include those with the following amino acid sequences: MHGKTQATSGTIQS (SEQ ID NO: 3), VSGSSPDS (SEQ ID NO: 4), and LKAHLPPSRLPS (SEQ ID NO: 5). Other peptides selected for such properties can similarly bind other specific metal or material contacts. For example, VPSSGPQDTRTT (SEQ ID NO: 6) is a known aluminum binding peptide, and MSPHPHPRHHHT (SEQ ID NO: 7) is a known silicon dioxide binding peptide. In various other embodiments, a biopolymer bridge molecule can comprise a peptide sequence that includes repetitions of an amino acid motif or motifs selected from one of the following amino acid sequence motifs known to favor the formation of stable alpha-helix conformations, providing for a linear, rigid, conductive bridge: EAAAR (SEQ ID NO: 8), EAAAK (SEQ ID NO: 9), EEEERRRR (EAN NO: 10), and EEEEKKKK (SEQ ID NO: 11). Such a peptide biopolymer bridge molecule can also comprise a modified amino acid consisting of a lysine residue with a covalently attached biotin to provide a conjugation point at a precisely atomically defined location for avidin-based conjugation to probe molecule complexes. A modified lysine can replace a standard lysine or arginine residue in such a peptide sequence motif, to otherwise maintain or minimally alter the properties of the alpha-helix.

Figure 4:
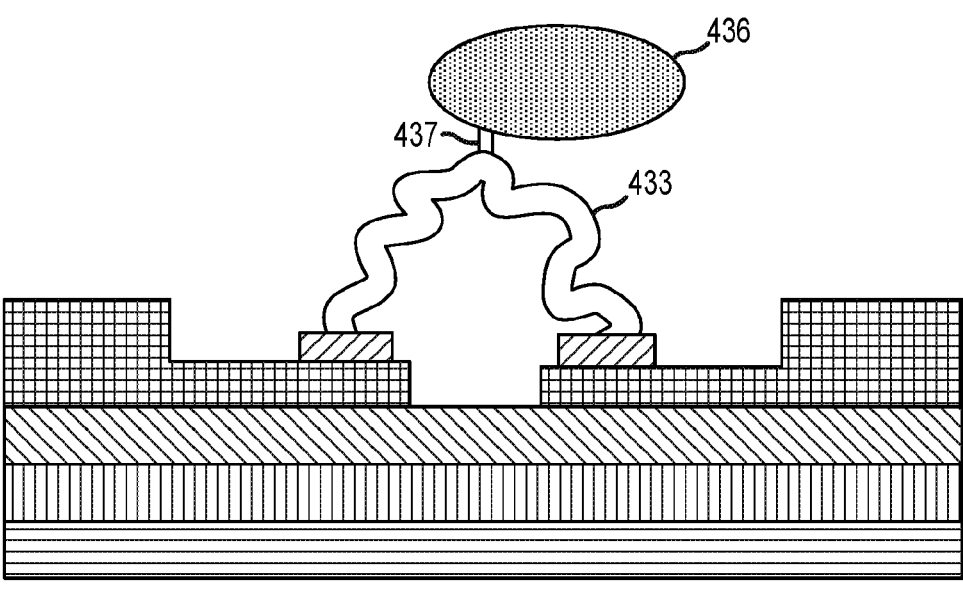
FIG. 4 illustrates a sensor comprising a biopolymer bridge molecule in accordance with various embodiments.
Figure 5:
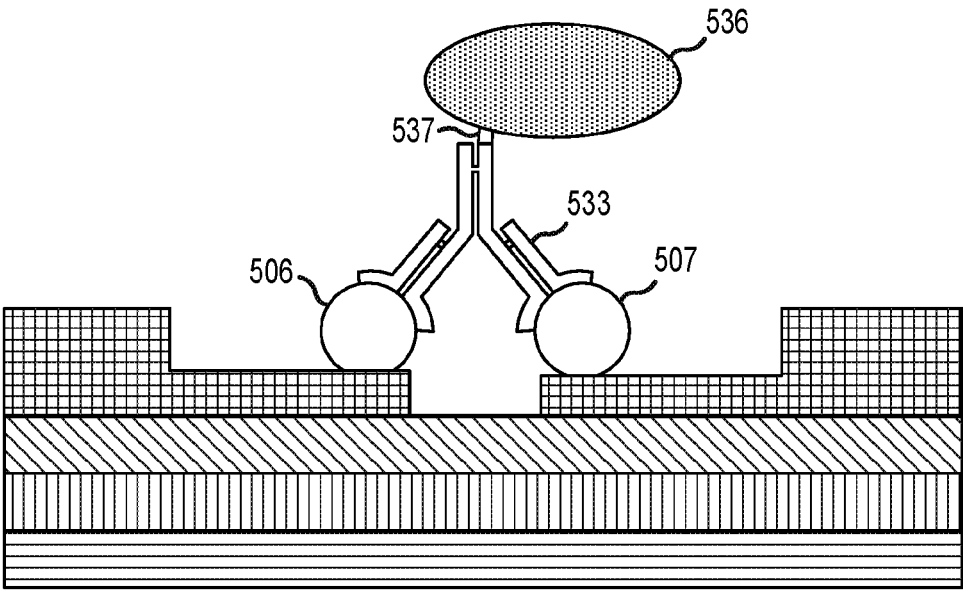
FIG. 5 illustrates a sensor comprising a biopolymer bridge molecule in accordance with various embodiments.

In various embodiments, a biopolymer bridge molecule can have other configurations. For example and as illustrated in FIG. 4, a biopolymer bridge molecule 433 can comprise a linear biomolecule that is flexed, folded, or comprises a certain degree of secondary structure. In various embodiments, a biopolymer bridge molecule can further comprise molecules having tertiary and/or quaternary structure, including globular proteins, antibodies, and multi-subunit protein complexes. An example is illustrated in FIG. 5, in which the biopolymer bridge molecule 533 comprises an immunoglobin G protein (IgG). In the illustrated embodiment, the electrical contacts (506, 507) are gold nano-particles, and the IgG has been established with a specific affinity to bind such particles.

Similarly to sensor 301, the configurations illustrated in FIG. 4 and FIG. 5 each comprise a probe (436 and 536, respectively) coupled to the biopolymer bridge molecules via linkers (437 and 537, respectively). The illustrated embodiments are intended to exemplify the range of possible biopolymer bridge molecule configurations that may be couple to electrodes or contacts comprising different materials and configurations, including different metallic or non-metallic conducting or semiconducting contacts in different structural configurations. In various embodiments, electrodes or contacts may further be coated, treated, or derivatized to facilitate bridge assembly and/or attachment using products such as InnovaCoat GOLD nanoparticles (Innova Biosciences).

A probe in accordance with various embodiments can comprise any suitable molecule or multicomponent molecular complex. A probe may be selected based on the molecule to be detected by the sensor or the biochemical reaction to be monitored. Various examples of probes include peptides, proteins, enzymes, nucleic acids, ribozymes, catalytic DNAs, and the like. In various embodiments, an enzyme can comprise a lysozyme, a kinase, or a polymerase. Any molecule or complex that exhibits a specific change in physical, chemical, or electronic configuration in response to binding or processing of a substrate or target molecule may be used as a probe in accordance with various embodiments of the present disclosure.

In various embodiments, a probe can comprise an enzyme such as polymerase or a reverse transcriptase suitable for interacting with individual DNA or RNA target molecules. Enzymes that catalyze the template-dependent incorporation of nucleotide bases into a growing oligonucleotide strand undergo conformational changes in response to sequentially encountering template strand nucleic acid bases and/or incorporating template-specified natural or analog bases (i.e., an incorporation event). Such conformational changes can modulate electrical current through a bridge molecule to which the probe is coupled, thereby provide a sequence-specific signal pattern in a manner that is dependent on the template molecule. As described above, the signal pattern may be detected by a signal processing system and translated to a sequence data output. Moreover, the presence of a modified nucleotide in a target nucleic acid sequence may produce unique conformational changes and corresponding signal features in a signal pattern that can enable a sensor device and signal processing system to directly determine, for example, methylation of bases in a target sequence on a base-by-base basis. Such a label-free, direct sequencing method may permit discrimination of a nucleotide-specific incorporation event in a sequencing reaction using nucleotide base mix comprising a mixture of natural and/or analog bases corresponding to all four bases of DNA, although a sequencing process comprising sequentially providing individual natural or analog bases in a serial and/or cyclic fashion may also be used. The use of a reverse transcriptase as the probe molecule can similarly enable the direct sequencing of RNA molecules without the need for an intermediate cDNA conversion step.

In various embodiments and as described briefly above, a probe can be attached to the bridge molecule via a self-assembling linker. A self-assembling linker can comprise any of a number of structures suitable to attach a first biomolecule to a second biomolecule. In various embodiments, a self-assembling linker can comprise a first linker component and a second linker component that is complementary to the first linker component. The first linker component and the second linker component may be joined by self-assembly to form an assembled linker based on an affinity of the first linker component for the second linker component. A first linker component can be associated, for example, with a bridge molecule, and a second linker component can be associated with a probe. A linker component associated with a bridge molecule can be engineered to a specific site in the bridge molecule, such that self-assembly of the probe to the bridge produces coupling of the probe to the bridge molecule at a predetermined location on the bridge molecule. A linker component selected for association with the probe may be configured to minimize interference between the probe and a target, both with respect to the size of the linker component and the position at which it is conjugated to the probe. In this manner, joining the complementary first and second linker components can provide functional attachment of the probe to the bridge molecule. A self-assembling linker can comprise a biotin-avidin coupling mechanism, with an avidin (or other avidin-like) protein first linker component and a biotin small molecule second linker component, which components form a strong non-covalent bond with one another. Other avidin-like proteins include streptavidin, rhizavidin, bradavidin, NeutrAvidin, other various amino-acid modified forms of avidin or streptavidin, as well as divalent or monomeric derivatives of such avidins which retain biotin-binding functionality. In various embodiments, for example, a biotin may be conjugated to the bridge molecule and a streptavidin conjugated to the probe molecule. A self-assembling linker can also comprise the well-known "click-chemistry" mechanisms for bioconjugation. A self-assembling linker can also comprise an antigen-antibody coupling, for example with an antigen present on the bridge molecule coupling to an antibody conjugated to the probe molecule. A self-assembling linker can also comprise, for example, a SpyCatcher peptide first linker component and a SpyTag peptide second linker component, with the two components binding to form an irreversible covalent bond. Any other self-assembling linker system in any configuration now known to, or that may be hereinafter devised by, a person of ordinary skill in the art may be used to couple a probe to a bridge molecule.

In various embodiments, a sensor need not comprise a probe molecule distinct from the bridge molecule. Instead, the bridge molecule itself may be configured to be acted on by a target molecule. For example, a bridge can comprise a protein binding site, such as a kinase binding site, and be used to detect the presence and/or activity of the corresponding protein in a sample based on binding of the target protein to the bridge and/or modification of the bridge by the target protein.

Figure 6A:
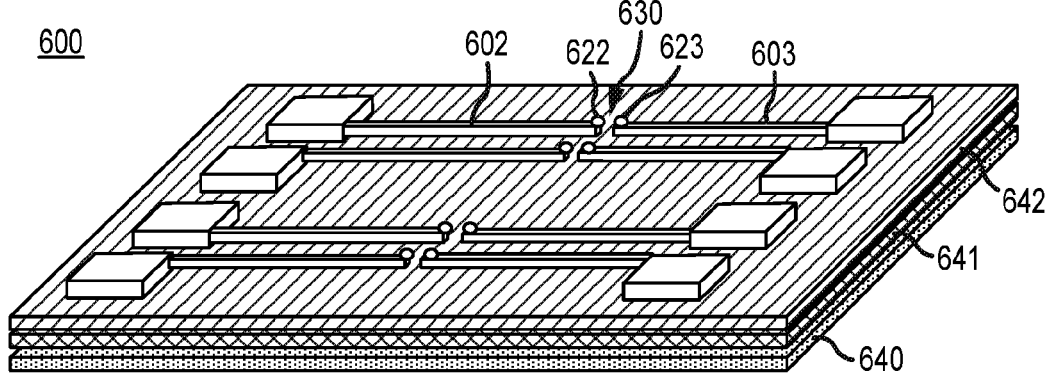
FIGS. 6A and 6B illustrate views of a sensor device in accordance with various embodiments.
Figure 6B:
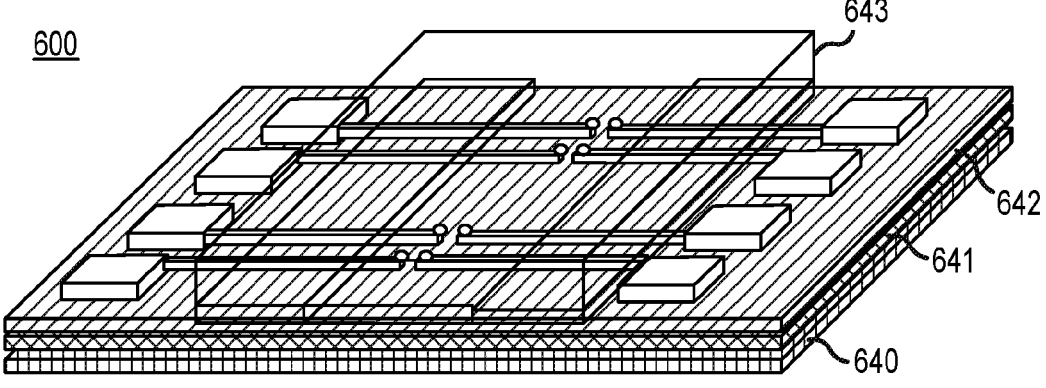

With reference now to FIGS. 6A and 6B, perspective views of a partially-fabricated sensor device 600 with and without a sensor enclosure are illustrated. Sensor device 600 is a three terminal sensor device comprising a buried gate 640. Device 600 illustrated in FIG. 6A comprises various features of a sensor device that may be produced using CMOS fabrication techniques, such as gate 640 underlying substrate 641 and oxide 642, along with first electrodes 602 and second electrodes 603 separated by electrode gaps 630, and each electrode having an attached contact 606/607. Attachment of the various sensor complex components described above, including a bridge molecule and probe, may be performed in downstream self-assembly steps. In various embodiments and as illustrated in FIG. 6B, sensor device 600 may first be configured with an enclosure 643 configured to enclose or form a flow cell around sensor gaps 630 prior to completing assembly of the sensors by contacting the sensor with a solution comprising the bridge and/or probe molecules. Likewise, enclosure 643 may also be used to perform assays such as sequencing reactions. Enclosure 643 can be separately formed and attached to a structure including device 600.

Biomolecule Detection and Nucleic Acid Base Discrimination

In various embodiments, a method for detecting the dynamics and kinetics of a single molecule sensing device such as device 100 (FIG. 1) is provided. Any method for measuring changes in electrical conductance of a sensor 101 comprising a bridge molecule can be used to monitor a sensor device described herein. In various embodiments, a voltage of less than about 10 V can be applied to a sensor comprising a biomolecular bridge molecule, and in various embodiments described in greater detail below, a voltage of about 0.5 V is applied. The current flowing through the sensor can be measured as a function of time using integrated circuit 120. Target binding and/or processing events by a probe (i.e., enzyme activity in the case of an enzymatic probe) in sensor complex 105 can produce changes to the conductivity of the sensor 101, modulating the measured current to produce a signal pattern 122 over time t comprising signal features 123. Such events, and the associated conformational changes, including structural, chemical, and electronic changes (i.e., charge distributions in an enzyme, substrates, and surrounding solution) can comprise kinetic features of target binding and processing, with the various events producing current fluctuations comprising signal features 123 that can be measured, recorded, discriminated, analyzed or stored using signal processing techniques which are known in the art. The signal features can comprise any of a range of possible forms, including wavelets with shapes that are triangular, sinusoidal, or have any number of Fourier components. For example, a polymerase used as a probe in a sensor can provide a polymerase kinetic signature for each discrete interaction with a template base (i.e., a target molecule feature) and/or a template-dependent nucleotide incorporation (i.e., the polymerase kinetic signature is template base-dependent), with a nucleic acid template target comprising a sequence of target molecule features at discrete positions in the target molecule (i.e., first, second, and nth target molecule features at first, second, and nth target molecule positions), each target molecule feature producing a corresponding signal feature during detection by a sensor in accordance with the present disclosure. The n target molecule features can correspond to n consecutive bases of a single stranded DNA template molecule (i.e., the target) which is processed by the polymerase enzyme to sequentially incorporate complementary nucleotides at these n target molecule features. The amplitudes, durations, and shapes of a signal pattern comprising a series of signal features can encode a target-specific sensor response that can be analyzed using signal processing system 121 to compare the signal pattern to a signal interpretation map to determine the identity of the target. Increasing the time resolution of signal detection and analysis may provide an ability to further resolve kinetic variability, transitions, and intermediate states of a probe-target interaction.

Since the fidelity of nucleotide incorporation is paramount to accurate nucleic acid sequencing, in various embodiments, a method of sequencing may rely on analog bases that increase the conformational changes of template-based nucleotide incorporation, thereby producing clearer signals, and/or otherwise provide an enhanced ability to discriminate incorporation of the analog base, thereby providing for enhanced sequencing accuracy. Non-labeled analog bases that can be used to enhance the kinetic or dynamic discrimination of template-dependent nucleotide incorporation are well known and can include modifications of the purine and pyrimidine bases and the deoxyribose or ribose and phosphate portions of a nucleotide. In particular, this can include adding additional groups to the gamma-phosphate of the nucleotide, which accepts large and diverse molecular modifications that are cleaved off during incorporation and therefore do not permanently impact the growing strand and its interaction with the polymerase.

In various embodiments, a method can provide detection of unmodified and modified nucleotide bases in a nucleic acid template sequence. For example, a method may be suitable to distinguish a modified template nucleotide, including $N^6$-methyladenosine, $N^4$-methylcytosine, 5-methylcytosine, 5-hydroxymethylcytosine, 5-formylcytosine, and 5-carboxylcytosine bases, as well as damaged template sequence positions such as abasic sites. Without wishing to be bound by theory, a DNA polymerase catalyzing incorporation of a nucleotide into a complementary nucleic acid strand during a sequencing reaction may exhibit differential polymerase kinetics in a manner dependent on the identity of the nucleotide in the template strand. Using devices and methods in accordance with the present disclosure, the identity of a nucleotide base in a nucleic acid template may be determined in near real-time based on detection of an electronic signature corresponding to the incorporation event. Unlike other systems and methods that rely on detection of a fluorescence signal associated with incorporation of a fluorophore-labeled nucleotide, fluorescence-based detection reagents and signal detection devices are not required, thereby reducing cost and complexity of the process.

Figure 7:
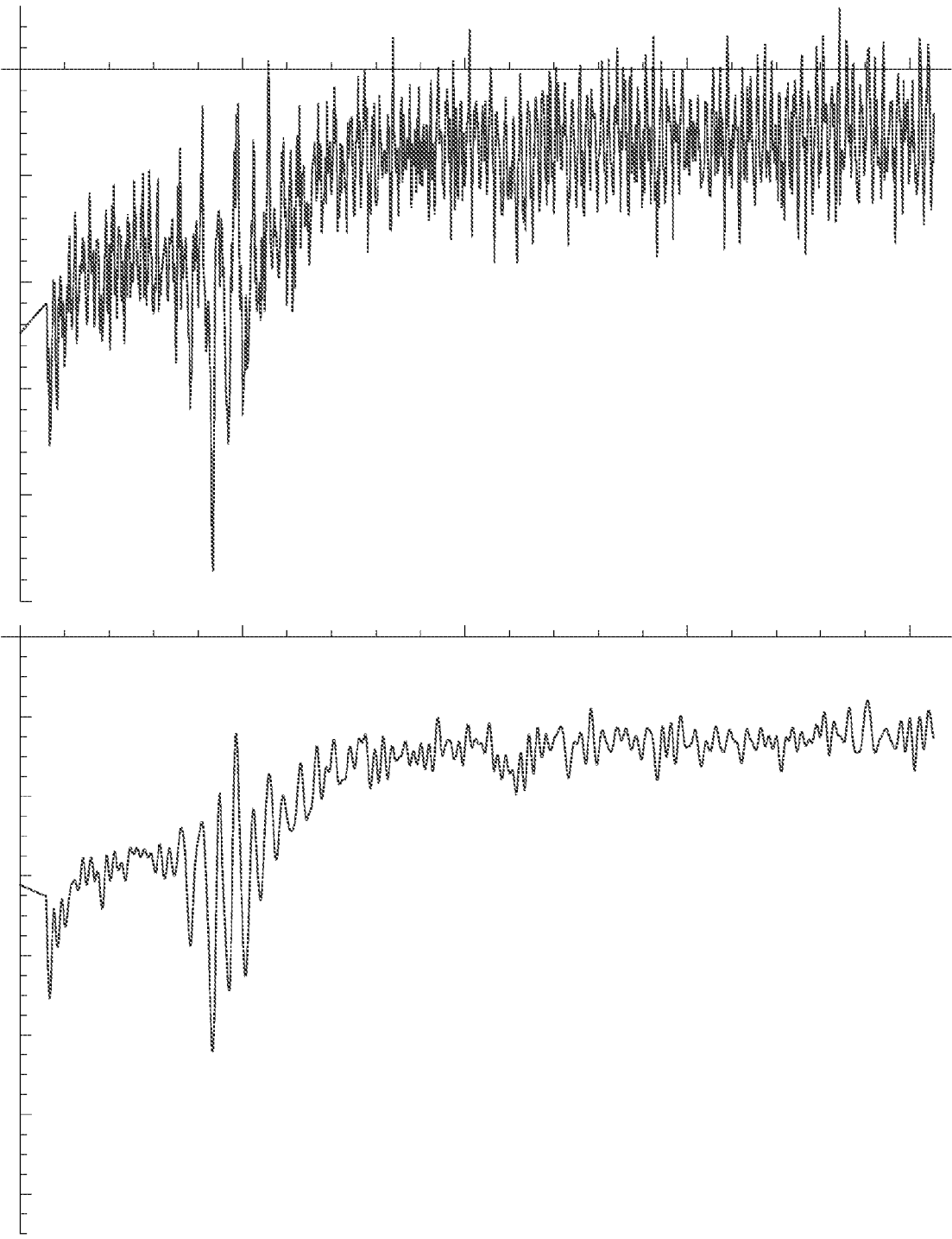
FIG. 7 illustrates a signal trace before and after noise removal in accordance with various embodiments.

In various embodiments, a method can comprise removing noise from a signal trace. Removing noise can comprise performing signal processing, such as to remove 60 Hz line noise. Removing noise from a signal trace can reduce the error of signal trace interpretation. An example of a signal trace produced by sequencing a 12-base nucleic acid template, before (upper signal trace) and after (lower signal trace) removal of 60 Hz line noise from the signal, is illustrated in FIG. 7. Various methods of noise removal may be used, depending on the character of such noise, and such methods are well known to a person of skill in the art in the field of signal processing.

In various embodiments, signal processing to determine the sequence of a target bound to a sensor may comprise a probabilistic determination of the identity of the target, rather than an exact determination of the sequence. The actual sequence of a target molecule may be one of a number of possible unique sequences, each possible unique sequence having a unique theoretical signal. A determination of the sequence of the target molecule may require a comparison of experimentally measured signal with a signal interpretation map comprising a database of unique theoretical signals. The signal interpretation map may be generated based on a training data set or library produced using known target sequences, signal processing based on positive and negative control measurements to reduce signal artifact such as noise, blur, drift, and the like, as well as application of machine learning and/or statistical methods such as neural networks, clustering, curve fitting, model fitting, Bayesian inference, etc.

Manufacturing and Assembly of a Sensor Device

In various embodiments of the present disclosure, a method of producing a molecular biosensor device as described herein is provided. A method of producing a molecular biosensor device can comprise a combination of CMOS fabrication processes and molecular biology methods. CMOS fabrications processes can comprise high-resolution optical lithography methods that are well known in the art and are suitable for commercial scale production of integrated circuits, including devices such as FETs. In various embodiments, CMOS fabrication processes can be used to produce integrated circuits comprising individual sensors having a first electrode and a second electrode deposited on a semiconductor base, with the first electrode and the second electrode separated by a precisely defined sensor gap. In a preferred embodiment, a nano-electrode, gap and contact design would be chosen so as to be manufacturable entirely within CMOS processes. In particular, if specific simple geometries are chosen for these elements, they can be fabricated using the high resolution optical lithography methods, such as Extreme UV (EUV) and Deep UV (DUV) sources, combined with phase-shifting masks, multiple-patterning, and other techniques used to achieve highest resolution CMOS fabrication nodes, including current and future 16 nm nodes, 14 nm nodes, 10 nm nodes, 7 nm nodes and 5 nm nodes as embodied by specific fabrication facilities, such as those at major foundry companies, (e.g., TSMC or GlobalFoundries). Such processes have uniquely high resolution for making certain specific pattern features, such as straight line segments, straight line cuts, and circular spots. Use of these process-specific geometric elements in the design of nano-electrode, nano-contact, and/or gap geometries can facilitate fabrication of a sensor device in accordance with various embodiments in the associated CMOS process. However, in general the manufacturing techniques employed may also comprise non-CMOS process methods, such as e-beam lithography, nano-imprint lithography, or milling and etching techniques such as focused ion beam milling and plasma etching. Molecular biology fabrication methods can comprise synthesis of the desired bridge molecules with precise control over the atomic configuration, and delivery of solutions of such biomolecules in a liquid phase under conditions suitable to permit interaction and coupling of the biomolecules with electronic sensor components produced in upstream CMOS or other fabrication method process, and/or with other biomolecules, in specifically designed self-assembly reaction processes.

In various embodiments, a method of manufacturing a sensor device described herein can comprise steps that including: manufacturing an integrated circuit microchip, fabrication of sensor electrodes and/or contacts, synthesis of a bridge biomolecule, assembling the bridge biomolecule to the electrodes and/or contacts, coupling a probe to the bridge biomolecule, and enclosing the sensor device in a flow cell. In various embodiments, a sensor can comprise a two terminal circuit, or a sensor can comprise a three terminal circuit with a gate. In various embodiments, a gate may have a buried gate configuration; however, lateral gate and other gate configurations, including finFET structures, may also be used.

In various embodiments, an electrode, contact, and/or gate may be comprised of conductive metal materials. For example, an electrode, contact, and/or gate may comprise aluminum, titanium, chromium, copper, gold, palladium, platinum, and the like. In various embodiments, an electrode, contact, and/or gate may comprise semiconductor materials, including doped semiconductor materials that may be used to produce n-type and p-type semiconductor electrodes. In various embodiments, an electrode and a contact attached to the electrode can comprise the same material, and in various other embodiments, a contact can comprise a material that is different from an electrode to which it is attached.

In various embodiments, an electrode may have any suitable structural configuration. For example, an electrode can comprise a generally rectangular cross-section, although other geometric and irregular cross-sectional profiles are possible and within the scope of the present disclosure. In various embodiments, an electrode can have a maximum cross-sectional dimension (i.e., the maximum dimension of the electrode in a cross-section of the electrode) of less than about 30 nm, or less than about 25 nm, or less than about 20 nm, or less than about 15 nm, or less than about 14 nm, or less than about 13 nm, or less than about 12 nm, or less than about 11 nm, or less than about 10 nm, or less than about 9 nm, or less than about 8 nm, or less than about 7 nm, or less than about 6 nm, or less than about 5 nm, or less than about 4 nm, or less than about 3 nm.

Similarly, in various embodiments, a contact may have any suitable structural configuration. For example, a contact can comprise a generally semi-spherical or hemi-spherical cross-sectional profile, although other geometric and irregular cross-sectional profiles are possible and within the scope of the present disclosure. In various embodiments, a contact can have a maximum cross-sectional dimension (i.e., the maximum dimension of the contact in a cross-section of the contact) of less than about 20 nm, or less than about 15 nm, or less than about 14 nm, or less than about 13 nm, or less than about 12 nm, or less than about 11 nm, or less than about 10 nm, or less than about 9 nm, or less than about 8 nm, or less than about 7 nm, or less than about 6 nm, or less than about 5 nm, or less than about 4 nm, or less than about 3 nm.

In various embodiments, the first electrode and the second electrode may be alternately referred to as a source and/or drain, and in various embodiments, a source and/or drain can comprise a distinct structural component from an electrode.

A method of manufacturing can comprise using lithography methods to define a first electrode location and a second electrode location on the surface of a substrate. The first electrode location and the second electrode location may be defined to produce a precisely defined electrode gap between them upon completion of electrode fabrication. Similarly, in various embodiments, a method of manufacturing can comprise using lithography methods to define a first contact position and a second contact position. The first contact position and the second contact position may be defined to produce a precisely defined contact gap between them upon completion of contact fabrication. Likewise, a contact can be configured with a defined structure. Various methods that may be used to manufacture a biosensor are described in greater detail below.

Figure 8:
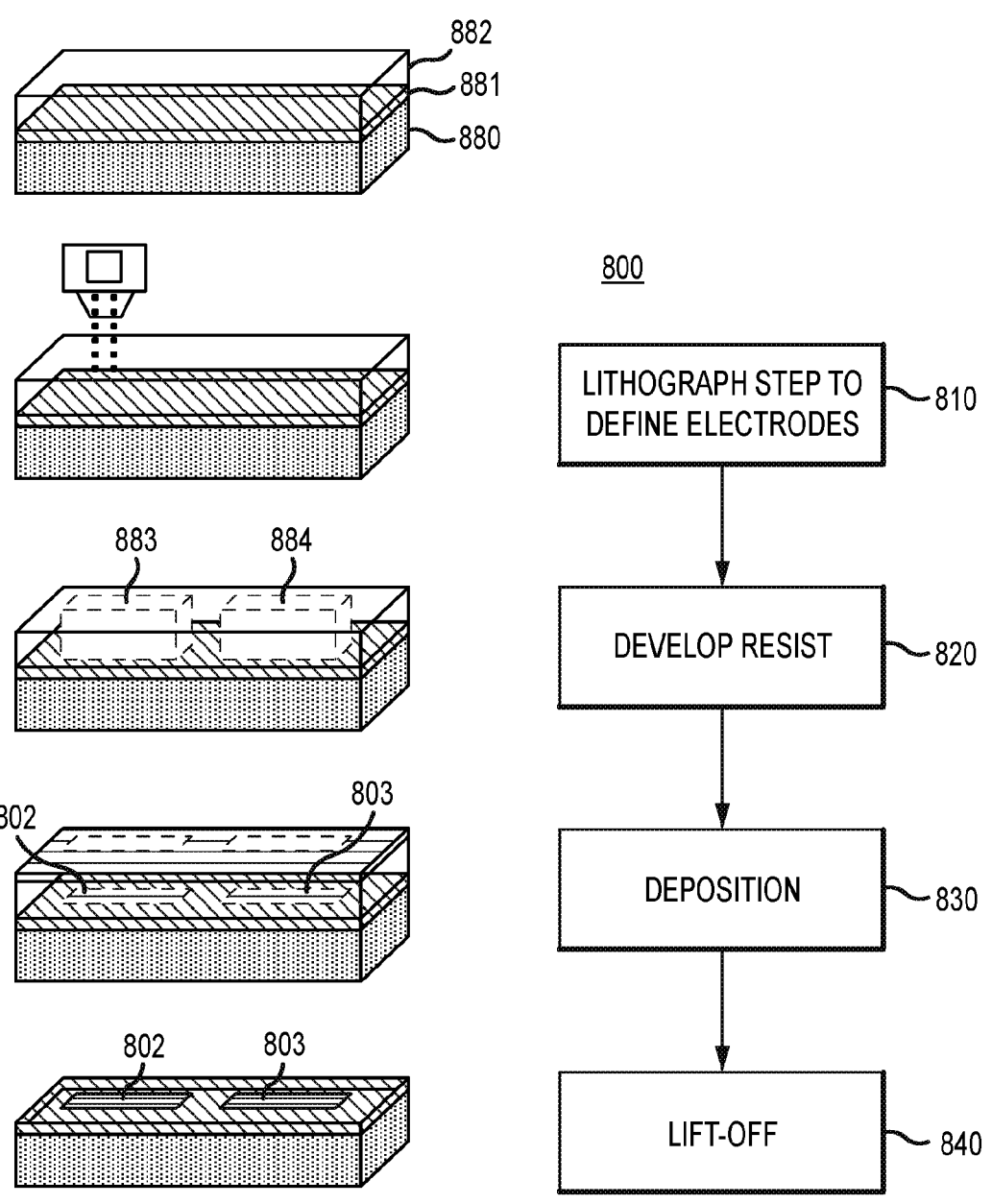
FIG. 8 illustrates a process flow for a method of fabricating electrodes using CMOS techniques in accordance with various embodiments.

With reference now to FIG. 8, a lithographic method 800 for fabricating electrodes is illustrated. In various embodiments, a fabrication method may begin with a microchip substrate such as a silicon substrate 880 overlayed with a silicon oxide layer 881 a resist layer 882. The resist layer can comprise any suitable resist material suitable, such as poly (methyl methacrylate). Adhesion promoters may also be used in a fabrication process in accordance with the present disclosure. In the illustrated embodiment, e-beam lithography is used to expose the resist layer and to define a first electrode track 883 and a second electrode track 884 in the resist layer (step 810). Following the lithography step, the resist is developed (step 820) to remove the resist in the areas defined in the lithography step. Next, a deposition step (step 830) may be performed to form a first electrode 802 and a second electrode 803 on the substrate surface. Any suitable material and deposition method may be used, including, for example, metal sputter coating. Likewise, any suitable substrate surface treatment, such as application of an intermediate attachment layer to provide suitable bonding between electrode and substrate, may be performed prior to performing the deposition step. In various embodiments, the first and second electrodes are fabricated from gold using a sputtering deposition method. Following the deposition step, a lift-off step (step 840) is performed to remove the remaining resist, leaving the first electrode and the second electrode disposed on the surface of the substrate.

In various embodiments, a lithographic method for fabricating nano-electrodes such as method 800 can achieve highly precise electrode configurations. For example, the electrodes can be configured with consistent length, width, and thickness specifications. In various embodiments, an electrode can have a width of between about 10 nm and about 40 nm, such as a width of about 20 nm. Likewise, the electrode gap defined by the first electrode and the second electrode can be configured with a precise electrode gap dimension. In various embodiments, the electrode gap dimension may be between about 3 nm and about 30 nm. For example, the electrode gap for a pair of electrodes in a sensor in accordance with various embodiments can be between about 3 nm and about 30 nm, or between about 4 nm and about 25 nm, or between about 5 nm and about 20 nm, or between about 6 nm and about 17 nm, or between about 7 nm and about 15 nm. In various embodiments, an electrode gap can be fabricated with a dimension of about 3 nm, about 4 nm, about 5 nm, about 6 nm, about 7 nm, about 8 nm, about 9 nm, about 10 nm, about 11 nm, about 12 nm, about 13 nm, about 14 nm, or about 15 nm. As will be evident to a person of ordinary skill in the art, the various method steps described above can be used to produce multiple pairs of electrodes in parallel at high density and with highly precise physical specifications in a process amenable to commercial-scale production of sensor devices using CMOS fabrication and/or other microelectronic fabrication methods.

Without wishing to be bound by theory, providing a sensor having an electrode gap (or a sensor gap) with an electrode gap dimension as described above may provide various advantages with respect to sensor performance and/or fabrication. For example, for an electrode gap having a dimension below about 3 nm, spurious sources of current conduction through the solution (i.e., the sample environment) and bulk will start to increase, creating added noise. In addition, such gaps may not be large enough to accommodate various probe molecules of interest, such as enzymes. Moreover, such gaps are not compatible with current CMOS manufacturing capabilities. The cost and complexity of manufacturing bridge molecules with atomically precise specifications for electrode gaps greater than about 30 nm, such as by using biopolymers or chemically synthesized molecules, rises substantially, and the rigidity various bridge molecules may decrease with lengths beyond about 30 nm. Likewise, the conductivity of many molecules drops substantially below useful parameters beyond those lengths, and greater lengths also limit the ability to closely pack sensors in high density arrays. Thus, sensors with electrode gaps in the range of about 3 nm to 30 nm may afford certain advantages with respect to the function, manufacturability, scalability and economics of a sensor device.

Figures 11A, 11B, 11C:
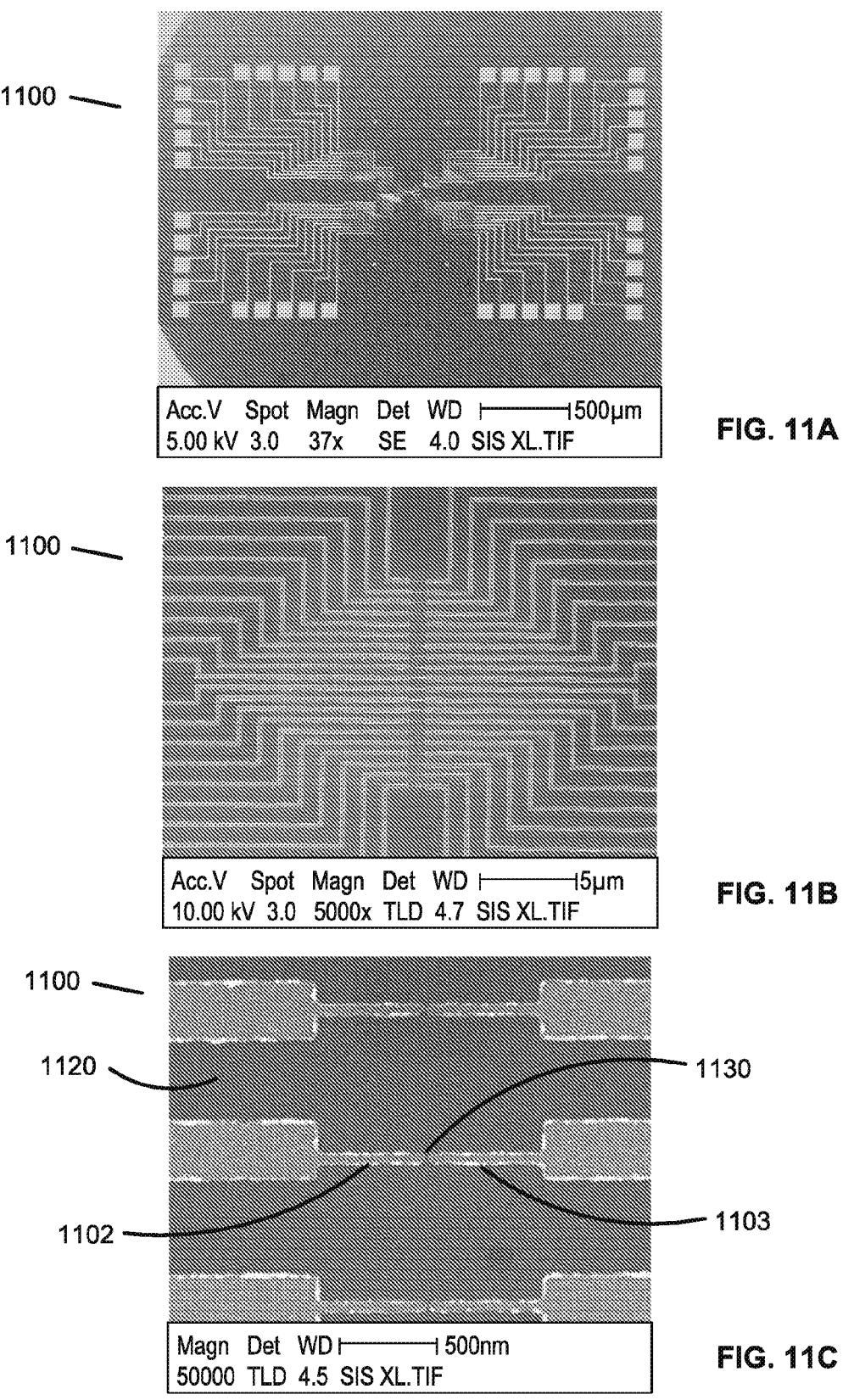
FIGS. 11A-11C illustrate views of a sensor device fabricated using CMOS techniques in accordance with various embodiments.

An example of a sensor device fabricated in accordance with the method described above is illustrated in FIGS. 11A-11C, which shows scanning electron micrographs of the surface of a sensor device 1000 at 37-fold, 5000-fold, and 50,000-fold magnification, respectively. Sensor device 1000 comprises nano-electrodes and nano-contacts for 20 sensors, as well as leads and pads for connection to an external current meter. Pads and leads located on the surface of the substrate are clearly visible in FIG. 11A. Sensor electrodes appear as a lighter vertical band in the center of FIG. 11B. In FIG. 11C, first electrodes 1102 and second electrodes 1103 can be seen clearly, along with electrode gap 1120 defined between the first and second electrodes.

Figure 9:
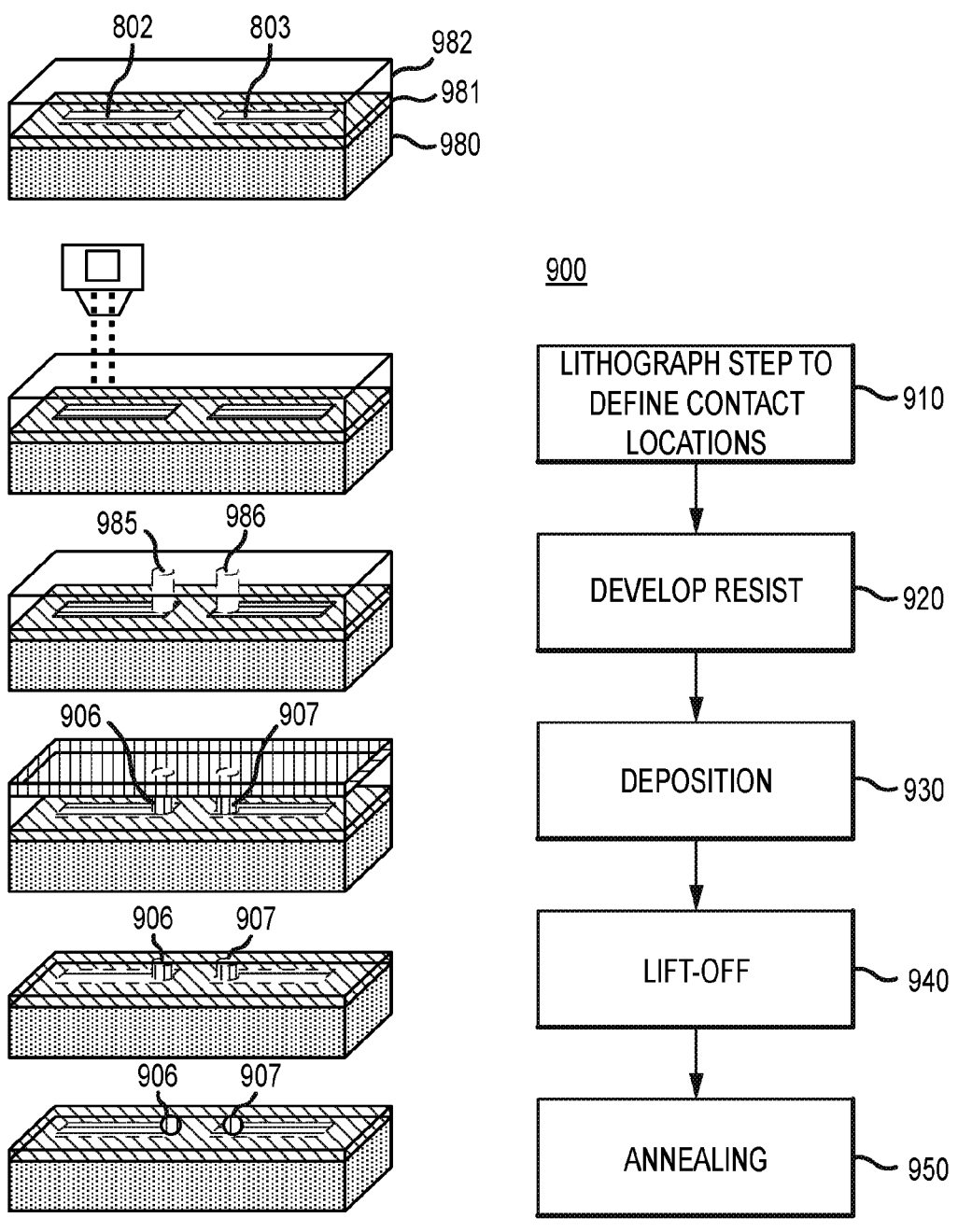
FIG. 9 illustrates a process flow for a method of fabricating contacts using CMOS techniques in accordance with various embodiments.

In various embodiments and with reference now to FIG. 9, a method of manufacturing a biomolecular sensing device can comprise a lithographic method 900 for fabricating and/or determining the location of a contact. In various embodiments, a fabrication method may begin with a microchip comprising a substrate on which a first electrode 802 and a second electrode 803 are disposed. The microchip can comprise silicon substrate 880 overlayed with silicon oxide layer 881 and a suitable resist layer 982. In the illustrated embodiment, e-beam lithography is used to expose the resist layer and to define a first contact position 985 and a second contact position 986 in the resist layer (step 910). In various embodiments, the location of the contact may be defined to overlay one of the first electrode and the second electrode, such as near a distal end of the electrode adjacent to the electrode gap. The size and pattern defined for the contact may contribute to determining the size and shape of the contact formed in later process steps, as described below. Following the lithography step, the resist is developed (step 920) to remove the resist in the contact positions defined in the lithography step. Next, a deposition step (step 930) may be performed to form a first contact 906 and a second contact 907 on the first and second electrode surfaces. As for the electrodes, any suitable material and deposition method may be used. Likewise, any suitable substrate surface treatment, such as application of an intermediate attachment layer to provide suitable bonding between electrode and substrate, may be performed prior to performing the deposition step. The contacts can comprise a different material from the electrodes, or the contacts can comprise the same material used to fabricate the electrodes. In various embodiments, the first and second contacts are fabricated from gold using an electrochemical deposition method. Following the deposition step, a lift-off step (step 940) is performed to remove the remaining resist, leaving the first contact and the second contact disposed on the surfaces of the first and second electrodes.

Alternately, in various embodiments, a method for fabricating a contact can comprise deposition of preformed contact nanoparticles. Preformed contact nanoparticles can be deposited into a void formed in a resist layer and configured to receive a contact nanoparticle and position it at a contact position, or contact nanoparticles can be deposited using a chemical derivatization layer to achieve attachment at a contact position.

Figure 10:
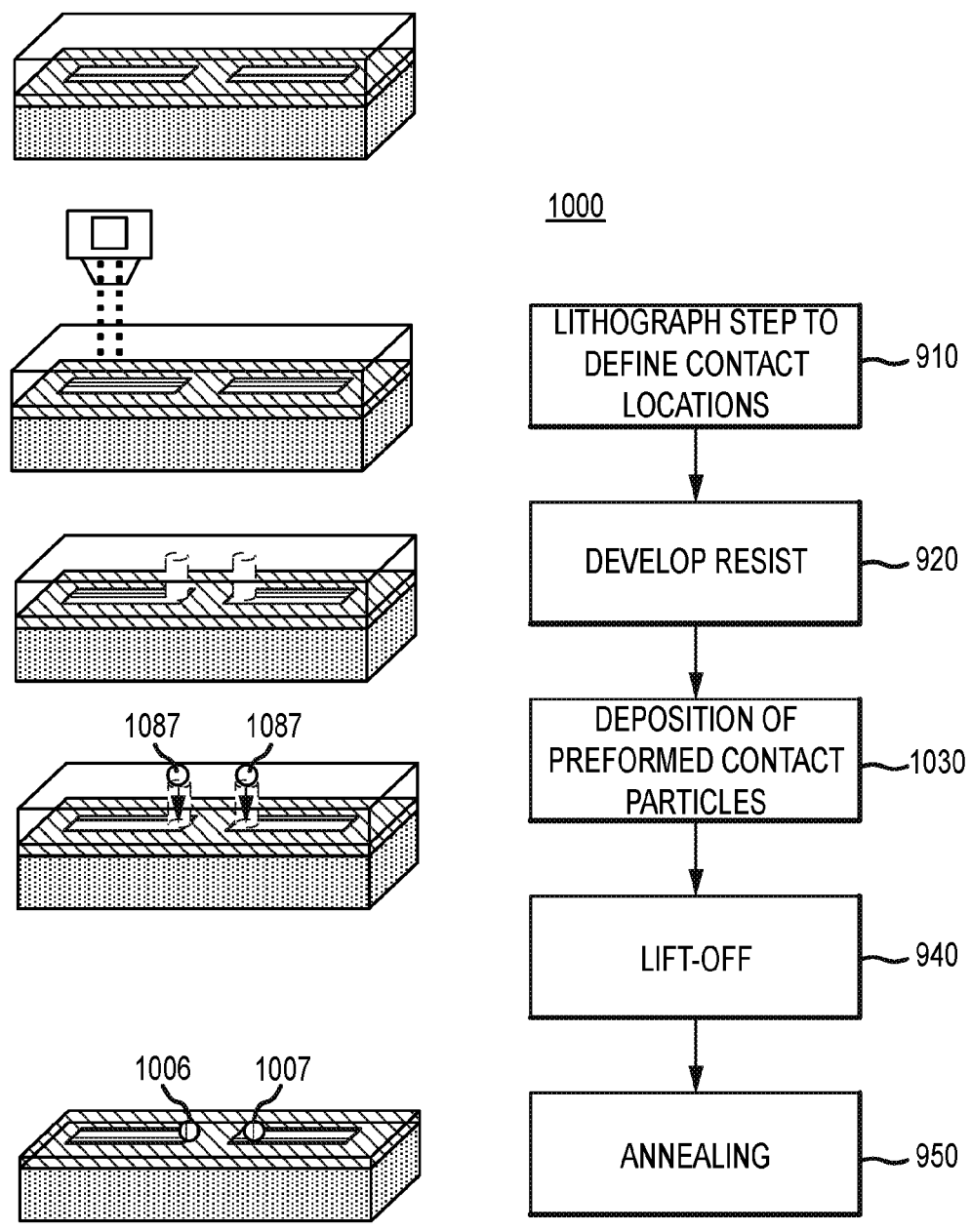
FIG. 10 illustrates a process flow for a method of fabricating contacts using CMOS techniques and deposition of preformed contact particles in accordance with various embodiments.

As illustrated in FIG. 10, a method 1000 of depositing a preformed contact particle into void formed in a resist layer can comprise the same steps described above for method 900 with respect to steps 910 and 920. Following creation of a void configured to receive a preformed contact particle, a solution comprising a plurality of preformed contact particles 1087 can be contacted with the device (step 1030) and the particles deposited into the voids using pressure, mixing, surface tension, buoyancy, centrifugal force, or other methods to introduce a particle into a void. Following deposition of the particles, excess solution and particles may be removed. A lift-off step can be performed to remove remaining resist as described above with respect to step 940, and the preformed contact particles can optionally be annealed to the electrodes in a subsequent as necessary to form strongly attached first and second contacts (1006, 1007).

Alternately, a method of depositing preformed contact nanoparticles using a chemical derivatization treatment can comprise steps similar to steps 910 and 920 described above with respect to the method illustrated in FIG. 9. For example, one such widely used surface derivatization compatible with a silicon substrate surface is silanization, which can include coating a substrate surface with molecules such as aminosilanes (for example, APTES) or mercaptosilanes (for example, MPTES). These molecules adhere to a silicon surface, and then their exposed ends readily cross-link to other materials such as gold nanoparticles to bind them to the surface. Then, in a step similar to step 930, such a derivatization treatment can be applied rather than depositing a contact metal or other material. After a lift-off step similar to step 940 is performed, the first electrode and the second electrode will comprise a surface derivatization at the locations intended for attachment of the first contact and the second contact. The device comprising the derivatized electrode surfaces can be contacted with a solution comprising a plurality of preformed contact particles. The particles may have a surface or coating that is complimentary to or otherwise binds specifically to the derivatized electrode surfaces, thereby localizing the contact particles to the defined contact positions. The derivatization treatment and any particle coating may be removed in a removal step, as necessary, and the preformed contact particles annealed to the electrodes as described above. An example of this approach is the use of an APTES-coated silicon surface to specifically bind a gold nanoparticle.

In various embodiments, contact structures can be created by various direct means, such as positioning gold nanoparticle beads on electrodes by use of atomic force microscopy (AFM), or by deposition of excess beads followed by AFM removal of unwanted beads.

In various other embodiments, contact structures and/or an electrode gap can be formed in place via material removal, such as by using focused ion beam (FIB) milling. For example, an electrode gap can be carved into a previously established continuous metal nanowire using FIB, thereby creating a first electrode and a second electrode simultaneously with forming the electrode gap.

Following fabrication of the electrodes and contacts of a sensor or array of sensors, the sensor(s) may be enclosed in a flow cell or similar device suitable to permit controlled introduction of a liquid solution to the sensor(s). Enclosing the sensor chip in a flow cell is typically done by molding a flow cell from PDMS or other polymer or plastic, and using this to encase the chip, leaving the fabricated electrodes and contacts suitably exposed for bridge and probe assembly as well as subsequent assays using the completed sensor(s). In various embodiments, a surface passivation treatment may be applied to the substrate surface and portions of the exposed electrodes to reduce electrical noise that can occur from contact with liquid samples. The passivation treatment can be applied to leave the electrodes and/or contacts in the area of the sensor gap untreated. For example in various embodiments, a 30 nm wide area aligned with the sensor gap may be left untreated. The passivation treatment may be performed prior to enclosing the sensor chip with a flow cell. A sensor in accordance with various embodiments can have electronic noise of less than about 1 pA, or less than about 0.9 pA, or less than about 0.8 pA, or less than about 0.7 pA, or less than about 0.6 pA, or less than about 0.5 pA, or less than about 0.4 pA, or less than about 0.3 pA, or less than about 0.2 pA, when a voltage of about 0.5 V is applied and the sensor is immersed in a low ionic strength buffer solution otherwise suitable to support activity of an enzyme, for example DNA polymerase I enzyme.

Fabrication of a biopolymer bridge can be performed by any of a variety of methods that may be used to synthesize biopolymer molecules, including in vivo synthesis methods, in vitro enzymatic synthesis methods, chemical synthesis methods, or any combination thereof. Various methods for producing biopolymer molecules suitable for use as a bridge molecule in accordance with the present disclosure will be well known to a person of ordinary skill in the art. Likewise, methods for derivatizing or modifying a biopolymer bridge molecule to provide an anchor or a linker component as described herein are likewise well known. The various specific biopolymer bridge molecules described herein are provided by way of example and should not be interpreted as limiting the scope of the present disclosure, and synthetic bridge molecules may be used in accordance with various embodiments of the present disclosure.

In various embodiments, attachment of a biopolymer bridge molecule to a probe may be performed by a self-assembly chemical reaction. Likewise, attachment of a biopolymer bridge molecule to electrodes or contacts may also be performed by a self-assembly chemical reaction. Such self-assembly reactions may be performed by putting the two components to be attached into contact with one another via a solution comprising at least one of the components. In various embodiments, attachment of a biopolymer bridge to a probe can be performed before, after, or simultaneously with attachment of the bridge to electrodes or contacts. Similar considerations apply to a bridge molecule produced by synthetic chemistry.

In various embodiments, a method of making a sensor device includes assembling a biopolymer bridge molecule to the first electrode and the second electrode. The bridge molecule assembly step can comprise a self-assembly step. Self-assembly can be performed by contacting the partially constructed sensor device comprising the first and second electrode with a solution comprising the bridge molecule. The bridge molecule can self-assemble to the first electrode and the second electrode based on an affinity between the first end and the second end of the bridge molecule and the first electrode and the second electrode. In various embodiments, self-assembly of the sensor components can be monitored electronically by the sensor device, as described below in Example 2 and with reference to FIGS. 13-15. Electronic monitoring can provide a quality control function and serve to identify sensors in a device that are properly assembled. Signal from sensors circuits that do not provide assembly process signals within predetermined parameters may be disregarded in downstream analyses, such as sequencing analyses, performed with the device.

Example 1

Biopolymer Bridge Self-Assembly

Figure 12:
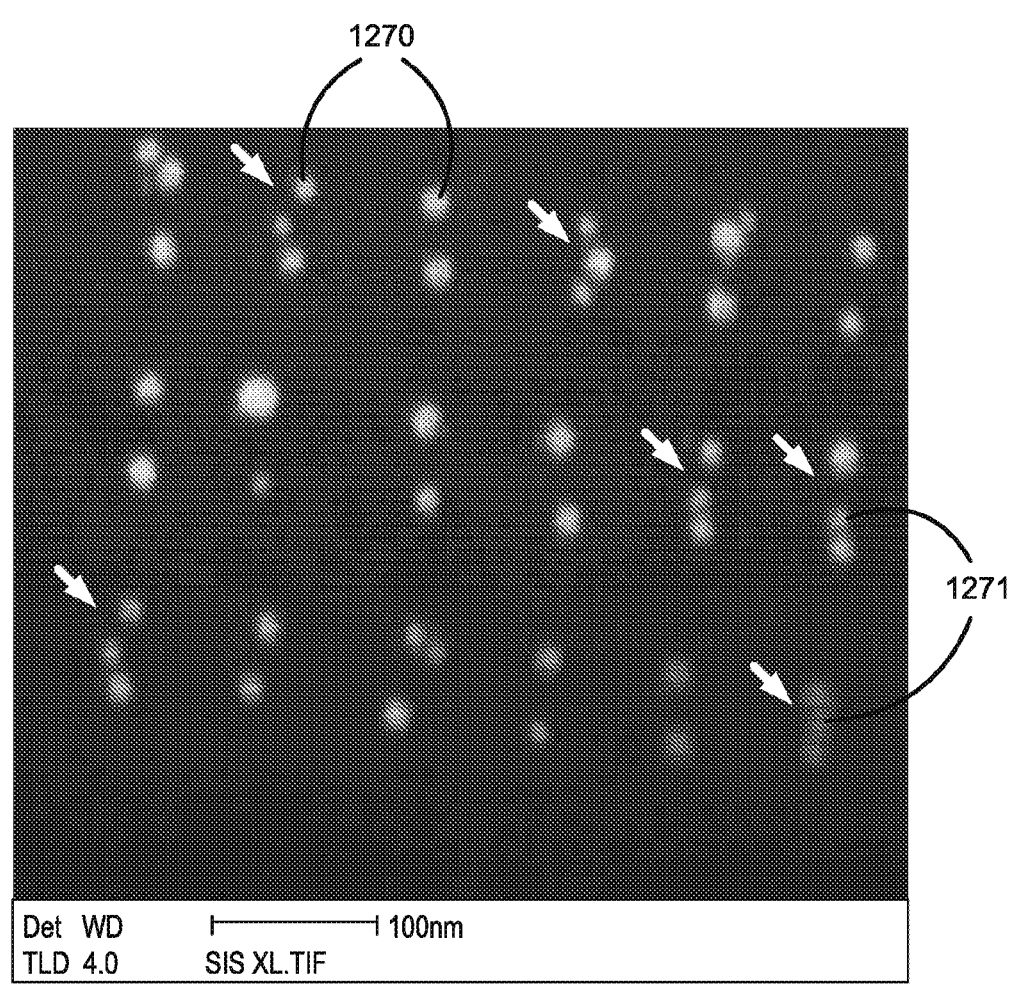
FIG. 12 illustrates a scanning electron micrograph of a contact array following biopolymer bridge self-assembly in accordance with various embodiments.

A double-stranded DNA biopolymer bridge molecule with an end-to-end length of about 20 nm was constructed using the oligo set forth in SEQ ID NO: 1 comprising a 5'-thiol modification and the oligo set forth in SEQ ID NO.: 2 comprising a 5'-thiol modification and an internal biotin modification. The bridge molecules were labelled for visualization purposes using a streptavidin-gold tag. A test array 1200 (FIG. 12) of gold nanoparticle contacts was fabricated using e-beam lithography techniques to deposit pairs of gold contacts, each pair of contacts defining a contact gap of about 20 nm, center-to-center. A buffered solution comprising the gold-labelled bridge molecules was placed in contact with the test array of gold nanoparticle contacts. Following a brief incubation period, excess solution was removed and the array was washed and imaged by scanning electron microscopy (SEM). An SEM image showing the arrangement of gold contacts 1270 and gold tags 1271 is illustrated in FIG. 12. For several contact pairs (indicated with arrows), a gold tag 1271 can be seen disposed between the contact pair, indicating successful self-assembly of the biomolecular bridge molecule to the pair of contacts.

Example 2

Detection of Self-Assembly Steps

Figure 14:
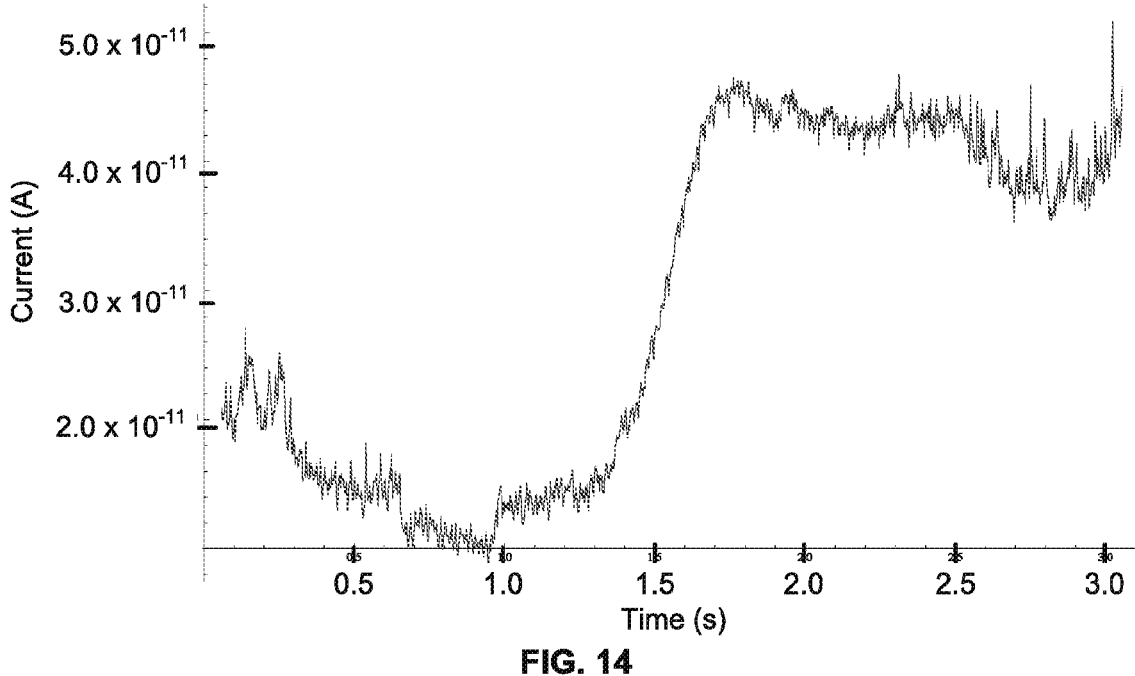
FIG. 14 illustrates a signal trace produced during a process of probe binding to a biopolymer bridge of a sensor in accordance with various embodiments.
Figure 15:
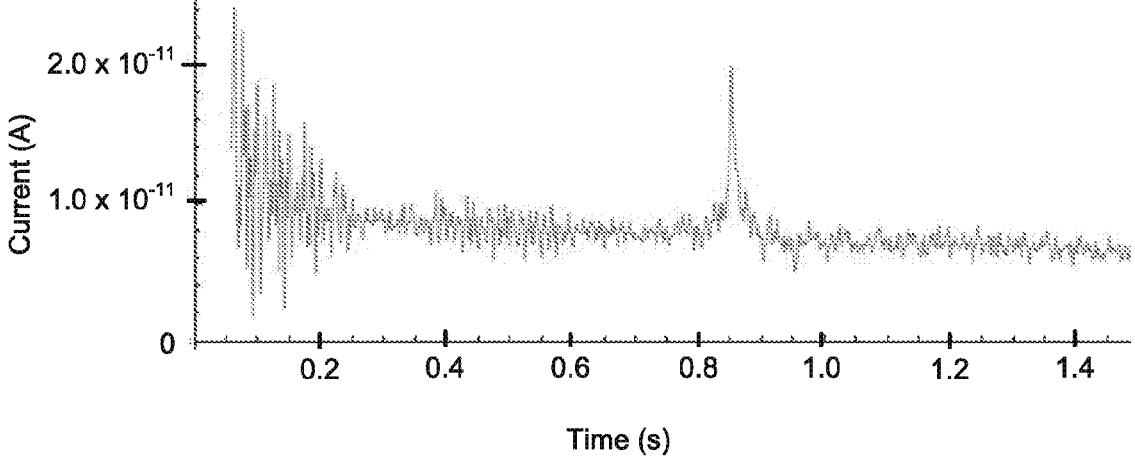
FIG. 15 illustrates a signal trace produced during template binding to a probe in accordance with various embodiments.
Figure 16:
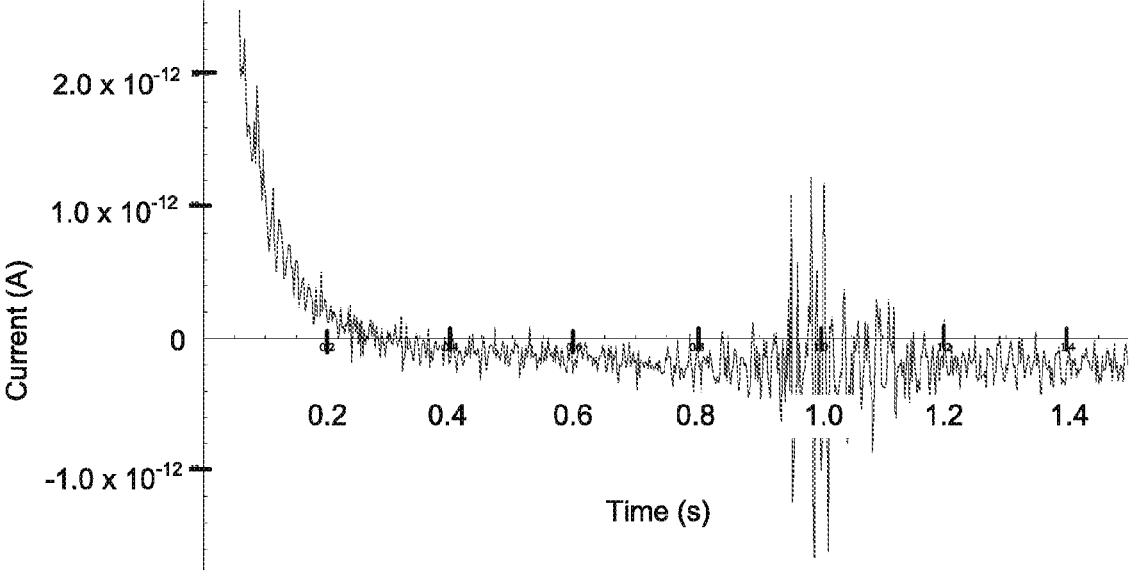
FIG. 16 illustrates a signal trace produce during template-dependent base incorporation by a probe in accordance with various embodiments.

A sensor device with a single sensor comprising gold contacts attached to electrodes with a contact gap of about 20 nm, center-to-center, was fabricated using e-beam lithography techniques. The sensor was enclosed with a PDMS flow cell comprising a 1 mm wide by 0.4 mm high channel that was open on either end to permit introduction of liquid into a first end of the flow cell interior and displacement of liquid from the second end of the flow cell, and solution the cell contacting the sensor. The flow cell channel was oriented orthogonally to the direction of the electrodes comprising the sensor, with the sensor located in approximately the middle of the length of the flow cell channel. A low ionic strength buffer solution was introduced into the flow cell, and a 0.5 V potential was applied to the sensor throughout subsequent serial steps of introduction and self-assembly of a double-stranded DNA bridge molecule (as described above for Example 1, but without a gold tag) (FIG. 13), introduction and binding of a streptavidin-tagged Klenow fragment (FIG. 14), introduction and binding of a 50 base primed single-stranded DNA molecule (FIG. 15), and introduction of a dNTP mix to initiate template-based synthesis by the Klenow fragment (FIG. 16). The sequence of the DNA template molecule include the following oligo sequence featuring a poly-A region:

```
                                 (SEQ ID NO: 16)
5'-cgc cgc gga gcc aag aaa aaa aaa aaa aaa aaa aa
ttgcatgtcctgtga-3'
``` and the primer used was:

```
                                 (SEQ ID NO: 17)
        3'-aac gta cag gac act-5'
```

In addition, similar sequences with the poly-A tract replaced by poly-C, G, and T tracts were used to investigate the effect of different template bases.

Figure 13:
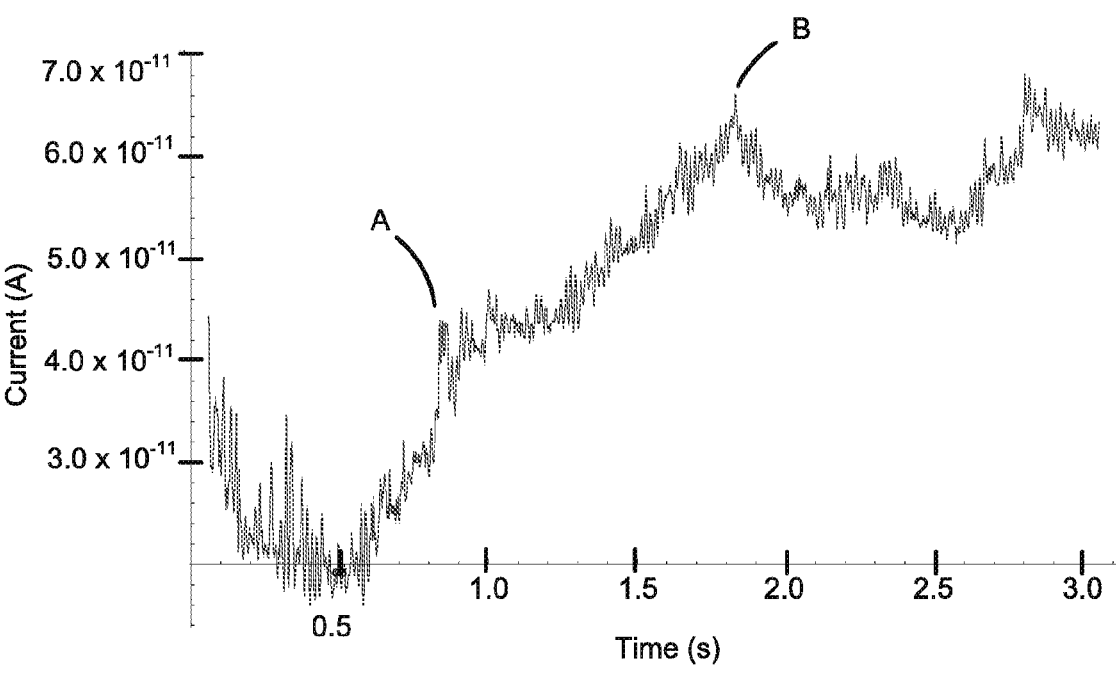
FIG. 13 illustrates a signal trace produced during a biopolymer bridge self-assembly event for a sensor in accordance with various embodiments.

As illustrated in FIG. 13, the measured current rises over a three second period. The two inflections points (A and B) in the signal trace are thought to correspond to binding of the 5'-thiol-modified terminal base anchors to the first and second contact. The signal trace following introduction of a solution comprising streptavidin-tagged Klenow fragment (FIG. 14) exhibits a sharp increase in current at about 1.5 s that is likely to correspond to a streptavidin linker component of a Klenow fragment enzyme contacting and binding the biotin linker component of the biopolymer bridge. In FIG. 15, a sharp signal peak is present in the signal trace following introduction of the template strand to the flow cell, with the peak interpreted to correspond to template binding by the Klenow fragment. The signal trace measured following introduction of a dNTP mix comprising all for DNA bases, illustrated in FIG. 16, likewise exhibits a distinct signal feature at about 1 s. This may represent dissociation of the synthesized duplex from the polymerase enzyme, and the signal trace from about 0.7 s to about 0.95 s may correspond to the kinetic signature produced by the sensor in response to nucleotide incorporation based on the bound template DNA.

Example 3

Detection of Nucleotide Base Incorporations

Figure 17:
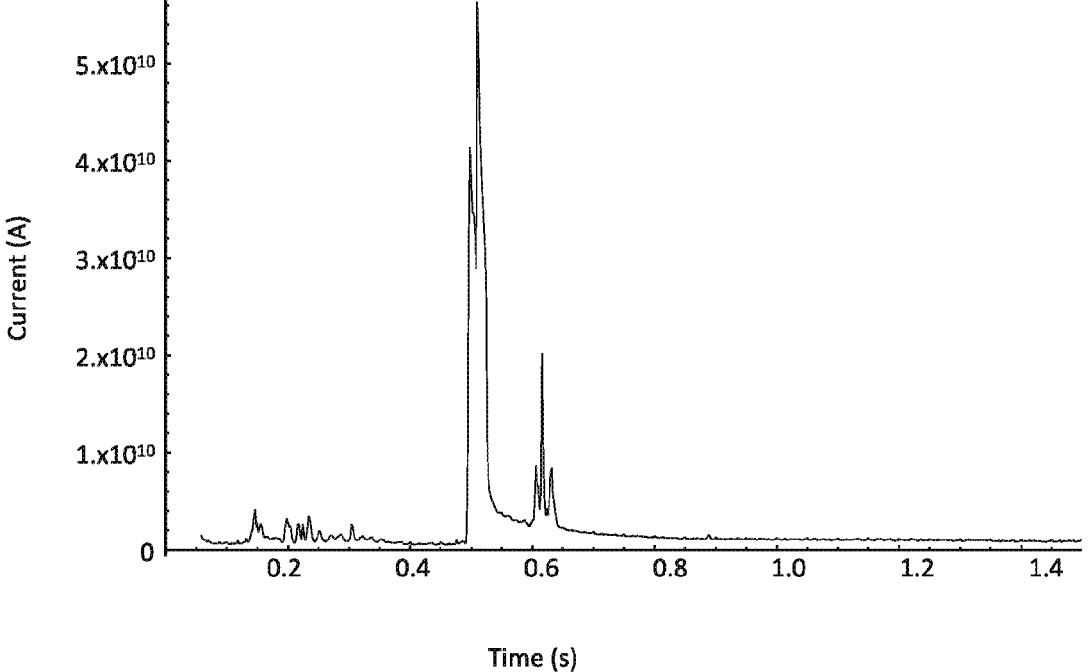
FIG. 17 illustrates a signal trace produced by a single template-dependent base incorporation event by a sensor in accordance with various embodiments.
Figure 18:
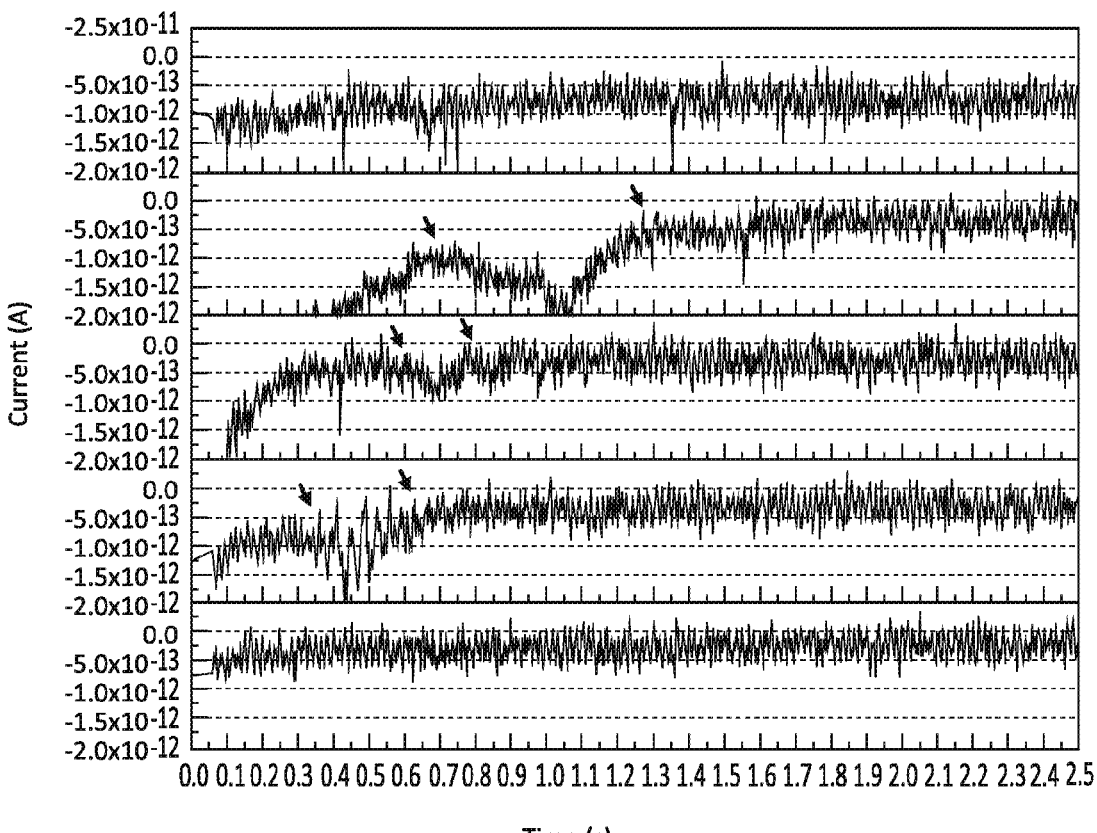
FIG. 18 illustrates signal traces produced by a sensor in accordance with various embodiments under various experimental conditions.

A sensor device comprising a biopolymer bridge molecule and Klenow fragment probe was fabricated and assembled as described above in Example 2. The sensor device was used to produce signal traces in response to DNA synthesis reactions performed using single-stranded DNA templates of various lengths and sequence compositions. FIG. 17 illustrates a signal trace for a template sequence that provides for the incorporation of a single base. The signal feature at 0.5 s is interpreted to correspond to the template-dependent activity of the Klenow fragment and base incorporation, and the much weaker signal features just after 0.6 s are interpreted to correspond to some form of noise or spurious signal in the system. FIG. 18 illustrates signal traces for various template tracts. The template and primer described above in Example 2 were used for the illustrated reactions.

The top and bottom signal traces are control experiments in which buffer without dNTPs is introduced to a sensor. The second, third, and fourth signal traces (from top to bottom) were produced in response to introducing dTTP into solution (expected to result in 20 incorporation events directed by the 20 A bases of the template), followed by addition of dCTP (expected to allow another 3 incorporations directed by the GAA triplet in the template, 3' to 5'), followed by the addition of dNTP (expected to polymerize as directed remaining 12 bases of the template) so that the signals produced result from 20, 3, and 12 incorporation events. The signal trace comprising the signal features located between arrows for each signal trace is interpreted to correspond to signal modulation due to template-dependent enzyme activity. The relative durations of these perturbed signal regions is in the expected proportion of 20:3:12, and the third such tract displays a clear spike that may correspond to the 12 discrete incorporation events. FIG. 7 illustrates an additional example of a signal trace produced by a DNA synthesis reaction performed using the device described above and the template described above with 12 unpaired template bases. These results demonstrate that a sensor in accordance with various embodiments can produce a signal trace comprising signal features in response to template-dependent DNA polymerase probe activity. This also demonstrates the value of noise removal in clarifying the signal: the upper panel in FIG. 7 is the raw measured signal, and the lower panel has undergone signal processing to remove noise, in this case specific 60 Hz line noise was eliminated with a bandpass filter.

Example 4

Detection of Methylated Template Bases

A sensor device comprising a biopolymer bridge molecule and Klenow fragment probe was fabricated and assembled as described above in Example 2. The sensor device was used to produce signal traces in response to DNA synthesis performed using a single-stranded DNA template comprising both cytosine and 5-methylcytosine modified nucleotides. The template sequence included unpaired base nucleotides having the sequence 5'-13x(N)-5x(GmC)-5x(GC)-G-3' (i.e., 5'-NNN NNN NNN NNN NGmC GmCG mCGmC GmCG CGC GCG CGC G-3' (SEQ ID NO: 12), where N is any standard nucleotide and where mC is 5-methylcytosine). This template sequence was designed to produce a complementary synthesized strand having the sequence 5'-C-5x (GC)-5x(<u>GC</u>)-13x(N)-3' (i.e., 5'-CGC GCG CGC GCG CGC <u>GCG</u> <u>CGC</u> NNN NNN NNN NNN N-3' (SEQ ID NO: 13)), with the underlined guanosine bases corresponding to the positions of the 5-methylcytosine modified nucleotides in the template strand. A 0.5 V was applied to the sensor, and current was measured through the course of sequential introductions and incubations with water, buffer, a buffered solution of dCTP, a buffered solution of dGTP, and a buffered solution with a mix of all four dNTP bases. The expected result of this would be a single dCTP incorporation event, then 20 dGTP and dCTP incorporation events, the first 10 of which are against the unmodified cytosine bases, and the latter 10 against the 5-methylcytosine modified nucleotides. Detection of methylation would show up as a different character of signal in the second 10 of these 20 events.

Figure 19:
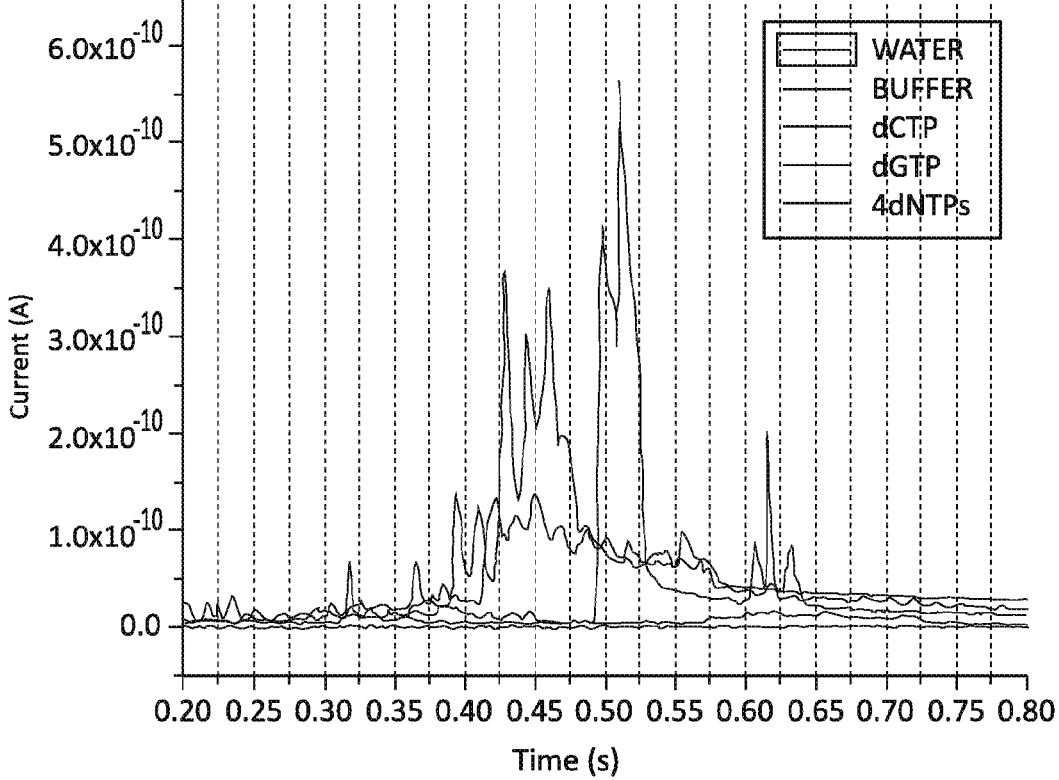
FIG. 19 illustrates a signal traces produced by a sensor in accordance with various embodiments under various conditions in response to a target comprising unmodified and 5-methylcytosine modified nucleotides.

Signal traces produced during incubation with each reagent are illustrated in FIG. 19. Incubation with water and buffer produced very low, baseline current with little variation. Addition of a solution comprising dCTP produced a sharp sequence feature corresponding to a single base incorporation of dCTP against the template lead base G. Addition of dGTP, creating a solution comprising both dCTP and dGTP, permitted synthesis through the 10 base incorporations corresponding to unmodified nucleotides followed by synthesis through the 10 base incorporations corresponding to the 5-methylcytosine bases in the template strand. The signal trace produced in this incubation period shows signal features with higher current from about 0.35 s to about 0.5 s, followed by signal features with lower current from about 0.5 s to about 0.65 s. This shift in signal amplitude is interpreted as a distinct change in the sensor signal in response to the effect of the methylation status of the template sequence on the polymerase and resultant signal modulation. This evidence supports the ability of a sensor in accordance with various embodiments of the present disclosure to directly distinguish the presence of modified nucleotides in a target sequence during a sequencing reaction.

Example 5

Detection of Signal Over Long DNA Strand Reads

A sensor device comprising a biopolymer bridge molecule and Klenow fragment probe was fabricated and assembled as described above in Example 2. The sensor device was used to produce signal traces in response to DNA synthesis performed using a single-stranded DNA template comprising an approximately 5400 bp template sequence derived from the genome of phi X 174 bacteriophage. A dNTP mix was provided in the experimental sequencing reaction, while a ddNTP (dideoxynucleotide triphosphate) mix was provided for a control reaction. The ddNTP mix terminates the polymerization process after one incorporation of such a dideoxy terminator, and thus essentially no sequencing sensing signal should result. The data was acquired at 20 ms time sampling resolution, which is too coarse to observe individual incorporation spikes, but allowed data collection for a timer period over 300 seconds, long enough to observe the entire polymerization process at the expected enzyme rate of approximately 20 bases per second.

Figure 20:
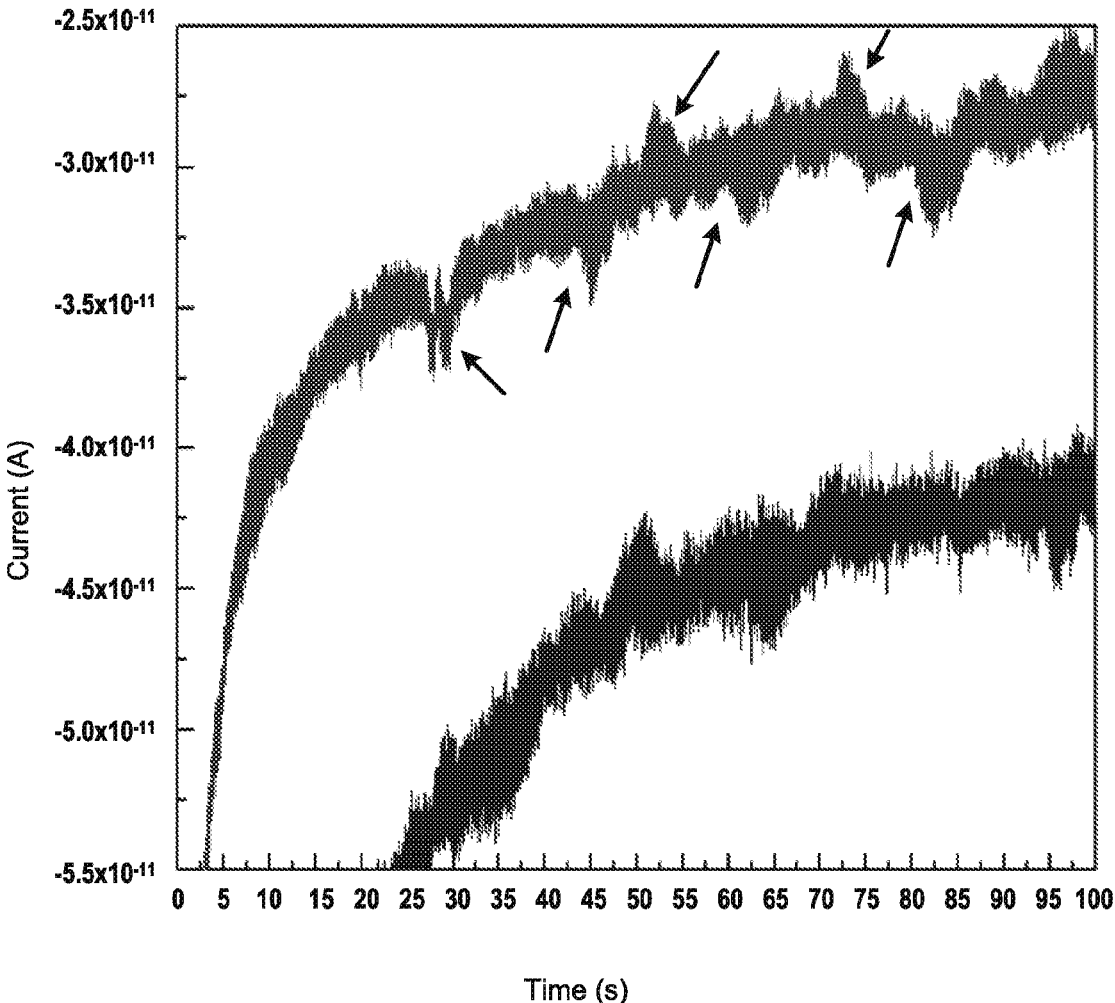
FIG. 20 illustrates signal traces produced by a sensor in accordance with various embodiments in response to a long template sequence under various experimental conditions.

FIG. 20 illustrates the signal trace produced by the experimental reaction with a dNTP mix (upper signal trace) compared to that for the control reaction using a ddNTP mix (lower trace). The signal trace for the experimental sequencing run included a number of distinct, gross signal features (noted with arrows) lacking in the control reaction and also produced a higher current than the control reaction. The signal trace produced over the 100 second period shown suggests that a sensor in accordance with various embodiments of the present disclosure may be suitable to produce a detectable signal in response to template-based nucleotide incorporation activity of a DNA polymerase probe over the course of an extended sequencing run for a long template sequence. Thus, there is no immediate limitation on the length or template such a sensor can process.

Example 6

Molecular Bridge Self-Assembly

Figure 22:
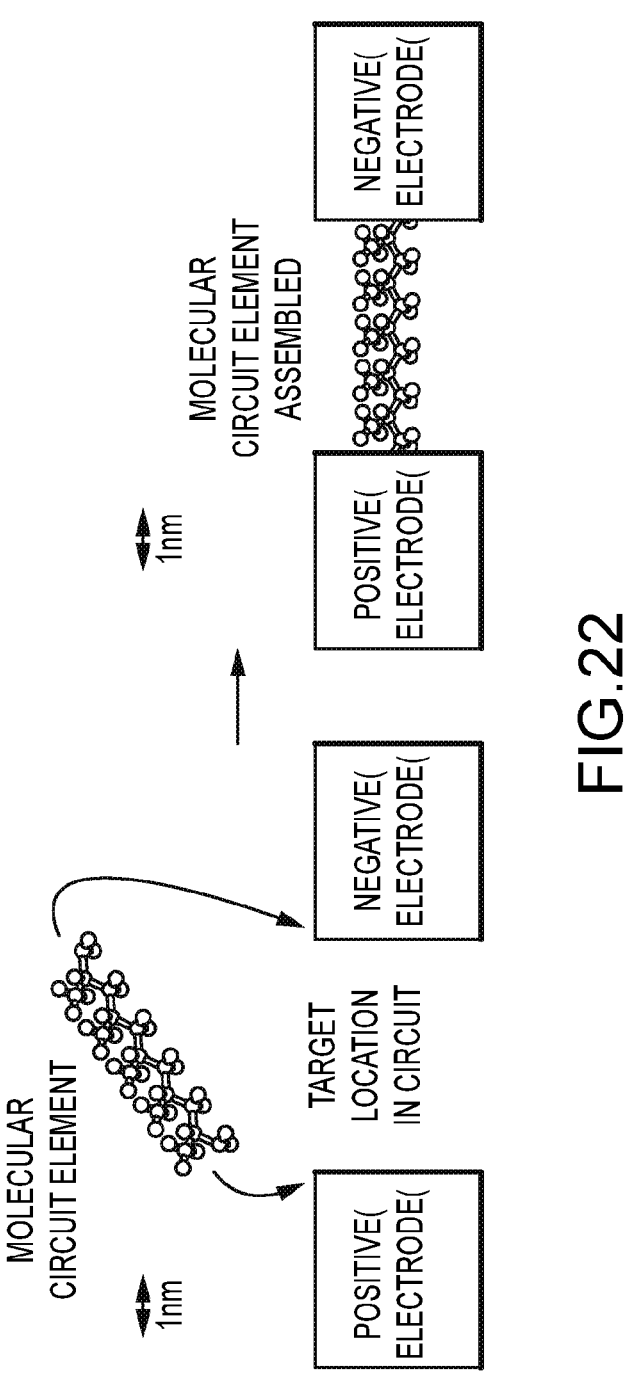
FIG. 22 illustrates the general self-assembly process wherein a molecular circuit element, such as a biopolymer, bonds within a target location in the circuit to both the positive and negative electrodes bridging them to form an assembled molecular circuit.

This example teaches new methods of manufacturing a molecular bridge component for a molecular electronics circuit. It is a common fabrication challenge in the field of molecular electronics to insert a bridge molecule into a nano-scale electrical circuit. Typically, a molecular element is to be connected between two electrodes, as shown in FIG. 22. A common problem in molecular electronics is to assemble a given molecular circuit element in between electrodes, as illustrated. The final device requires both good mechanical and good electrical connection between the electrodes and the molecule forming the bridge. It is also preferable that the device self-assemble into this bridged configuration because of the nano-scale size and the large number of electrode pairs that make any manual assembly impractical.

The object of this example is to provide molecular bridge structures for molecular electronics applications. These are precise self-assembling circuit elements spanning electrodes that provide for various electronics uses. This includes specific compositions of matter, manufacture for establishing these, and methods related to ensuring the quality of these structures. This includes specific preferred embodiments of such bridge molecule systems.

Figure 23:
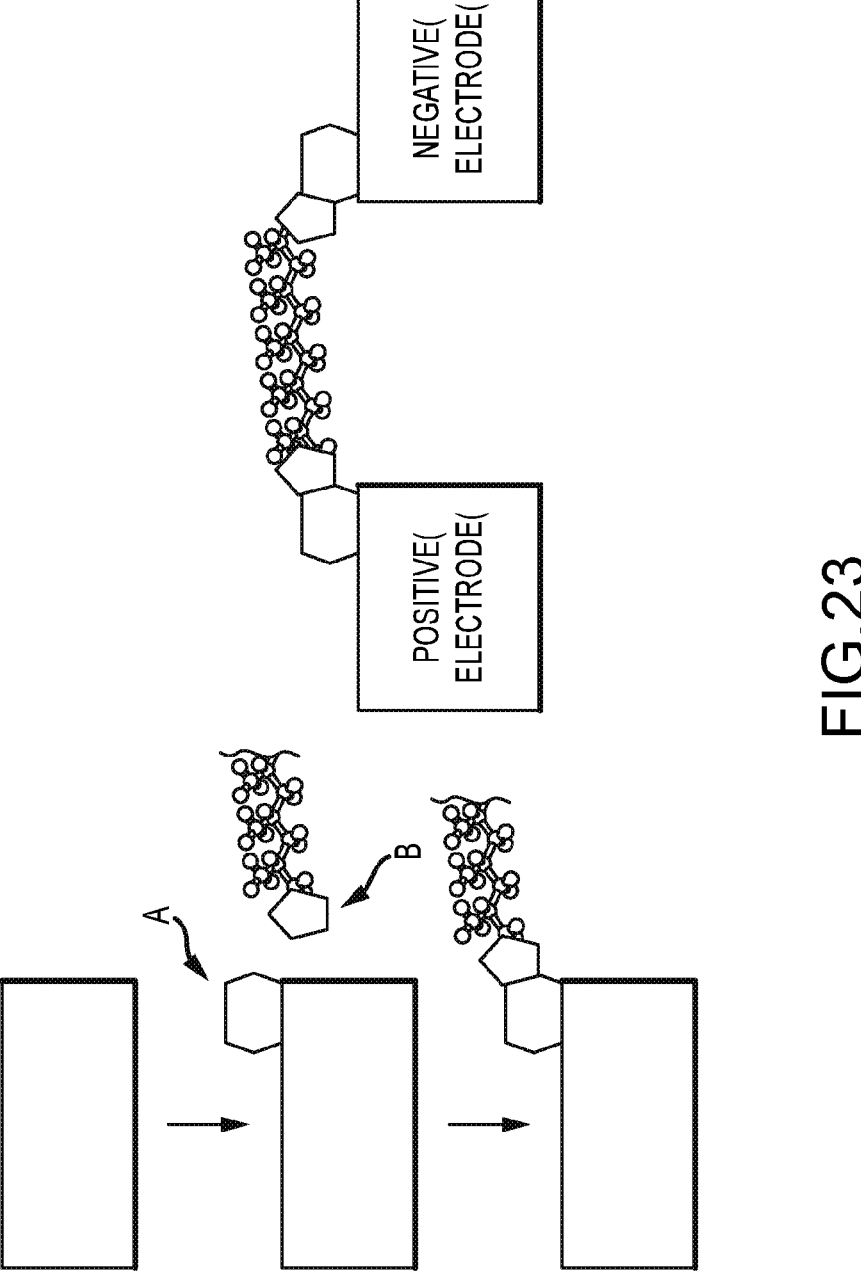
FIG. 23 illustrates the use of a material contact point in circuit self-assembly. The contact point, shown as "A," is a spatially localized, precisely positioned material element that can guide precise self-assembly, and provide electrical or mechanical connection. The basic steps of adding a contact point and attaching the molecular element are shown on the left. How this can result in a desired circuit is indicated at right. The group "B" is a conjugate group on the bridging molecule that can selectively bind to the contact point.

This example teaches a specific system for establishing a class of circuits, and its specific preferred embodiments. A preferred way to solve this is to introduce a highly localized, precisely positioned, material particle or patch, which is referred to herein as a nano "contact point" that serves some or all of the needs of guiding self-assembly, and which provides mechanical and electrical connection. The use of such a contact point for these purposes is illustrated in FIG. 23. For this purpose, a contact point is made of a suitable material that (i) selectively binds a conjugate group on the target molecule; (ii) is highly spatially localized; (iii) is precisely located at a desired position; and (iv) is bound in place to the substrate. As illustrated in FIG. 23, a contact point "A" is a spatially localized, precisely positioned material element that can guide precise self-assembly and provide electrical or mechanical connection. The basic steps of adding a contact point "A" to an electrode and then attaching the molecular element are shown at the left in FIG. 23. The end result is the desired circuit shown at the right of FIG. 23. The element "B" is a conjugate group on the bridging molecule that can selectively bind to the contact point "A."

The key properties of the contact point-bridge molecule system required for this are: (1) the contact point is highly spatially localized ("small" or "point-like"); (2) the contact point has precisely pre-defined, specified location; (3) the contact point be made of the right material configuration to support its functional role; and (4) the bridge molecule is constructed with a conjugate group on both ends, which specifically binds the contact point.

The same properties have broader utility than just the example of circuit construction shown here, such as playing a role in directed assembly of various nano-electro-mechanical devices, either directly, or in-directly as supporting scaffolding.

Figure 24:
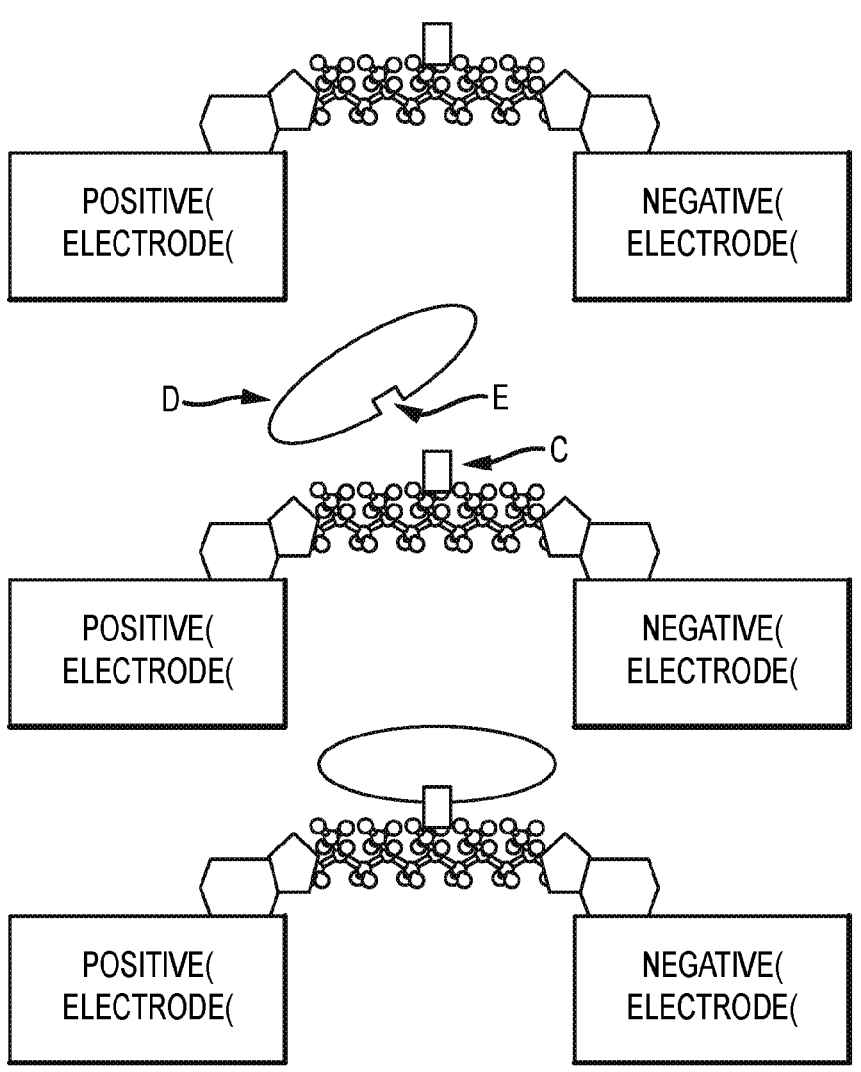
FIG. 24 illustrates use of an additional contact group "C" to specifically bind in additional molecular components "D" represented as an ellipse, with conjugate binding site "E" to the primary bridge molecule, in a series of assembly steps.
Figure 25:
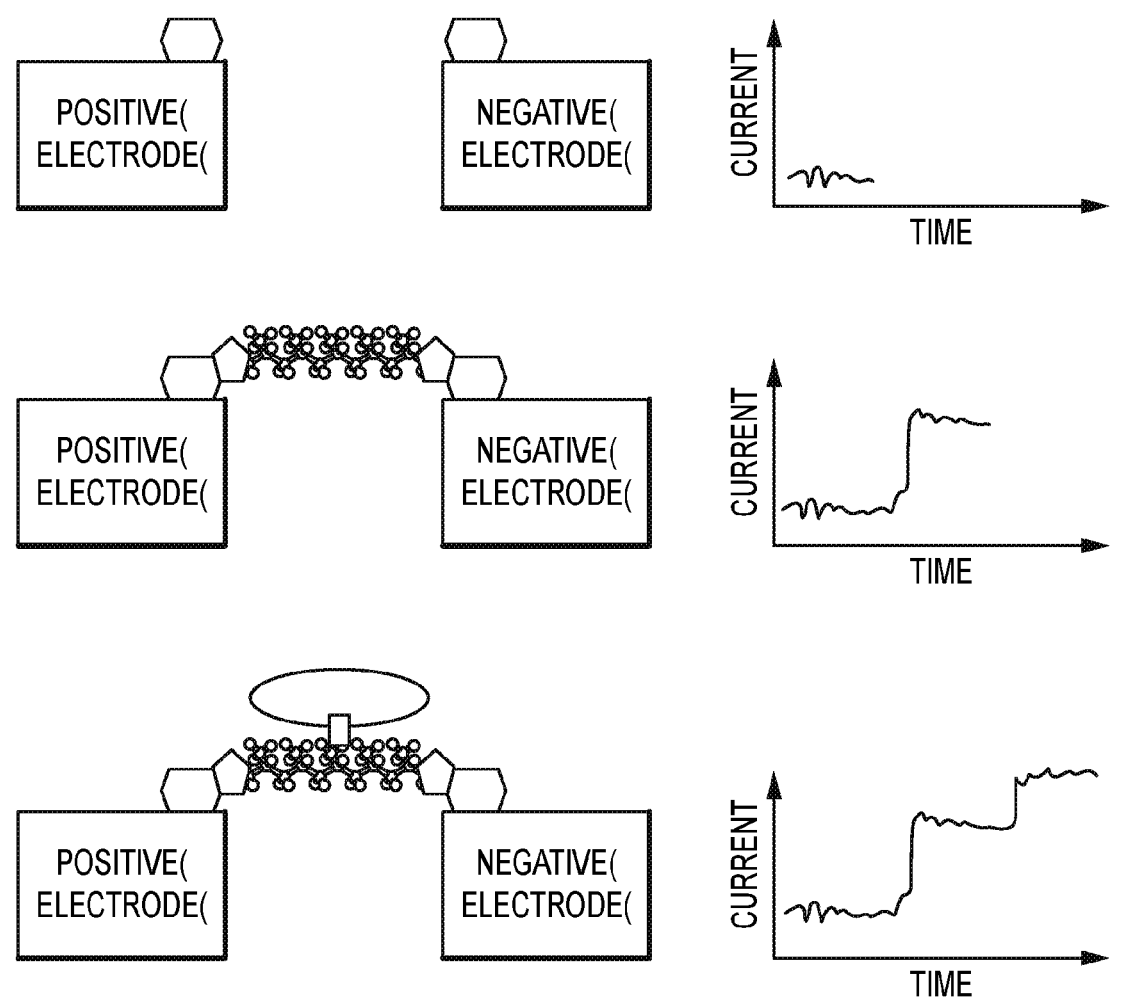
FIG. 25 illustrates how spikes in electrical current relate to each steps in the self-assembly of a sensor device.

Such a contact point/bridge molecule system may further have an internal contact where subsequent molecules can be attached to form more complex molecular constructs through a series of assembly steps that are most effective if carried out in situ. This series of assembly steps, directed by contact points on the electrodes and internal to the bridge molecule, is shown in FIG. 24. As shown in FIG. 24, an additional contact group "C" is used to specifically bind in additional molecular components "D" with conjugate binding site "E" to the primary bridge molecule, in a series of assembly steps. In particular, when performed in situ, these steps of assembly can be monitored electronically with the underlying circuit, to provide a means of knowing when/if proper assembly has been achieved. This assembly monitoring via the current internal to the device, is shown in FIG. 25. FIG. 25 illustrates how spikes in electrical current relate to each steps in the self-assembly of a sensor device. The ability to monitor the assembly is an advantage of the in situ assembly process combined with the current sensing properties of the underlying circuit. In general, the present example provides a system where, for given electrodes: (i) nano-contact points are established on the electrodes; (ii) conjugate specific binding groups are provided at two points of a bridge molecule capable of spanning the gap between contact points; (iii) an internal binding group is identified in the bridge molecule having a conjugate specific binding group; (iv) other molecular elements to be attached to the bridge have specifically attached the conjugate; (v) the series of binding events are performed in situ on the electrodes, including primary bridge binding and secondary molecule binding; and (vi) the binding events are monitored for completion by following the internal current in circuit under an applied voltage.

In particular, the contact points may be beads of a first material, deposited by any means of nano-fabrication on an electrode comprising a second material, such that material-specific binding can be used to direct the self-assembly.

Herein, dissimilar materials may be referred to as "material 1" and "material 2," for example.

In particular, the beads may be metallic, and in a preferred embodiment the beads are gold. In this case, the group on the bridge molecule can be any group containing a thiol substituent (—SH), or a sulfide group that can be reduced to a free thiol group (e.g. through activation, cleavage of a disulfide, or transiently), which will then engage on the specific, well known thiol-gold bonding.

In addition, there are well known short peptides that bond to gold, as well as other materials, including metals and semiconductor materials. Given such a peptide for contact bead material 1, the bridge can be any protein that bears two such peptide domains at two distinct "end" sites that can span the contact points. The peptide-material binding can then provide the specific contact point binding. In particular, if the bridge molecule is an engineered protein, it can have engineered into the linear sequence these peptides, preferably with linker groups that make the peptide more available for external binding. Preferred linker groups are glycine and serine rich peptide linkers, such as GS or GGGS (SEQ ID NO: 18). Such peptides can be engineered into two sites on a single chain that forms the protein bridge, or on multiple chains that may assembly to form a multi-chain protein.

One preferred embodiment consists of a specific system, wherein a gold bead is established as the contact material 1, which is different from electrode material 2. The gold is derivative with a cysteine-terminated peptide that further contains a spacer and linker, and is then terminated with a peptide antigen for which there is a specific Immuno-globin-G (IgG) Antibody, or any other antibody that has at least two identically binding arms. The cysteine will specifically bind to the gold, by thiol linkage. Then, the specific antibody to the peptide antigen can bind to form the bridge between the gold bead contacts. Furthermore, in this system, anti-IgG antibodies that are crosslinked to any other proteins, such as enzymes, can play the role of the specifically binding additional molecular component. For a specific preferred embodiment, the derivatizing peptide can consist of the CALNN (SEQ ID NO: 19)

peptide, with a GS-rich flexible linker, followed by the "FLAG-tag" antigen peptide (DYKDDDDK) (SEQ ID NO: 20), for example CALNNGSGSDYKDDDDK (SEQ ID NO: 21). This peptide has well-established anti-FLAG IgG antibodies commercially available, which in this specific context form a molecular bridge that will self-assemble against these gold-peptide contact points. If, for example, this is a mouse anti-FLAG antibody, then anti-mouse IgG, such as goat-anti-mouse IgG, will specifically bind the bridge, and can be crosslinked to any other protein that is desired to be coupled to the bridge.

Another preferred embodiment is where the contact point material comprises a gold bead, established by nanofabrication at the end of each electrode, and the bridge molecule comprises a double stranded DNA (dsDNA) molecule, that has thiol-groups integrated as modified nucleotides (thio-lated nucleotides) at the 5' and/or 3' ends of each single strand, such that there is one or two thiol groups at either end. Additional thiolated nucleotides could reside near the ends of the dsDNA, to provide for more thiol-gold linkages. This will preferentially self-assemble in the bridge molecule framework. In addition, a single biotinylated nucleotide can be specifically incorporated into the interior of the dsDNA, preferentially at the middle base of one strand. This provides a specific linkage site for a Streptavidin molecule (native or altered). The streptavidin can be crosslinked to any other desired protein, such as an enzyme, to form the secondary coupling molecule of this system.

Another preferred embodiment is that the contact point material comprises a gold bead, established by nanofabrication at the end of each electrode, and the bridge molecule be a protein alpha-helix molecule, that has cysteine amino acids at/near the amino and carboxyl termini, so that these can form specific thiol-gold linkages to the gold contact points. This will preferentially self-assemble in the bridge molecule framework. In addition, a single biotinylated amino acid can be specifically incorporated into the interior alpha-helix, preferentially at the middle base of one strand. This provides a specific linkage site for a streptavidin molecule (native or altered). The streptavidin can be cross linked to any other desired protein, such as an enzyme, to form the secondary coupling molecule of this system.

Another preferred embodiment is based on an IgG antibody as a bridge molecule. Such an antibody can be raised against an antigen, and any means of creating the contact point comprising the antigen will allow the associated IgG antibody to specifically bind the two contact points using the specific antigen-antibody binding of the two Fab arms on the IgG. Furthermore, in this system, anti-IgG antibodies that are cross linked to any other proteins, such as enzymes, can play the role of the specifically binding additional molecular component.

In a further preferred embodiment of this IgG system, the antibodies would be raised against gold nanoparticles, injected into host animals, preferably mouse or rabbit. The antibodies produced by such animals can have various forms of gold particle binding specificity, and can therefore play the role of the above IgG component, when the material 1 contact is a gold bead, sufficiently similar to the gold nanoparticles used for the vaccination. The specificity such antibodies have can be material specific (gold), as well as potentially size specificity, for the approximate size of the vaccination nanoparticle.

In a further preferred embodiment of this IgG system, gold nanoparticle in the 3 to 10 nm size range (diameter) would be used in the vaccination, and a distinct manufacturing process would establish gold bead contact points of comparable size on the electrodes.

In a further preferred embodiment of this IgG system, gold nanoparticle in the 3 to 10 nm size range (diameter) would be used in the vaccination, and animals are selected by testing their serum and/or isolated, purified IgG (e.g. via ELISA assay) for their binding response to a range of sizes of gold nanoparticles, so as to identify specific IgG sources that have specific affinity for either a size range of gold particles, or gold particles in general. These IgG then form bridge molecule systems for the associated gold contact points (size range specific, or gold bead in general).

In a further preferred embodiment of this IgG system, the animals identified as producing desirable IgG with contact-specific binding then undergo the hybridoma fusion process to produce a panel of monoclonal antibodies. Antibodies from the panel are then screened for their IgG binding properties, to select desirable monoclonals. These are then the preferred source for the IgG for a molecular bridge system. This provides a precise molecule with specific properties that can be mass-produced indefinitely.

In an alternative preferred embodiment of this approach to establishing an IgG system, the animals identified as producing desirable IgG with contact-specific binding then undergo B-cell receptor deep sequencing, to identify candidate DNA sequences for the underlying IgG variable domains, and desirable receptor sequences are cloned and expressed, and re-tested fro their gold particle binding activity, to obtain specific mono-clonal forms of the desirable IgG antibodies.

In a further preferred embodiment of this IgG system, IgG molecules are directly engineered from a starting template that has material binding peptides in the variable domains of the biding pockets. This could include inclusion of a cysteine amino acid, which has specific thiol-gold linkage, or could include a standard or novel gold binding peptide, preferably with a suitable GS-rich linker to enhance availability. Entirely engineered IgG would form a molecular bridge system with gold bead contacts. Alternatively, peptides that bind other materials can be used, compatible with contact points made from said material. In addition, methods of molecular screening, such as phage display screening, can be used to identify new such material binding peptides for use in the molecular bridge system, to further extend the type of materials that can be used for contact points, or improve the binding properties of given material contact points for the bridge molecule.

In an alternative embodiment of the IgG bridge systems above, the secondary binding molecule could be based on Protein A or protein G, instead of a cognate anti-IgG antibody.

In another embodiment, an enzyme can be engineered directly to form a primary bridge molecule in this system. This can be achieved by engineering the enzyme protein to carry material binding peptide domains or cysteine residues in the manner described above, and/or by engineering in the standard Spy-Catcher peptide conjugation system, with either Spy or Catcher domains on the protein, and the conjugate peptide comprising part of the contact point. In general, for the two connections to be made, combination of thiol-linkage, material binding peptides, and Spy-Catcher peptide couples could be sued to achieve the two attachment points, and even to define preferred orientations of the contacts, if two distinct contact point coupling systems are employed (e.g. thiol-gold linkage for one contact point, and a Spy-Catcher linkage at the other).

For all such molecular bridge systems, the preferred means of establishing the bridge composition is to do a series of in situ binding reactions, with active monitoring of the device current. Changes in current then identify the point at which discrete steps of assembly have been achieved: open circuit, primary bridge bound, secondary molecule bound. In a further preferred embodiment, a third electrode (buried gate) is used to apply a gate voltage, which can be used to further tune the observed current levels. In addition, in other embodiments, voltage spectroscopy/response to AC signals can be used to provide identifying fingerprints for the various conformations of the system during and after assembly.

In a further preferred embodiment, that gate and applied voltages can be used to "reset" the junction, by voltage-induced ejection of the bridge structure. Suitable high voltages/currents will in general rupture/degrade any molecular bride structures, partial or complete. This can be done in conjunction with a suitable "stripping buffer" that may have voltage inducible acidity or pH changes, or other voltage induction of local degrading factors from the solution.

Also, in certain embodiments, applied voltages (source-drain or gate) can potentially provide voltage-enhanced assembly, to accelerate or drive the assembly process.

In a further preferred embodiment, all the methods described above are compatible with creating large arrays of such molecular bridge systems. In his context, real-time monitoring of device current from individual devices in the array identifies which devices are well formed, and control over individual device voltages will, in certain systems, enable voltage directed or accelerated assembly, and voltage-directed resetting/re-initialization/stripping of devices.

In various embodiments, a system and process for creating molecular bridges comprises establishing nano-contact points on electrode ends; establishing conjugate binding groups at two points on the primary bridge molecule; optionally establishing an internal contact point within the bridge molecule and a secondary molecule with conjugate group for the internal contact point; and allowing self-assembly in a series of reactions, monitored by the current through the underlying circuit, to establish that discrete assembly events have indeed occurred. In various examples, the contact points are beads of a first material, material 1, the electrodes are of a different material, material 2, and the conjugate binding groups are groups having material 1-specific binding capability. For example, material 1 comprises a material specific binding peptide, and this peptide is used as the conjugate group.

In various embodiments, material 1 is gold, and the material specific binding peptide is one of the known gold binding peptides. In other aspects, material 1 is gold, and the conjugate group contains a thiol group, for gold-thiol linkage as the specific binding. Further, material 1 may be gold, and the material specific binding peptide is the amino acid cysteine, which is contained in the conjugate binding group.

In other embodiments, material 1 is gold, and the bridge molecule is double stranded DNA, with thiol-containing nucleotides present at both ends. Or, material 1 is gold, the bridge molecule is double stranded DNA, with thiol-containing nucleotides present at both ends, and there is an internal biotinylated nucleotide, and the secondary molecule is streptavidin (native or mutated), optionally cross-linked to an additional protein, in particular an enzyme, in particular, polymerase. In other aspects, material 1 is gold, and the bridge molecule is an alpha-helix protein containing cysteine at or near both termini to provide the material specific binding via the gold-thiol linkage.

In various embodiments, there may be an internal biotinylated amino-acid, and the secondary molecule is streptavidin (native or mutated), optionally cross-linked to an additional protein, in particular an enzyme, in particular, polymerase. Material 1 may comprise an antigen for a specific IgG antibody, A, wherein A forms the bridge molecule by specific binding to the antigen.

In other examples, an anti-A anti-IgG antibody, cross-linked to another protein, in particular, an enzyme, in particular, a polymerase, forms the secondary molecule of the system. In these IgG systems, material 1 may be a gold bead, established by a nano-manufacturing process, derivatized with a peptide that has a cysteine group at one end, and includes a peptide antigen with specific IgG antibody, A. The derivatizing peptide may consist of CALNN (SEQ ID NO: 19), with a GS-rich spacer of 0 or more amino acids, followed by the FLAG-tag peptide antigen, and the antibody A is [host]-anti-FLAG IgG, and the secondary binding molecule is anti-[host]-IgG, where [host] is any of the standard antibody host animals, and particularly mouse, goat, rabbit, and the secondary IgG is optionally conjugated to any other protein, in particular an enzyme, and in particular, a polymerase.

The bridge molecule may be an IgG antibody raised by vaccinating host animals with nanoparticles of material 1, and this material 1 specificity is the basis for the bridge binding. In this system, the secondary molecule is a cognate anti-IgG, which can be optionally cross linked to another protein, specifically an enzyme, specifically polymerase. Alternatively, the secondary molecule could be Protein A or Protein G, which specifically bind IgG, optionally cross-linked to another protein, specifically an enzyme, specifically polymerase. Material 1 may be gold, and the antibodies raised by vaccination of host animals with gold nanoparticles. For example, gold nanoparticles in a 3 nm to 10 nm size range, and in particular, in host animals of mice or rabbits, and in particular, where antibodies undergo preselection based on their binding profile against a range of sizes of gold nanoparticles.

Antibodies may be produced as monoclonal antibodies derived from host animals selected to have good antibody binding response, and further selected to have good binding response against a gold bead contact manufactured by a given nano-manufacturing process.

Antibodies may be engineered, based on B-cell receptor sequencing and cloning, from animals selected to have good antibody binding response, and with clones further selected to have good binding response against a gold bead contact manufactured by a given nano-manufacturing process.

In some examples, the bridge molecule may be a synthetic protein engineered on a IgG template, with specified amino acid sequences in the variable domains of the Fab binding pockets, such sequences comprising material 1-binding peptides, in conjunction with GS-rich peptide linkers. The secondary binding is provided by a cognate anti-IgG antibody, possibly cross-linked to another protein, particularly an enzyme, and particularly a polymerase. For such engineered proteins, for an alternative approach to secondary binding, it is further possible to engineer in the secondary contact site in the form of a specific binding peptide, that can bind to conjugate peptides in other engineered proteins, especially engineered enzymes, and especially engineered polymerases, and specifically using the Spy-Catcher peptide conjugation system in this fashion (with Spy or Catcher peptide engineered into the IgG template). Material 1 may be gold, and the material specific peptides engineered into the binding pockets may comprise Cysteine's, gold-binding peptides, in conjunction with GS-rich linkers and spacers.

In various embodiments, the primary bridge molecule may comprise a protein, preferably an enzyme, preferably a polymerase enzyme, that has been engineered to directly include binding groups conjugate to contact points into its linear protein sequence, or the sequence of its composite chains if it is a multimeric protein.

Contact points may include Spy or Catcher domains, and the protein may include the conjugate peptides, and the Spy-Catcher peptide conjugation system provides the coupling to the contact points. The contact material may be gold, and the protein contains cysteine amino acids or gold binding peptides as binding groups, in conjunction with GS-rich linkers, to provide the coupling to the electrode contact points.

In various embodiments, a gate voltage is used to provide another voltage control in the process monitoring aspect. For example, the gate voltage and an applied source/drain voltage are used to perform voltage spectroscopy, I-V characterization, or AC-signal response to further characterize the stages of construction and resulting molecular bridge configurations, and to identify well-formed structures. The gate voltage and applied source/drain voltage are used to accelerate bridge formation, and to eliminate improperly formed bridge constructs.

In various examples, molecular bridge constructs may be disposed in large arrays, such as on an array of electrodes, including identification of well-formed sites, and resetting/
stripping/re-initializing sites with voltage directed sensing
and actuating.

Herein in EXAMPLE 6, FIGS. 26 through 34 show
experimental results for the above embodiments, discussed
in more detail below. A first group of figures shows various
types of bridge molecules binding/bridging on test arrays of
gold contact dot pairs, via thiol-gold directed binding. This
covers DNA, peptide and antibody bridges. The next group
of figures shows binding/bridging to the electrodes with gold
contact dots or targets via thiol-gold directed binding, with
results assessed by both imaging and electrical measure-
ments.

FIGS. 26 through 34 further provide: Binding Test Array:
dsDNA bridge; Binding Test Array: dsDNA bridge,
improved binding; Binding Test Array: peptide alpha helix
bridge; Binding Test Array: IgG Antibody bridge; Schematic
of Test setup for electrical bridge/binding measurements;
Test electrodes with gold dot contacts; Electrical Signals of
bridging and molecular assembly; Electrical Signals of
bridge molecule binding with imaging; and Image of an
electrode with labeled bridge in place.

Figure 26:
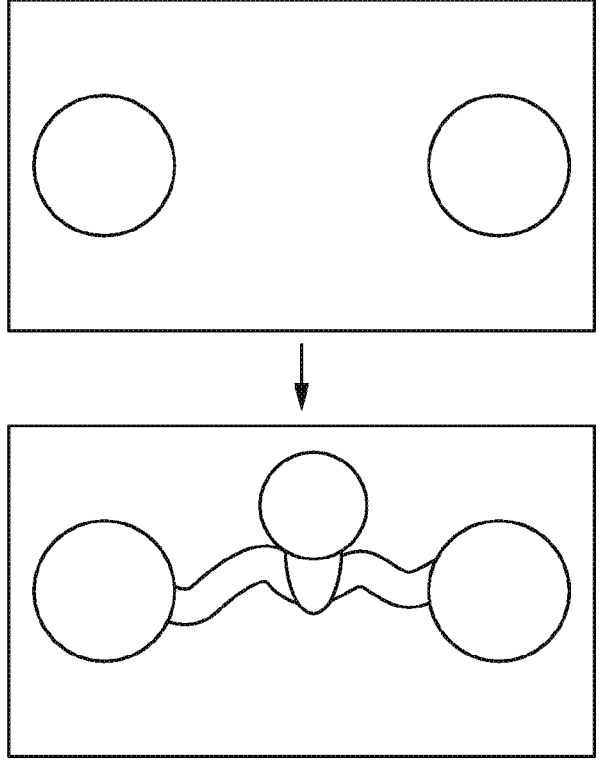
FIG. 26 is a diagrammatic representation of ideal images of bridged contacts (green box) and un-bridged contacts (red box)
Figure 27:
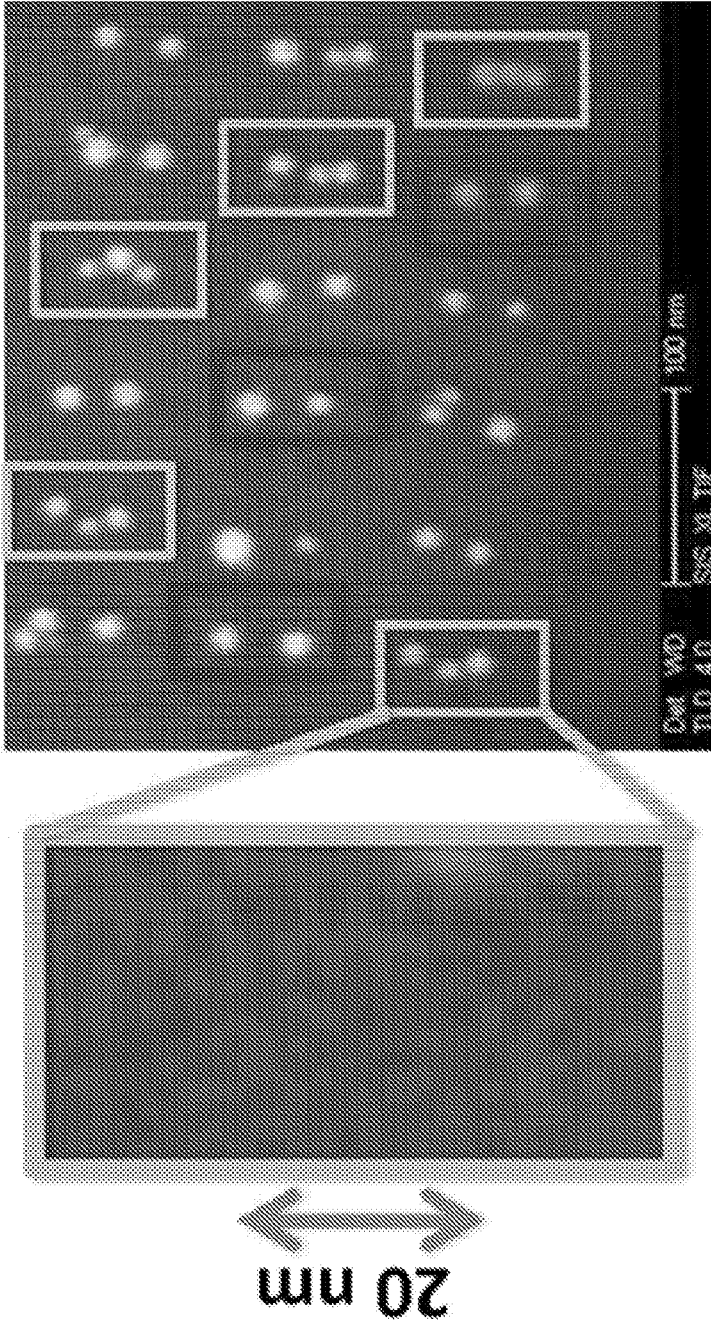
FIG. 27 is an electron microscope image of a substrate after bridging reactions and labeling reactions. Green squares highlight contacts having a well formed bridge.

With reference now to FIG. 26, diagrammatic represen-
tations of ideal images of bridged contacts (green box) and
un-bridged contacts (red box) are illustrated. In FIG. 27,
double stranded DNA molecules were used to form bridges
between gold-dot contact points. In this example, the bridge
molecule is a double stranded DNA molecule 20 nm in
length (60 bases), with thiol groups on the 5' ends of each
strand for thiol-gold binding to contact dots. Gold dots are
formed via e-beam lithography on a silicon substrate. The
DNA bridge has a biotinylated base 30 on one strand, for
binding of a biotin-gold label to allow electron microscope
imaging of the labeled bridge. FIG. 27 shows the EM image
of the substrate after bridging reactions and labeling reac-
tions. Green squares highlight contacts having a well formed
bridge.

Figure 28:
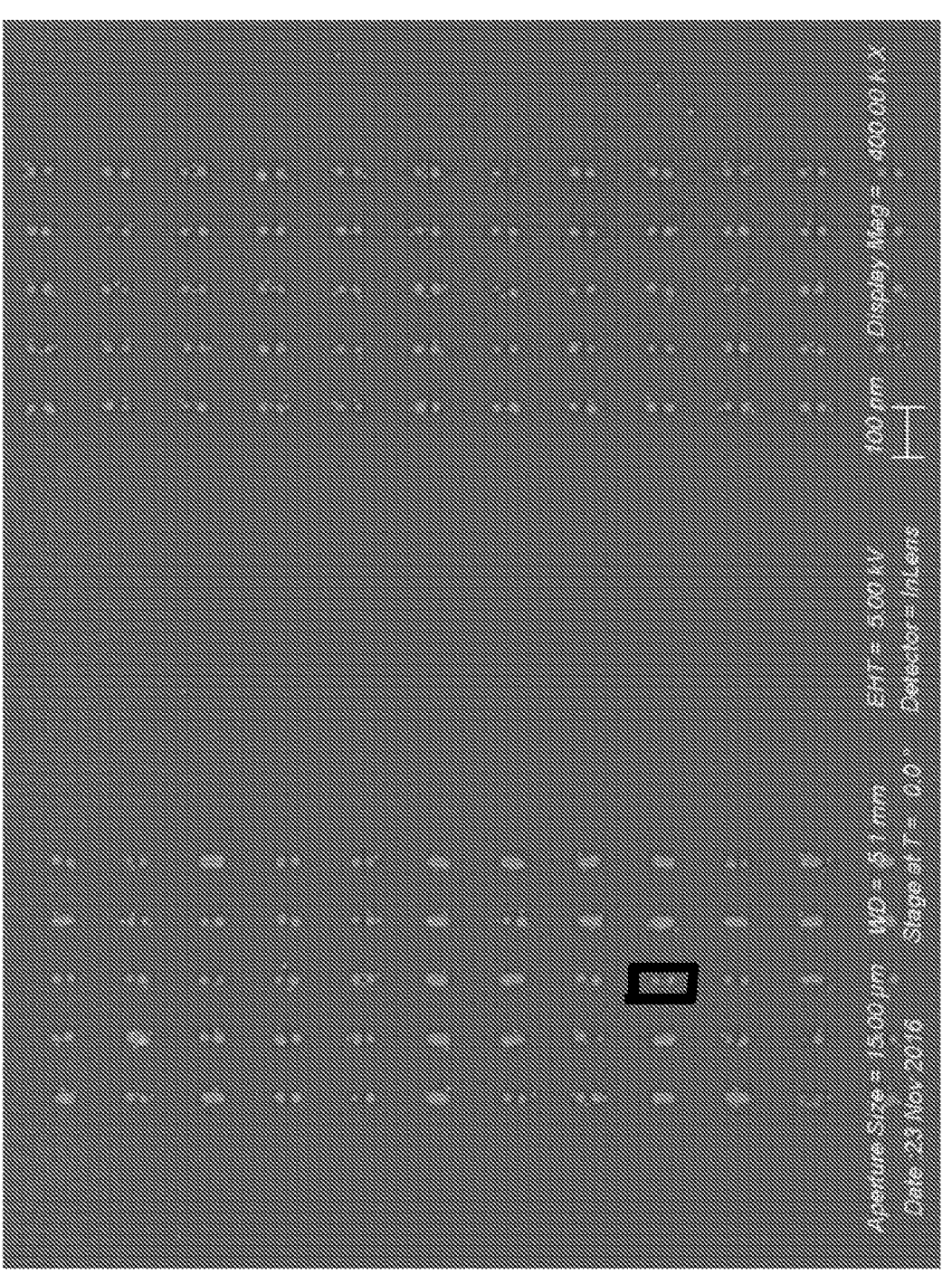
FIG. 28 is an image of higher efficiency 20 nm double-stranded DNA bridge-binding to an array of gold contact points. Bridges are labeled with a small gold dot for imaging purposes. Green squares highlight examples of well-formed bridges. Higher levels of binding to gold contact points, and bridge, due to deposition in a high salt buffer solution (bridge reaction conditions: 1 µM bridge concentration incubated with binding array for 1 hour in a 5×TBS buffer)

FIG. 28 is an image of a higher efficiency 20 nm double-
stranded DNA bridge binding to an array of gold contact
points. Bridges are labeled with a small gold dot for imag-
ing. Green square highlights on well-formed bridge
example. Higher levels of binding to gold contact points,
and bridge, are due to deposition in a high salt buffer
solution, (bridge reaction conditions: 1 μM bridge concen-
tration incubated with binding array for 1 hour in a 5×TBS
buffer).

Figure 29:
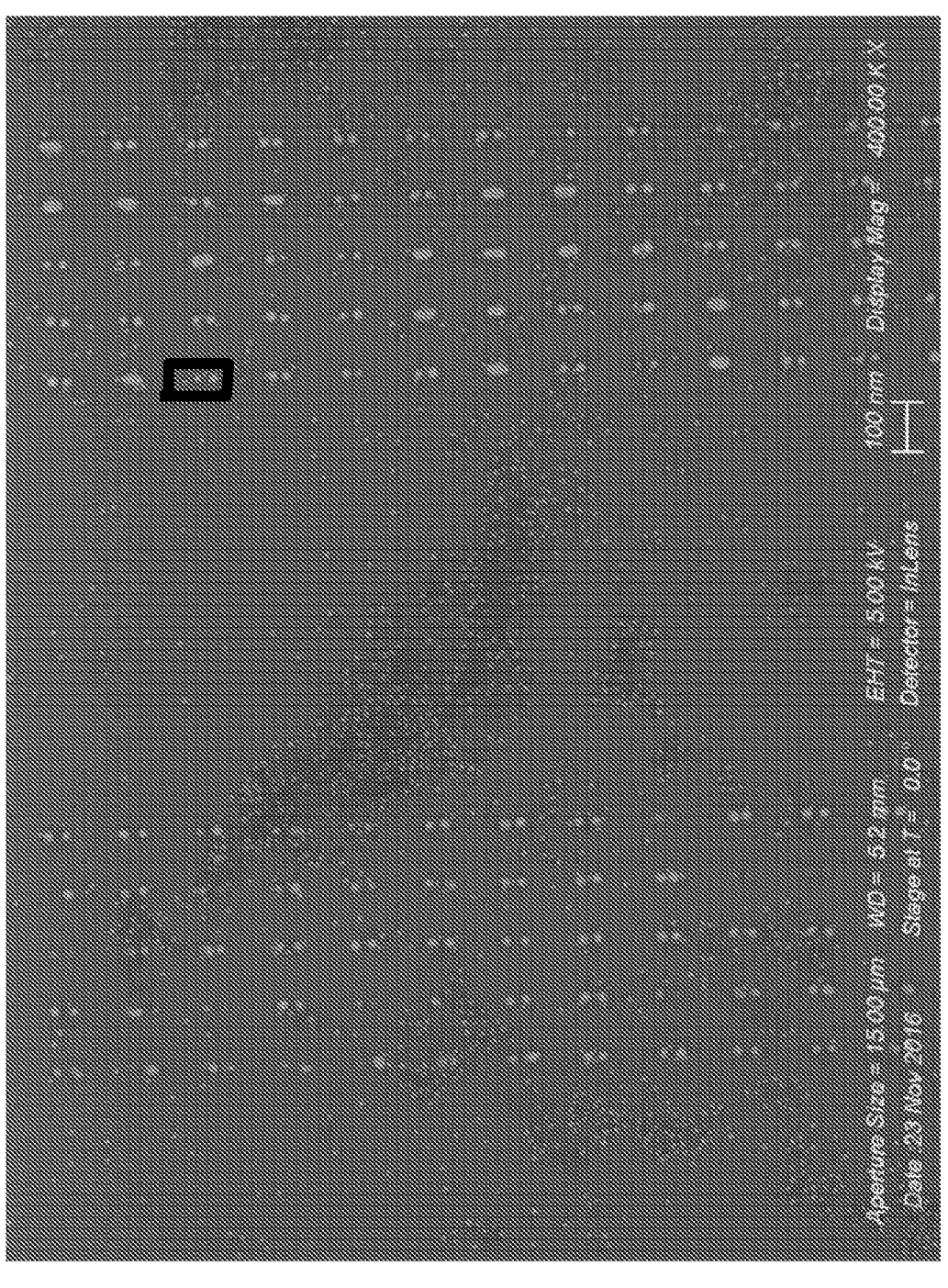
FIG. 29 is an image of alpha-helix peptide bridge binding to test array of gold dot contact points.

FIG. 29 is an image of an alpha-helix peptide bridge
binding to test array of gold dot contact points. The bridge
molecule is a peptide alpha-helix 10 nm in length, with
cysteine amino acids at the termini for thiol binding to gold
via thiol groups of the cysteines. Bridges are labeled via an
internal lysine-biotin, labeled with streptavidin-gold bead.
Not many of the contact gold dots have a bound bridge, and
many pairs of gold dots have a bridge located between the
dots, consistent with a dot-to-dot bridge. For this experi-
ment, peptide bridging reaction conditions were: 1 μM
bridge concentration incubated for 1 hour in 1×PBS buffer.
Green square highlights on well-formed bridge example.

Figure 30:
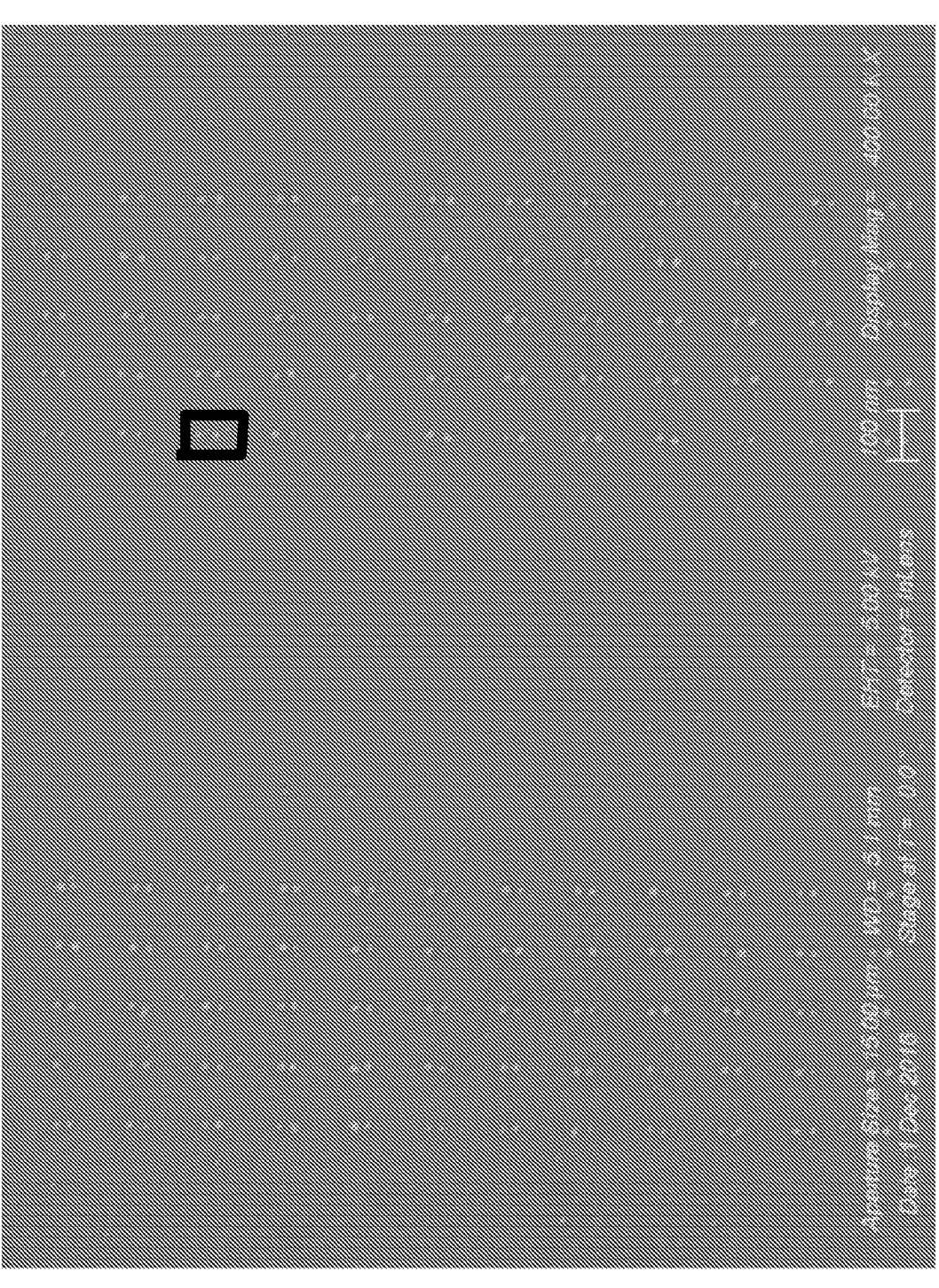
FIG. 30 is an image of IgG antibody bridge binding.

FIG. 30 is an image of IgG antibody bridge binding. Gold
dot contact arrays are first derivatized with the CALNN
(SEQ ID NO: 19)-FLAG-tag peptide, via cysteine/thiol-gold
binding. Anti-FLAG tag IgG is bound to the FLAG-tags, via
specific affinity binding. Antibody location is labeled for
imaging using a gold-dot-Protein-A label that binds to the
IgG constant domain. FIG. 30 shows anti-IgG bound to gold
contact/CALNN (SEQ ID NO: 19)-FLAG. Several dot pairs
show antibody located between dots, suggesting complete bridge formation, with the IgG arms spanning the dots.
Green squares highlight well-formed bridge examples.

Figure 31:
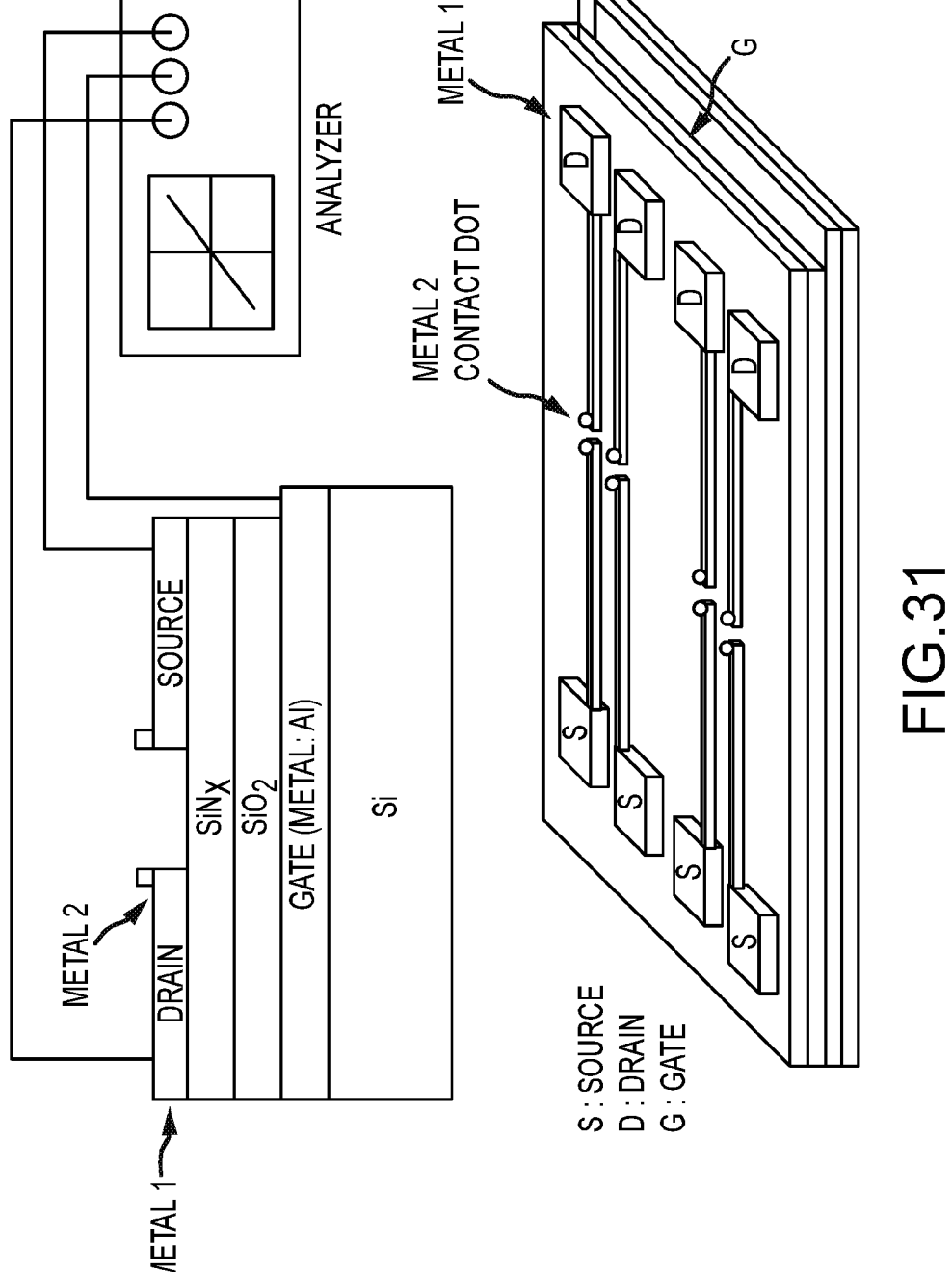
FIG. 31 illustrates a schematic of test set-up for electrical measurements on bridge molecules.

FIG. 31 illustrates a schematic of a test set-up for elec-
trical measurements on bridge molecules. In the upper
portion of the figure is illustrated a cross section of the
electrode-substrate structure, and attachment to analyzer for
applying voltages and measuring currents through the bridge
molecule. In the lower portion of the figure, a perspective
view of electrode array for bridging circuits is illustrated.
Each pair of electrodes has Metal-2 contact points on
Metal-1 electrodes.

Figure 32:
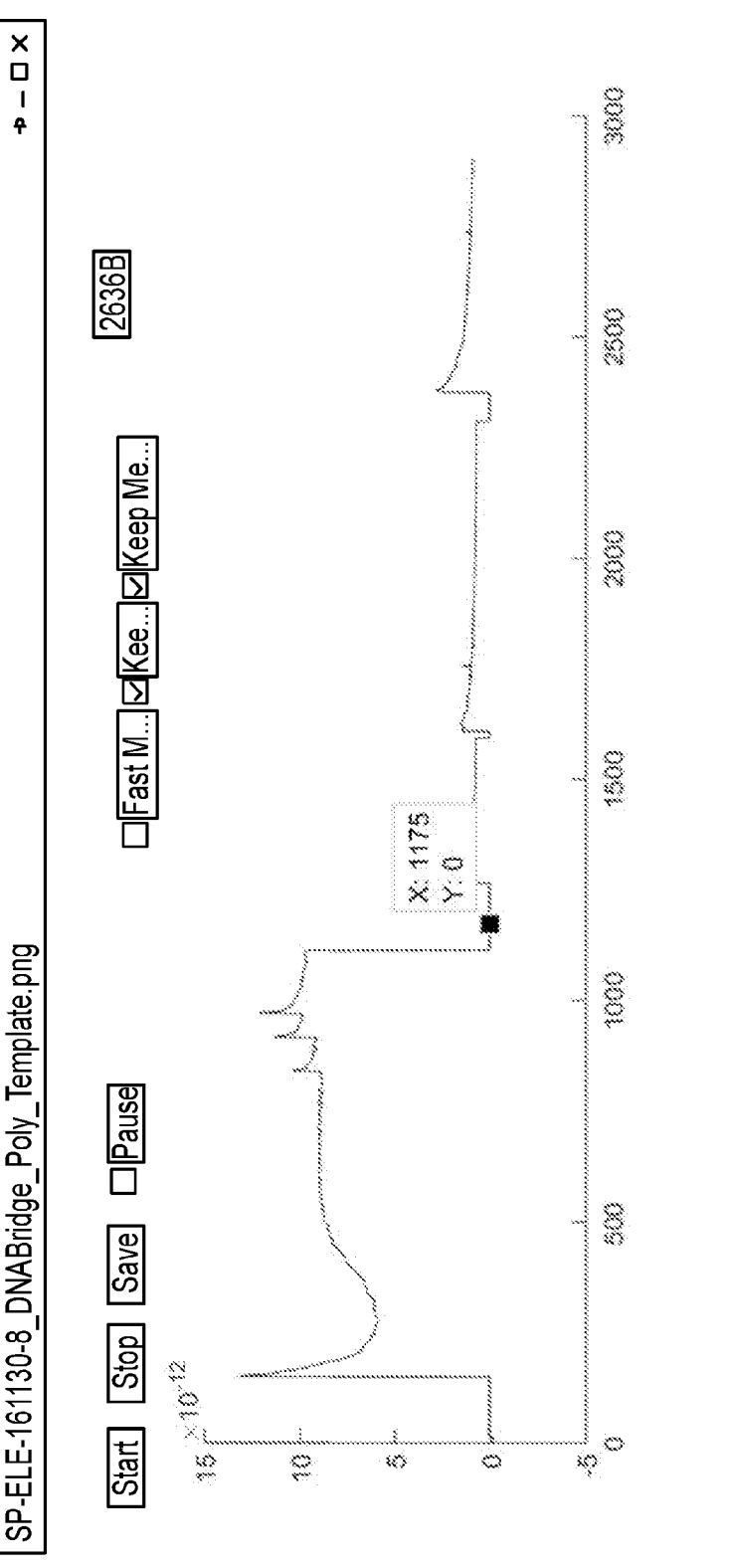
FIG. 32 illustrates a plot of current vs time showing three spikes indicative of bridge-electrode binding events.
Figure 33:
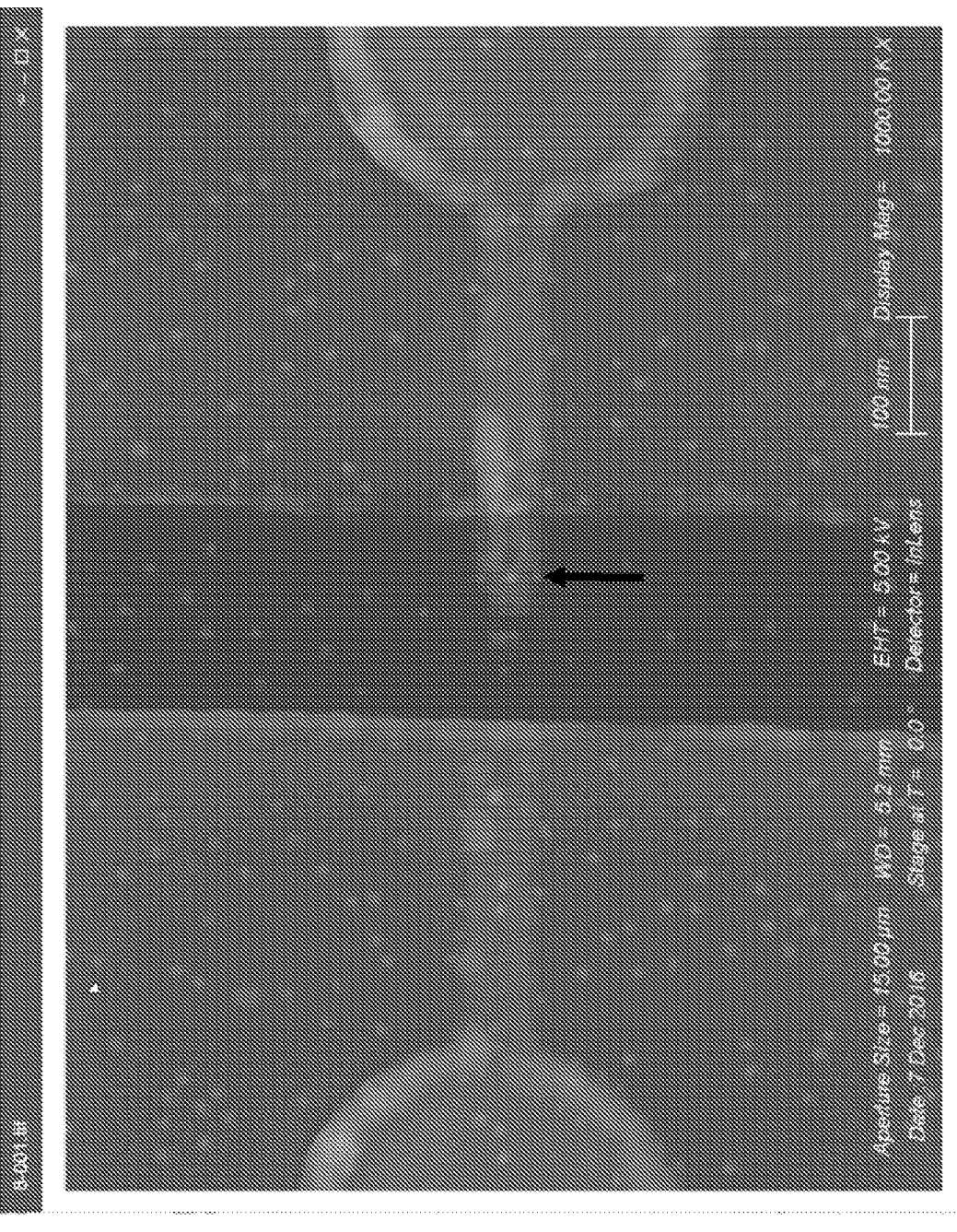
FIG. 33 is an EM image of labeled bridges.

FIGS. 32-33 illustrate electrical signature of bridge mol-
ecule binding. In FIG. 32, Current vs time shows three
spikes, indicating bridge-electrode binding events. FIG. 33
is an EM image of labeled bridges, for same electrode,
showing three bridges bound to right-most electrode (green
arrow), in agreement with the three signal spikes observed.
These do not bridge the electrode gap, but show that binding
of the bridge molecule even without spanning electrodes can
produce a detectable electrical signal.

Figure 34:
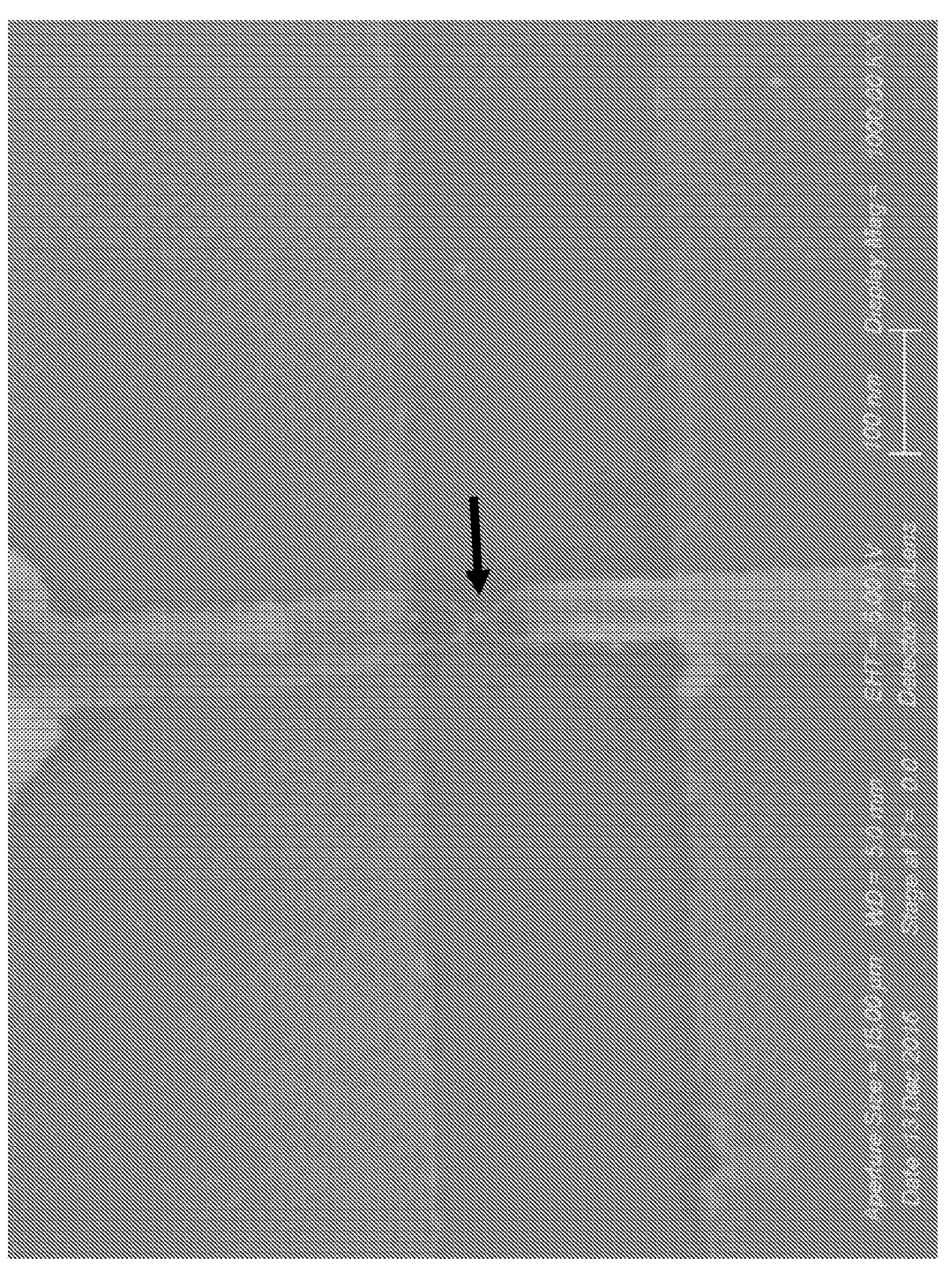
FIG. 34 is an EM image of dSDNA bridging of gold electrodes.

FIG. 34 is an EM image of dSDNA bridging of gold
electrodes. A 20 nm dsDNA bridge with thiol groups on 3'
and 5' end of one strand is shown bound as a bridge between
gold-coated electrodes (green arrow). The bridge is labeled
with a gold dot at a central biotinylated base via a gold-dot-
streptavidin label. Electrodes have a 15 nm gold layer on a
5 nm chromium substrate, on silicon. Surface is passivated
by a silicon oxide layer, with open region 20 nm wide to
expose gold surface of electrodes for bridging (dark hori-
zontal band is exposed region, no silicon-oxide covering).

Example 7

Introducing Nano-Contact Points on the Electrodes

This example demonstrates new methods of manufactur-
ing for preparing beads on a substrate, such as an electrode,
with precise location, shape and size. A key novel feature of
these methods is that they provide a way to position beads
on a substrate that are smaller in diameter than the basic
pattern features of the pattering methods used in the process.

This example concerns nanoparticles that are to be
deployed on a solid substrate, with precise position and
small size. One preferred application is the use of nanoscale
material particles as "contact points" on a substrate, in order
to spatially localize the following types of events to well
defined, desirable locations at the nanometer scale, particu-
larly mechanical connections, electrical connections, and
self-assembly.

One possible need for this was discussed above and
illustrated in greater detail in FIG. 22 in the context of
creating a desired molecular scale circuit. Here a molecular
element is to be connected between two electrodes. This is
a common problem in the field of molecular electronics.

One preferred way to solve this problem is to introduce a
highly localized, precisely positioned, material particle,
referred to herein as nano "contact points," which serve
some or all of the needs of guiding self-assembly, and
providing mechanical and electrical connection. The use of
such a contact point is discussed above and illustrated in
FIG. 23, wherein element "A" is the contact point. For this
purpose contact point is made of a suitable material that
selectively binds the target molecule, is highly spatially
localized, and is precisely located at a desired position.

The key properties of the nano-particle required for this
application are (1) that it is highly spatially localized (must
be "small" or "point-like"); (2) that it has a precisely pre-defined specified location; and (3) that it be made of the appropriate material to support its functional role.

The same properties have broader utility than just the example of circuit construction shown here. For example, in the area of plasmon resonance devices, where the nanoparticle interaction with electromagnetic energy is a critical concern.

It is generally challenging to efficiently fabricate nanoscale beads that have a desired small size and precise location on a substrate. Standard methods of nanoscale lithography or milling can be used to create a disk of a desired material on a substrate, with shape and diameter of the disk set by the primary patterning process. These include well-known patterning methods such as e-beam lithography, photo lithography, UV lithography, Extreme-UV lithography and imprint lithography, as well as ion beam milling, combined with various material deposition methods such as sputtering or vapor deposition. The foremost limitation of this standard approach is that the diameter of the material disk is set by the patterning process, and the minimum resolution of the patterning process may not be small enough to provide the desired nanoscale bead size. This is especially the case if the desired bead has a diameter below 10 nm, which is near or beyond the resolution limits of most modern optical, UV or e-beam lithography systems, or ion beam milling systems. The present invention is a means for using these standard, efficient patterning methods to manufacture precisely positioned beads on a substrate, wherein the beads are smaller in diameter than the resolution limit of the primary patterning process. These beads are also precisely positions, with precisely defined shapes.

Figure 35:
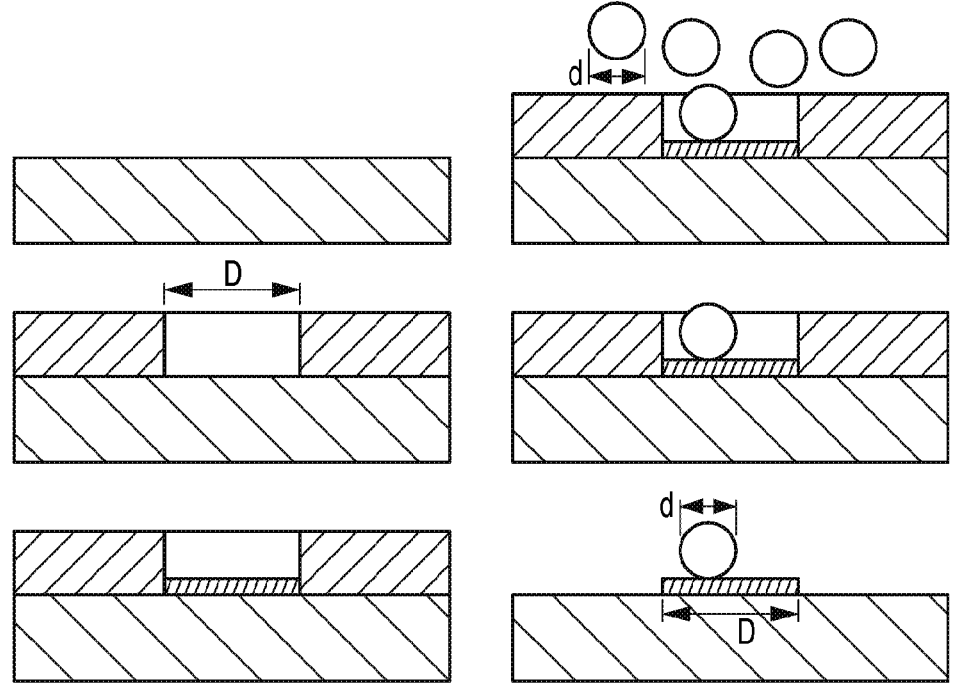
FIG. 35 illustrates the steps of process (1) used to manufacture a small bead at a desired location. Beginning from the upper left in the figure, a layer of resist (grey) is pattered on a substrate (blue), with an open disk of diameter D. Then a layer of adhesive (green) is deposited into the disk. Then a solution of pre-made beads, fabricated by standard means is exposed to this, where the beads have diameter d such that steric hindrance allows only one bead per adhesive disk. After removal of resist, what remains is a bead of diameter d, positioned near the center of the adhesive disk, but of a size smaller that the disk diameter D.
Figure 36:
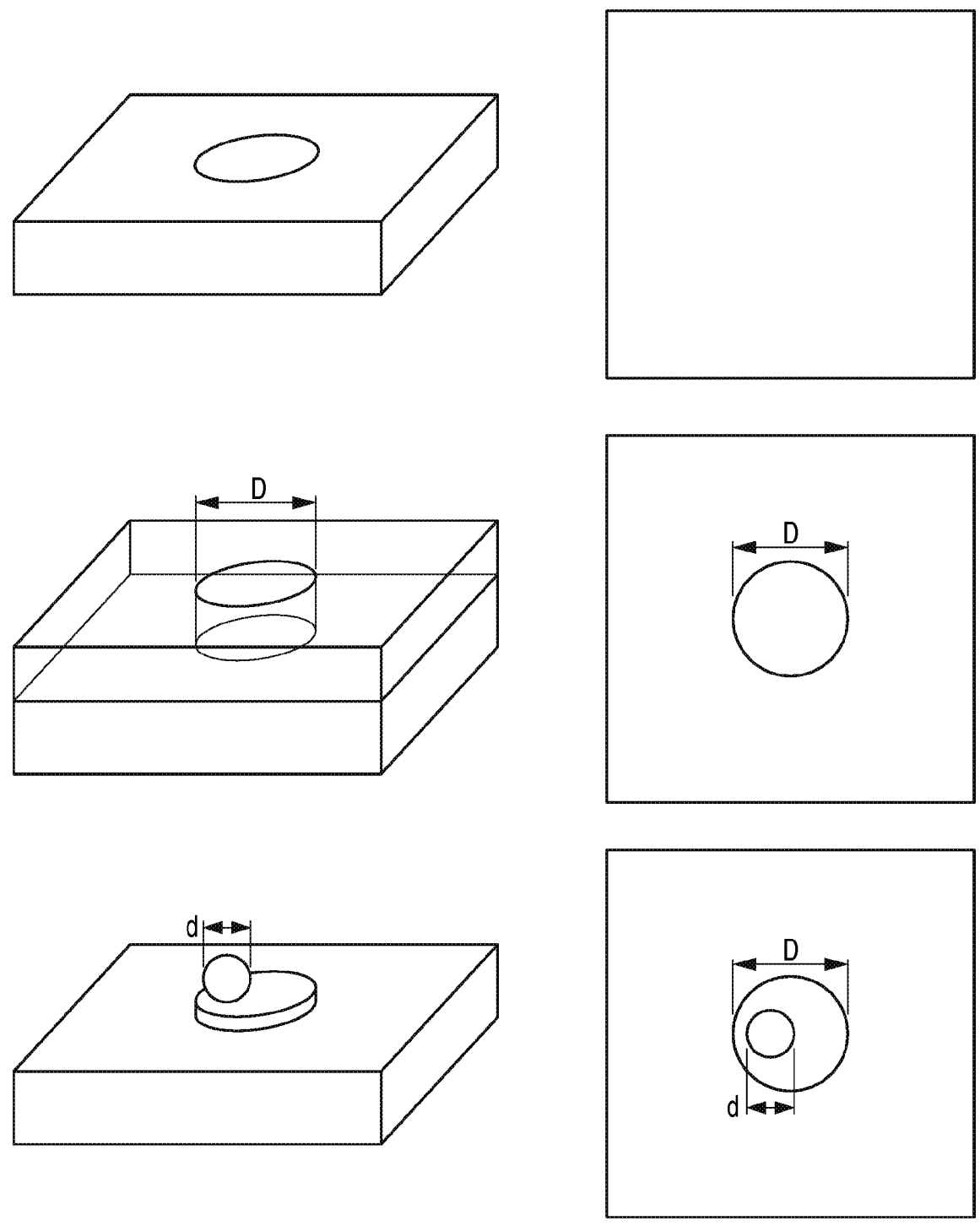
FIG. 36 illustrates the steps of process (1) for establishing a small bead from FIG. 35, shown in 3D perspective and overhead views. Starting from a substrate, standard patterning and deposition methods are used to deposit an adhesive disk of material of diameter D into a pattern rendered in a resist coating (grey). Exposure to beads and removal of resist results in a bead attached to the adhesive patch, and steric hindrance allows for only one bead per adhesive disk. Thus, this process established a bead in a desired location, with a diameter smaller than what is dictated by the patterning process. In particular, this allows manufacture of contact points at resolution exceeding that of the patterning method.

This example teaches three exemplary methods of manufacturing beads of precisely controlled size, shape and location, which are substantially smaller in diameter than the minimum feature size of the primary pattern generation method used in the process. The methods are as follows:

The first method, referred to herein as "process (1)," is illustrated in FIGS. 35 and 36. The first method consists of patterning a disk into a protective resist layer by a standard patterning method. This step results in a protective resist layer, in which the desired disk region on the substrate is exposed. This is followed by a deposition process to deposit an adhesive material, which can again be done by standard deposition or coating methods, depending on the chemical nature of the adhesive material. The adhesive material should be capable of binding to the substrate, and also to the bead material. This is then exposed to a solution contained the desired beads, previously fabricated by standard means of making bulk quantities of nano-particles (such as colloidal suspensions), which can then bind in place on the adhesive disk. If the beads are large enough, and at low concentration, physical size constraints (commonly known as "steric hindrance") will allow at most one bead to bind at the disk. Then the resist is dissolved way, leaving the attached bead. As an alternative embodiment, the resist can be removed first in this sequence of steps, although its presence helps restrict additional beads from accessing the adhesive region, once a primary bead is in place, so the former approach is a preferred embodiment. The adhesive may be permanent in this processes, or, in an alternative embodiment, it could be a transient aspect of the procedure, to be removed by dissolution, leaving the bead in place, perhaps in conjunction with addition process steps that bind the bead to the substrate. In any case, note that in particular, this bead can be smaller in diameter than the disk itself, and is otherwise positioned near the center of the adhesive disk.

In particular, a bead that has half the diameter of the disk would provide the appropriate size exclusion so that only one bead may bind per disk.

FIG. 35 illustrates steps of process (1) used to manufacture a small bead at a desired location. Beginning from the upper left portion of FIG. 35, a layer of resist (grey) is patterned on a substrate (blue), with an open disk of diameter D. Then a layer of adhesive (green) is deposited into the disk. Then a solution of pre-made beads, fabricated by standard means is exposed to this, where the beads have diameter d such that steric hindrance allows only one bead per adhesive disk. After removal of resist, what remains is a bead of diameter d, positioned near the center of the adhesive disk, but of a size smaller that the disk diameter D. This process is depicted in 3D for greater clarity in FIG. 36, showing both perspective and overhead views of key elements of process (1).

The second method, "process (2)," is illustrated in FIGS. 37, 38, 39A and 39B. Starting from a substrate, any standard patterning method is used to pattern a rectangular region, of width W, longer than it is wide, and any standard deposition method is used to deposit a solid-phase, thin layer of the desired bead material, M, of some thickness, into this rectangular pattern. This configuration is then annealed using a suitable annealing process, which will allow the system for evolve towards a configuration of minimal energy. Under appropriate conditions, this will cause the deposited material strip to break up into beads under the action of surface tension, forming a row of smaller diameter beads, which collectively contain the same volume of material. The resulting beads of material M have smaller diameter than the width W of the strip, and are still precisely centered near the same centerline. The bead-to-bead spacing will be statistically similar, and again this spacing can be substantially larger than the bead diameter. The final step of this process is intended to result in just a single exposed bead near a preferred end of the original strip.

Two alternative embodiments of such a process for achieving this are:

(a) protect the bead nearest the end of the strip with a deposited layer of removable material/resist patterned by a standard patterning method, then wash away all other beads, then expose the protected bead to reach the desired single exposed bead near the end of the initial strip; or (b) deposit, with standard patterning and deposition methods, a layer that cover the beads except that nearest the end of the strip, again leaving exposed only a desired bead nearest the preferred end of the strip.

By either means, a single exposed bead, nearest the referred end of the strip, remains. This bead will also have a precisely defined shape, which can be nearly spherical but in general is defined by the bulk and surface interaction energies of materials involved and the annealing process. Annealing is typically performed by immersing the system in a suitable ambient medium (which in preferred embodiments may be a vacuum, or air, or inert gases such as nitrogen), and then elevating the temperature of the system for a period of time. In order for this bead-up process to occur, the deposition material, substrate material, and ambient medium must have suitable physical properties. The preferred embodiment would have the following properties: (i) the material-substrate surface tension exceeds the substrate-ambient surface tension; and (ii) the material will anneal or melt at a temperature that does not disrupt the substrate.

Under these favorable conditions, upon heating to a suitable annealing temperature, typically well below the melting point, the material will become mobile and, allowing suitable annealing time to pass, the material will break up into a row of beads under the action of surface tension, generally forming much smaller, rounded beads. The bead will be nearly spherical if there is a very large surface tension between the material and substrate, and otherwise shaped according to the surface tension forces. The diameter of this bead, d, will be smaller than the width of the initial deposition pattern, W. Thus, this process achieves a contact point of diameter d, substantially smaller than the limits of the initial patterning process. This bead location will remain centered near the center of the original spot, as well, thus also retaining precisely specified position while enhancing the spatial localization. Another key, novel advantage of this process is that the resulting bead has a well-defined shape, even if the initial deposited material layer has irregularities, because the final bead shapes are defined by the surface tension forces, not the initial deposition pattern.

Figure 37:
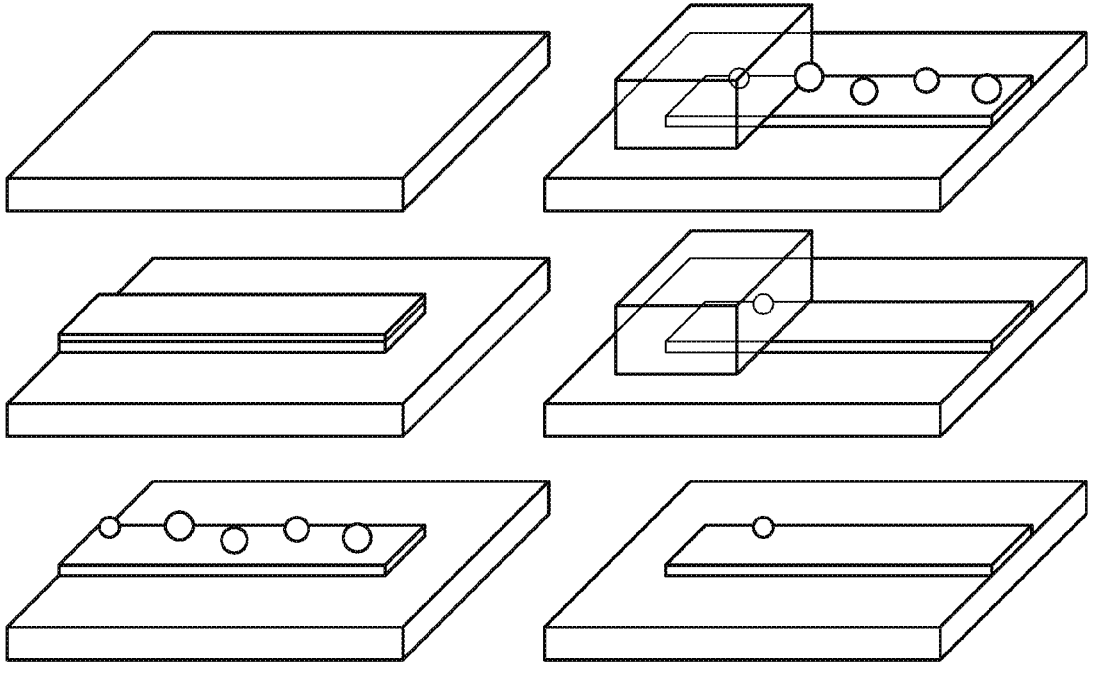
FIG. 37 illustrates the steps of process (2) embodiment (a): Beginning from the upper left, deposition of a rectangle of bead material (gold) of width W on a suitable substrate (blue), which, upon annealing, and under the action of surface tension, breaks up into a line of beads. Then, a protective layer of removable resist (red) is patterned and deposited, protecting region that would contain a single bead. The remaining beads are removed, and then the resist is removed, leaving a single bead near a preferred end of the original rectangle of material.
Figure 38:
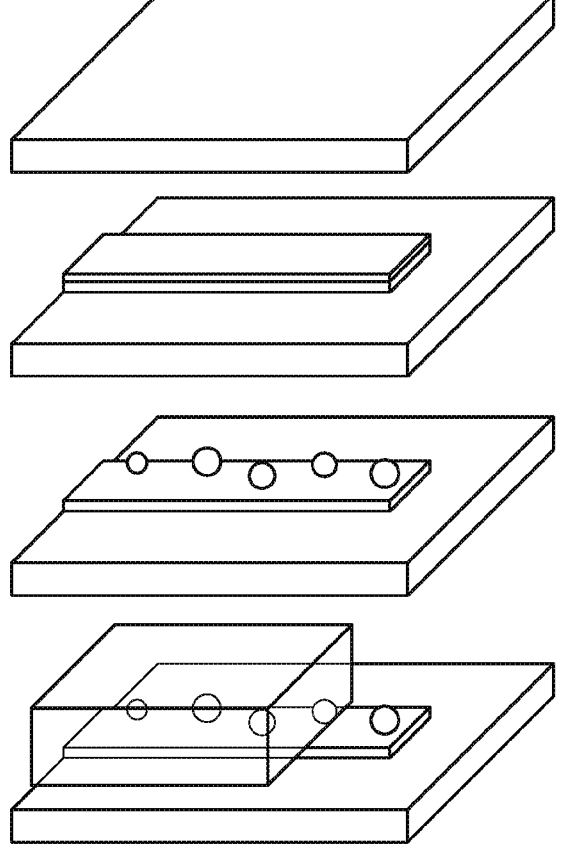
FIG. 38 illustrates an alternative embodiment, b, of process (2), where, in contrast to that shown in FIG. 37, the final deposited layer (red) is used to cover the un-wanted beads, leaving only the bead at the preferred end exposed and available for use in the greater nano device.

This second method is captured in FIGS. 37, 38, and 39A-B as follows:

FIG. 37 illustrates the steps of process (2) embodiment (a): beginning from the upper left of the figure, deposition of a rectangle of bead material (gold) of width W on a suitable substrate (blue), which, upon annealing, and under the action of surface tension, breaks up into a line of beads. Then, a protective layer of removable resist (red) is patterned and deposited, protecting region that would contain a single bead. The remaining beads are removed, and then the resist is removed, leaving a single bead near a preferred end of the original rectangle of material. FIG. 38 illustrates an alternative embodiment, b, of process 2, where, in contrast to that shown in FIG. 37, the final deposited layer (red) is used to cover the un-wanted beads, leaving only the bead at the preferred end exposed and available for use in the greater nano device.

Figure 39A:
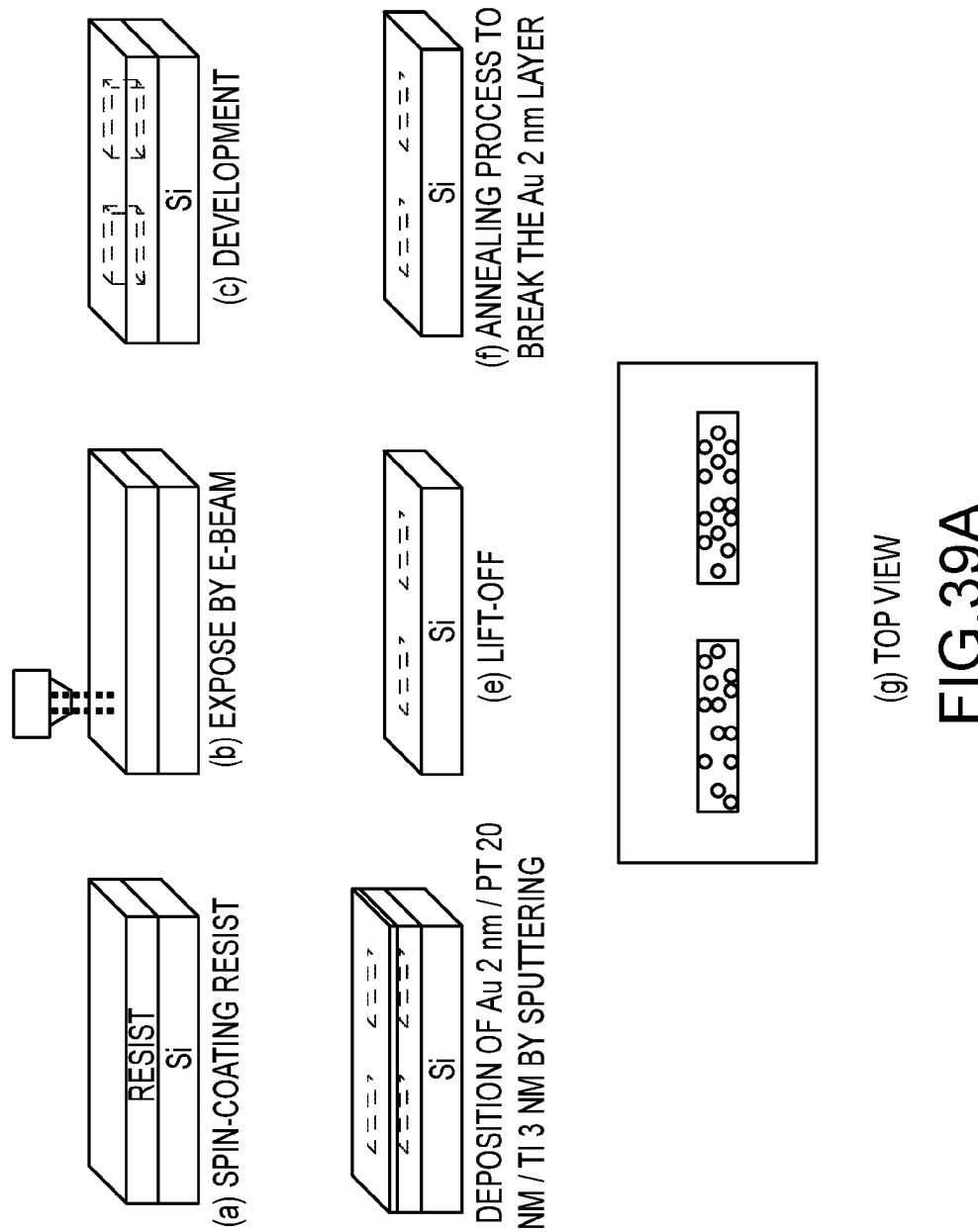
FIG. 39A illustrates an example of one preferred embodiment of process (2), wherein the patterning method used is e-beam lithography, and the goal is to make beads at the proximal ends of two electrode strips. The illustration depicts the process through the point of breaking up the rectangular layers into beads, and prior to final steps to achieve a single bead at a preferred end of each rectangle.
Figure 39B:
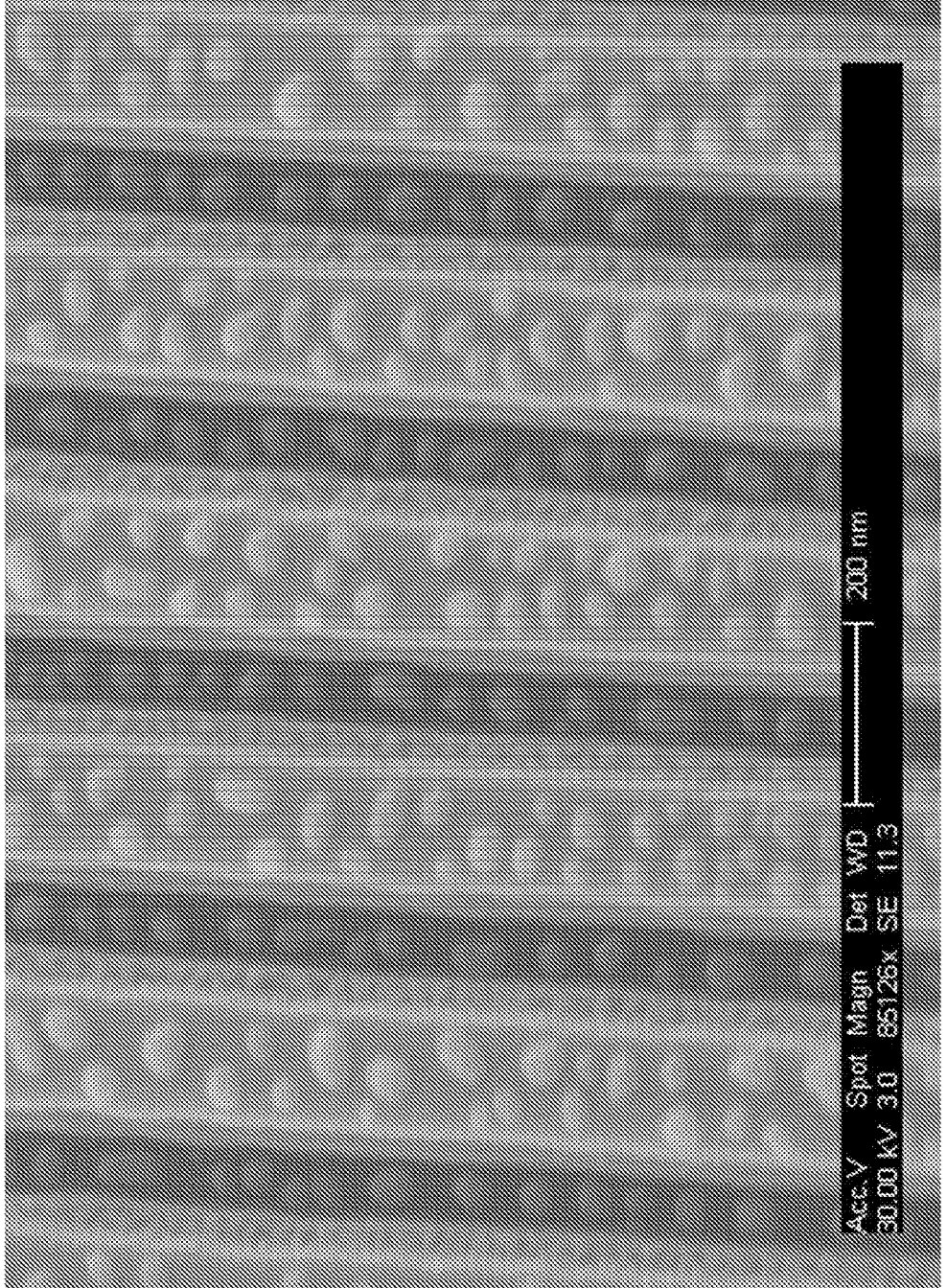
FIG. 39B is an electron microscopy image showing the process of FIG. 39A reduced to practice on a substrate that consists of elevated and depressed substrate ridges, onto which the gold layer is deposited and allowed to break up into beads. The image shows that the beads are substantially smaller in diameter than the underlying width of the rectangular strips, and the narrowed (depressed) strips are small enough that a single line of beads form.

FIG. 39A illustrates an example of one preferred embodiment of process (2), wherein the patterning method used is e-beam lithography, and the goal is to make beads at the proximal ends of two electrode strips. The illustration depicts the process through the point of breaking up the rectangular layers into beads, and prior to final steps to achieve a single bead at a preferred end of each rectangle. FIG. 39B is an electron microscopy image showing the process of FIG. 39A reduced to practice on a substrate that consists of elevated and depressed substrate ridges, onto which the gold layer is deposited and allowed to break up into beads. The image shows that the beads are substantially smaller in diameter than the underlying width of the rectangular strips, and the narrowed (depressed) strips are small enough that a single line of beads form.

Figure 40:
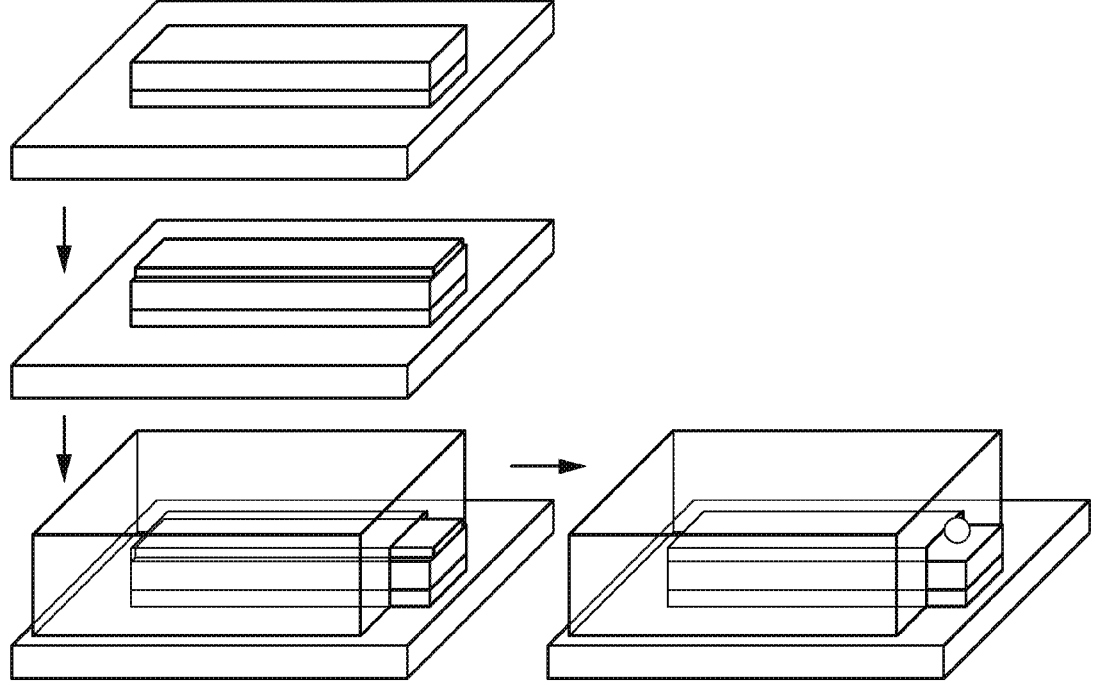
FIG. 40 illustrates bead formation process (3), in which a rectangular pattern is produced, and deposition of an adhesion material 1 (blue), followed by material 2 (gold), followed by an interfacial layer, such as oxidation induced by a vacuum break, (grey), to establishing the uppermost left configuration. Then (arrow) material 3 is deposited in a thin layer (shown as gold again), which may be the same material as 2, then (arrow) a protective layer (red) is patterned and deposited, such as silicon oxide, leaving exposed a small region of a preferred end. Then (arrow) annealing is performed, which causes the small patch of material 3 bounded by the protective layer and interfacial layer to break off and bead up, forming a bead of material 3 of smaller diameter than and of the primary patterning dimensions, located at the end of the rectangular region.

A third method, "process (3)," is illustrated in FIG. 40. Starting from a substrate, any standard patterning method is used to pattern a rectangular region, of width W, longer than it is wide. This rectangular pattern may further be blunt, but in a preferred embodiment is also pointed on the designated end at which the bead is to be created, which may enhance bead location precision. Then, any standard deposition method is used to deposit a layer of first material 1 (blue) into this pattern, that is an adhesion material for a second material 2, meaning material 2 strongly adheres to it, to the point that beading up, such as in FIG. 37, does not occur upon annealing. The second material 2 is also deposited into this same pattern. Then a thin interfacial layer (grey) is established at this surface, which is any layer of material, or an alteration in the molecular lattice structure, that produces a disruption in the bulk structure that would otherwise exist; in a preferred embodiment, this is done by introducing a break in the vacuum system, allowing exposure to air, which allows an oxidation layer to form at the surface. After the interfacial layer is established, an additional thin-layer deposition of material 3, which is the desired bead material, is made, in the same pattern, and where in a preferred embodiment material 3 is the same as material 2. This configuration is then protected by deposition of a thick passivation layer that leaves only a preferred end of small dimensions exposed. This configuration then undergoes annealing, under the same considerations as in method 2 above. In the present configuration, the thin layer of material 3 that is exposed will break off and bead up under the action of annealing, as discussed in method 2 above, forming a bead of small dimensions than the exposed region. Because of the material 1 being an adhesion layer, the material 2 layer will not bead up under this annealing process, even in the preferred embodiment where material 2 and 3 are the same material. The interfacial layer is transient and will be displaced during this process, especially in the preferred embodiment where it is an oxidation layer and the annealing is done at elevated temperature. The result is a bead of the desired material 3, of smaller diameter than and of the patterned dimensions, positioned near the desired end of the original rectangular pattern. As noted, in a preferred embodiment material 2 and 3 are the same material, with an oxidation layer as an interfacial layer, and in a further preferred embodiment, this material would be gold, producing a gold bead of super-resolved dimensions, on a gold supporting surface.

Figure 41:
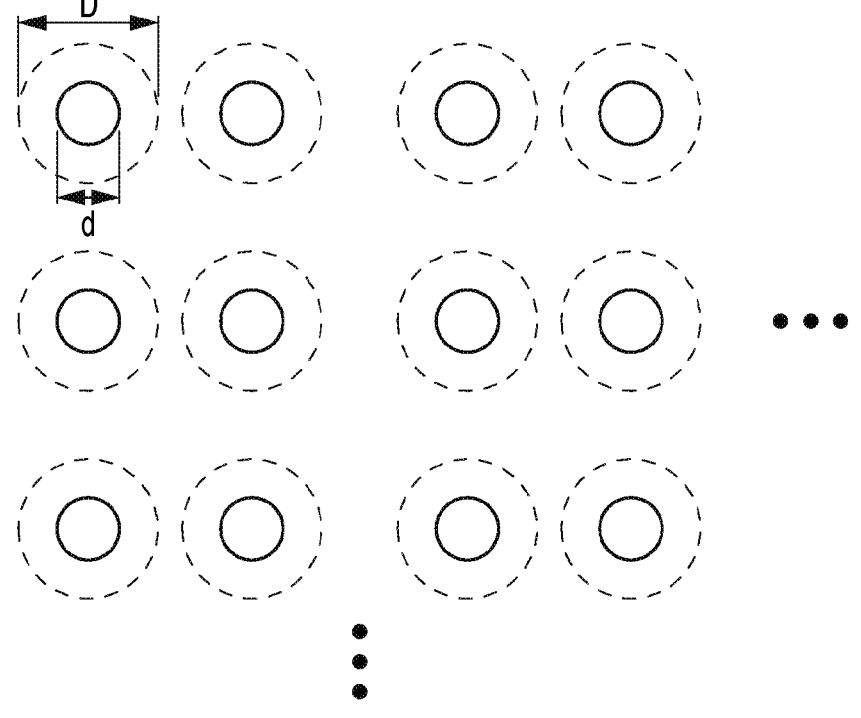
FIG. 41 illustrates an array of beads produced using the processes (1) or (2). In the case of process (1), the initial patterning and material deposition processes can be used to create an array of adhesive material disks on the substrate (original footprints indicated by dashed circles), The process will then deposit the preformed beads shown. Alternatively, if method (2) is used, entire columns of beads can be established with a single protection step, based on an array of deposited initial material rectangles.

In general, these three processes (1), (2) and (3) can be used to create beads laid out in orderly, specified array patterns, in support of broader nanofabrication needs. FIG. 41 illustrates how process (1) can easily be used to create an array of adhesive disks, and thus will efficiently transform a patterned deposition of adhesive material into an array of super-resolved, precisely positioned and precisely shaped beads. Thus, it provides a highly efficient manufacturing process for ordered arrays of nanoscale beads, at a resolution beyond that achievable by the primary patterning process. FIG. 41 illustrates an array of beads produced using the processes (1) or (2). In the case of process (1), the initial patterning and material deposition processes can be used to create an array of adhesive material disks on the substrate (original footprints indicated by dashed circles). The process will then deposit the preformed beads shown. Alternatively, if method (2) is used, entire columns of beads can be established with a single protection step, based on an array of deposited initial material rectangles. FIG. 41 illustrates a portion of an orderly, patterned array of beads, of potentially any extent on the substrate.

Figure 42:
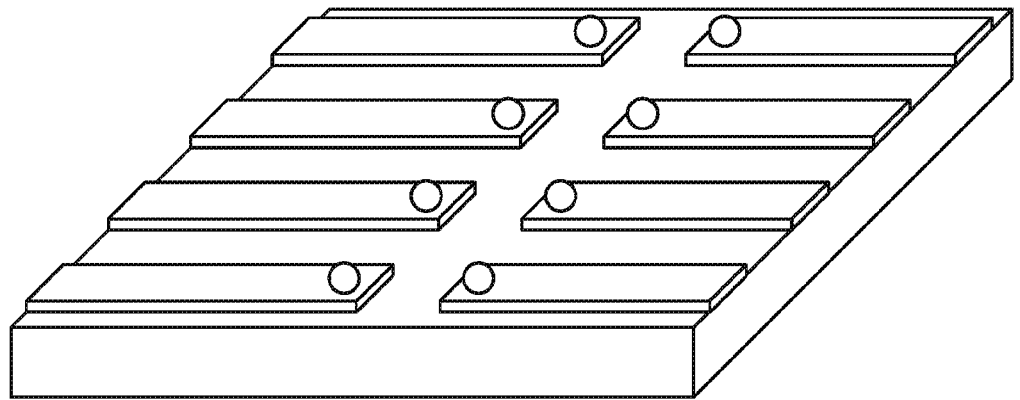
FIG. 42 illustrates the use of the bead-up process in order to produce nano-contact points for an array of molecular electronics devices. The array of beads are positioned such that each pair of electrodes receives a pair of beads as contact points, positioned near the ends of the electrodes.

FIG. 42 illustrates one preferred application for using these manufacturing processes to produce an array of beads would be in manufacturing arrays of molecular electronics devices, of the type indicated in FIG. 34. The array process described would be used to manufacturing an array of beads positioned at the tips of electrode pairs, as indicated in FIG. 40. Note that method (2) and (3) are especially well suited to this specific type of pattern, because a single protection step (red layer, in FIGS. 38 and 39A) can protect and establish an entire row of beads at the end of the electrodes. Such beads as in FIG. 41 can act as nano-contact points for molecular electronic circuits, as indicated in FIG. 34. Use of the bead of process would be part of the overall manufacturing process used to produce the final molecular electronics devices, in a scalable array format. This could be used to produce an array of many such devices on a single integrated circuit chip, in particular.

In various embodiments, the present disclosure provides a process for depositing a bead having a diameter smaller than that of an original pattern comprises: providing a substrate material; providing pattern generation and adhesive deposition processes; providing a multiplicity of pre-fabricated beads in solution; establishing a disk or patch of adhesive material on the substrate using the pattern generation and adhesive deposition processes, with diameter set by the patterning process, and protecting the remainder of the substrate by a resist coating; and exposing the multiplicity of pre-fabricated beads in solution to the adhesive, binding thereon, wherein the prefabricated beads have a diameter large enough such that there is only room for one bead to bind on the disk of adhesive material; and either prior to bead binding, or after, the resist coating is removed, leaving the bead in isolation, bound to the adhesive patch. In various embodiments, the final bead may have a diameter less than about 20 nanometers. In other examples, bead diameter may be less than about 10 nanometers.

In various aspects, the pattern generation processes may include any one of Electron-beam lithography; Photo lithography; UV lithography; Extreme UV lithography; X-ray lithography; Nano-imprint lithography; and Ion beam milling.

In various examples, the foregoing processes may be used to form an ordered array of beads, where the pattern of bead locations is directed by the primary patterning process. For example, the bead pattern may be such that it places the beads in contact point locations relative to a pattern of electrodes for an array of molecular electronic devices. In some aspects, the process may comprise fabricating more than 100 contact points on a single chip. In other examples, the process may comprise fabricating more than 10,000 contact points on a single chip, or even more than 1,000,000 contact points on a single chip.

In various embodiments, pre-fabricated beads may comprise metallic nano-particles, such as for example, colloidal gold nano-particles. In some examples, the pre-fabricated beads comprise gold nano-particles and the adhesive comprises a thiolated silane material.

In various aspects of the foregoing processes, when the adhesive material is subsequently removed, the particle is left in place on the substrate bound by other active or passive means. In some examples, the diameter of the pre-fabricated nano-particle is equal to or larger than ½ the diameter of the adhesive disk, allowing at most one such particle to bind.

In other examples, the adhesive may be patterned into some other shape than a disk.

In variations of the foregoing processes, means are used to favor a single particle deposited per adhesive site, such as for example: particle size (larger diameter is favorable) in conjunction with any or all of these other limiting factors: aspect ratio of the depression in the resist (high depth/width is favorable), concentration of the solution of pre-fabricated particles (lower concentration is favorable), mixture of primary beads with another species of beads that cannot bind, present for size exclusion purposes (more such displacement beads are favorable) to prevent multiple primary beads from contacting one site, (and duration of the binding reaction (shorter time is favorable).

Beads may be deposited in such a way that there can be more than one bead attached per site, but such that, in accord with the stochastic process of loading a site, which is random in the precise point of attachment and time of attachment (Poisson loading statistics), some fraction of sites will get a single bead as desired for a well-formed site.

The nano-particle may further comprise a removable coating that increases its effective diameter, in order for size exclusion to limit deposition to 1 particle per adhesive site, and where said coating is removed in a subsequent processing step, after the exposure to the solution of nanoparticles is completed.

EXAMPLE 7 sets forth experimental results for the invention in which pre-formed nanoscale beads are deposited on a surface, and adhere to a patterned region, in order to establish beads at desired locations for use as contact points for self-assembling molecular devices. The ELISA assay results shown further demonstrate that beads bound to surfaces as taught retain the functional ability to have specific molecular binding, which is the basis for molecular self-assembly reactions.

FIGS. 43 through 46A-D further explain these results, and include: an EM image of Binding of Beads to a properly derivatized surface regions; an EM image showing absence of beads on un-derivatized surface regions; an AFM image of beads bound to derivatized surface region; and functional molecular binding assay on surface-bound gold beads.

Figure 43:
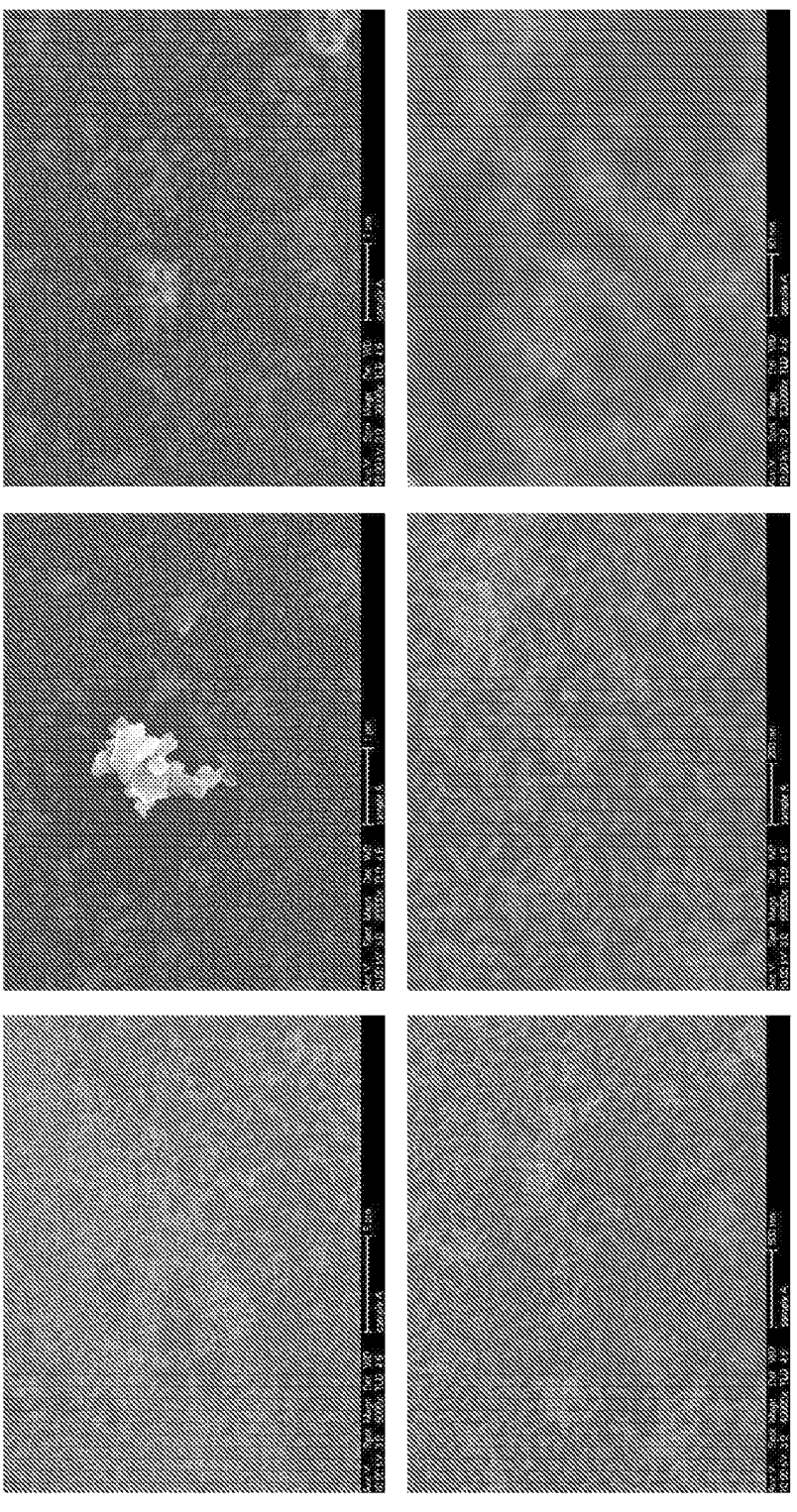
FIG. 43 shows electron microscope images of gold beads deposited on an adherent surface. Beads are gold nanoparticles approximately 5 nm to 10 nm in diameter.

FIG. 43 shows electron microscope images of gold beads deposited on an adherent surface. Beads are gold nanoparticles approximately 5 nm to 10 nm in diameter. The adherent surface is a silicon wafer derivatized with commercially available "molecular glue" that conveniently binds a wide variety of material surfaces using a nanoscale polymer matrix (Mix & Go™, from Anteo Diagnostics, Inc.). The deposition buffer uses is a carbonate buffer. The images show beads adhered to the surface, at a high density, indicating efficient deposition.

Figure 44:
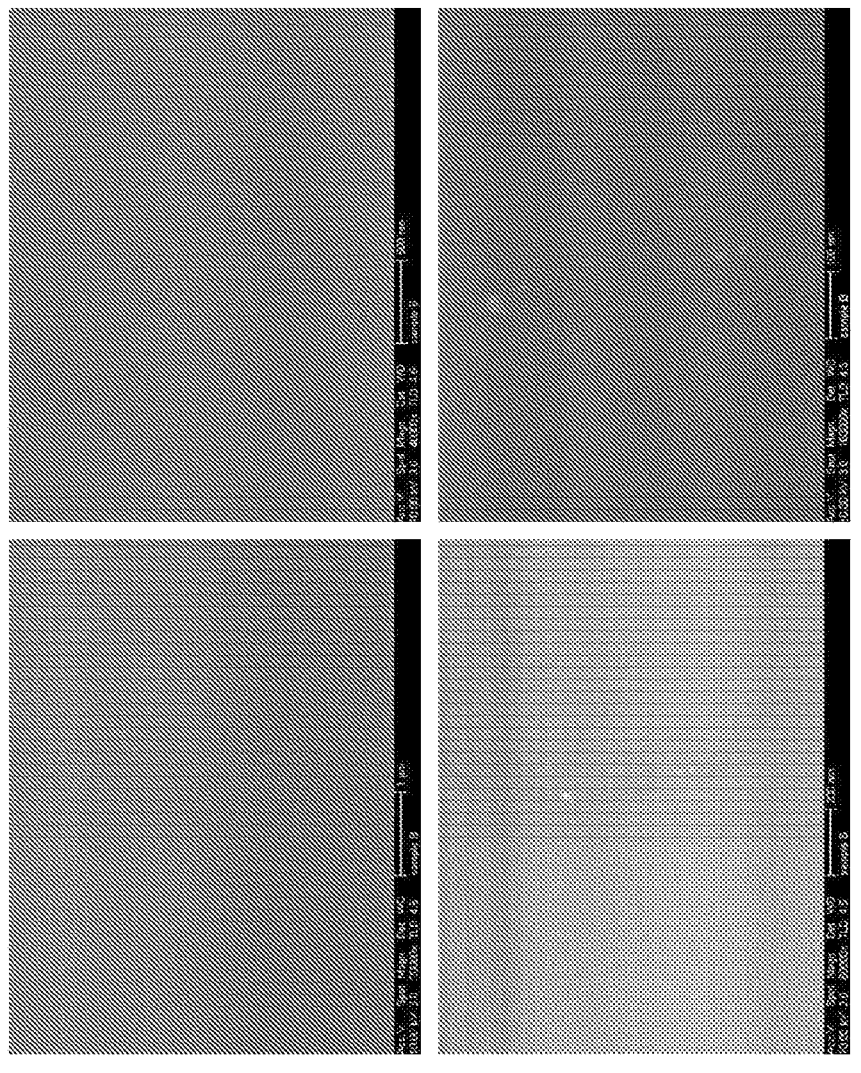
FIG. 44 shows electron microscope images of a control sample comprising gold beads adherent to un-derivatized silicon surface.

FIG. 44 shows electron microscope images of a control sample comprising gold beads adherent to un-derivatized silicon surface. This shows there is very low background level of surface adhesion of beads without proper derivatization to guide the surface binding, and without proper deposition buffer. Therefore, patterned derivatization of the surface can be used to direct bead binding precisely to the patterned regions, with no deposition on the un-derivatized regions.

Figure 45:
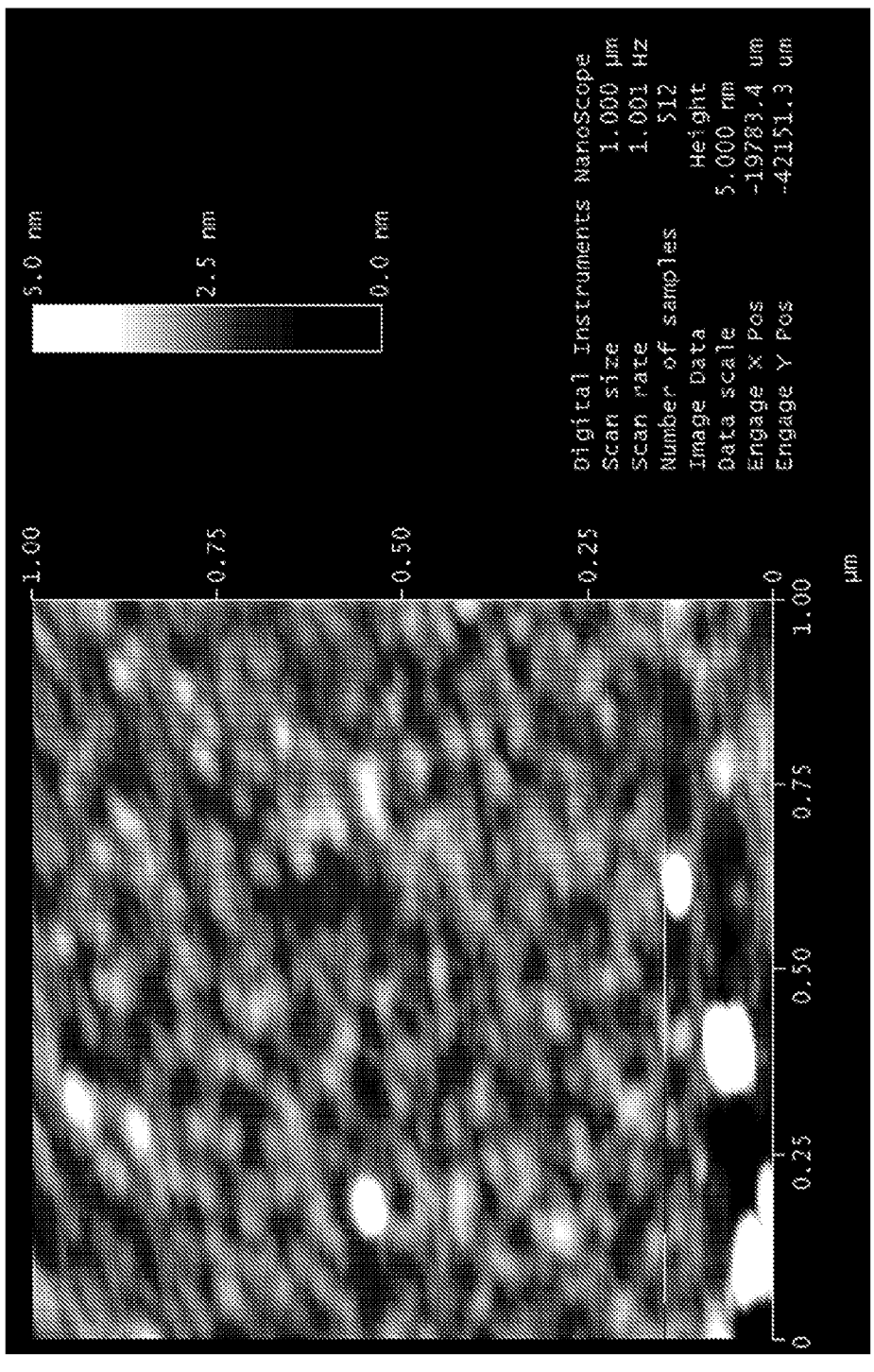
FIG. 45 shows Atomic Force Microscope (AFM) images of gold beads deposited on a derivatized adherent surface. Beads are gold nanoparticles approximately 5 nm to 10 nm in diameter.

FIG. 45 shows Atomic Force Microscope (AFM) images of gold beads deposited on a derivatized adherent surface. Beads are gold nanoparticles approximately 5 nm to 10 nm in diameter. The adherent surface is a silicon wafer derivatized with commercially available "molecular glue" that conveniently binds a wide variety of material surfaces using a nanoscale polymer matrix (Mix & Go™, from Anteo Diagnostics, Inc.). The deposition buffer uses is a carbonate buffer. The images show the surface structure with nanometer resolution of topography. Bright white regions are concentrations of gold nanoparticles adhered to the surface.

Figure 46B:
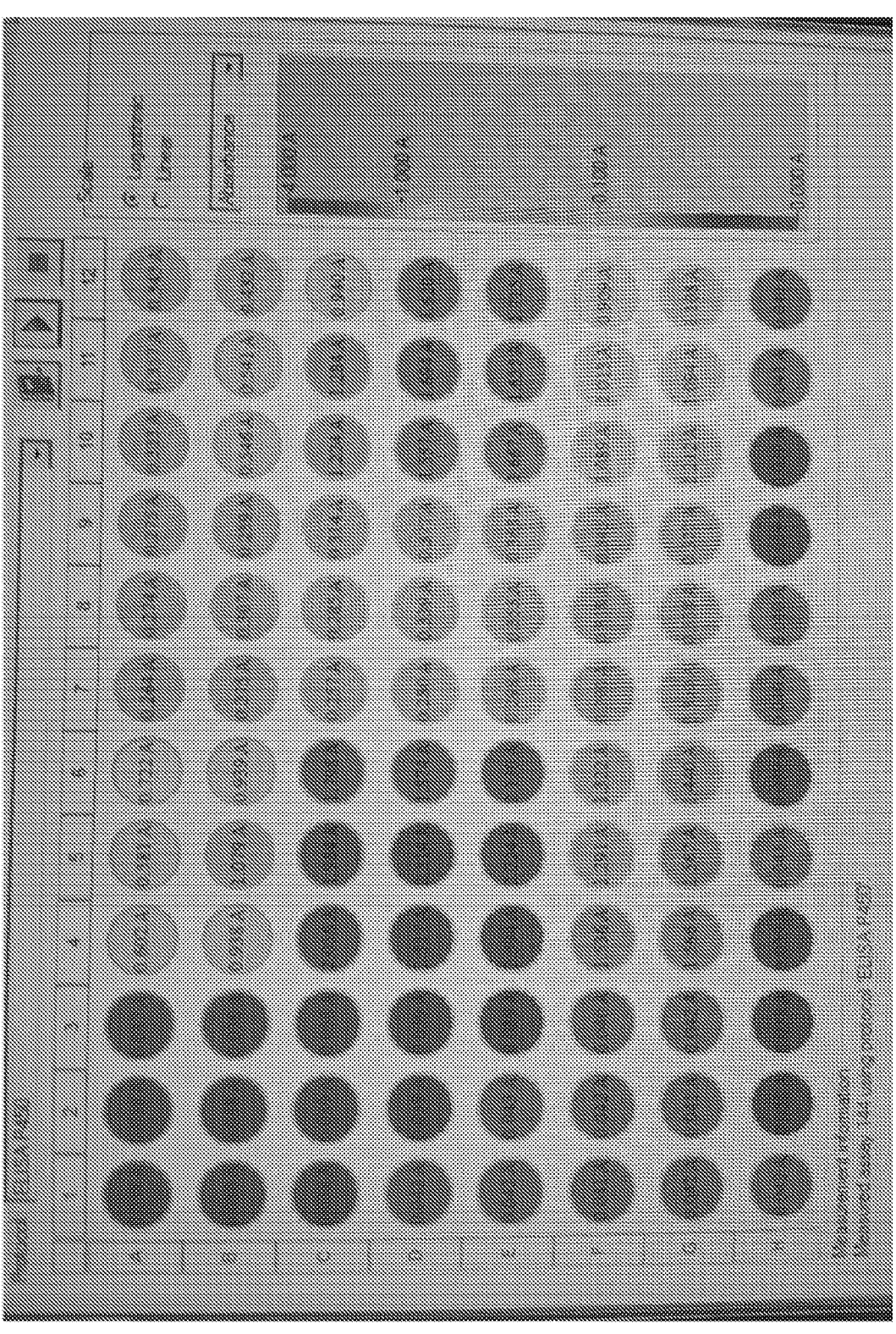
FIG. 46B is a color coded intensity map of final readings from the ELISA plate.
Figure 46D:
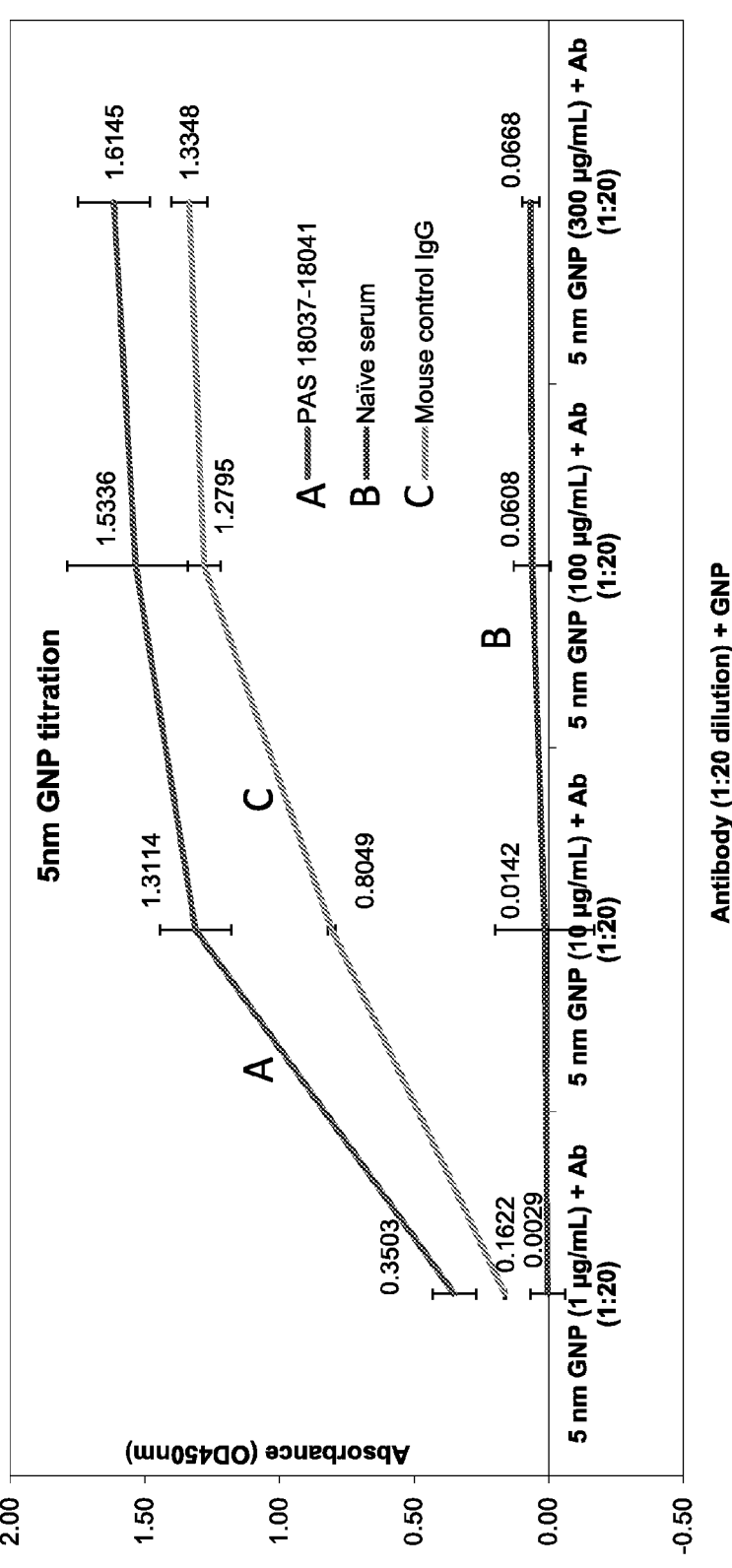
FIG. 46D depicts the final data results summarized in graphical form, showing that the antibody with specific affinity has greater binding than the surface beads than various controls, across the entire range of bead concentrations deposited on the surface.

FIGS. 46A-46D show functional testing of gold beads bound to a surface. Data illustrate that bound beads retain functionality for binding single molecules with specific affinity to the beads, thereby demonstrating suitability for molecular self assembly uses. The FIGS. 46A-46D show details of an ELISA assay performed in a well plate with gold beads bound into wells via the method discussed herein above. In this assay, antibodies raised in a mouse (PAS 18037-18041) to have specific binding to the pre-formed 5 nm gold beads are assayed for binding affinity to beads from the same batch, attached to the well bottoms of the ELISA plate with a Mix & Go™ (Anteo Diagnostics, Inc.) derivatized adherent surface. FIG. 46A shows the plate map, setting forth the various concentrations of gold nanoparticles deposited into wells, with triplicate columnar repeats of buffer, affinity antibodies, naïve serum, and control non-specific mouse IgG, at various dilutions indicated in rows. FIG. 46B is a color coded intensity map of final readings from the ELISA plate. FIG. 46C is the corresponding table of numeric ELISA readings. Lastly, FIG. 46D depicts the final data results summarized in graphical form, showing that the antibody with specific affinity has greater binding than the surface beads than various controls, across the entire range of bead concentrations deposited on the surface. This shows that beads remain bound to the surface through the rigorous binding and washing conditions of the ELISA assay, and also retain specific molecular binding properties established previously for a molecule of interest (here a specific IgG antibody).

Example 8

Nucleic Acid Analysis Using Molecular Electronics Sensors

Figure 47:
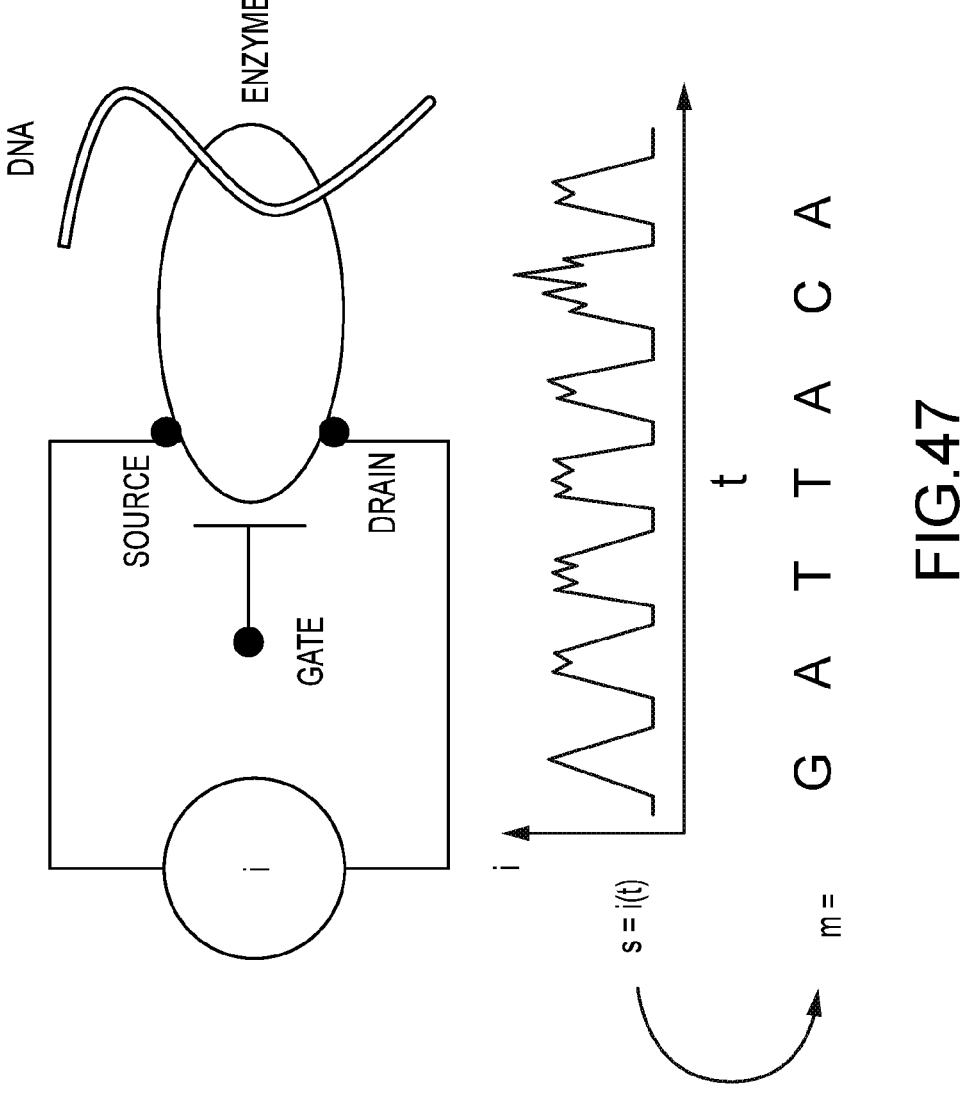
FIG. 47 illustrates one preferred form of a molecular electronics circuit for measuring DNA sequence. An enzyme is coupled between source and drain electrodes, to form a circuit that includes a meter for measuring an electrical property, such as current under applied source-drain and gate voltages, or a similar system properties (such as voltage at constant applied current). The measured property S(t) as a time trace reflects the underlying sequence of the DNA, due to the processive action of the enzyme on DNA, and its variable properties as an electrical component during this processing.

This example teaches methods of Sequencing nucleic acids, and specifically DNA or RNA, using molecular electronics sensors. An embodiment of such a sensor is illustrated in FIG. 47, discussed below.

Determination of the sequence of DNA is a fundamentally important measurement process in biological research, as well as in the biomedical and healthcare applications of genetics. Since the structure of DNA and its fundamental role in molecular biology were first elucidated by Watson and Crick in 1953, there has been a major focus on developing efficient methods to determine the sequence of nucleic acid bases that make up a given DNA molecule. A native DNA molecule is a double stranded helix, formed of complementary strands, each of which is a biopolymer composed from four nucleic acid bases, typically denoted A, G, T, and C. To sequence the DNA is to determine the precise sequence of these nucleic acid bases in this polymer. The first general method for determining DNA sequence was introduced by Sanger in 1977. Through the work of Hood and others, automated machines performing this Sanger sequencing process were developed and commercialized in the late 1980's. These instruments powered the Human Genome Project, which determined a reference sequence for humans in 2001, at a total sequencing cost in excess of one billion dollars. In the course of this work, there were substantial efforts to develop more efficient DNA sequencing methods. In 2004, the first of these massively parallel systems was introduced and commercialized by Rothberg. Subsequently, several other massively parallel sequencing platforms were introduced, including those that can analyze single DNA molecules, analyze molecules rapidly in real-time at the speed of processive enzymes, or sense DNA sequence using electronic semiconductor chip sensor devices. Systems capable of sequencing a human genome for under $1000 were also commercialized in 2014. In spite of this enormous progress, there is still substantial potential for sequencing technology to become faster, cheaper, and to provide higher quality sequence data in the form of lower errors, longer contiguous reads of sequence, or reading RNA or modified bases. There is also substantial potential for the instruments to become smaller or portable, more robust, less costly and mass-producible. In addition, there are related problems of interest such as sequencing of RNA molecules, and in determining the sequence of modified nucleotides that may be present in naturally occurring DNA, such as the methylated nucleotides shown in FIG. 48. When these commonly occurring methylated forms are present in DNA, it is desirable to be able to read out their presence in the sequence as well, as this may have biological relevance. More generally, if DNA contains modified or analogue nucleotides, or damaged bases, it may be desirable to determine the sequence of these as well, in conjunction with that of the standard bases present.

The field of Molecular Electronics emerged in the 1970's, from a convergence of foundational work on the theory of molecular bonds and electron transfer in molecules in the 1940's and 1950's, as well as the emergence of nanotechnology as championed by Feynman in 1959. The central premise is that individual molecules can form critical components in nano-scale electronic circuits, acting as circuit components such as rectifiers, switches or sensors. The unique value of this is that it enables the ultimate in miniaturization and low power circuitry. A further value is that individual molecules can have unique properties as sensors, through their molecular interactions, and especially for sensing properties of individual molecules. This is especially true in the area of bio-sensing, using biomolecules such as proteins or enzymes, as these have evolved highly sophisticated and specific molecular iterations.

While early work on molecular electronics devices began in the 1970's, only in the late 1990's and early 2000's did the state of nano-engineering reach the degree of sophistication needed to begin extensive investigation of the properties of circuits integrated with a single molecule as a component. Typically, such a molecule is integrated into a circuit as a bridge between electrodes, so that voltages can be applied. For application as a sensor, such a bridge molecule will change its conducting properties as it interacts with the target analytes. There may further be a "gate" voltage applied, to further tune the sensing properties of the molecule via an imposed gate field.

The object this example is to demonstrate determination of a DNA sequence, and related nucleic acid analyses, using molecular electronics sensor devices. This includes specific device embodiments useful for this purpose, as well as the methods of using such devices to determine or characterize the sequence of DNA or RNA molecules.

Herein are taught two general forms of a molecular electronics sensor that are useful for nucleic acid analysis. This consists of an enzyme (native or engineered to have augmented properties) that processes the target nucleic acid in some form, coupled into a three termal device have source and drain electrodes, and a gate electrode for additional voltage control. One preferred schematic embodiment is shown in FIG. 1, in which the enzyme 105 is coupled in as a primary circuit element, and the overall circuit is configured with a meter measuring an electrical property (such as current in the circuit under applied voltages, or voltage under applied currents), and where measured trace is thereby related to the sequence of the DNA molecule 108 engaged with the enzyme 105. This configuration is preferred when the enzyme-DNA conformations substantially alter the conduction of charge through/around the complex. In this context, the concept of an "enzyme" can be broader than the strict meaning in molecular biology, to be any molecule that produces detectable signals of interaction with a DNA molecule, that can be related to underlying DNA sequence.

In the context of this example, FIG. 47 illustrates a schematic of one preferred form of a molecular electronics circuit for measuring DNA sequence. An enzyme is coupled between source and drain electrodes, to form a circuit that includes a meter for measuring an electrical property, such as current under applied source-drain and gate voltages, or a similar system properties (such as voltage at constant applied current). The measured property S(t) as a time trace reflects the underlying sequence of the DNA, due to the processive action of the enzyme on DNA, and its variable properties as an electrical component during this processing.

Figure 49:
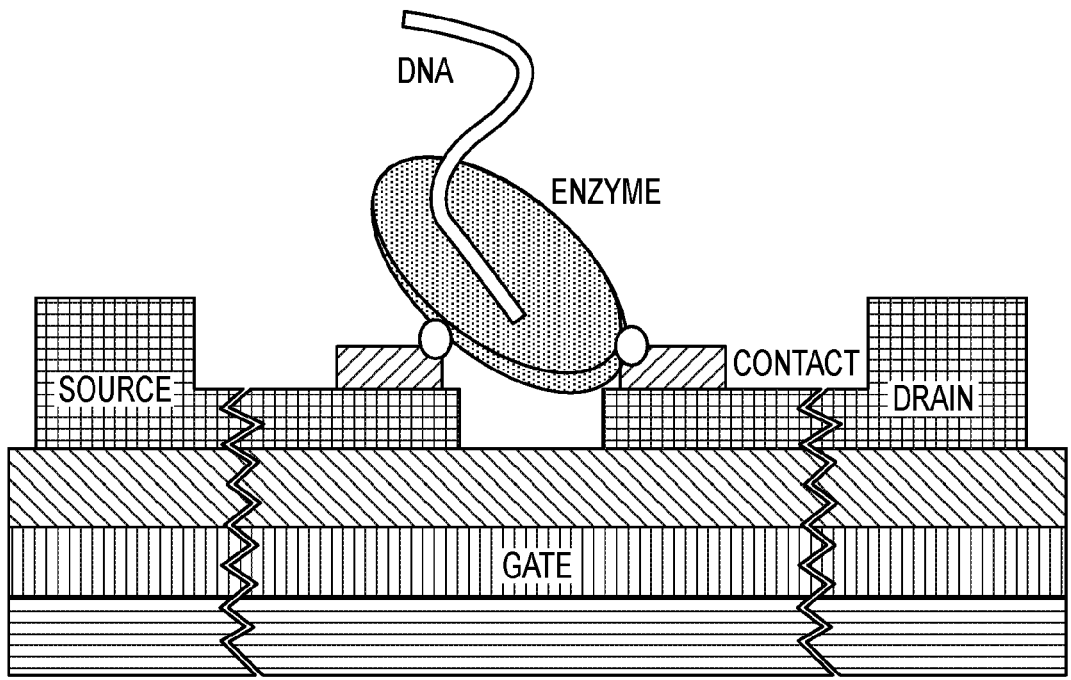
FIG. 49 illustrates FIG. 1 in a more standard source-drain-gate geometry.

FIG. 49 depicts another preferred schematic embodiment in which the enzyme is coupled in as a secondary or parallel circuit element, which may have both conducting and gating activity relative to a primary conductive element, and where the overall circuit is configured with a meter measuring an electrical property (such as current in the circuit under applied voltages, or voltage under applied currents), and where measured trace is thereby related to the sequence of the DNA molecule engaged with the enzyme. The schematic is realized in a more standard source-drain-gate geometry. This configuration is preferred when the enzyme-DNA conformation changes can apply variable gating voltages to the primary conducting element, acting principally as another gate electrode applying sequence-dependent gate voltages. In this context, the concept of an "enzyme" can be broader than the strict meaning in molecular biology, to be any molecule that produces detectable signals of interaction with a DNA molecule, that can be related directly or indirectly, to underlying DNA sequence.

Figure 50:
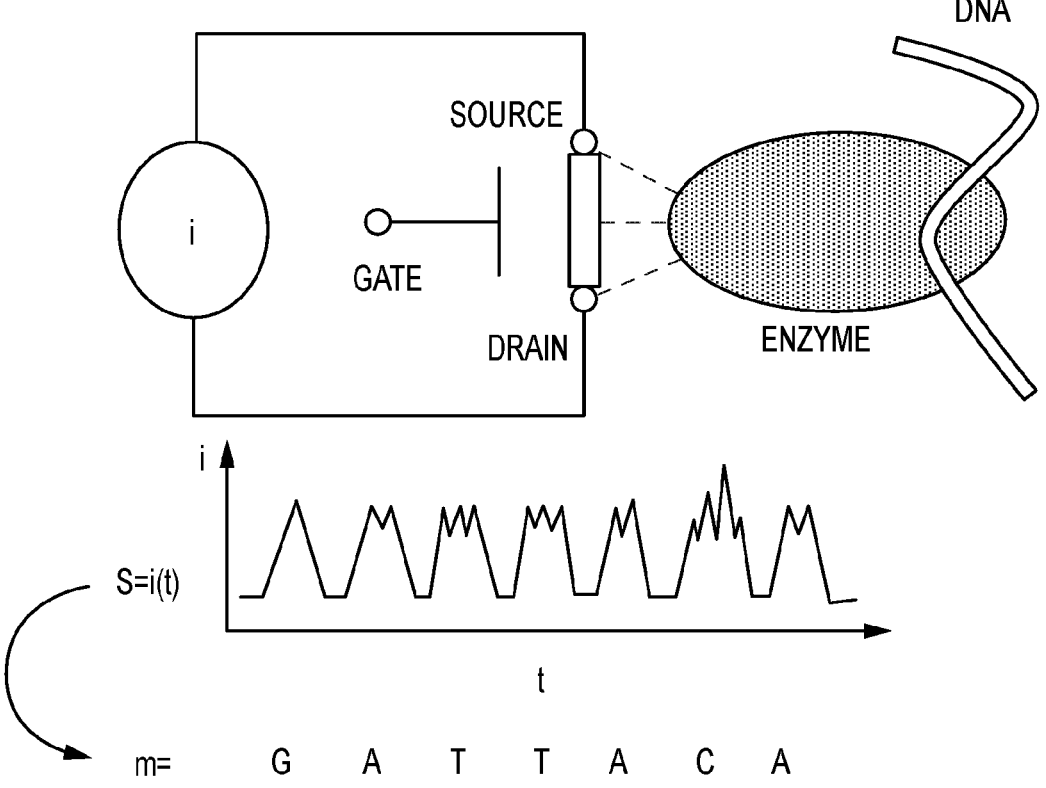
FIG. 50 illustrates a schematic of another preferred form of a molecular electronics circuit for measuring DNA sequence. An enzyme is coupled as a secondary element to a primary conducting element between source and drain electrodes, to form a circuit in which the enzyme may provide gating function as well as conduction. The circuit includes a meter for measuring an electrical property, such as current under applied source-drain and gate voltages, or similar system properties (such as voltage at constant applied current). The measured property S(t) as a time trace reflects the underlying sequence of the DNA, due to the processive action of the enzyme on DNA, and its variable properties as an electrical component during this processing.

FIG. 50 illustrates a schematic of another preferred form of a molecular electronics circuit for measuring DNA sequence. An enzyme is coupled as a secondary element to a primary conducting element between source and drain electrodes, to form a circuit in which the enzyme may provide gating function as well as conduction. The circuit includes a meter for measuring an electrical property, such as current under applied source-drain and gate voltages, or similar system properties (such as voltage at constant applied current). The measured property S(t) as a time trace reflects the underlying sequence of the DNA, due to the processive action of the enzyme on DNA, and its variable properties as an electrical component during this processing.

Figure 51:
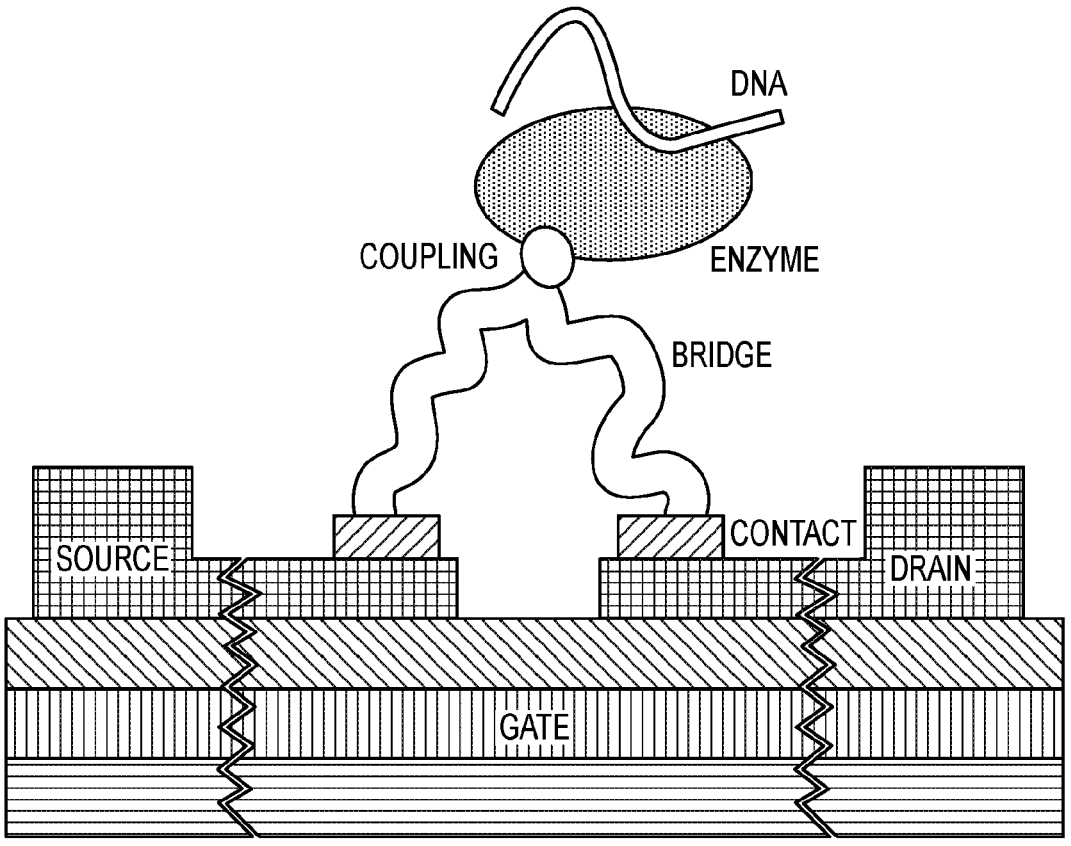
FIG. 51 depicts the schematic of FIG. 1 in a more descriptive preferred embodiment with a source-drain-gate geometry from semiconductor devices, and a molecular bridge between electrodes as the primary conducting element, and a coupling point or conjugation group that couples the enzyme to the bridge, as one means of ensuring proximity, and potentially electrical connection.

FIG. 51 depicts the schematic of FIG. 1 in a more descriptive preferred embodiment with a source-drain-gate geometry from semiconductor devices, and a molecular bridge between electrodes as the primary conducting element, and a coupling point or conjugation group that couples the enzyme to the bridge, as one means of ensuring proximity, and potentially electrical connection.

Having taught these general classes of molecular electronic sequencing sensing devices, we now teach specific preferred embodiments and methods of using these for measuring or characterizing sequence.

Figure 52:
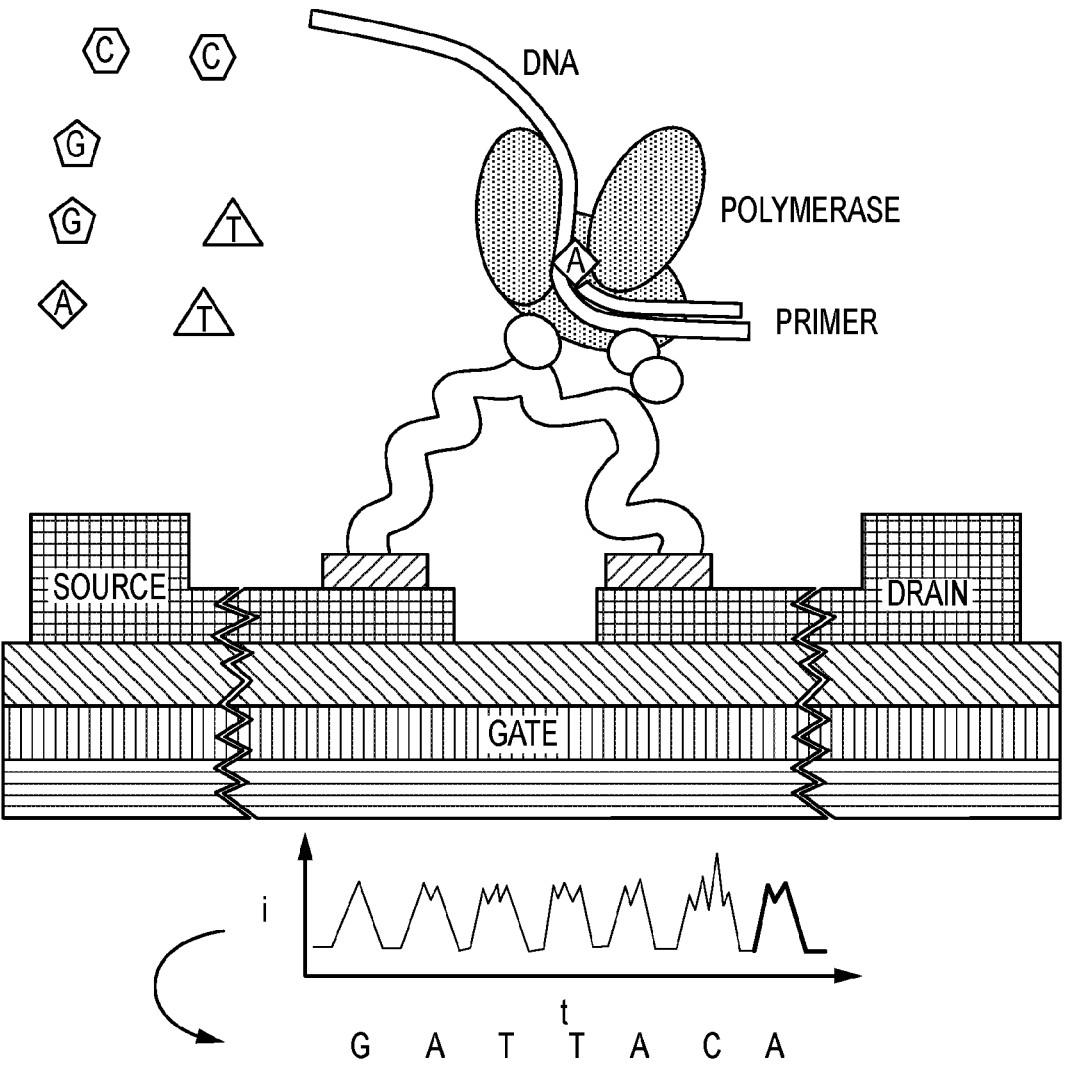
FIG. 52 illustrates a preferred embodiment wherein the enzyme comprises polymerase, which is extending a primed single stranded DNA template, assuming a suitable buffer is present that contains dNTPs. The incorporation process (incorporation of A nucleotide shown) produces a corresponding identifiable feature in the measured current trace, thereby determining sequence.

In one preferred embodiment, shown in FIG. 52, the enzyme is a polymerase, and the DNA molecule is a primed single strand, and the processive action of the enzyme is synthesis of the complementary strand from dNTPs in solution. The polymerase is extending a primed single stranded DNA template, assuming a suitable buffer is present that contains dNTPs. The incorporation process (incorporation of A nucleotide, as shown in FIG. 52) produces a corresponding identifiable feature in the measured current trace, thereby determining sequence. The circuit parameter being measured, such as current, is monitored, and specific trace features can be used to detect which base is incorporated, thereby determining the sequence of the template DNA in an asynchronous fashion. In one preferred embodiment, it is current being monitored, under constant applied voltages for the source-drain and gate. In another preferred embodiment, the circuit parameter being measured may be an I-V characteristic obtained by sweeping the source-drain voltage or gate voltage, and this I-V curve may be measured repeatedly at high frequency, such that a complete I-V curve could be obtained which a base is in the process of incorporation. In another preferred embodiment, response to an alternating current pulse could be used as the measured circuit parameter, this pulsing being performed at sufficiently high frequency to obtain information while the base in question is undergoing incorporation.

Figure 53:
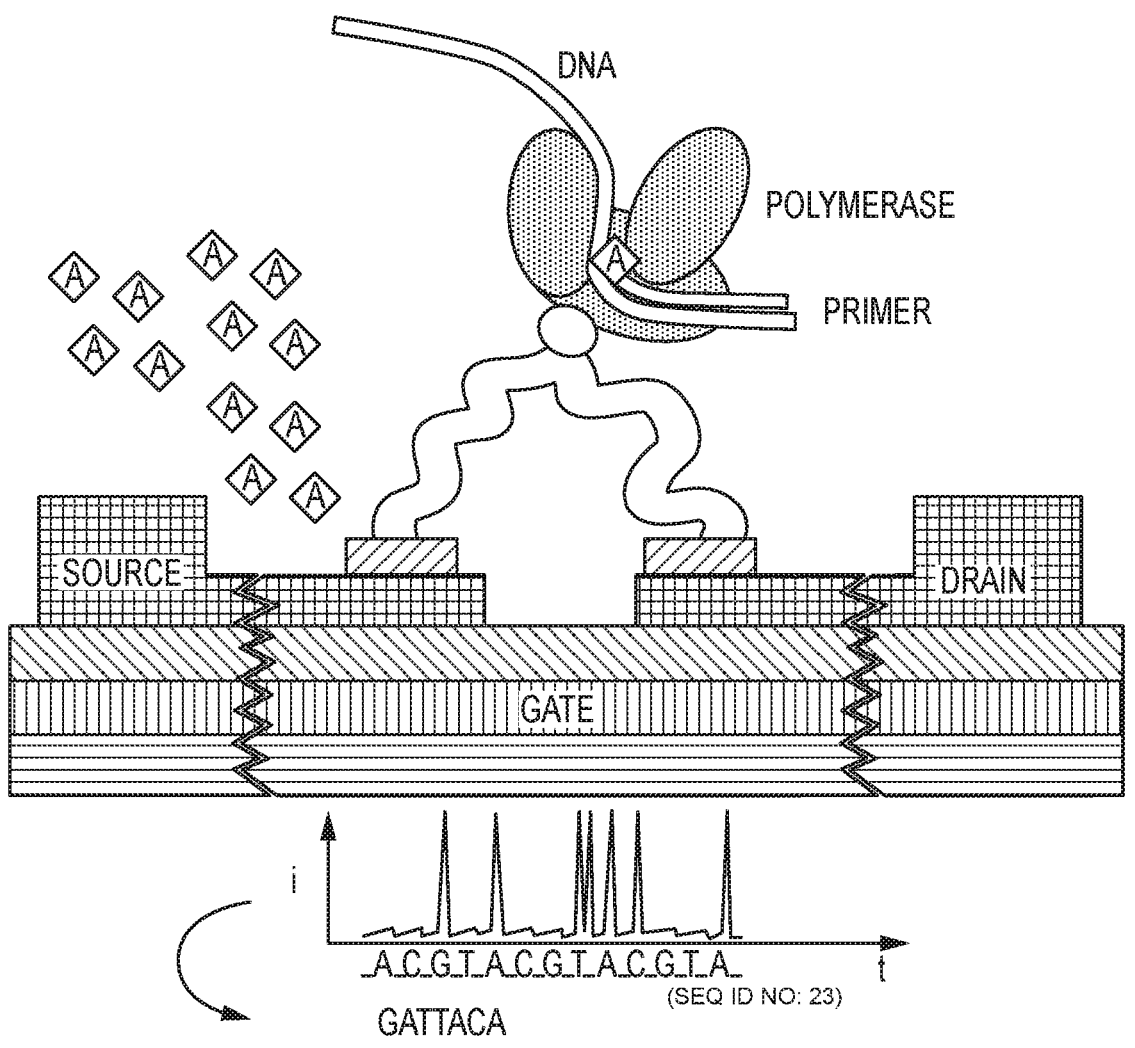
FIG. 53 illustrates an embodiment of sequencing when there is a detectable signal of incorporation, indicated as a signal spike in the measured circuit parameter, such as current, i. Trial flows of single nucleotide types, A, C, G, T, are performed, separated by wash steps (timing of nucleotide flows and washes indicated by letters and underscores on the time axis), and the resulting observed signal spikes determine sequence as indicated. Note that homopolymer sequence series, such as "TT", are indicated as multiple incorporation spikes during the corresponding trial flow. Shown is the result of flowing the A base, in a situation in which A is incorporated and produces a signal spike, and corresponding next base of the resulting DNA sequence.

In another preferred embodiment, shown in FIG. 53, sequencing can be performed when incorporation produces a detectable signal, but does not necessarily determine the identity of the base incorporated. In this scenario, trial solutions containing only one base can be added sequentially, separated by wash/flushing steps, such for example, trial of A, wash, trial of C, wash, trial of G, wash, trial of T, wash, and repeat, and the resulting signals observed during the specific base trial indicate the incorporation of one or more of that base, and therefor indicate corresponding sequence. This trial process repeated indefinitely determines sequence in a semi-synchronous fashion.

Further disclosed herein is another variation of the above two sequencing methods wherein a reversible terminator nucleotide is incorporated in a first phase, by exposure to a solution of ddNTP dideoxy terminators, followed by a second phase where circuit sensing continues in subsequent nucleotide exposures, collecting signals while nucleotides transiently reside in the binding pocket of the polymerase, but are not incorporated due to the terminator present. These exposures may be done in a mixture of all dNTPs (preferred when A/C/G/T having distinguishable traces when they reside in the polymerase binding pocket) or in trial exposures to individual A, C, G, T solutions (preferred when signals of residence in the binding pocket are not distinguishable between bases). In either case, such signals will differ in some detectable way between a correctly paired base in the pocket, versus an incorrectly paired base in the pocket, reflecting the fact that correctly paired nucleotides have different residence properties in the binding pocket than do incorrectly paired nucleotides, even though neither can be incorporated due to the terminator. From collecting signal information from such an exposure or exposures over a sufficiently long time, identification of the correctly paired base is achieved due to the signal differences, such as duration of in-pocket spikes. At this point, the terminator is removed through the reversing reaction, and a next terminated base is incorporated, and the process repeated. In this way, sequence is determined. Because data can be collected for an arbitrarily long time, it is possible to achieve any desired level of certainty about the correct next base, by accumulating sufficiently much discriminatory signal.

In the foregoing methods, it is taught that similar untargeted or targeted priming may be used, as described above, to achieve either un-targeted or targeted sequencing.

Further disclosed are that the above general sequencing methods can be enhanced by a variety of methods, as set forth below.

Nucleotides

Figure 54:
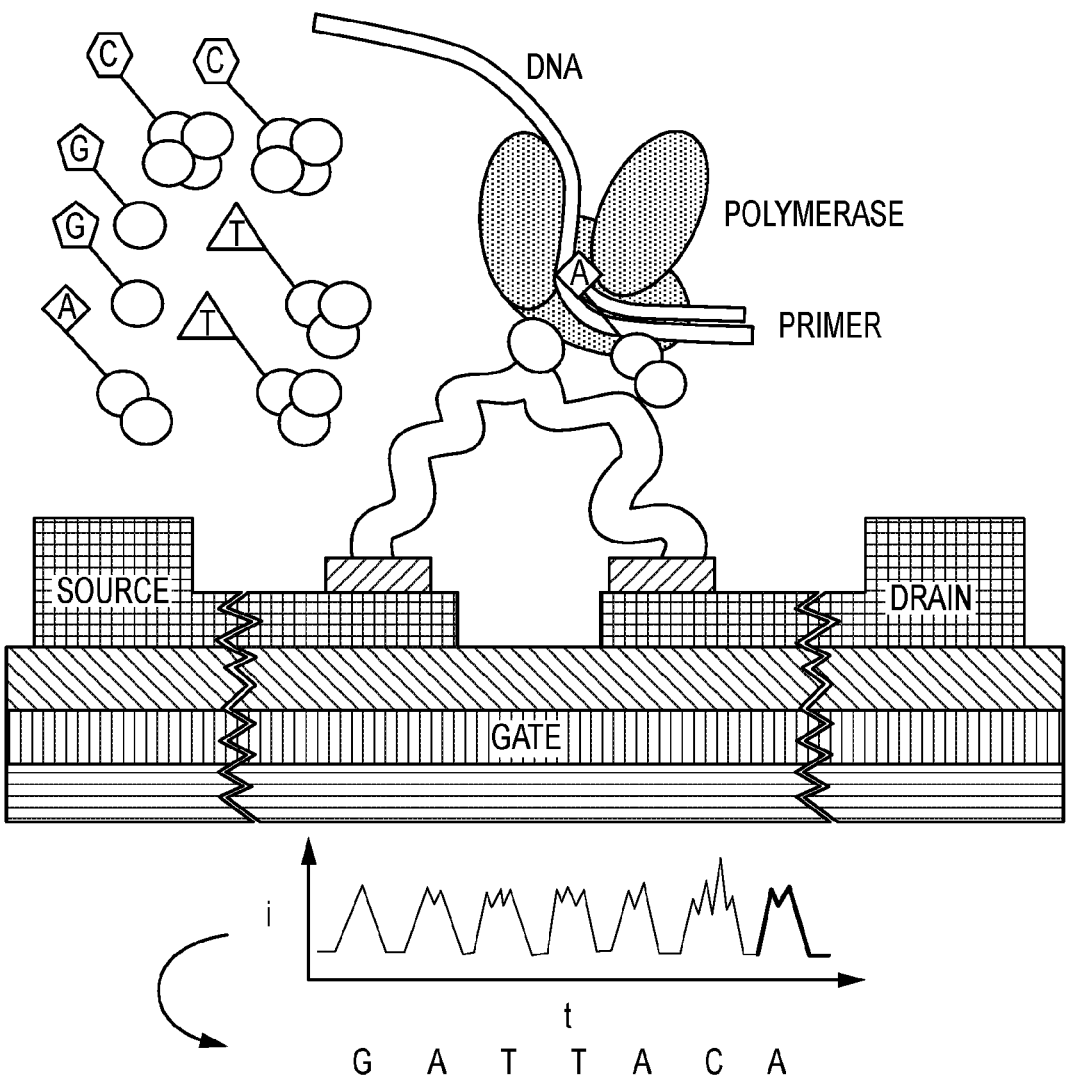
FIG. 54 depicts use of modified nucleotides to produce detectible signals. Indicated is a case where each dNTP carries a modification group (indicated as red balls) that have detectible influence on the current the incorporation process. Such a modification could be on the cleavable gamma phosphate, and therefore removed by the polymerase, or could be cleavable in a separate cleavage reaction, performed after a sensing reaction. Shown is the instance in which a modified A base in incorporated. The concept is illustrated here with the four different modification groups represented as four different numbers of attached balls (G:1, A:2, T:3, C:4), resulting in enhancing the traces to have the same number of minor spikes within the trace for each nucleotide.
Figure 55:
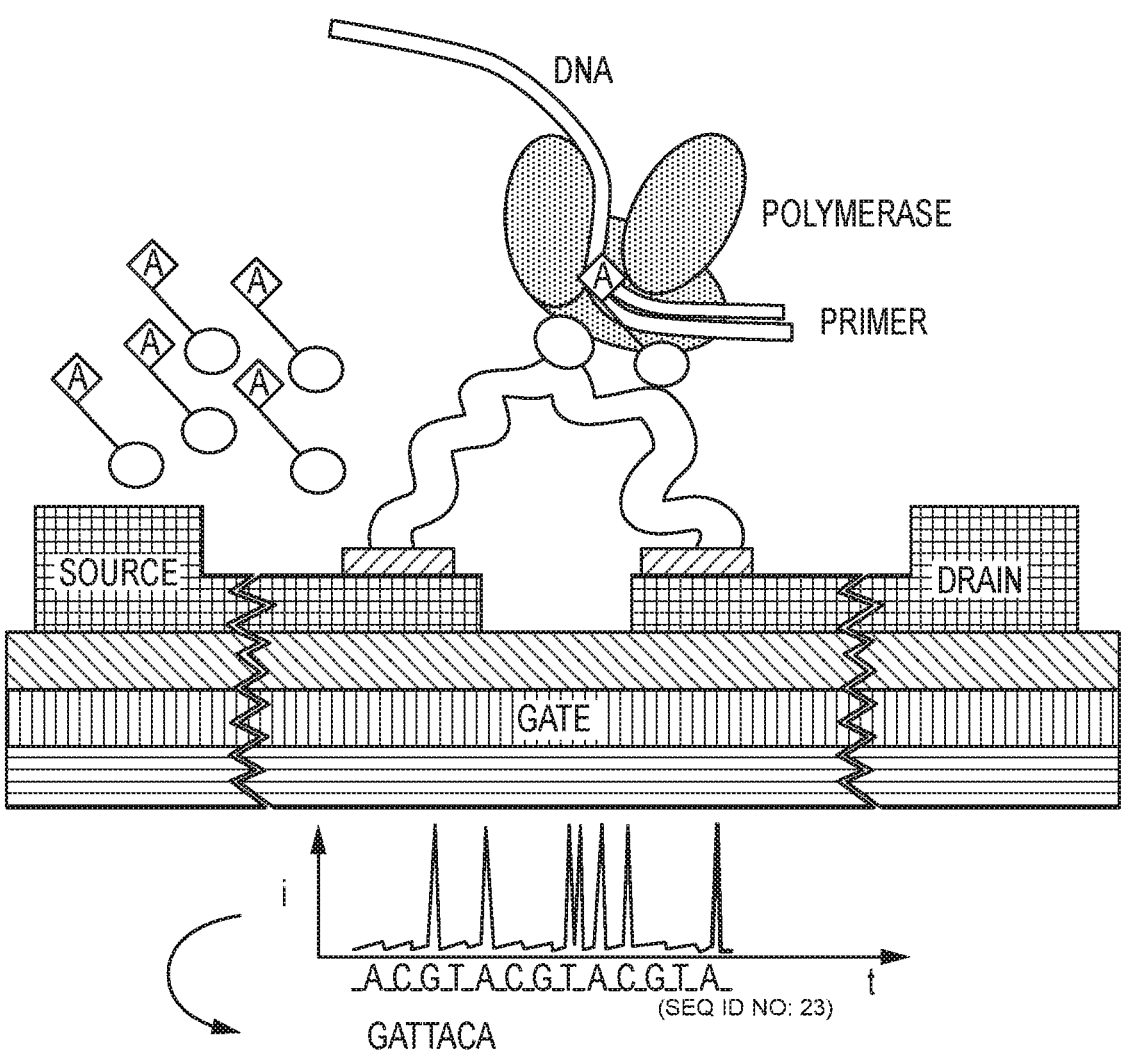
FIG. 55 depicts use of a modified nucleotide to enhance incorporation signal in the embodiment of sequencing when there is a detectible signal of incorporation used in a trial flow method. Indicated is a case where each dNTP carries a modification group (indicated as red ball) that has detectible influence on the current in the incorporation process. Such a modification could be on the cleavable gamma phosphate, and therefore removed by the polymerase, or could be cleavable in a separate cleavage reaction, performed after a sensing reaction. Shown is the A step of the trial flow process, where the A is the correct base for incorporation.

As indicated in FIG. 54 and FIG. 55, modified nucleotides can be used to produce distinguishable or detectable signals, that either enhances detection of incorporation, or discrimination of different bases undergoing incorporation in the above methods. In particular, nucleotides with groups on the gamma phosphate can be used to produce distinguishable signals transiently, wherein the enhancing group is cleaved off in the course of the polymerase incorporation process. In particular, this disclosure teaches that charged groups can be used to produce local, transient field-effect gating that enhances the measured current signal strength or features. This disclosure also teaches that nucleotides that have a removable detectable group can be used, in a trial incorporation fashion, and after each such trial incorporation, there can be a spate a detection step, and then a step to remove the detectable group. This disclosure teaches that such groups could be charged groups, and the detection can be using electrical detection properties of the circuit, such as the current, or response to specific applied voltages, voltage sweeps, or AC voltages, possibly in the presence of a different buffer that facilitates detection, such as a low conductivity buffer, or a buffer that activates the detectable group. This disclosure teaches that such modified nucleotides could also have a terminator group, and then the sequencing process can be done in the manner of reversible terminator sequencing by synthesis, cleaving the terminator and detectable group after each incorporation and detection step is completed.

Further, in the methods taught, the different nucleotides could be prepared to have distinguishable kinetic signatures, such that the kinetics of incorporation as monitored by the system real-time electrical parameters can be used to identify each incorporated base. In particular, different Kinetic signatures could be due to different concentration of different nucleotides in the solution, or modifications to them that alter incorporation kinetics. The kinetic signatures could include the height or width of an incorporation spike, or the time-spacing between incorporation spikes, as indicated in FIG. 56.

Figure 56:
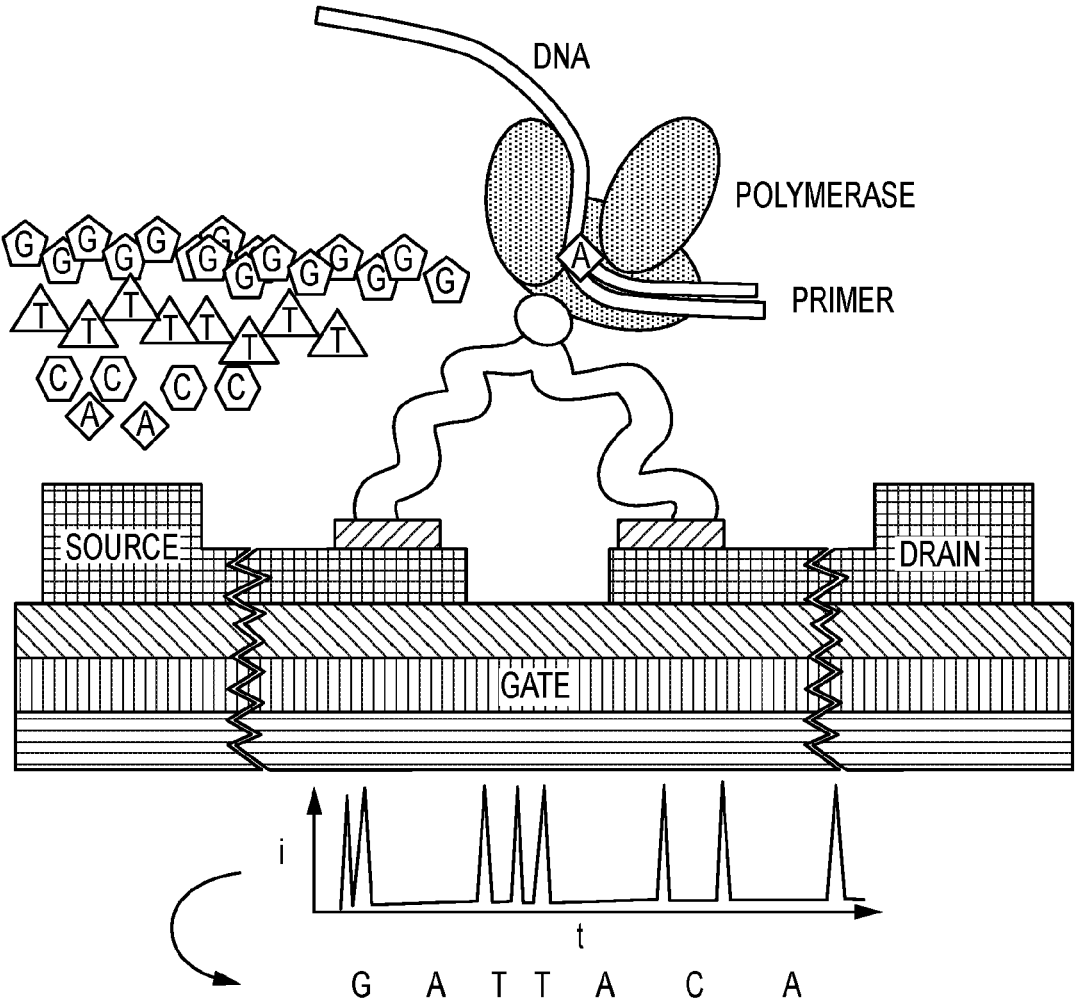
FIG. 56 illustrates kinetic encoding of sequence information. The time between incorporation spikes indicated the base being incorporated, here do to difference in dNTP concentrations indicates: A is at the lowest concentration, therefore a long time between spikes indicates the waiting time expected for A incorporation, while G is at the highest concentration, so that the shortest time between spikes indicates a G incorporation (first interval)

FIG. 56 shows kinetic encoding of sequence information. The time between incorporation spikes indicated the base being incorporated, here do to difference in dNTP concentrations indicates: A is at the lowest concentration, therefore a long time between spikes indicates the waiting time expected for A incorporation, while G is at the highest concentration, so that the shortest time between spikes indicates a G incorporation (first interval).

Enzyme

Further disclosed is that the polymerase enzyme can be modified by protein engineering to enhance the signals produced. One preferred embodiment of this is to place charged amino acid groups on its surface, which can induce current fluctuations as the enzyme changes conformation and correspondingly changes the local electric field structure.

Circuit Parameters

Further disclosed is that the gate voltage can be set to maximally enhance these signals of incorporation or base discrimination. We teach that applied AC voltages or voltage spectroscopy or response to specific applied voltage waveforms can be used to enhance detection of incorporation, or base discrimination. In particular, the gate-drain voltage, and/or gate voltage may be swept to obtain I-V characteristics for the system during the time in which a particular nucleotide (native or modified) is resident, under incorporation, incorporated, or undergoing a detection phase of the process. Such an I-V characteristic can determine which base or bases are present.

Buffer

Further disclosed is that the buffer used in this process, which generally contains salts and nucleotides, can be optimized to produce signals. In particular, the buffer may be diluted substantially, for example to reduce the noise from current carried by buffer ions, or to increase the Debye length and corresponding extent to which electric fields penetrate through the solution. In such a dilute buffer, we also teach that the dNTPs to be incorporated could be pre-complexed with magnesium, to increase their availability to the polymerase, while maintain a relatively low concentration of magnesium ions in the solution.

Bridge

Figure 57:
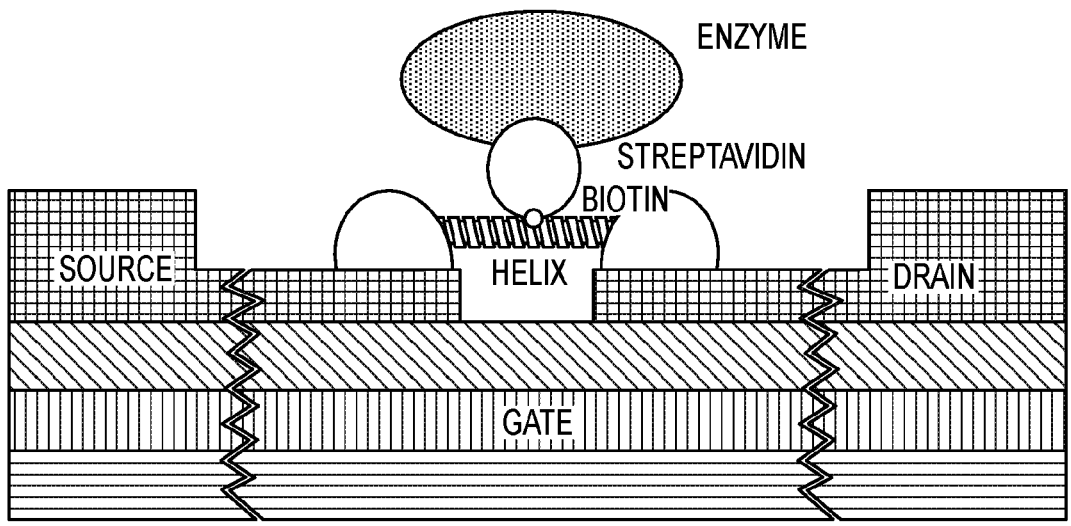
FIG. 57 illustrates a preferred embodiment of the bridge, which is a helical polymer (dsDNA or protein alpha helix) coupled to gold contacts via a thiol linkage (thiolated nucleotides in DNA ends, or cysteine placed at alpha helix termini), and with a specifically synthesized internal biotin, for coupling to streptavaidin conjugated to an enzyme.
Figure 58:
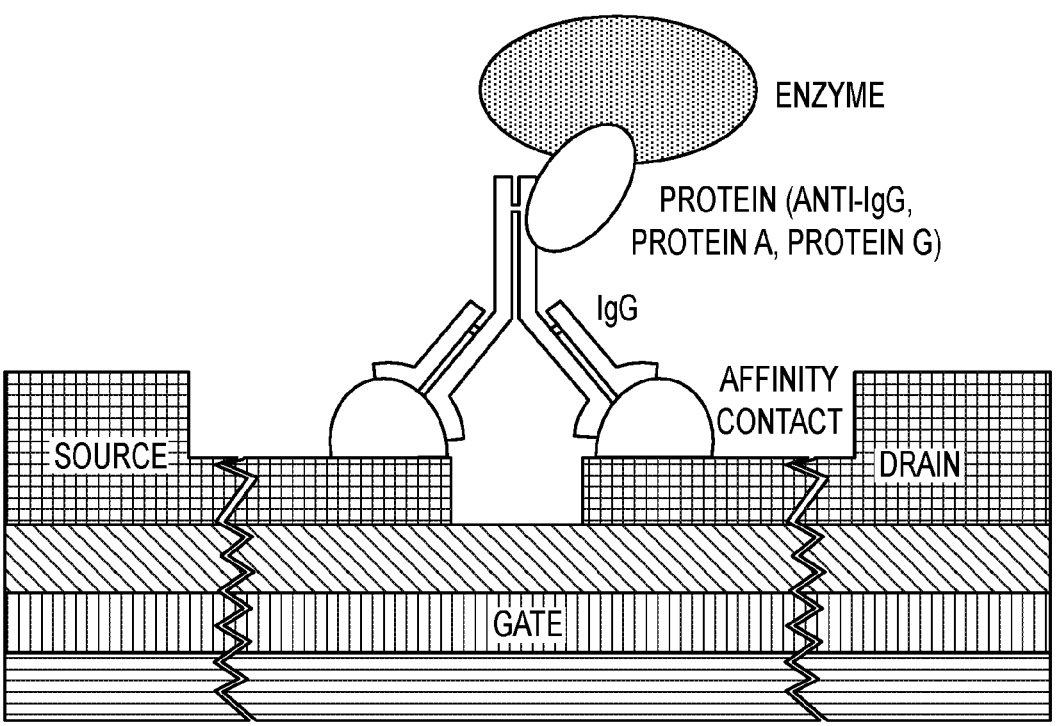
FIG. 58 illustrates another preferred embodiment of the bridge, as an IgG protein (native or engineered) with specific affinity to contact points on the electrode (affinity to primary contact point material, or antigen derivatization of surface), with coupling via IgG specific binding proteins (such as anti-IgG antibody, or Protein A or Protein G) that is otherwise conjugated to the protein of interest, or the protein of interest could be directly conjugated to the IgG, using native or engineered conjugation sites.

Additional preferred embodiments are illustrated in FIGS. 57 and 58. FIG. 57 illustrates a preferred embodiment of the bridge comprising a helical polymer (dsDNA or protein alpha helix) coupled to gold contacts via a thiol linkage (thiolated nucleotides in DNA ends, or cysteine placed at alpha helix termini), and with a specifically synthesized internal biotin, for coupling to streptavaidin conjugated to an enzyme. FIG. 58 illustrates another preferred embodiment of the bridge, as an IgG protein (native or engineered) with specific affinity to contact points on the electrode (affinity to primary contact point material, or antigen derivatization of surface), with coupling via IgG specific binding proteins (such as anti-IgG antibody, or Protein A or Protein G) that is otherwise conjugated to the protein of interest, or the protein of interest could be directly conjugated to the IgG, using native or engineered conjugation sites. The bridge molecule is a double stranded DNA molecule, coupled to gold contact beads on the electrodes via thiolated nucleotides at the end of the molecule. The coupling is achieved by using a biotinylated nucleotide internal to the DNA, which can conjugate to Streptavidin, which in turn could be conjugated to the polymerase. Similarly, the bridge can be a protein alpha-helix, otherwise similarly coupled and linked. Another preferred embodiment of the bridge is an IgG antibody molecule (native or engineered), with suitable specific affinity for contact points on the source and drain, and with coupling mediated by a IgG-binding protein (such as an Anti-IgG, Protein A or Protein G) conjugated to the polymerase, as indicated in FIG. 58.

Replication & Integration

Figure 59:
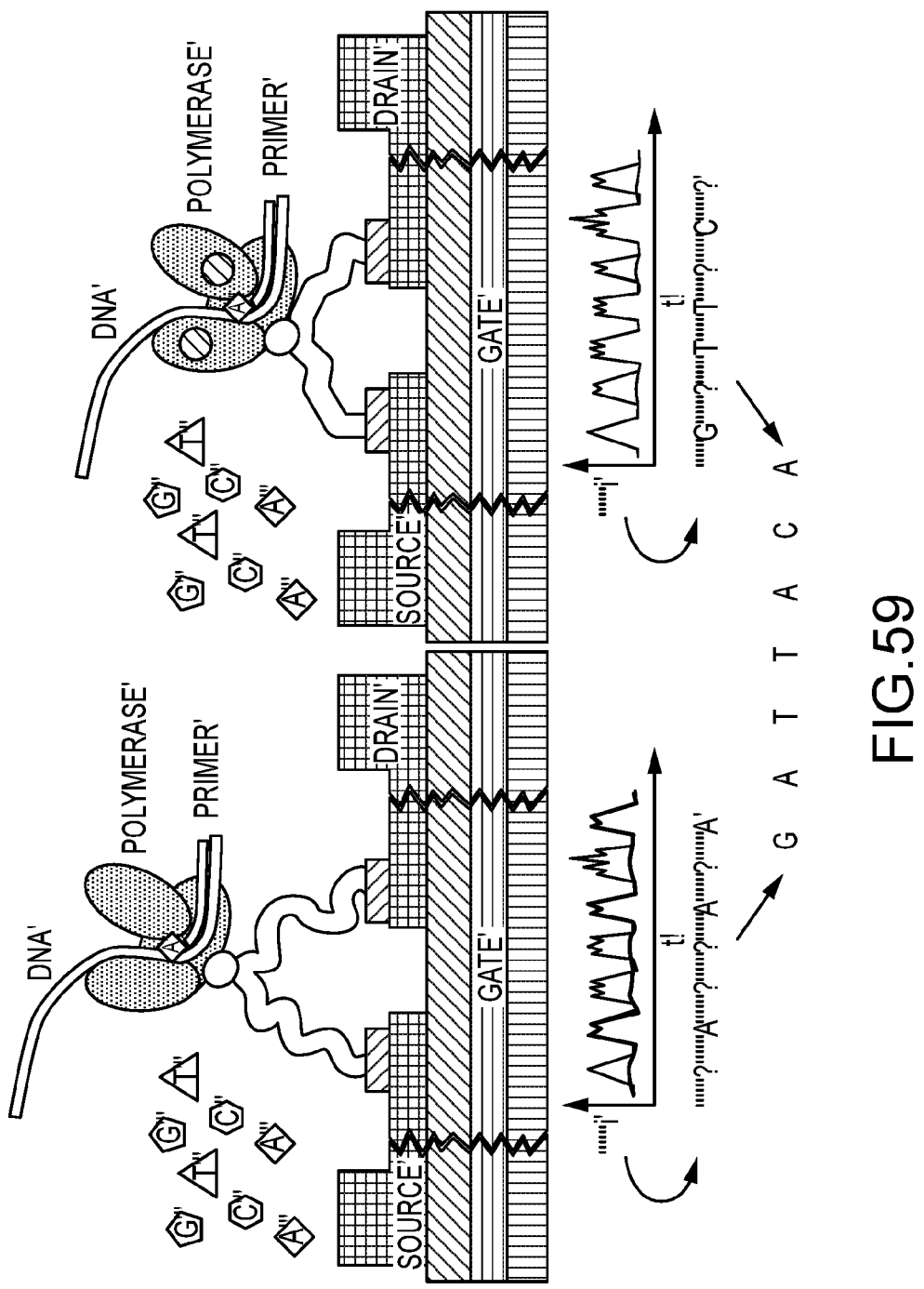
FIG. 59 illustrates combination of partial sequence information from replicate sequencing of the same (or replicated) DNA templates using different embodiments of the methods described, to achieve complete information. Blue traces indicate partial information from each separate instance, relative to the grey trace of combined information (which is not directly observable in a single sequencing run). Indicated here, a template is sequenced (left embodiment) to produce partial information (shown, only A bases can be detected), and again (right embodiment, indicating a change to the bridge and the enzyme), to produce complementary or auxiliary sequencing information (shown, G, T, C are detected), which is then combined to obtain complete sequence. The two sequencing embodiments could be physically or temporally isolated and independent, using replicate templates, or could be different states of the same sensor system at different times—perhaps produced by a buffer change, temperature change or change in applied voltages such as gate voltage—re-reading the same template. Any number of such complementary embodiments could have their information combined to improve the final sequence determination.

As illustrated in FIG. 59, that data acquired from independent sequencing runs performed with different specific embodiments from the above may be integrated to produce complete sequencing information from partially acquired information. FIG. 59 shows combination of partial sequence information from replicate sequencing of the same (or replicated) DNA templates using different embodiments of the methods described, to achieve complete information. Blue traces indicate partial information from each separate instance, relative to the grey trace of combined information (which is not directly observable in a single sequencing run). Indicated here, a template is sequenced (left embodiment) to produce partial information (shown, only A bases can be detected), and again (right embodiment, indicating a change to the bridge and the enzyme), to produce complementary or auxiliary sequencing information (shown, G, T, C are detected), which is then combined to obtain complete sequence. The two sequencing embodiments could be physically or temporally isolated and independent, using replicate templates, or could be different states of the same sensor system at different times—perhaps produced by a buffer change, temperature change or change in applied voltages such as gate voltage—re-reading the same template. Any number of such complementary embodiments could have their information combined to improve the final sequence determination. In one preferred embodiment, this could be the same sensor-DNA conjugate, but under different systemic conditions, such as changes to the buffer, dNTPs, temperature, applied voltages, circuit parameters monitored, metrology process, etc., in which the DNA template is re-read in some manner (strip and re-extend, reading through circular or hairpin templates to interrogate the same strand again, or the complementary strand). In another preferred embodiment, one device make may contain a diversity of sensors (different bridge molecules, enzymes, etc., or, in one preferred embodiment, different applied voltages) integrated on a single chip format. A multiplicity of replicate templates (clones, or PCR replicates), is applied, such that in parallel, the different sensors interrogate their respective copies of the DNA. These independent sensor measurements are then integrated to obtain complete sequencing information for the template under investigation. In one preferred embodiment the sensors could be substantially identical in their controlled properties, and the diversity just provides a means of average out noise or uncontrolled variations in sensor properties and performance. In another preferred embodiment, different bridges and modified enzymes that have complementary detection power can be deployed on one chip, exposed to the same template, and same primary solutions in the sequencing chemistry, to produce complementary information in parallel. In another preferred embodiment, the sensor in question retains its template, which is suitably read multiple times (via stripping of extended strand, or use of circular or hairpin templates), under different conditions (buffers, temperature, applied voltages, circuit metrology, concentrations of dNTPs or mixtures of dNTPs (native or modified), or different sequencing methods as above in the different sequencing runs, to produce a series on time of complementary acquisitions of partial sequence information, which can be integrated to achieve more complete sequence information.

Figure 48:
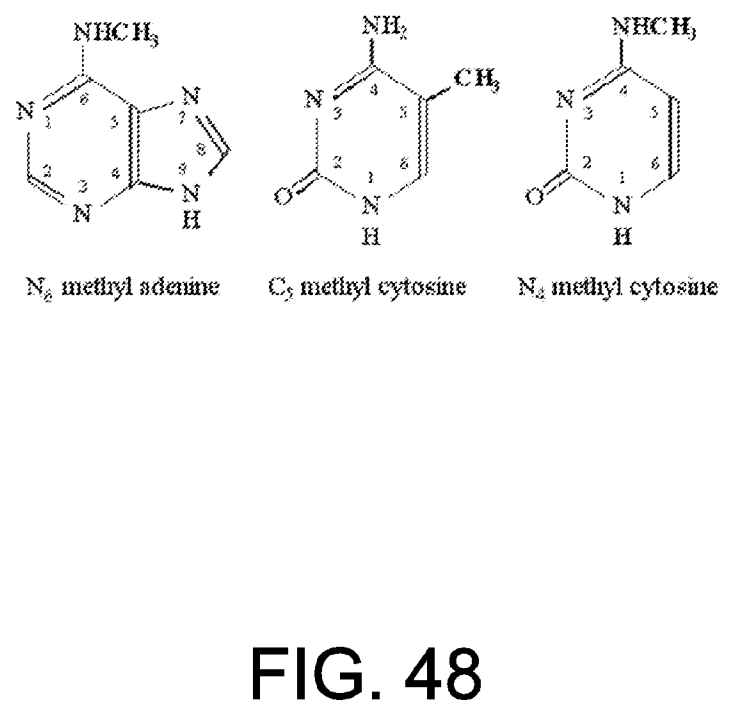

Further disclosed is that systems such as the above can also distinguish various modified nucleotides or base analogues present in the DNA strand, such as the methylated bases of FIG. 48.

In the methods above, incorporation steps could involve nucleotides that are not distinguishable from the acquired signals, so that partially determined sequence information results (e.g., the dNTP mixture applied could contain a subset of the nucleotides, such at {A,T}), and an incorporation spike would therefore indicate that a member of the subset was incorporated. This can yield partial sequence information. Such information can be combined in complementary ways (different nucleotide subsets) via replicate sequencing as described above, to further determine the underlying sequence that is compatible with the different partial observations.

Molecular Fingerprinting

The methods above, such as based partly or solely on a distinguishable incorporation spike, can be used to perform long range molecular fingerprinting. In this application, any of the methods of generating local sequencing information can be employed, to generate a stretch of local sequencing information. Then, all four dNTPs are added, and the system is allowed to freely incorporate for a length of time, during which time the incorporation spikes are detected and counted, to provide a measure of the number of bases spanned by this incorporation phase. Then, this phase is arrested, for example by flushing out the dNTP buffer, and the local sequencing method is resumed, to determine another local sequence feature. This process can be repeated across the span of a long DNA template. The resulting sequence contexts (Si), and base distance estimates between them (di), as a list, {S1, d1, S2, d2, S3, d3 . . . } form a fingerprint that identifies the gross structure of the DNA fragment. This information can be used for large scale structural mapping of a collection of overlapping fragments, or for such mapping relative to a given reference genome.

Other preferred embodiments where the enzyme could be a RNA polymerase or Reverse Transcriptase, with a corresponding DNA or RNA template that is being sequenced.

Signal Processing and Sequence Analysis Algorithms

Signal processing methods may be necessary determine the sequence from the acquired signal. This may include training or machine learning of a classifier system using training or calibration training data, and the use of various deconvolution or classification or hidden Markov models to determine or restrict the underlying sequence. This disclosure teaches that these methods are often integral parts of the overall sequence determination process. In preferred embodiments, this includes signal processing methods to segment features, and to discriminate/classify features from noise, as well as between features associated with alternative candidate sequence elements. This process may includes parameter extraction from segmented signals, including parameters such as time between spikes, spike height, duration, and such features as sub-features within segmented signals. The final sequence determination analysis may then further includes algorithms to deconvolute or fit processed signals to models of the underlying sequence, and seeking the model that best fits the data, as well as assigning confidence levels or odds to such fits. In particular, one preferred embodiment of the analysis where there may be pre-preprocessing to denoise the raw signals, and segmentation of the raw signals, as well as normalization of the raw signals, and then in general there is a model of the signals produced from underlying sequencing, and odds are assigned that the observed data come from underlying sequencing candidates. Maximum likelihood sequence can then be determined. In another preferred embodiment, the sequence prediction can be defined as an optimization of a cost functional measured the difference between observed and predicted signals, and methods of optimization theory may be used to efficiently solve such formulations for the underlying sequence.

The above methods may measure some property of the DNA that is less informative than complete sequence, such as just the length of the fragment, or partial sequence information, or information that can be used to classify the DNA template into one of several possible sequence groups. This includes single base sequencing or genotyping applications. This also includes fragment length analysis such as is used in microsatellite marker typing, or typing indel polymorphisms.

Sequence information so obtained may be combined from multiple trials of the same DNA molecule, or replicates thereof, to filter out errors and determine the underlying sequence. We teach the second strand could be removed, and the same molecule re-sequenced, to improve accuracy by combining these data. We teach that if the DNA molecule is circular, it may be sequenced repeatedly by reading linearly, to improve accuracy, and if it has a hairpin form, both strands may be read linearly to obtain forward and reverse sequence information to improve accuracy. These and other such methods known to those skilled in the arts of sequencing techniques are compatible with the present inventions.

The enzyme may be a ligase, and ligation of DNA oligos are detected and used to derive sequence information, or classify the sequence. Multiple rounds of serial ligation may be used to determine sequence, whether done on the same molecule serially, or in different rounds. Signals of ligation can be enhanced by the various means above.

Figure 60:
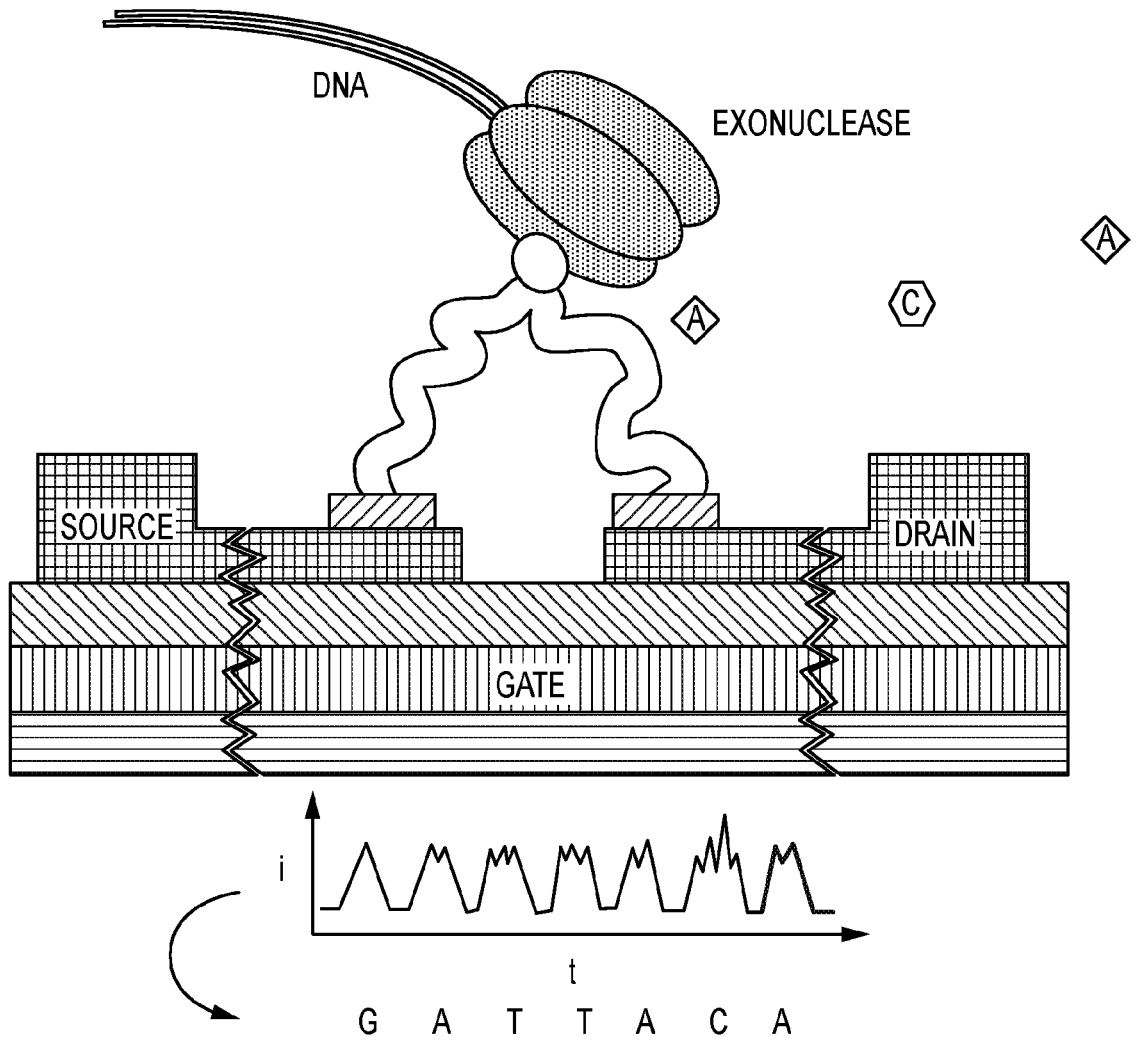
FIG. 60 illustrates an embodiment wherein the enzyme is an exonuclease. Signals are produced by the effect of enzyme conformation, DNA conformation, and freed nucleotides on circuit parameters.

The enzyme can be an exonuclease, as shown for example in FIG. 60, whereby the number or identity of bases is detected as they are processed and released. Signals of excision or base discrimination could be enhanced by the various means above. FIG. 60 illustrates an embodiment where the enzyme is an exonuclease. Signals are produced by the effect of enzyme conformation, DNA conformation, and freed nucleotides, on circuit parameters.

Figure 61:
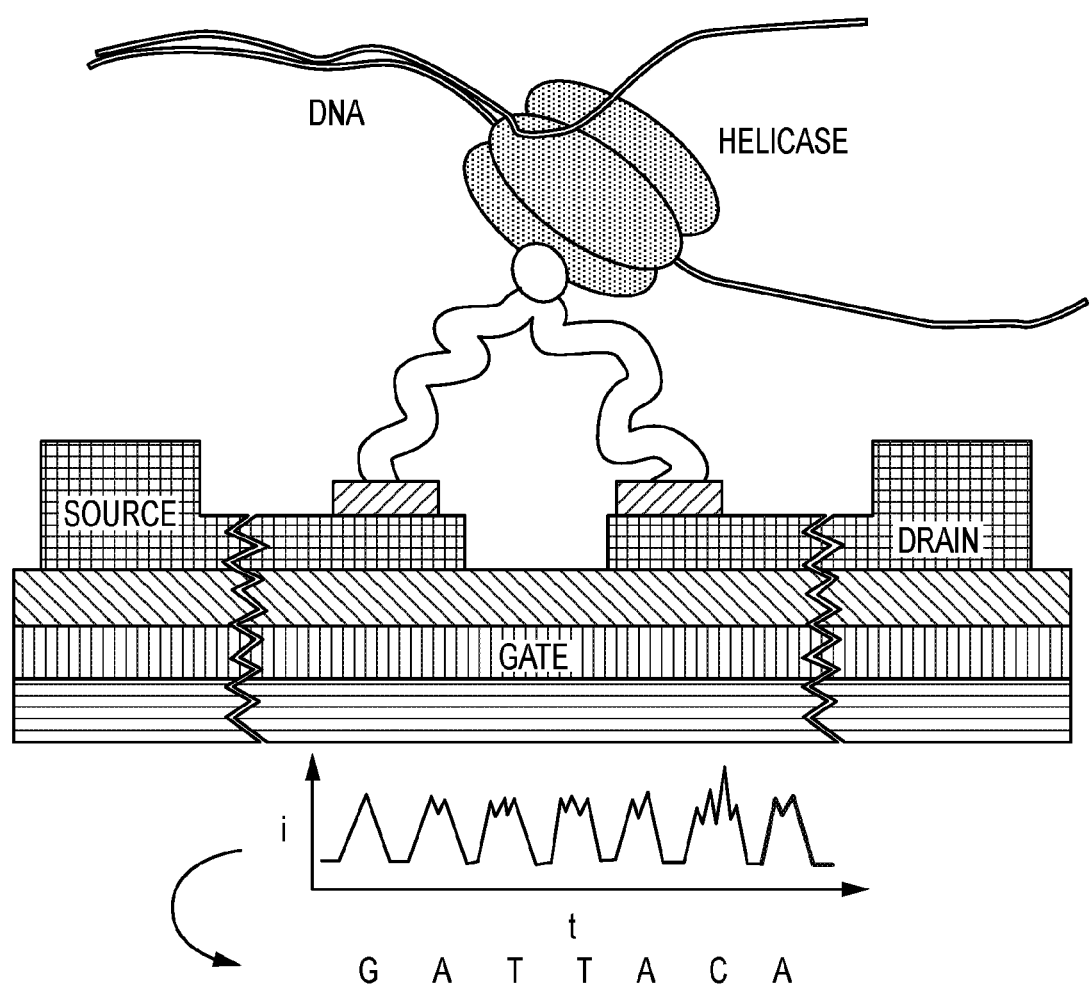
FIG. 61 illustrates an embodiment wherein where the processive enzyme is a DNA helicase, unwinding a double stranded DNA template.

In other embodiments, the enzyme may be a helicase, as shown in FIG. 61, and that the number or identity of bases is detected as they pass through the helicase. Signals of excision or base discrimination could be enhanced by the various means above, including in particular by modification of the nucleotides that comprise the DNA, or engineered changes to the helicase, FIG. 61 illustrates an embodiment where the processive enzyme is a DNA helicase, unwinding a double stranded DNA template.

Figure 62:
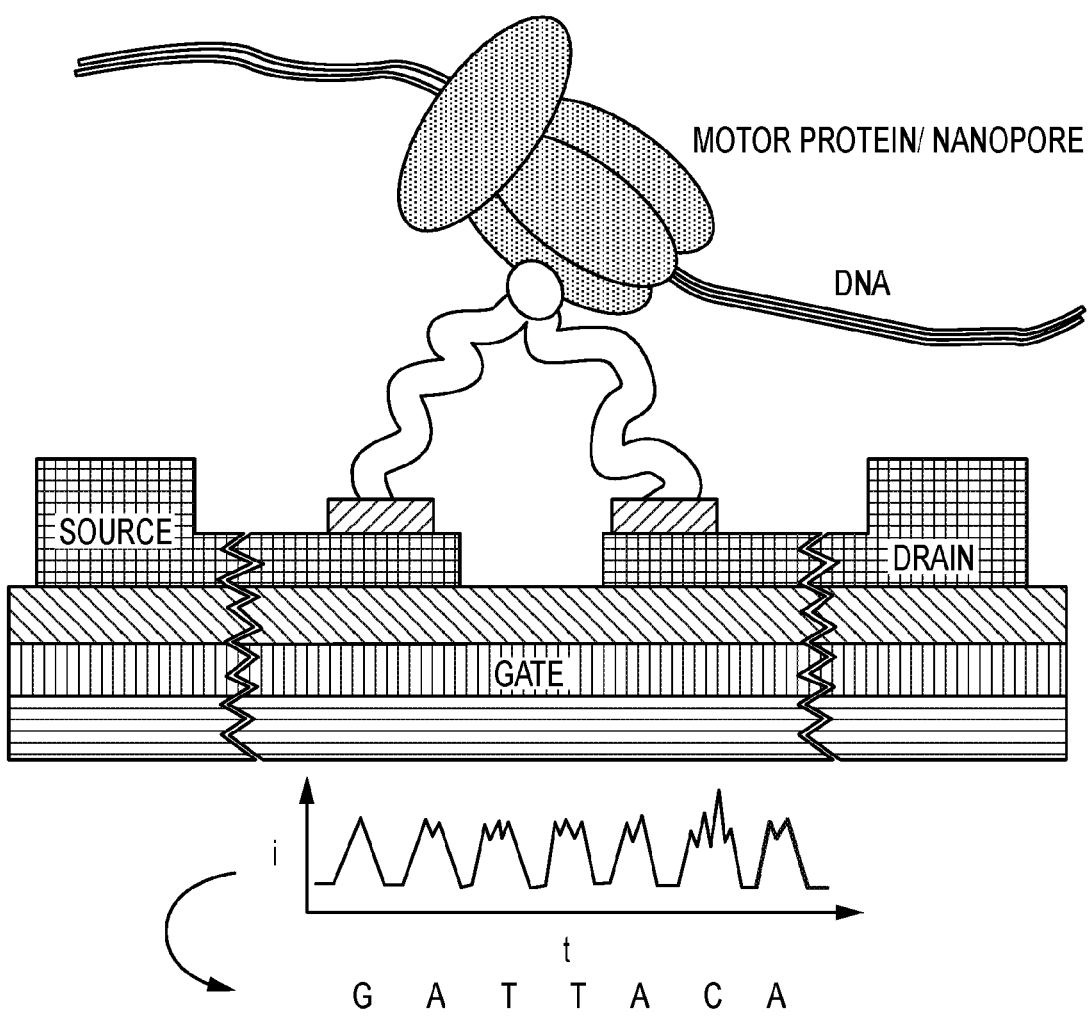
FIG. 62 illustrates an embodiment wherein where the enzyme is a complex formed of a protein nanopore and motor protein enzyme having DNA translocation capability.

The enzyme may also comprise a protein nanopore, as shown in FIG. 62. FIG. 62 illustrates that embodiment where the enzyme is a complex formed of a protein nanopore and motor protein enzyme having DNA translocation capability. In particular, it could be a complex of a processive enzyme with DNA translocation function (e.g. helicase, polymerase, or viral motor protein) and a protein nanopore. In this embodiment, changes in system current or other electrical parameters or response reflect the bases that are traversing the nanopore. Deconvolution methods can be used to reconstruct the underlying sequence. If the DNA is circular in this context, the same molecule can be read repeatedly for improved accuracy. Signals of base discrimination could be enhanced by the various means above.

Those skilled in the art of sequencing chemistry also understand how to combine many of the above elements of invention to produce improved sequencing results.

Figure 63:
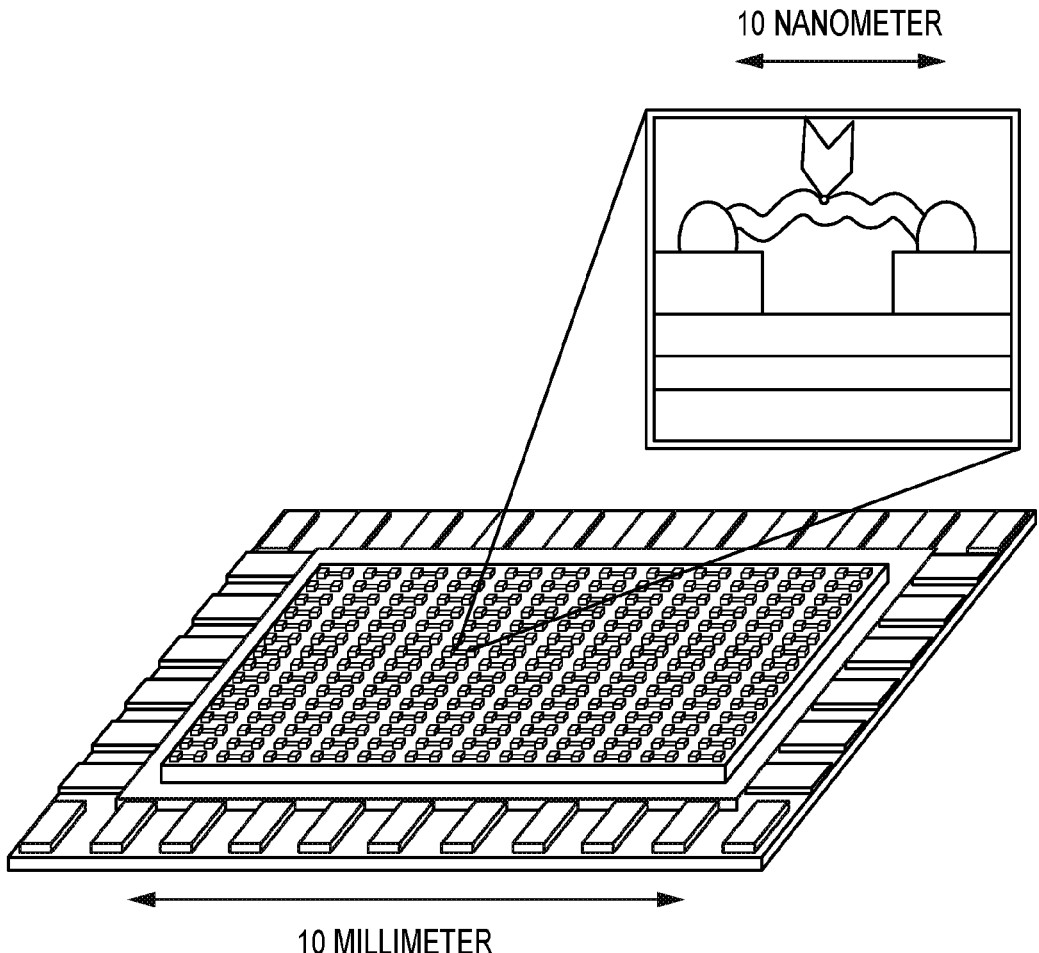
FIG. 63 illustrates an integrated chip sensor array device. This format provides a way to perform massively parallel sensing of sequence from many sequences at the same time, as well as the option of deploying diverse or identical sensor constructs at each site, for robust averaging or data integration of sequence data for replicates of a single DNAS fragment.

All the above methods can be performed on a sensor array integrated circuit chip, indicated in FIG. 63, containing an array of such sensors and supporting measurement circuitry and data read-out circuitry, in a massively parallel fashion, to achieve massively parallel sequencing of many DNA fragments on mass manufacturable devices. FIG. 63 illustrates an integrated chip sensor array device. This format provides a way to perform massively parallel sensing of sequence from many sequences at the same time, as well as the option of deploying diverse or identical sensor constructs at each site, for robust averaging or data integration of sequence data for replicates of a single DNAS fragment. In particular, the entire sensor can be a nano-scale device, with 10 nm dimensions, and supporting measuring electronics can be locally integrated if desired using CMOS semiconductor nodes at or below 14 nm, allowing a very high density array of integrated sensors on chip. This could enable up to 10,000,000 sensors on a single chip of standard dimensions (i.e. single stepper exposure area). Also, if a clonal or replicate population of DNA molecules is applied in this format, against an array of sensors that could be diverse or identical as described above and in FIG. 59, so that the multiple reads of the same molecule can be combined to filter out errors in the sequencing, to produce a much more accurate sequencing result.

Multi-site Analysis on Sensor Arrays

A long single-stranded DNA fragment, primed at multiple sites, could be introduced to such a sensor array, and sequencing initiated at a multitude of the primed sites that are captured by the polymerase enzymes at different sensor locations, using any of the described sequencing methods. This provides a novel way to obtain multiple sequencing reads simultaneously from a long fragment. This can both accelerate reading such a fragment, and provide information that can be used to assemble long range structure of the fragment, such as phasing of variants, or haplotyping, or large scale structural analysis.

Terminator Sequencing

Figure 64A:
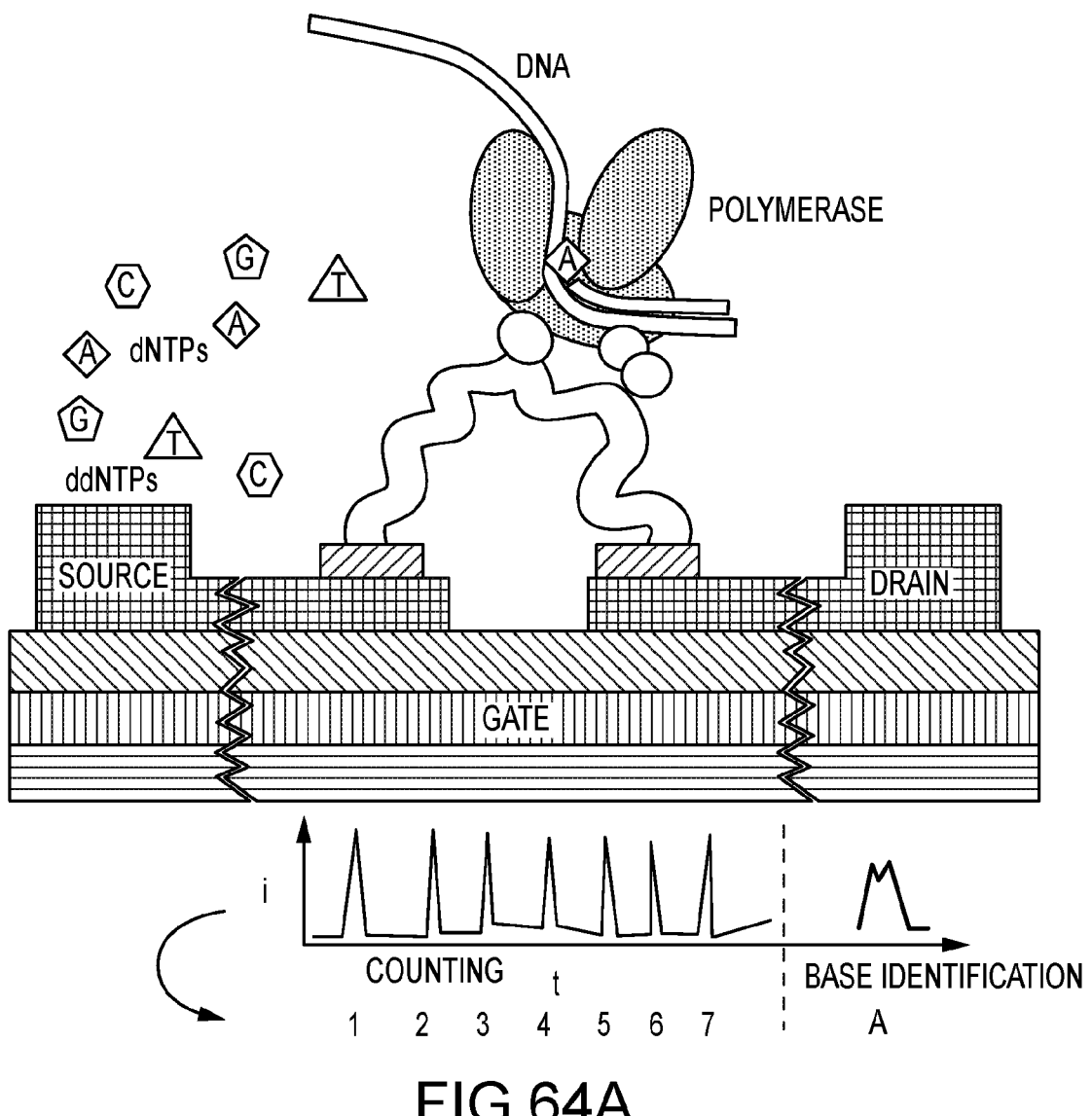
FIG. 64A illustrates a trial run in the terminator sequencing process. In the presence of a mixture of dNTPs (blue) and dideoxy terminators, ddNTPs (purple), polymerization and sensing proceeds, producing incorporation spikes used to count base position (to position 8 shown) as indicated, until a terminator is randomly incorporated. At the end of the reaction, a sensing measurement takes place, to identify the terminator base (in this case, A). Thus the underlying sequence has A at position 8. By repeating such measurements on this template, or replicate templates, and combining the information, the complete sequence of bases at all locations along the template can be determined.
Figure 64B:
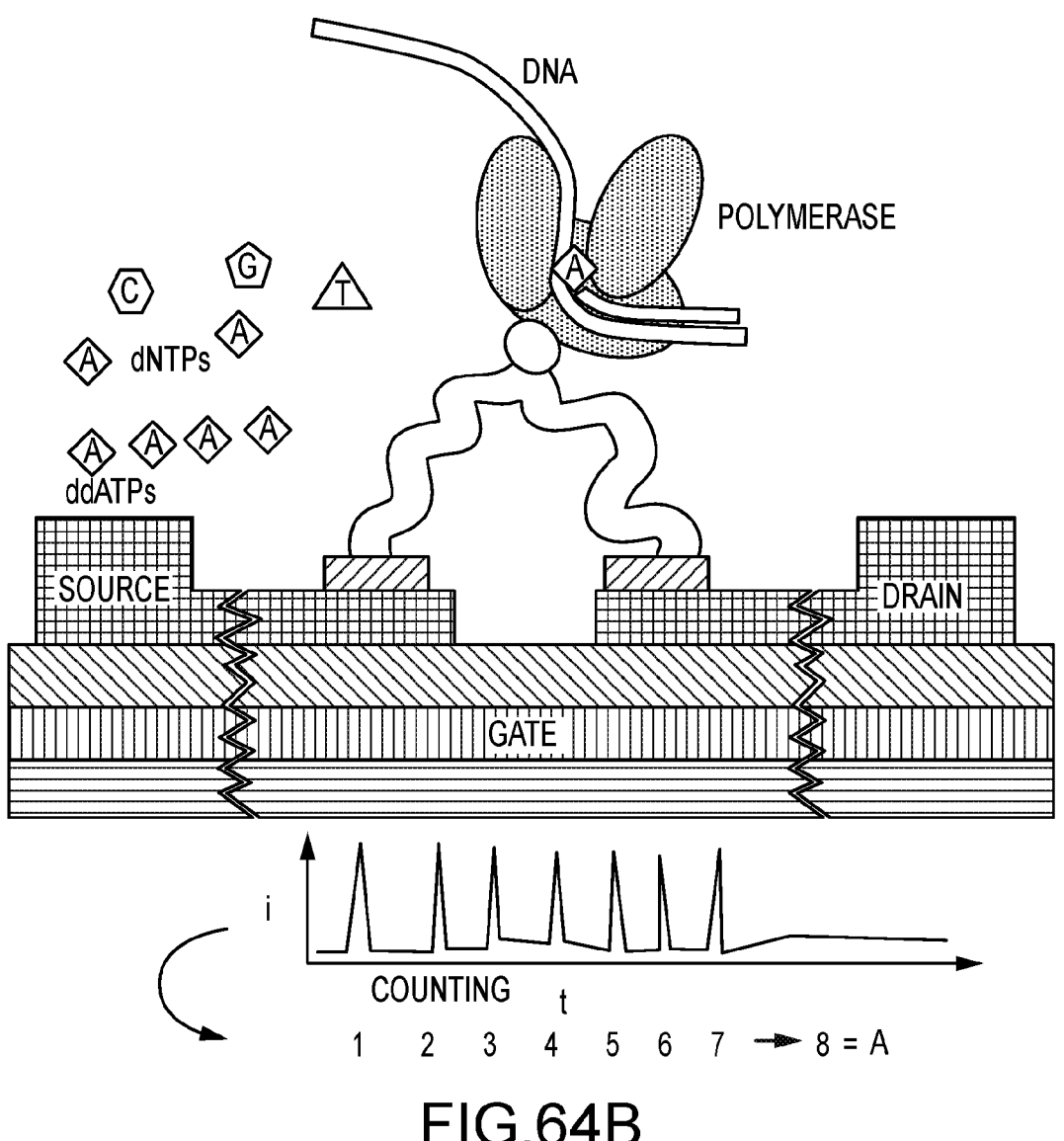
FIG. 64B illustrates an Alternative embodiment of terminator sequencing, where only a single base terminator, in the case shown, A dideoxy termination (ddATP, purple), is used in a given reaction. In this mode, when the reaction terminates, it is implied that the base in question is A, the terminator, and the count of the number of incorporation spikes gives the position of this A in the template. Repeating many runs for A with replicate templates will randomly determine all A locations in the template, and performing similar series of runs for the other terminator bases C, G, T, respectively, will determine the respective locations of all these bases in the template, thereby determining the entire sequence.

Terminator sequencing, wherein a mix of dideoxy terminator ddNTP and dNTPs are supplied, such that incorporation signal spikes from the dNTP (native or modified to enhance signal) incorporations provide a count of the base position along the template (position 1, 2, 3, . . . , L, where L is template length in bases), until a terminator is incorporated (native or with added detection group). Said terminator is then interrogated through a detection procedure, which may be a sensing of the same form, or different such as use of different detection buffer, temperature, or, in a preferred embodiment, use of voltage sweeps or waveforms or AC response or I-V characteristics to identify the ddNTP present and thereby identify the base at the designated position along the template. By combining the data from many such test runs, preferably performed in parallel on a sensor array chip as in FIG. 63, supplied with replicated templates, and assembling the results, the identity of the base at each possible base location (1, 2, 3, . . . , L) can be determined and thereby the entire sequence. In another preferred embodiment of terminator sequencing, shown in FIG. 64B, separate reactions can be run with dNTPs mixed with just ddATP terminators, and each such run will identify the position of an A base in the template where the reaction terminates through random incorporation of ddATP instead of dATP. Performing many such runs will identify the locations of all the A bases in the template. This is preferentially done in a single parallel reaction run on a sensor array chip to accumulate all such A-termination data in one parallel reaction. Similarly separate reactions for C-, G-, and T-termination are performed, respectively, to determine the locations of these bases in the template, respectively, and the combination of all such single base termination results will determine the entire sequence. FIG. 64A illustrates a trial run in the terminator sequencing process. In the presence of a mixture of dNTPs (blue) and dideoxy terminators, ddNTPs (purple), polymerization and sensing proceeds, producing incorporation spikes used to count base position (to position 8 shown) as indicated, until a terminator is randomly incorporated. At the end of the reaction, a sensing measurement takes place, to identify the terminator base (in this case, A). Thus the underlying sequence has A at position 8. By repeating such measurements on this template, or replicate templates, and combining the information, the complete sequence of bases at all locations along the template can be determined.

Figure 64C:
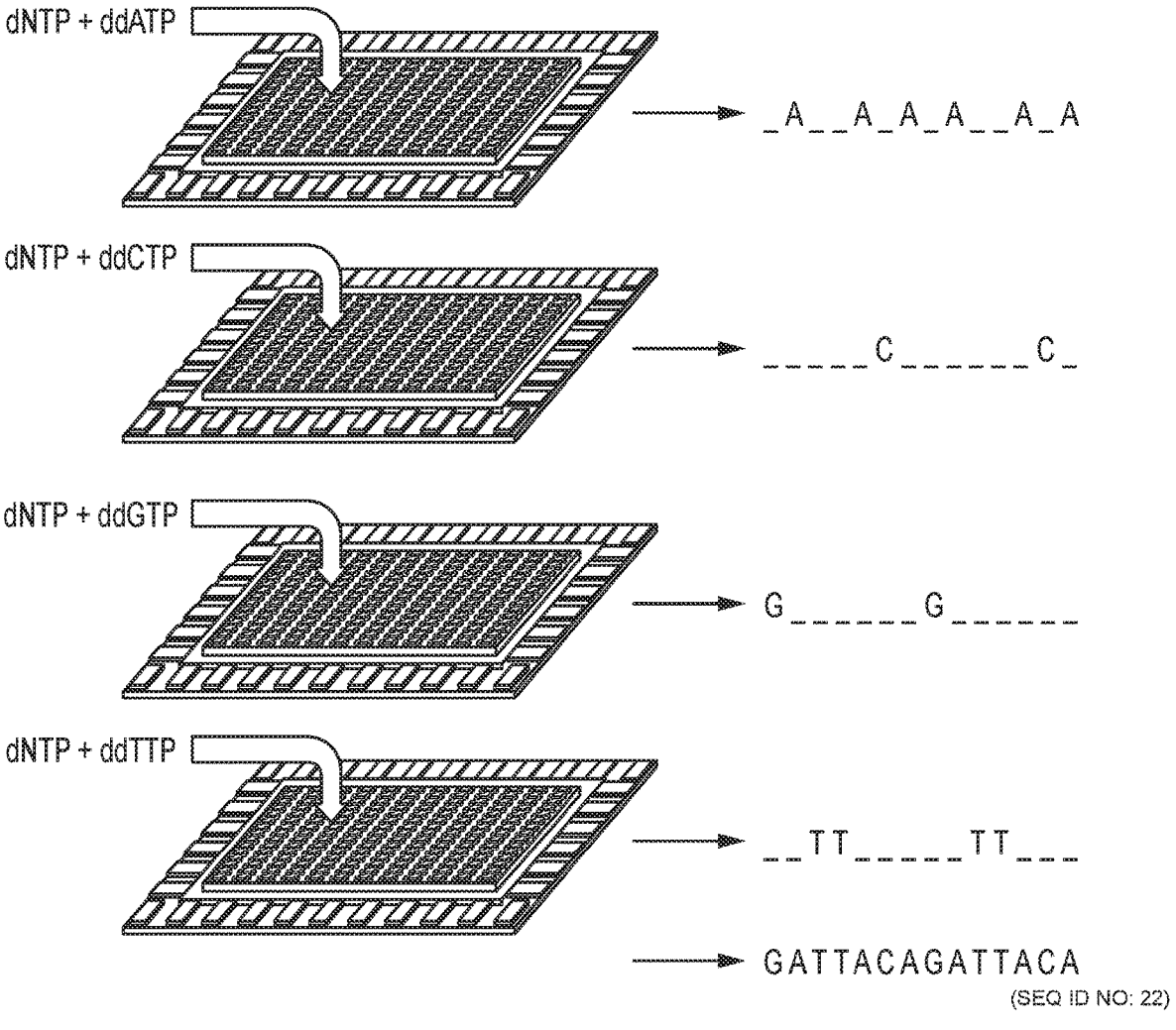
FIG. 64C illustrates an embodiment of terminator sequencing, where a replicated template of interest is loaded into each chip indicated, and all A termination data is accumulated from one run on a parallel sensor array, indicated in the top series, and similarly for the C-, G-, and T-termination reactions, and the single base results from each are accumulated (red arrow) to determine the full sequence of the template in question.

A preferred embodiment of this is to use four sensor array chips, dedicated respectively to the A-, C-, G-, and T-termination reactions, as indicated in FIG. 64C, to efficiently determine the sequence of an underlying template DNA, with one high level reaction run per array.

Sequencing by Hybridization

Figure 65:
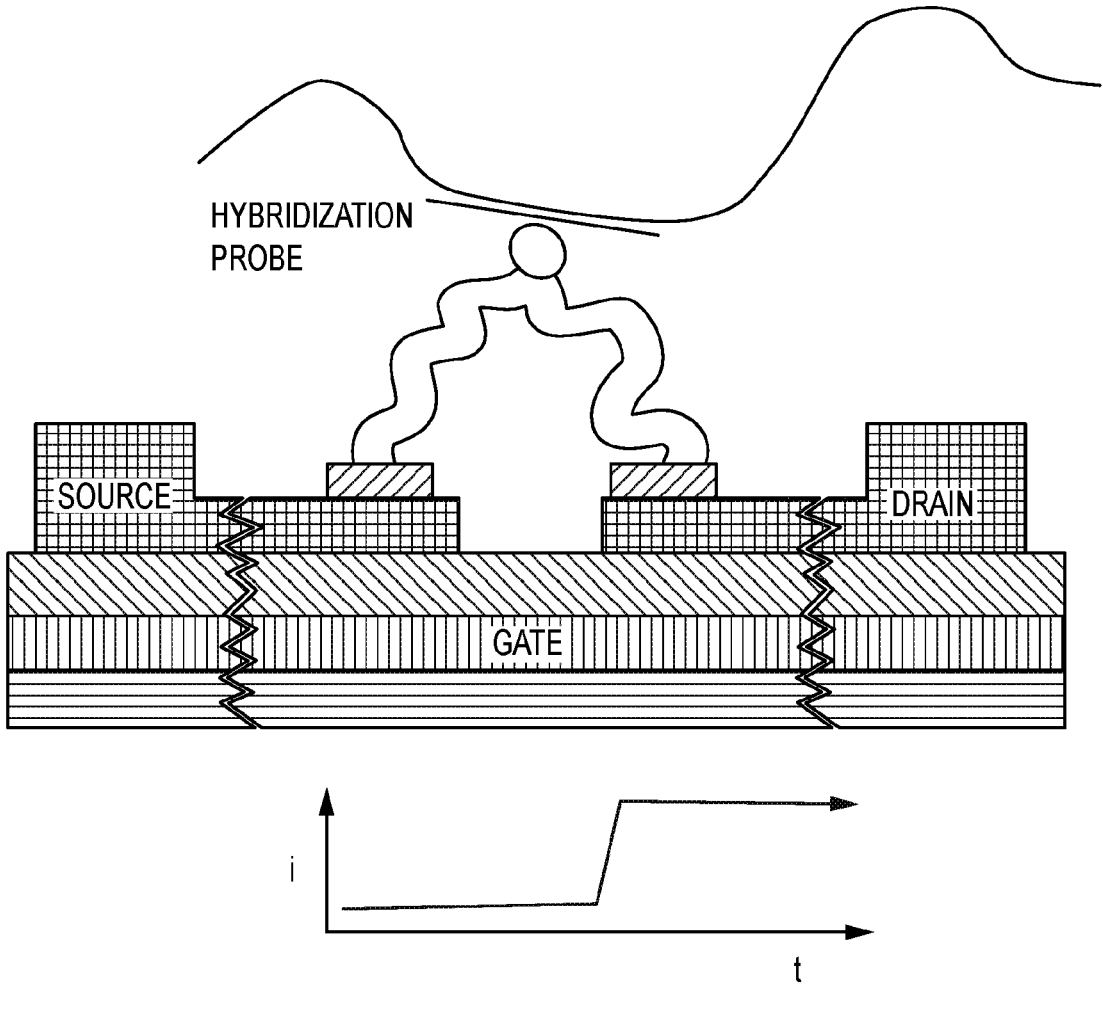
FIG. 65 illustrates use of a DNA hybridization probe in the molecular sensor, in place of an attached enzyme, and the detection of hybridization by monitoring a circuit parameter such as current. Hybridization is indicated by a different current level. One preferred embodiment would couple the DNA hybridization probe, to a streptavidin (orange group), via a biotinylated base located in the probe. This form of probe and detection measurement supports sequencing by hybridization, which is based on aggregating many such measures, using a set of informative probes, against replicated template molecules.
Figure 66:
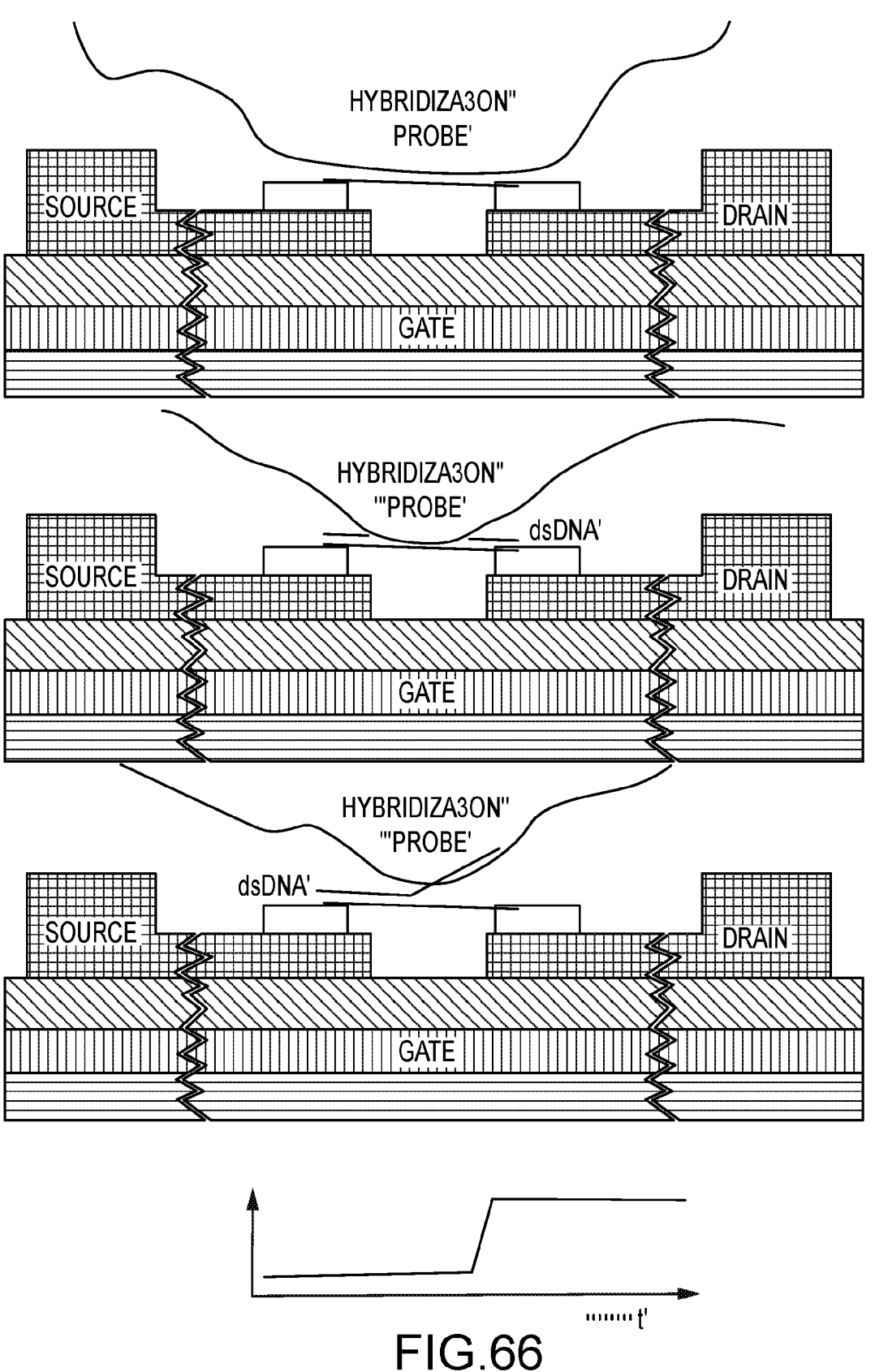
FIG. 66 illustrates alternative embodiments of incorporating a hybridization probe into the sensor, wherein the probe forms all or part of the bridge molecule. In a preferred embodiment, the DNA containing the probe would be coupled to the contact points using gold-thiol linkage, with gold contact points and thiolated nucleotides in the DNA. The figure illustrates three different ways such a hybridization probe could be configured as all or part of a DNA bridge molecule. In the lower instance, the probe could further partially hybridize to the underlying DNA, to set up competitive hybridization with the target for added stringency.
Figure 67:
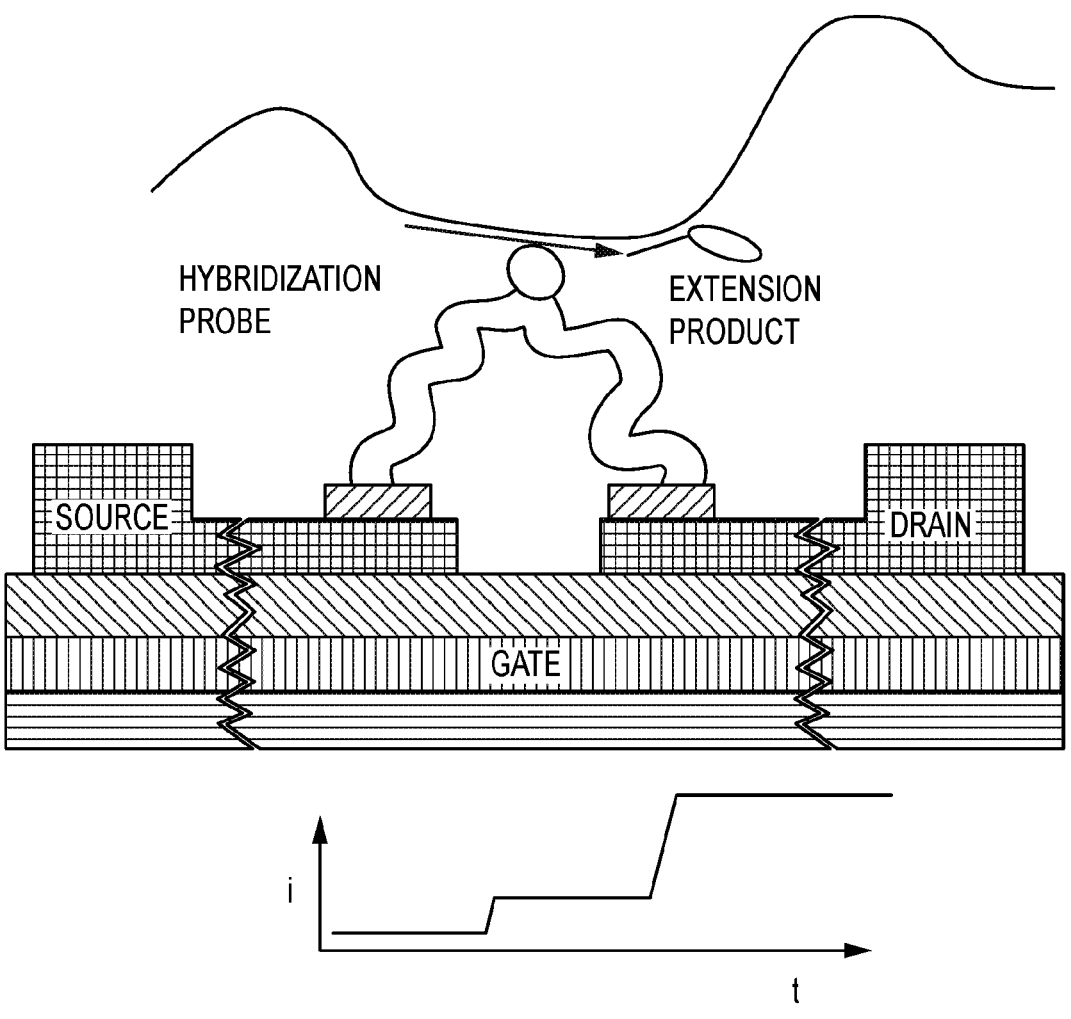

Further disclosed is sequencing by hybridization, using a special case of the sensor construct, where there attached molecule is not an enzyme, but rather a DNA hybridization probe, tethered to a bridge, or, in another preferred embodiment, the probe is acting as all or part of the bridge, as illustrated in FIGS. 65 and 66. Most generally, the bridge complex comprises an available hybridization probe, and there are many possible embodiments. The sensor signal in this case indicates whether hybridization to a target DNA single strand has occurred. As in the generally known sequencing by hybridization process, the aggregate data on which probes do or do not hybridize to the target DNA, based on many such measurements—preferably performed in parallel on a sensor array such as in FIG. 63—can be used to deduce what possible underlying sequences are most compatible with the data, up to full determination of the template sequence. In this process, the signal can be enhanced through extension reactions, as indicated in FIG. 67, wherein enzymatic extension can incorporate on or more bases comprising groups that increase the detectable signal. In addition, electronic stringency can be applied using the gate voltage to discriminate against/destabilize improperly paired hybridizations, thereby reducing erroneous hybridization detection. Stringency can also be based on the recorded signal, which may discriminate perfect pairing from imperfect, to eliminate erroneous hybridization detection. Further taught is that a variety of methods known to those skilled in the art to increase stringency can also be applied, such as the use of hairpin configurations, probes made from RNA or nucleotide acid analogues (LNAs, PNAs, etc), use of inosine or other universally binding probe bases, and also enzymatic processing such as polymerase extension or ligation as specificity measures. In a chip format, the sequencing by hybridization can be performed in parallel. Combination of probe hybridization to on chip probes, in conjunction of binding/ligation of a combinatorical set of detectable, distinguishable hybridization probes applied in solution, or some number of bases of sequencable extension of the primary ligation probe, can further extend the sequencing capacity of this approach, i.e. the ability to require more sequence information. We also teach that hybridization probes placed anonymously on chip can be decoded and identified by including detectable labels on said probes, or by a combinatorical binding process to decode binding barcodes on the probes. In particular, the probes could carry combinatorical DNA barcodes, decodable by a series of detectable oligo hybridizations. The probes could carry optical labels or barcodes, decoded by a prior optical imaging process. We further teach that electronic addressing of sensor sites could be used to deposit hybridization probes in directed fashion, so that known probes are put at desired sites. We teach that voltage can be used to accelerate the hybridization process, in particular the gate voltage may be used to attract the free DNA templates to the probe, increasing speed of hybridization, and reducing the amount of template required.

Further disclosed is the use of the array, with the molecular fingerprinting sequencing chemistry described above, to perform massively parallel fingerprinting of long fragments, for de novo structural assembly or structural assembly against a reference.

The probe molecules or enzymes used in the above processes could be controllably electronically—either in the native form, or through engineered modification, or through properties of the buffer (such as induced acid or base)—to either enable or enhance their interaction with DNA, or disable or inhibit that interaction. In particular, this could be influenced by the gate voltage, for example. We further teach that his could be use to gather data more quickly, or under more stringent (better signal to noise) conditions, and in either way increase the net amount of information collected per unit of operational time. In particular, in an array setting, different electronic control of the different sensor probes or enzymes on the array could be used to gather a diversity of complementary information that could provide overall greater informativeness for the sequence or sequence properties in question. For example, if electronic control can speed up or slow down the enzyme processing, the different sensors could process more quickly to different regions of the fragments, and then focus in on more accurate local information, to obtain more accurate assessment along the length of a long template supplied to the sensor array in replicate.

The probe molecules may be made to release their DNA template under electronic control, such as gate voltage. This can be used to retain desirable fragments, based on acquired sequencing information, and eject undesired fragments, by releasing and flushing them from the system. Desired fragments can subsequently be released and collected from the ambient solution for further uses, such as more extensive sequencing, or determination of modified or damaged bases that may be present via subsequence analyses. Such subsequent analysis could be via present means or other means such as mass spectrometry. For example, this could be of interest in the context of analyzing DNA from cancerous cells, to study the DNA damage that has occurred, or in studying modification of DNA that occur in special environments, such as in neuronal cells or stem cells.

Liquid Transfers and Processing

The various sequencing methods described entail working with one or more buffers. We teach several ways of efficiently working with these devices in this context. We teach placing the sensor or sensor array in a flow cell, and using a microfluidic system to pump buffers into and out of the cell. We also teach transfer the sensor or sensor array chip itself between differing buffer containers, dipping it in each, to achieve more rapid fluid exchange than is possible with pumping systems.

Microwell Isolation

In a special case of this general consideration of liquid transfer, which also enables additional detection methods, we also teach that individual sensors in the array may reside in their own microwell depressions (i.e. wells having microsized capacity), or a plurality of such per microwell, and that the entire array of sensors is contained within a large number of such microwells, as shown in FIG. 68. A single macroscopic covering/uncovering or sealing/unsealing process is used to seal and un-seal such wells for processing and liquid transfer simultaneously. The advantage is that in a sealed microwell, reactants and reaction products are localized and not lost to the bulk fluid, and furthermore any such trapped molecules repeatedly pass in proximity enclosed sensor, which may facilitate different types of sensing reactions that require a reactant to accumulate locally to produce an electronic detectable signal, or require a given target to engage and disengage multiple times from the same sensor to achieve a detectable signal. Or, an initial trigger molecule may lead to cascade production of signaling molecule that must build up over time locally. In particular, this can be useful if the primary sequencing reaction releases molecule (such as polymerase extension, releasing H, Pyrophosphate, and tags attached to gamma phosphate, or exonuclease, releasing the next base clipped off), and the molecular sensor comprises a probe molecule that needs to detect this molecule, accumulations of such molecules, or cascades of molecules resulting from the trigger molecule. FIG. 68 illustrates a sensor enclosed in microwells or nanowells that can be sealed and unsealed in a bulk/macroscopic process. This localizes reactants and reaction products, to facilitate other modes of detection. This may also benefit from multiple sensor types per well, or multiple probe molecules per sensor, so that a processive enzyme can be present with a probe to detect a reaction product.

In various examples, a three terminal molecular electronic sensor comprises primary source and drain electrodes and a field effect gate electrode, wherein a probe molecule is coupled between source and drain electrodes or a probe molecule is coupled to a bridge molecule coupled between source and drain electrodes, and wherein the probe molecule engages in a detectible interaction with a nucleic acid polymer, where the detection comprises the monitoring of circuit parameters. In various examples, the detectable interaction can be related to the sequence composition of the nucleic acid polymer interacting thereby, relative to some set of candidate sequence elements. The polymer may be a form of DNA or RNA, for example, and the set of candidate sequence elements may be {A,C,G,T} for DNA or {A,C,G, U} for RNA, respectively.

In various examples, candidate sequence elements may include modified nucleotides, and the related sequencing process thereby identifies modified nucleotides in the DNA template. Modified nucleotides may contain the various forms of methyl C, such as, 5-methyl-C, and the related sequencing process thereby identifies these modified nucleotides in the DNA template.

In various embodiments, the probe molecule is an enzyme, or a DNA or RNA hybridization probe. Preferred configurations of the latter two embodiments are shown in FIG. 66. As an example, the probe molecule comprises a DNA polymerase, such as, for example, Phi29 or a mutant thereof, or Pol I or a mutant thereof.

In various other non-limiting examples, the probe molecule may comprise any one of a Reverse Transcriptase, a ligase, an exonuclease, an enzyme that translocates DNA, a helicase, a protein nanopore, a protein nanopore complexed with an enzyme that translocates, or a Ribosome.

In non-limiting examples, the bridge molecule may be for example double-stranded DNA, a protein alpha-helix, an IgG antibody, an IgG antibody having specific affinity to the contact points on the source and drain electrodes, or an IgG antibody template engineered to have a specific affinity to the contact points on the source and drain electrodes.

In various aspects, the contact point coupling to the source and drain electrodes is via a thiol-gold bond between a gold contact, such as a gold bead, and a thiol containing group in the bridge molecule. In a more specific example, the internal couple point of may be via a biotin in the bridge molecule, a streptavidin (native or modified), and the probe molecule conjugated to the streptavidin.

The assembly of the elements of the sensor may be monitored through electrical parameters during the course of a multi-step, in situ assembly process. For example, the electrical parameter monitored may be any one of: the sourced-drain current under an applied source-drain voltage and gate voltage; the sourced-drain or gate voltage under an applied source-drain current; the sourced-drain current under an applied source-drain voltage and gate voltage; an I-V characteristic, as the source-drain voltage and/or gate voltage are swept through a range of values; and the current response relative to an applied voltage waveform, applied to the source-drain or gate.

In other aspects, the probe molecule may be a polymerase, whereby a detectable signal is a signal of incorporation monitored through a series of nucleotide trial flows to determine the sequence of a primed, single-stranded DNA molecule template bound to the polymerase. In more specific examples, the polymerase is modified to enhance the signal of incorporation. Likewise, nucleotides may be modified to enhance the signal of incorporation.

In various aspects, the probe molecule is a polymerase, and the detectable signal is a signal of incorporation that also distinguishes the different bases, and this is monitored while the system is exposed to a mixture of dNTPs, to determine sequence. Further, the polymerase may be modified to enhance the signal of incorporation, and the nucleotides may be modified to enhance the distinguishable signals of incorporation of the different bases.

In various examples, the sensor can be used to distinguish (in addition to {A,C,G,T}), the presence of additional modified bases, such as 5-methyl-C, in the template.

In examples wherein the probe molecule is a polymerase, the detectable signal may be a signal of incorporation, and this can be used to perform terminator sequencing reactions, and for each distinct terminator-A, -C, -G, -T, and thereby assemble the sequence of a template molecule. For example, electrical measurement can discriminate the four different terminators, and the terminator sequencing is performed through assembly the results of many runs of a mix of terminators, with identification of the terminator.

In other examples, the probe molecule comprises a DNA or RNA hybridization probe, and the signals of DNA interaction from a diversity of such probes can be used to sequence or categorize a DNA fragment supplied in replicated to the corresponding reactions.

In various examples, a sensor array format may be deployed. For example, an array of 1,000 or more such sensors, or of 10,000 or more such sensors, or of 100,000 or more such sensors, or of 1,000,000 or more such sensors, or of 10,000,000 or more such sensors, or of 100,000,000 or more such sensors. Deployment may be on a chip that comprises CMOS sensor electronics. Such a chip system may be used to sequence DNA by collecting in parallel a large number of detectable signals of interaction of probes and DNA, and aggregating this information. In these various embodiments, the chip system may be used to perform massively parallel sequencing of a multitude of DNA molecules, or to perform terminator sequencing of a DNA fragment supplied in replicate, through various terminator sequencing reactions, each being applied in massively parallel fashion on four distinct chips, or in series of four reactions on a single chip.

Chip systems may be used to perform terminator sequencing of a DNA fragment supplied in replicate, through various terminator sequencing reactions, each being applied in massively parallel fashion on four distinct chips, or in series of four reactions on a single chip, to achieve the requisite number of individual reactions of each type. Chip systems may be used to perform terminator sequencing of a DNA fragment supplied in replicate, through various terminator sequencing reactions being performed in massively parallel fashion on a single chip to achieve the requisite number of individual reactions. Chip systems may be used in conjunction with a sequencing method as outlines, and a incorporation detection signal as outlined, to produce molecular fingerprinting of fragments applied to the array, so as to collectively achieve de novo fragment assembly or assembly against a reference.

In these various chip systems, the probes may be a collection of DNA hybridization probes sufficiently informative to perform sequencing by hybridization on a fragment. Probe identities may be encoded in a combinatorical fashion that can decoded through a series of decoding reactions. For example, the decoding reactions may comprise hybridization reactions against pools of hybridization tags, and the reading of said reaction outcomes is via electronic detection of the hybridization signals, using the observable circuit parameters.

In some examples, the probes may be a collection of DNA hybridization probes sufficiently informative to perform sequencing by hybridization on a fragment, and said fragment is applied to the array in replicate to determine its sequence.

In various embodiments, buffer modifications or conditions may be used to improve the signal detection in any of the aforementioned examples, such as more dilute/low-ionic strength buffers.

A diversity of sensors may be used on a chip-based sensor array to make complementary measures as in the above sequencing methods, which are further combined to achieve greater aggregate accuracy. In particular, when one DNA fragment is supplied to the array in replicate, and the information from the independent sensors on the array is used to determine the sequence of this fragment with increased accuracy. The diversity of sensors may be provided through diversity in the bridge structure, or in the diversity in modified probe molecules. In various aspects, the diversity of sensors is through random (uncontrolled) diversity in the configurations and operating conditions of the sensors on the array, and the aggregation of this information constitutes a way of removing such noise to obtain a more accurate sequence.

In examples where the probe molecule is polymerase, nucleotides may be prepared and supplied in such a way as to have different kinetic signatures, which thereby provide the detectable signal. Different kinetics may be due to different concentrations of the nucleotides in solution, and the signature includes the timing between incorporation signals.

In various embodiments, the enzyme of the sensor is an exonuclease, and the DNA template may be prepared with modified bases to enhance detection, and the exonuclease may be further modified to enhance this detection of said nucleotides, and sequencing signals are obtained occurs as the exonuclease cleaves bases in order.

In various examples, the probe molecule (native or modified) has the ability to be electronically controlled, so that its reaction with DNA can be enabled or enhanced or inhibited or disabled. For example, the probe molecule may be an enzyme that can be electronically controlled, in terms of enabling or enhancing or inhibiting or disabling its processivity, and this is used to improve the informativeness of the sequence data collected. In particular, in the chip sensor array format, this allows a diversity of such differently acquired measures to be acquired in parallel, to increase overall informativeness. In particular, in the case of a polymerase, this could be used to move individual polymerases along the templates faster, to reach and then slow and interrogate more distant regions of a long, replicate fragment applied to all sensors.

In various embodiments, the gate voltage may be set so as to improve the signal detection.

In the examples pertaining to sequencing by hybridization, electronic controls may be applied to improve performance, such as voltage driven concentration of template DNA near probes to accelerate hybridization, voltage based stringency to repel improperly paired hybrids, or voltage cycling of this stringency to rapidly anneal correctly hybridized fragments, or applied voltages that alter the detected signal in a way that distinguishes proper hybridization from mismatched or improper hybridization.

In various embodiments, DNA/RNA templates may be held or released electronically, and, based on sequence determination, certain fragments are retained, the rest released and removed, and the retained ones released and captured in the solution for subsequent uses or additional analysis.

In some examples, a reversible terminator base is used to provide a terminated reaction to allow time for more extensive electronic discrimination sensing to identify the terminated base in question, followed by removal of the terminator and repetition of this processes out to the desired number of bases to be sequenced. For example, the reversible terminator may be used to enable probing of the next base, past the terminator, by introduction of one or more trial nucleotide dNTP mixtures, and acquiring signal data that allows determination of the next base due to detectable differences in transiently signals produced while in the binding pocket between correctly paired and incorrectly paired bases, followed by removal of the terminator, and incorporation of another reversible terminator to advance the process to the next step, and repetition of this processes out to the desired number of bases to be sequenced.

The primer may be used is a non-extendable/terminator primer, and the interrogation therein is used to perform single base sequencing the obtain the identity of the first base following the primer.

In various examples, the enzyme may be a polymerase, the use of which may be targeted primers for priming templates, either prior to introduction of the templates, or such primers tethered in place on the bridge or polymerase molecules, to achieve in situ targeted sequencing, potentially without a separate targeting reaction step. Herein, such primers may be standard oligo primers, or primers of increased affinity, or primers enhanced by recombinase, the latter for priming of double stranded DNA.

In the chip array system, a long DNA molecule primed at multiple sites may be used and introduced to the array to be captured by multiple polymerase, and undergo multiple simultaneous sequencing reactions, or used to determine variant phasing, haplotype, or structure of a contiguous, long DNA molecule.

In some examples, a plurality of molecular sensors within micro-well chambers may be disposed on a chip, with a large number of such microwell on the chip, and a single macroscopic process to seal and unseal such wells, in such a way that independent contained reactions and detections can occur within the enclosed wells. This enables a number of signal detection modalities in which the molecular sensor probe molecule detects a byproduct molecule released or created from the processive reaction itself (polymerization, or exonuclease), or subsequent molecular cascade molecules stemming from such primary molecules.

A microfluidic system and flow cell provides the needed reaction mixtures and buffers to the sensor or sensor array.

In the chip array system, the chip may be directly transferred between different containers of reaction buffers, in order to achieve rapid exposure to different buffers used in the sequencing process.

In the examples wherein the probe molecule is polymerase, these examples provide the use of a strand displacing polymerase, in conjunction with a circularized template, or a hairpin-adapted template, so that reading of both strands, or repeated reading of the same strand, is achieved to produce multiple reads of the same template that enhance the accuracy. Further, stripping and re-sequencing of the same template can achieve the same end directly.

EXAMPLE 8 sets forth the experimental results for construction of a basic sensor, its properties, and its application to observing signals of incorporation by a polymerase in several important application settings (e.g. homopolymer length, single base determination, methylation, and long reads). This example establishes reduction to practice for a critical application, and provides a strong basis for the premise that the other applications can be similarly reduced to practice. This example sets forth results, e.g. illustrated in the drawing figures, for Molecular Sensor Structure, Electrical Measurement Set-up, Electrode images, Sensor chip image, Chip passivation, Flow Cell, Chip packaging, I-V characteristics of sensor, Electrical observation of sensor self-assembly, Discrete polymerase incorporation event signals in homopolymer DNA, single base detection signal, Methylated DNA detection, and Long read capability.

Determination of the Sequence of DNA is a Fundamentally Important Measurement Process.

FIG. 69 illustrates the Molecular Structure used for this experimental work. FIG. 69 shows details of the bridge and probe molecule structure typically used for experimental work. The bridge in this case is double stranded DNA molecule, of 20 nm length shown (60 bases), with thiol groups at both 5' ends for coupling to gold contacts on a metal electrode. The probe molecule is a polymerase, here *E. Coli* Pol I, chemically crosslinked to a Streptavidin protein, which in turn is coupled to the bridging at a biotinylated nucleotide in the synthetic DNA oligo. FIG. 69 is shown to scale for the sixes of the molecules and atoms.

Referring now to FIG. 70, a schematic of a test set-up for electrical measurements on molecular sensors is shown. In the upper portion of FIG. 70, a cross-section of the electrode-substrate structure and attachment to an analyzer for applying voltages and measuring currents through the bridge molecule is shown. In the lower portion of FIG. 70, a perspective view of an electrode array for bridging circuits is illustrated. Each pair of electrodes has Metal-2 contact points on Metal-1 electrodes (that is, dissimilar metals). In the present experiments, contact points are gold beads or gold coated electrode tips, which support self-assembly of thiolated molecules into place via thiol-gold binding.

FIGS. 71A, 71B and 71C show electron microscope images of electrodes at various levels of magnification. The images are of electrodes with gold metal dot contacts used for bridge binding. Electrodes are on a silicon substrate, and were produced via e-beam lithography. FIG. 71A is the EM image of an array of electrodes. Here, the electrodes are titanium, with gold dot contacts. FIG. 71B is the EM image of a close-up showing an electrode gap of 7 nm and gold dot contacts having 15 nm gold-to-gold spacing. FIG. 71C is an EM image close-up showing approximately 10 nm gold dots at the tips of the electrodes.

FIG. 72 illustrates electrode test chip architecture. In this case, the electrode array was formed on a 1 cm silicon substrate, using e-beam lithography. The series of three SEM images in FIG. 72 shows the 20 electrode pairs at increasing resolution, down to the 10 nm scale of the electrode gap.

FIG. 73 illustrates use of a passivation layer on a device to protect the electrodes from the solution. In this case, the passivation layer is silicon oxide. Openings in passivation expose the electrode area on the nanometer scale, and the electrical contact pads on a 10 micron scale.

FIG. 74 illustrates a flow cell used to support controlled exposure of liquid solutions to the sensor chip surface. In this case, the flow cell comprises molded PDMS polymer.

FIG. 75 illustrates a chip mounted in a chip carrier for electrical measurements.

FIG. 76 sets forth a characterization of conductivity of the assembled sensor complex. FIG. 76 shows the measured Current-versus-Voltage (I-V) characteristics of DNA bridge molecules and complete sensor complexes (bridge with polymerase) in wet (dilute salt buffer) and dry (air) conditions, along with controls of open circuit electrodes in air, water and dilute salt buffer. FIG. 76 shows that the bridge and sensor complex conduct on the order of 100 mpico-Amp currents at 1 Volt of applied source-drain voltage. Measurements are done on semiconductor parameter analyzer via an SMU.

FIG. 77 illustrates electronic monitoring of the self-assembly of a molecular sensor having gold-dot contact electrodes. Current versus time measurements were used to monitor progress of the self-assembly of the bridge and molecular sensor complex. The plot at the top left in FIG. 77 shows Phase 1: wherein double stranded DNA bridge assembles with thiol groups on 5' ends assembles onto electrode gold contact point, as indicated by a jump in current. The plot at the upper right in FIG. 77 shows Phase 2: polymerase-streptavidin complex binds to biotinylated site on the dsDNA bridge, as indicated by jump up in current. The plot at the lower right in FIG. 77 shows Phase 3: primed single-stranded DNA template binds to polymerase to complete the complex, as indicated by a spike in current versus time.

FIG. 78 provides the images of the final assemblies. In the higher resolution image, the bridge-complex is directly visible without labeling, and is seen as a blurry high contrast region joining the electrodes (pointed to by the green arrow).

FIG. 79 are four plots measuring incorporation signals with the sensor. The plots in FIG. 79 show the current signals resulting from the sensor being supplied with various primed, single stranded DNA sequencing templates and dNTPs for incorporation and polymerization. In each case, the major signal spikes represent signals from discrete incorporation events, wherein the polymerase enzyme adds another base to the extending strand. In the plot in the upper left portion of FIG. 79, the template is 20 T bases; In the plot at the upper right, template is 20 G bases; In the plot at the lower left, template is 20 A bases; In the plot at the lower right, the template is 20 C bases. The approximate rate of incorporation observed is 10 to 20 bases per second, which is consistent with standard enzyme kinetics except for the lower rate of ~1 base per second due to rate limiting factors (e.g. lower dNTP concentration).

FIG. 80 is a close up of signal produced from a single base incorporation event. In this case, the signal has a double-peak structure which could potentially be used to help identify the base, in addition to detecting the incorporation event.

FIG. 81 provide plots showing electrical sensing of methylated bases. FIG. 81 demonstrates the potential use of the sensor to sense the methylation state or individual methylated bases in the template. The plots show different signals resulting from un-methylated versus methylated portions of the template (green trace). Higher signals result from the un-methylated portion, rather than methylated portion. The experiment shown consists of measuring traces for a series of different solution additions onto the sensor chip as indicated, for the template sequence indicated. The dCTP flow produced a single base incorporation spike, and the addition of dGTP then enabled incorporation to proceed across the CG tract of the template, highlighting a difference in signal from methylated versus un-methylated template.

FIG. 82 illustrate the long-read capability of the sensor. This figure shows the potential to read or analyze long DNA fragments, which is important for applications where long range continuity of the data is important, such as de novo assembly of whole genome sequences. The DNA template is the 5.4 kb PhiX viral genome. In the current versus time plot at left, differential signals from a low-time-resolution read of the template (dNTP mix), versus a follow on control (terminator ddNTP mix, polymerase activity blocked) without polymerization is recorded. The SEM image at the right shows the electrodes with the long template DNA visible.

Example 9

Molecular Sensor Having a Peptide Bridge Sensor Detecting Base Incorporation Signals with Modified dNTPs Another preferred embodiment of the sensor utilizes a protein alpha-helix as a bridge molecule. Protein alpha-helices are favorable structures because they are relatively rigid, are known to allow electron transfer and current conduction, and they can be synthesized as peptides with atomically precise specifications of structure and with coupling groups for self-assembly. Such a peptide alpha helix bridge and associated sensor is illustrated in FIGS. 83A and 83B. The particular peptide used in the experimental work of this example is a peptide with the following 66 amino acid sequence:

```
                                    (SEQ ID NO: 14)
CAEAAAREAAAREAAAREAAAREAAAREAAA{Lys-Ahx-Biotin}
EAAAREAAAREAAAREAAAREAAAREAAARC
```

This features a 61-amino peptide based on repeats of the motif EAAAR (SEQ ID NO: 8), which is known to favor an alpha-heix structure for the peptide. Cysteine amino acids at the termini provide for thiol-gold coupling to the gold contacts on a chromium electrode. A central lysine placed in the peptide is modified to include biotin on an Ahx (six carbon linear aminohexanoic) linker, to support binding of a neutravidin protein for coupling purposes. The alpha helical from of the peptide is approximately 9 nm in length. The polymerase couples to the neutravidin via a biotin-maleimide group bound to a surface cysteine amino acid on the polymerase via the known maleimide-cysteine covalent binding reaction.

FIG. 83A shows this embodiment with a peptide alpha-helix bridge, reduced to practice using the 66 amino acid sequence peptide mentioned. FIG. 83B illustrates the fully assembled sensor, with the alpha-helix bridge coupled to a neutravidin via the known biotin-neutravidin binding reaction, and also the polymerase attached, via an additional biotion-maleimide linker that has been conjugated to a surface cysteine on the polymerase, via the known maleimide-cysteine covalent coupling reaction.

The experimental reduction to practice of this embodiment is shown in FIGS. 85A-D. A test chip with 20 electrode pairs was fabricated by e-beam lithography as in other examples. The electrodes were chromium, with a gold layer deposited for coupling to the peptide bridge. The chip was cleaned for 240 seconds in an oxygen plasma cleaner immediately prior to bridge deposition. The peptide bridge was incubated with the chip in PBS buffer, at 1 µM concentration, for one hour. Subsequent to that, in PBS, the current-voltage characteristics of the electrodes was measured, varying the source-drain voltage from 0 to 2 volts. The electrode pair with the highest current was selected for time monitoring during the assembly and sequencing. Current versus time was monitored through the process of supplying neutravidn for bridge binding, polymerase-maleimide-biotin for binding to the neutravidin-bridge, and DNA template+dNTPs for polymerase incorporation activity. As shown in FIGS. 85A-D, a signal spike was produced corresponding to the neutravidin binding and polymerase binding phases of the sensor assembly process. The polymerase showed activity when exposed to the template-nucleotide solution, which could be interpreted (as indicated) as a series of three events of the sensor capturing a DNA template, and incorporating the complementary bases.

The template sequence had 4 major tracts of 10-GT repeats. Specifically, the template sequence included:

```
                                    (SEQ ID NO: 15)
GTGTGTGTGTGTGTGTGTGTGTTTTGTGTGTGTGTGTGTGTGTGTAAAGTG
TGTGTGTGTGTGTGTGTCCCGTGTGTGTGTGTGTGTGTGT
```

In the data interpretation shown, the GT tracts produce the spikes of sustained activity, within three successive engagements of the sensor with different incoming templates. This example illustrates that other preferred forms of bridge molecule can produce the incorporation signals that are the basis of sequence analysis.

In order to enhance the incorporation signal from this G-rich template, a modified C was used for the incorporation reaction mixture. Specifically, the standard dCTP nucleotide in the dNTP nucleotide mixture was replaced with a mixture of equal parts of two different modified dCTP molecules, shown in FIGS. 84A and 84B, whose forms were chosen to make substantial electro-chemical changes relative to the standard dCTP. These forms, dC4P-lactose, depicted in FIG. 84A, and d4CP-Cy7, depicted in FIG. 84B, are produced through a CLICK chemistry reaction. Both forms replace the triphosphate linkage with a tetra-phosphate linkage, and, via the DBCO CLICK chemistry linker, add an additional group onto the terminal phosphate. The groups used herein were the sugar, lactose, and the dye molecule "Cy7," resulting in dCP4-lactose and dCP-Cy7 modified forms of dCTP. Modifications are added to the gamma of the primary dCTP, such that during incorporation, the modifications are excised by the polymerase, leaving only native product DNA. This approach allows for large molecular perturbations, and thus signal enhancement, without altering the form of the DNA which could impair enzyme function or proccessivity.

FIG. 85A depicts data from s Sequence Sensing Experiment with the alpha-helix peptide bridge. The plot is Current-vs-Voltage traces for the electrodes on a test chip that has been incubated with the peptide bridge molecule for 1 hour in PBS buffer, at 1 µM peptide concentration, in order to attach bridge to gold contacts. The highest current trace, which achieves a 3 nano-amp current at 2 volts applied source-drain, indicates an electrode with a bridge molecule in place.

Further, FIG. 85B depicts additional data from s Sequence Sensing Experiment with the alpha-helix peptide bridge. The plot is Current-vs-Time trace showing the signature of the subsequent neutravidin binding to the bridge, at time of approximately 10 seconds to 50 seconds, when bridged sensor is exposed to a neutravidin solution with applied source-drain voltage of 2 volts.

FIG. 85C depicts additional data from s Sequence Sensing Experiment with the alpha-helix peptide bridge. The plot is Current-vs-Time trace showing the signature of the polymerase-maleimide-biotin binding the neutravidin-bridge complex, at the time of 10-20 seconds, when the latter is exposed to a solution of the former.

Lastly, FIG. 85D depicts additional data from s Sequence Sensing Experiment with the alpha-helix peptide bridge. The plot sets forth the resulting sequencing signals when the assembled sensor is provided with solution containing a template DNA, with sequence having a series of GT repeats: (10×GT) TTT (10×GT) AAA (10×GT) CCC (10×GT) (SEQ ID NO: 15). FIG. 84D is annotated with one possible interpretation of these signals, where major spikes corresponding to the GT repeat tracts of the template, and overall three different template DNA molecules, engage with the sensor during the 45 seconds shown.

Additional Examples

Additional non-limiting examples of the disclosure include the following.

A sensor comprising: a first contact coupled to a first electrode; a second contact coupled to a second electrode; a sensor gap defined between one of the first contact and the first electrode and one of the second contact and the second electrode; and a bridge molecule comprising a first end and a second end; wherein the bridge molecule is a biopolymer bridge molecule; and wherein the bridge molecule is coupled to the first contact at the first end and coupled to the second contact at the second end.

A sensor comprising: a first electrode overlying a substrate surface; a second electrode overlying the substrate surface; a sensor gap defined between the first electrode and the second electrode; and a bridge molecule comprising a first end and a second end; wherein the sensor gap comprises a sensor gap dimension of between about 5 nm and about 30 nm; and wherein the bridge molecule is coupled to the first contact at the first end and coupled to the second contact at the second end.

In various embodiments, the sensor may further comprise a gate electrode.

In various embodiments, the sensor gap has a sensor gap dimension of between about 5 nm and about 30 nm.

In various embodiments, the first end of the bridge molecule comprises a first self-assembling anchor, and/or the second end of the bridge molecule comprises a second self-assembling anchor.

In various embodiments, the bridge molecule comprises a biopolymer bridge molecule. In various embodiments, the first and/or second ends of the biopolymer bridge molecule are chemically modified by various chemical reactions.

In various embodiments, the bridge molecule comprises a chemically synthesized bridge molecule.

In various embodiments, the bridge molecule comprises a linear biopolymer.

In various embodiments, the bridge molecule comprises an end-to-end length of less than a persistence length of the bridge molecule.

In various embodiments, the bridge molecule comprises an end-to-end length configured to approximate the sensor gap dimension.

In various embodiments, the bridge molecule comprises a nucleic acid duplex.

In various embodiments, the nucleic acid duplex comprises one of a DNA duplex, a DNA-RNA hybrid duplex, a DNA-PNA hybrid duplex, a PNA-PNA duplex, and a DNA-LNA hybrid duplex.

In various embodiments, the nucleic acid duplex comprises a thiol-modified oligo.

In various embodiments, one of the first self-assembling anchor and the second self-assembling anchor comprises a 5'-thiol modified nucleotide.

In various embodiments, the nucleic acid duplex further comprises an internal biotin-modified nucleotide.

In various embodiments, the bridge molecule comprises a peptide sequence, and wherein one of the first self-assembling anchor and the second self-assembling anchor comprises an L-cysteine residue.

In various embodiments, the bridge molecule is configured to self-assemble to produce a bridge molecule conformation when a fluid medium comprising the bridge molecule is contacted with one of the first contact and the second contact.

In various embodiments, the sensor further comprises a probe, wherein the probe is attached to the bridge molecule.

In various embodiments, the sensor further comprises a linker attached to the bridge molecule.

In various embodiments, the probe is configured to engage a single target molecule.

In various embodiments, the molecular bridge and/or probe comprises an enzyme.

In various embodiments, the enzyme is one of a polymerase and a reverse transcriptase.

In various embodiments, the target molecule comprises a plurality of target molecules features, each target molecule feature having a discrete position, including a first target molecule feature at a first position, a second target molecule feature at a second position, and an nth target molecule feature at an nth position.

In various embodiments, the probe is an enzyme configured to engage the target molecule during a reaction in a solution comprising a plurality of different target molecules, wherein the reaction comprises a time period t, and wherein contacting the target molecule produces a plurality of conformation changes in the enzyme in response to the plurality of target molecule features, wherein each of the plurality of configuration changes modulates an electrical current in the sensor to produce a signal feature.

In various embodiments, a system comprises a sensor as described herein above.

In various embodiments, the system further comprises a signal processing system coupled to the sensor and configured to detect the signal feature.

In various embodiments, a system and/or sensor is configured to produce a signal trace comprising a plurality of signal features detected over time period t.

In various embodiments, the system further comprises a signal interpretation device.

In various embodiments, the signal interpretation device comprises a signal interpretation map.

In various embodiments, the signal interpretation map is calibrated against a signal trace from a known target sequence.

In various embodiments, the signal interpretation device is configured to return a signal interpretation in response to the signal trace produced by a target sequence.

In various embodiments, the signal interpretation includes a probabilistic evaluation of a likelihood that a signal trace interpretation matches a possible actual sequence.

In various embodiments, a method comprises: providing a sensor according to any of examples hereinabove; contacting a nucleic acid template with a polymerase, wherein the polymerase is coupled to a bridge molecule comprising a portion of a sensor; optionally applying an electrical potential to the sensor; providing a nucleotide base mix; performing, by the polymerase, an incorporation event comprising incorporation of a nucleotide from the nucleotide base mix into a synthesized nucleic acid; and detecting a signal produced by the incorporation event.

In various embodiments, the method further comprises a series of incorporation events performed in a time period t, wherein the series of incorporation events produces a signal trace comprising a sequence of signal features.

In various embodiments, each signal feature corresponds to one of the series of incorporation events.

In various embodiments, the signal trace further comprises noise, and wherein the method further comprises removing the noise from the signal trace.

In various embodiments, each incorporation event produces polymerase kinetic signature that is template base-dependent.

In various embodiments, the polymerase kinetic signature contributes to the signal feature.

In various embodiments, the method is suitable to distinguish a first signal feature produced in response to an unmodified template nucleotide and a second signal feature produced in response to a modified template nucleotide.

In various embodiments, the modified template nucleotide is one of $N^6$-methyladenosine, $N^4$-methylcytosine, 5-methylcytosine, 5-hydroxymethylcytosine, 5-formylcytosine, and 5-carboxylcytosine.

In various embodiments, the modified template nucleotide is an abasic site.

In various embodiments, a biomolecular sensing device comprises: forming a first electrode and a second electrode on a substrate surface, wherein the first electrode and the second electrode are separated by an electrode gap; placing a first contact on the first electrode and a second contact on the second electrode, wherein the first contact and the second contact are separated by a contact gap; and attaching a bridge molecule to the first contact and the second contact.

In various embodiments, the biomolecular sensing device further comprises contacting the bridge molecule with a probe to couple the probe to the bridge molecule, wherein the probe is coupled to the bridge molecule by self-assembly.

In various embodiments, attaching the bridge molecule to the first contact and the second contact comprises a self-assembly step.

In various embodiments, the electrode gap and/or the contact gap is between about 5 nm and about 30 nm.

In various embodiments, the first contact and/or the second contact comprise gold nanoparticles with a diameter of about 5 nm.

In various embodiments, a first contact position and/or a second contact position is determined using a lithography method.

In various embodiments, a photoresist layer is placed over the substrate surface comprising the first electrode and the second electrode, and defining a first contact position and a second contact position using a lithography method.

In various embodiments, the method further comprises applying a surface derivatization treatment to the substrate surface at the first contact position and the second contact position.

In various embodiments, the surface derivatization treatment comprises silanization.

In various embodiments, the method further comprises depositing a gold layer and performing a lift-off step to leave a first gold contact disposed on the first electrode and/or a second gold contact disposed on the second electrode.

In various embodiments, the method further comprises contacting the device with a solution comprising a plurality of gold nanoparticles and introducing a first gold nanoparticle at the first contact position and/or a second gold particle at the second contact position.

In various embodiments, the bridge molecule is attached to the first contact and the second contact by self-assembly prior to contacting the bridge molecule with a/the probe.

In various embodiments, the bridge molecule is contacted with the probe to produce a sensor complex by self-assembly prior to attaching the bridge molecule to the first contact and the second contact by self-assembly.

In various embodiments, the method further comprises fabricating an integrated circuit electronically coupled to the first electrode and the second electrode.

In various embodiments, the integrated circuit, the first electrode, and the second electrode comprise a mixed-signal integrated circuit.

In various embodiments, the integrated circuit, the first electrode, and the second electrode are fabricated using a CMOS fabrication method.

In various embodiments, the first and second contact are fabricated using a CMOS fabrication method.

In various embodiments, the integrated circuit, the first electrode, and the second electrode are fabricated using a fabrication method suitable to produce a field effect transistor.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions. The scope of the inventions is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. Although the various examples and embodiments described herein refer to methods of signal detection in relation to nucleic acid targets, the devices and methods of the present disclosure are in no way limited to applications comprising detection and sequencing of nucleic acids. Likewise, although the various examples and embodiments described herein refer to sensors comprising biopolymer bridges molecules, chemically synthesized bridge molecules are within the scope of the present disclosure. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35

U.S.C. 112(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

---

What is claimed is:

1. A sensor comprising:
a source electrode comprising a metal contact;
a drain electrode comprising a metal contact and spaced apart from the source electrode by a sensor gap, wherein the source and drain electrodes cooperate to form an electrode circuit;
a bridge molecule comprising a protein alpha helix or a nucleic acid duplex bridging across said sensor gap, coupling the source and drain electrodes, wherein the bridge molecule comprises two thiol containing groups coupled to the metal contacts of the source and drain electrodes by a thiol-metal bond; and
a probe coupled to the bridge molecule by a linker comprising a molecular complex configured to connect the probe to the bridge molecule, the probe configured to receive and interact with a nucleic acid;
wherein interaction of the probe with the nucleic acid is detectable by monitoring at least one parameter of the electrode circuit, and
wherein a molecular complex formed by the probe and the linker is interposed between the bridge molecule and the nucleic acid.

2. The sensor of claim 1, wherein the nucleic acid that interacts with the probe comprises DNA or RNA, or variants thereof.

3. The sensor of claim 1, wherein the probe comprises an enzyme.

4. The sensor of claim 3, wherein the enzyme comprises a DNA polymerase, a reverse transcriptase, an exonuclease, or a helicase.

5. The sensor of claim 4, wherein the enzyme comprises a DNA polymerase.

6. The sensor of claim 5, wherein the DNA polymerase is Phi29, PolI, or a mutant thereof.

7. The sensor of claim 1, wherein the bridge molecule comprises a double-stranded DNA having a thiol-modified nucleotide configured for self-assembling to one of the source or the drain electrodes.

8. The sensor of claim 7, wherein the bridge molecule comprises one of a DNA duplex, a DNA-RNA hybrid duplex, a DNA-PNA hybrid duplex, a PNA-PNA duplex, and a DNA-LNA hybrid duplex.

9. The sensor of claim 1, wherein the bridge molecule comprises a peptide or protein alpha-helix.

10. The sensor of claim 1, wherein the metal contacts on the source and drain electrodes comprise gold.

11. The sensor of claim 1, wherein the probe is configured to attach to the bridge molecule via a self-assembling linker.

12. The sensor of claim 1, wherein the at least one detected parameter of the electrode circuit correlates to a specific and identifiable nucleotide incorporation.

13. A sensor comprising:
a first electrode overlying a substrate surface, the first electrode comprising a metal contact;
a second electrode overlying the substrate surface, the second electrode comprising a metal contact;
a sensor gap defined between the first electrode and the second electrode;
a biopolymer bridge molecule comprising an sDNA or dsDNA and having a first end and a second end; and
a probe molecule coupled to the biopolymer bridge molecule through a linker;
wherein one or both of the first end and second end of the biopolymer bridge molecule comprises a thiolated nucleotide at a respective end in which a thiol group is coupled to the metal contact of the first and second electrodes by a thiol-metal bond; and
wherein the probe molecule interacts with a nucleic acid to generate a signal, and wherein a molecular complex formed by the probe and the linker is interposed between the bridge molecule and the nucleic acid.

14. The sensor of claim 13, wherein the biopolymer bridge molecule comprises a nucleic acid complex.

15. The sensor of claim 14, wherein the nucleic acid duplex comprises one of a DNA duplex, a DNA-RNA hybrid duplex, a DNA-PNA hybrid duplex, a PNA-PNA duplex, and a DNA-LNA hybrid duplex.

16. The sensor of claim 13, wherein the biopolymer bridge comprises a peptide alpha-helix.

17. The sensor of claim 13, wherein the biopolymer bridge comprises a synthetic molecule.

18. The sensor of claim 13, wherein the biopolymer bridge comprises an antibody.

19. The sensor of claim 13, wherein the metal contacts on the source and drain electrodes comprise gold.

* * * * *